(12) United States Patent
Turner et al.

(10) Patent No.: US 10,786,534 B2
(45) Date of Patent: Sep. 29, 2020

(54) PRODUCTION AND USE OF RED BLOOD CELLS

(71) Applicant: Taiga Biotechnologies, Inc., Aurora, CO (US)

(72) Inventors: Brian C. Turner, Denver, CO (US); Yosef Refaeli, Denver, CO (US); Gregory A. Bird, Littleton, CO (US)

(73) Assignee: TAIGA BIOTECHNOLOGIES, INC., Aurora, CO (US)

( * ) Notice: Subject to any disclaimer, the term of this patent is extended or adjusted under 35 U.S.C. 154(b) by 0 days.

(21) Appl. No.: 15/643,133

(22) Filed: Jul. 6, 2017

(65) Prior Publication Data

US 2018/0177827 A1 Jun. 28, 2018

Related U.S. Application Data

(62) Division of application No. 13/797,648, filed on Mar. 12, 2013, now Pat. No. 10,272,115.

(60) Provisional application No. 61/776,732, filed on Mar. 11, 2013.

(51) Int. Cl.
*A61K 35/18* (2015.01)
*C12N 5/078* (2010.01)
*C12N 5/0789* (2010.01)
*A01K 67/027* (2006.01)

(52) U.S. Cl.
CPC .......... *A61K 35/18* (2013.01); *A01K 67/0271* (2013.01); *C12N 5/0641* (2013.01); *C12N 5/0647* (2013.01); *A01K 2207/12* (2013.01); *A01K 2207/15* (2013.01); *A01K 2227/105* (2013.01); *A01K 2267/0331* (2013.01); *A01K 2267/0381* (2013.01); *C12N 2501/14* (2013.01); *C12N 2501/2303* (2013.01); *C12N 2501/26* (2013.01); *C12N 2501/48* (2013.01); *C12N 2501/606* (2013.01)

(58) Field of Classification Search
CPC ................ A61K 35/18; A01K 67/0271; A01K 2207/12; A01K 2207/15; A01K 2227/105; A01K 2267/0331; A01K 2267/0381; C12N 5/0641; C12N 5/0647; C12N 2501/14; C12N 2501/2303; C12N 2501/26; C12N 2501/48; C12N 2501/606
See application file for complete search history.

(56) References Cited

U.S. PATENT DOCUMENTS

| | | |
|---|---|---|
| 4,900,322 A | 2/1990 | Adams |
| 4,963,489 A | 10/1990 | Naughton et al. |
| 5,289,858 A | 3/1994 | Grabenkort |
| 5,476,996 A | 12/1995 | Wilson et al. |
| 5,652,122 A | 7/1997 | Frankel et al. |
| 5,670,617 A | 9/1997 | Frankel et al. |
| 5,674,980 A | 10/1997 | Frankel et al. |
| 5,698,767 A | 12/1997 | Wilson et al. |
| 5,747,641 A | 5/1998 | Frankel et al. |
| 5,804,604 A | 9/1998 | Frankel et al. |
| 5,811,301 A | 9/1998 | Cameron |
| 5,824,837 A | 10/1998 | Chen et al. |
| 5,843,728 A | 12/1998 | Seed et al. |
| 5,847,082 A | 12/1998 | Rother et al. |
| 5,849,288 A | 12/1998 | Reisner |
| 5,851,828 A | 12/1998 | Seed et al. |
| 5,912,170 A | 6/1999 | Seed et al. |
| 6,004,811 A | 12/1999 | Seed et al. |
| 6,040,177 A | 3/2000 | Riddell et al. |
| 6,284,240 B1 | 9/2001 | Seed et al. |
| 6,358,739 B1 | 3/2002 | Baetge et al. |
| 6,392,013 B1 | 5/2002 | Seed et al. |
| 6,410,014 B1 | 6/2002 | Seed et al. |
| 6,451,558 B1 | 9/2002 | Cooke et al. |
| 6,451,601 B1 | 9/2002 | Baetge et al. |
| 6,645,501 B2 | 11/2003 | Dowdy |
| 6,753,162 B1 | 6/2004 | Seed et al. |
| 7,135,287 B1 | 11/2006 | Lonberg et al. |
| 7,311,920 B1 | 12/2007 | Devico et al. |
| 7,582,745 B2 | 9/2009 | Sah et al. |
| 7,767,453 B2 | 8/2010 | Zhang |
| 8,034,334 B2 | 10/2011 | Dudley et al. |
| 8,211,422 B2 | 7/2012 | Eshhar et al. |
| 8,481,492 B2 | 7/2013 | Edenhofer et al. |
| 8,637,307 B2 | 1/2014 | June et al. |
| 8,697,854 B2 | 4/2014 | Schendel et al. |
| 8,784,825 B2 | 7/2014 | Refaeli et al. |
| 8,828,723 B2 | 9/2014 | Refaeli et al. |
| 8,986,702 B2 | 3/2015 | Refaeli et al. |
| 9,150,831 B2 | 10/2015 | Cambier et al. |
| 9,365,825 B2 | 6/2016 | Turner et al. |
| 9,775,897 B2 | 10/2017 | Refaeli et al. |
| 9,789,135 B2 | 10/2017 | Turner et al. |

(Continued)

FOREIGN PATENT DOCUMENTS

| AU | 2762802 | 5/2002 |
|---|---|---|
| AU | 2006304392 B2 | 5/2014 |

(Continued)

OTHER PUBLICATIONS

Hirose et al., Stem Cell Reports I: 499-508, 2013.*

(Continued)

*Primary Examiner* — Thaian N. Ton
(74) *Attorney, Agent, or Firm* — Foley & Lardner LLP

(57) ABSTRACT

The present disclosure relates to the production of red blood cells from hematopoietic stem cells, by differentiating such cells in the presence of a protein that induces cell survival and proliferation.

10 Claims, 35 Drawing Sheets

Specification includes a Sequence Listing.

(56) References Cited

U.S. PATENT DOCUMENTS

| | | | |
|---|---|---|---|
| 10,442,853 | B2 | 10/2019 | Refaeli et al. |
| 2001/0049393 | A1 | 12/2001 | Coller et al. |
| 2002/0076787 | A1 | 6/2002 | Baetge et al. |
| 2002/0098166 | A1 | 7/2002 | Havemann et al. |
| 2002/0155502 | A1 | 10/2002 | Balint et al. |
| 2003/0072794 | A1 | 4/2003 | Boulikas |
| 2003/0138859 | A1 | 7/2003 | Barbera-Guillem et al. |
| 2003/0220286 | A1 | 11/2003 | Abruzzese et al. |
| 2004/0224402 | A1 | 11/2004 | Bonyhadi et al. |
| 2005/0220705 | A1 | 10/2005 | Brooks et al. |
| 2005/0281816 | A1 | 12/2005 | Lamping et al. |
| 2006/0068369 | A1 | 3/2006 | Coelho et al. |
| 2006/0068469 | A1 | 3/2006 | Payne et al. |
| 2006/0115898 | A1 | 6/2006 | Zhang et al. |
| 2006/0154331 | A1 | 7/2006 | Avidan et al. |
| 2006/0156422 | A1 | 7/2006 | Dalrymple et al. |
| 2006/0222657 | A1 | 10/2006 | Dowdy et al. |
| 2007/0011753 | A1 | 1/2007 | Ito et al. |
| 2007/0047583 | A1 | 3/2007 | Assa et al. |
| 2007/0067854 | A1 | 3/2007 | Habu et al. |
| 2007/0082397 | A1 | 4/2007 | Hasson et al. |
| 2007/0093420 | A1 | 4/2007 | Yeomans et al. |
| 2007/0098715 | A1 | 5/2007 | Ettenberg et al. |
| 2007/0116691 | A1 | 5/2007 | Cambier et al. |
| 2007/0130628 | A1 | 6/2007 | Brown |
| 2007/0248618 | A1 | 10/2007 | Cohen |
| 2009/0291094 | A1 | 11/2009 | Refaeli et al. |
| 2010/0047217 | A1 | 2/2010 | Refaeli et al. |
| 2010/0055129 | A1 | 3/2010 | Refaeli et al. |
| 2010/0233804 | A1 | 9/2010 | Zhou et al. |
| 2010/0279351 | A1 | 11/2010 | Refaeli |
| 2010/0297763 | A1 | 11/2010 | Cambier et al. |
| 2011/0218210 | A1 | 9/2011 | Refaeli et al. |
| 2012/0003189 | A1 | 1/2012 | Pelus et al. |
| 2012/0027792 | A1 | 2/2012 | Pavlakis et al. |
| 2012/0244133 | A1 | 9/2012 | Rosenberg et al. |
| 2012/0251563 | A1 | 10/2012 | Nicchitta et al. |
| 2013/0177586 | A1 | 7/2013 | Refaeli et al. |
| 2014/0109246 | A1 | 4/2014 | Jimeno et al. |
| 2014/0255369 | A1 | 9/2014 | Turner et al. |
| 2014/0356392 | A1 | 12/2014 | Refaeli et al. |
| 2015/0164950 | A1 | 6/2015 | Turner et al. |
| 2015/0218515 | A1 | 8/2015 | Altrichter et al. |
| 2017/0044500 | A1 | 2/2017 | Cooper et al. |
| 2018/0036396 | A1 | 2/2018 | Refaeli et al. |

FOREIGN PATENT DOCUMENTS

| | | |
|---|---|---|
| CN | 1357620 | 7/2002 |
| CN | 101330830 A | 12/2008 |
| EP | 0 367 76 A2 | 9/1981 |
| EP | 0 213 469 A2 | 3/1987 |
| EP | 1 103 615 A1 | 5/2001 |
| EP | 1 357 184 | 10/2003 |
| EP | 1 792 627 | 6/2007 |
| GB | 2 387 599 | 10/2003 |
| JP | 2000-189157 | 7/2000 |
| JP | 2001-518300 | 10/2001 |
| JP | 2002-541786 | 12/2002 |
| JP | 2003-513672 | 4/2003 |
| JP | 2003-514565 | 4/2003 |
| JP | 2004-519245 | 7/2004 |
| JP | 2005-523012 | 8/2005 |
| JP | 2005-525085 | 8/2005 |
| JP | 2005-527211 | 9/2005 |
| JP | 2009-511081 | 3/2009 |
| JP | 2011-528567 A | 11/2011 |
| JP | 2012-501347 A | 1/2012 |
| JP | 2014-527980 A | 10/2014 |
| JP | 2015-524415 A | 8/2015 |
| JP | 6167130 B2 | 8/2015 |
| JP | 2015-525209 A | 9/2015 |
| JP | 2016-510996 A | 4/2016 |
| JP | 6484293 B2 | 3/2019 |
| JP | 6655050 B2 | 2/2020 |
| WO | WO-86/03780 A1 | 7/1986 |
| WO | WO-92/15322 | 9/1992 |
| WO | WO-94/04686 | 3/1994 |
| WO | WO-94/19465 | 9/1994 |
| WO | WO-95/14078 | 5/1995 |
| WO | WO-98/10058 | 3/1998 |
| WO | WO-98/52614 | 11/1998 |
| WO | WO-99/16884 | 4/1999 |
| WO | WO-99/45962 | 9/1999 |
| WO | WO-99/53023 | 10/1999 |
| WO | WO-99/53028 | 10/1999 |
| WO | WO-00/09669 | 2/2000 |
| WO | WO-00/61617 | 10/2000 |
| WO | WO-00/62067 | 10/2000 |
| WO | WO-01/34824 | 5/2001 |
| WO | WO-01/38548 | 5/2001 |
| WO | WO-02/057436 | 7/2002 |
| WO | WO-02/074968 | 9/2002 |
| WO | WO-03/020763 | 3/2003 |
| WO | WO-03/033701 | 4/2003 |
| WO | WO-03/038057 | 5/2003 |
| WO | WO-03/039462 | 5/2003 |
| WO | WO-03/057171 | 7/2003 |
| WO | WO-03/089580 | 10/2003 |
| WO | WO-03/089630 | 10/2003 |
| WO | WO-03/094849 | 11/2003 |
| WO | WO-03/097675 | 11/2003 |
| WO | WO-2004/033685 | 4/2004 |
| WO | WO-2004/035535 | 4/2004 |
| WO | WO-2004/044004 | 5/2004 |
| WO | WO-2004/050885 | 6/2004 |
| WO | WO-2004/074322 | 9/2004 |
| WO | WO-2004/084805 | 10/2004 |
| WO | WO-2005/014785 | 2/2005 |
| WO | WO-2005/084158 | 9/2005 |
| WO | WO-2005/113595 | 12/2005 |
| WO | WO-2005/114215 | 12/2005 |
| WO | WO-2006/000830 | 1/2006 |
| WO | WO-2006/032876 | 3/2006 |
| WO | WO-2006/116512 | 11/2006 |
| WO | WO-2006/125962 | 11/2006 |
| WO | WO-2007/047583 | 4/2007 |
| WO | WO-2007/067183 | 6/2007 |
| WO | WO-2008/038002 | 4/2008 |
| WO | WO-2008/039818 | 4/2008 |
| WO | WO-2008/112922 | 9/2008 |
| WO | WO-2009/059304 | 5/2009 |
| WO | WO-2009/139930 A2 | 11/2009 |
| WO | WO-2010/011644 | 1/2010 |
| WO | WO-2010/025421 | 3/2010 |
| WO | WO-2011/100477 A2 | 8/2011 |
| WO | WO-2012/055170 | 5/2012 |
| WO | WO-2013/039889 | 3/2013 |
| WO | WO-2013/166321 | 11/2013 |
| WO | WO-2014/018863 | 1/2014 |
| WO | WO-2014/083173 | 6/2014 |
| WO | WO-2014/133567 | 9/2014 |
| WO | WO-2014/133568 | 9/2014 |
| WO | WO-2014/164606 | 10/2014 |
| WO | WO-2016/105542 | 6/2016 |
| WO | WO-2017/123978 A1 | 7/2017 |

OTHER PUBLICATIONS

Opferman et al., Cell Death and Differentiation (2018) 25, 37-45.*
Chinese Office Action, dated May 24, 2018, issued in corresponding Chinese Patent Application No. 201380048261.4.
European Office Action, dated May 15, 2018, issued in corresponding European Patent Application No. 09747016.5.
Japanese Office Action, issued in Japanese Patent Appln. No. 2017-166334, 6 pages (dated Apr. 24, 2019).
Coeytaux et al., "The Cationic Amphipathic alpha-Helix of HIV-1 Viral Protein R (VPR) Binds to Nucleic Acids, Permeabilizes Membranes, and Efficiently Transfects Cells," The Journal of Biological Chemistry, vol. 278, No. 20, May 16, 2003, pp. 18110-18116.
Final Office Action on U.S. Appl. No. 14/873,296, dated Jan. 24, 2018.

(56) References Cited

OTHER PUBLICATIONS

Non-Final Office Action on U.S. Appl. No. 15/179,735 dated Feb. 26, 2018.
Non-Final Office Action on U.S. Appl. No. 15/244,138 dated Jan. 22, 2018.
Notice of Reasons for Rejection issued on Japanese Application 2014-108137, dated Nov. 1, 2017.
Notice of Reasons for Rejection issued on Japanese Application 2016-501113, dated Dec. 28, 2017.
Australian Examination Report, issued in Australian Patent Application No. 2014249200, 4 pages. (dated Mar. 15, 2019).
De Korte, "New additive solutions for red cells", ISBT Science Series 11: 165-170 (2016).
Decision of Rejection, issued in Chinese Patent Application No. 201380048261.4, 6 pages (dated Apr. 16, 2019).
European Extended Search Report, issued in European Patent Appln. No. 19157513.3, 13 pages (dated Apr. 1, 2019).
Final Office Action on U.S. Appl. No. 15/244,138 dated Mar. 14, 2019.
Japanese Office Action, issued in Japanese Patent Application No. 2018-017287, 13 pages (dated Apr. 18, 2019).
Laurentl, et al., "Hematopoietic Stem Cell Function and Survival Depend on c-Myc and N-Myc Activity", Cell Stem Cell 3: 611-624 (2008).
Maite, et al., "Erythropoietin Can Promote Erythroid Progenitor Survival by Repressing Apoptosis Through Bcl-XL, and Bcl-2", Blood Journal 88(5): 1576-1582 (1996).
Momir, et al., "Is erythropoietin a survival factor for red blood cells", Journal of the American Society of Nephrology, 7(8): 1178-1182 (1996).
Penuela, et al., "Erythropoietin reduces storage lesions and decreases apoptosis indices in blood bank red blood cells", Revista Brasileira de Hematologia e Hemoterapia 38(1): 15-20 (2016).
Song, "Cloning and expression of PTD-BDNF fusion gene and purification of expressed product", Bioengineering Pharmaceutical Research and Practice, Anhui Science and Technology Press, 1st Ed., pp. 200-201 (Feb. 2009).
Canadian Office Action, dated Jul. 4, 2018, issued in Canadian Patent Application No. 2,626,525.
European Office Action, dated Jun. 29, 2018, issued in European Patent Appln. No. 14779483.8.
Israeli Office Action, dated Jun. 27, 2018, issued in Israeli Patent Application No. 208810.
Israeli Office Action, dated Jul. 29, 2018, issued in Israeli Patent Application No. 256512.
Israeli Office Action, dated Jul. 30, 2018, issued in Israeli Patent Application No. 241192.
Japanese Office Action, dated Jul. 18, 2018, issued in Japanese Patent Application No. 2017-123838.
Second Office Action issued on Chinese Application 201480026500.0, dated Apr. 27, 2018.
Examination Report issued on EP Application 13820331.0, dated Apr. 24, 2018.
Examination Report issued on EP Application 14778538.0, dated Apr. 16, 2018.
Non-Final Office Action on U.S. Appl. No. 13/797,648 dated Apr. 19, 2018, includes Accession NP 002458.2, 2018.
Japanese Office Action, issued in Japanese Patent Application No. 2018-048138, 3 pages (dated Feb. 12, 2019).
Non-Final Office Action on U.S. Appl. No. 15/717,675 dated Feb. 14, 2019.
Aubry et al., "N-Myc Shares Cellular Functions with c-Myc", DNA and Cell Biology, vol. 19, No. 6, Jun. 2000, pp. 353-364.
Austrian Search Report and Written Opinion received for Singapore Patent Application No. 201101367-9, dated Mar. 23, 2012, 17 pages.
Baum, Christopher, "Insertional Mutagenesis in Gene Therapy and Stem Cell Biology", Current Opinion in Hematology, vol. 14, Jul. 2007, pp. 337-342.

Beerens et al., "Protein Transduction Domains and their Utility in Gene Therapy", Current Gene Therapy, vol. 3, No. 5, 2003, pp. 486-494.
Berkson et al., "Pilot Screening Programme for Small Molecule Activators of p53", International Journal of Cancer, vol. 115, 2005, pp. 701-710.
Bird et al., Expansion of Human and Murine Hematopoietic Stem and Progenitor Cells Ex Vivo without Genetic Modification Using MYC and Bcl-2 Fusion Proteins, PLOS ONE, vol. 9, No. 8, Aug. 29, 2014 p. 20 pages.
Bissonnette et al., "Apoptotic cell death induced by c-myc is inhibited by bcl-2," Nature, vol. 359, Oct. 8, 1992, pp. 552-554.
Bouchard et al., "Control of cell proliferation by Myc", Trends in Cell Biology, vol. 8, pp. 202-206, (1998).
Bunting et al., "Restoration of lymphocyte function in Janus kinase 3-deficient mice by retro-viral-mediated gene transfer," Nature Medicine 4:58-64 (1998).
Buske et al., "Deregulated Expression of HOXB4 Enhances the Primitive Growth Activity of Human Hematopoietic Cells", Blood, vol. 100, No. 3, Aug. 1, 2002, pp. 862-868.
Capecchi, Mario R., "Altering the Genome by Homologous Recombination", Science, vol. 244, No. 4910, Jun. 16, 1989, pp. 1288-1292.
Caron, et al., "Endosome disruption enhances the functional nuclear delivery of Tat-fusion proteins", Biochem Biophys Res Commun, (2004), vol. 319, pp. 12-20.
Carotta et al., "Directed Differentiation and Mass Cultivation of Pure Erythorid Progenitors from Mouse Embryonic Stem Cells", Blood, vol. 104, No. 6, Sep. 15, 2004, pp. 1873-1880.
Chadwick, et al., "Notch Signaling Induces Apoptosis in Primary Human CD34 Hematopoietic Progenitor Cells", Stem Cells, (2007), vol. 24, pp. 203-210.
Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.
Cheng et al., "BCL-2, BCL-XL, Sequester BH3 Domain-Only Molecules Preventing BAX- and BAK-Mediated Mitochondrial Apoptosis", Molecular Cell (2001) vol. 8, pp. 705-711.
Chin et al., "Essential Role for Oncogenic Ras in Tumour Maintenance", Nature, vol. 400, 1999, pp. 468-472.
Chinese 3rd Office Action dated Nov. 28, 2016 in Chinese Patent Application No. 201410168106.2.
Choi et al., "Myc Protein is Stabilized by Suppression of a Novel E3 Ligase Complex in Cancer Cells", Genes & Development, vol. 24, 2010, pp. 1236-1241.
Choi, et al., "Status Epilepticus-Induced Somatostatinergic Hilar Interneuron Degeneration Is Regulated by Striatal Enriched Protein Tyrosine Phosphatase", Journal of Neuroscience, (2007), vol. 27, No. 11, pp. 2999-3009.
Coller, et al., "Expression Analysis with Oligonucleotide Microarrays Reveals that MYC Regulates Genes Involved in Growth, Cell Cycle, Signaling, and Adhesion", PNAS, (2000), 97(7):3260-3265.
Communication issued on EP Application 09747016.5, dated Jun. 12, 2017.
Conti, et al., "Gene therapy using neural stem cells," Methods Mol. Biol. 198:233-244 (2002).
Coppola et al., "Constitutive c-myc oncogene expression blocks mouse erythroleukaemia cell differentiation but not commitment," Nature, vol. 320, Apr. 24, 1986, pp. 760-763.
D'Alessandro et al, "Red blood cell storage: the story so far," Blood Transfus, Mar. 29, 2010, pp. 82-88.
Dang et al., "Identification of the Human c-myc Protein Nuclear Translocation Signal", Molecular and Cellular Biology, vol. 8, No. 10, Oct. 1988, pp. 4048-4054.
Dang et al., "Nuclear and Nucleolar Targeting Sequences of c-erb-A, c-myb, N-myc, p53, HSP70 and HIV tat Proteins". Journal of Biological Chemistry, vol. 264, No. 30, pp. 18019-18023 (1989).
Dang, Chi V., "c-Myc Target Genes Involved in Cell Growth, Apoptosis, and Metabolism", Molecular and Cellular Biology, vol. 19, No. 1, Jan. 1999, pp. 1-11.
Daugas et al, "Erythrocytes: Death of a Mummy, "Cell Death and Differentiation, vol. 8, 2001, pp. 1131-1133.

(56) References Cited

OTHER PUBLICATIONS

Decision of Rejection issued on Japanese application 2014-108137, dated Jun. 2, 2016, English translation only.
Delgado et al., "Myc Roles in Hematopoiesis and Leukemia," Genes and Cancer, 2010, pp. 605-616.
Deocampo, et al., "Cooperation of BCL-2 and MYC in the Neoplastic Transformation of Normal Rat Lever Epithelial Cells is Related to the Down-Regulation of Gap Junction-Mediated Intercellular Communication", Carcinogenesis, vol. 21, No. 8, pp. 1501-1506,(2000).
Dmitrovsky et al., "A Transfected c-myc Oncogene Inhibits Mouse Erytholeukemic Differentiation," Current Topics in Microbiology and Immunology, vol. 132, 1986, 4 pages.
Domashenko et al., "TAT-mediated transduction of NF-Ya peptide induces the ex vivo proliferation and egraftment potential of human hematopoietic progenitor cells," Blood, Oct. 14, 2010, vol. 116, No. 15, pp. 2676-2683.
Dvorak et al., "Cytochemical Localization of Peroxidase Activity in the Developing Erythrocyte," Am. J. Pathol. 1972, 67(2), pp. 303-326.
Eilers, et al., "Chimeras of MYC Oncoprotein and Steroid Receptors Cause Hormone-Dependent Transformation of Cells," Nature 340(6228):66-68 (1989).
Eischen, et al., "Apoptosis Triggered by Myc-Induced Suppression of Bcl-XL or Bcl-2 Is Bypassed during Lymphomagenesis", Molecular Cell Biology, 2001, 21: 5063-5070.
English Translation of Decision of Rejection on Japanese Application No. 2011-520133, dated Nov. 26, 2014, 6 pages.
English Translation of Decision of Rejection on Japanese Application No. 2011-525258, dated Dec. 3, 2014, 11 pages.
English Translation of Fourth Office Action received for Chinese Patent Application No. 200880015602.7 dated Nov. 11, 2013, 6 pages.
English Translation of Notification of Defects in Israeli Patent Application No. 190946 dated May 14, 2015, 2 pages.
English Translation of Notification of Reasons of Refusal for Japanese Patent Application No. 2012-221023 dated Jun. 24, 2014, 2 pages.
English Translation of Office Action on Chinese Appln. No. 200980127166.7 dated Apr. 11, 2014, 3 pages.
English Translation of Office Action on Israeli Application No. 208810 dated Jan. 13, 2015, 3 pages.
English Translation of Office Action on Israeli Application No. 232432 dated Mar. 8, 2015, 3 pages.
English Translation of Office Action on Israeli Patent Application No. 200919 dated May 19, 2014, 3 pages.
English Translation of Office Action on Japanese Patent Application. No. 2012-221023 dated Apr. 22, 2014, 3 pages.
English Translation of Office Action on Korean Patent Application No. 10-2013-7020078 dated Sep. 17, 2014, 5 pages.
English Translation of Office Action received for Chinese Patent Application No. 200980126312.4 dated Jan. 22, 2014, 3 pages.
English Translation of Office Action received for Eurasian Patent Application No. 201001762/28, posted Oct. 16, 2013, 1 page.
English translation of Office Action received for Israeli Patent Application No. 190946, dated Apr. 22, 2013, 1 page.
English Translation of Office Action received for Israeli Patent Application No. 209968 dated Jan. 2, 2014, 2 pages.
English translation of Office Action received for Japanese Application No. 2008-536713 dated Aug. 5, 2013, 2 pages.
English Translation of Office Action received for Japanese Patent Application No. 2011-525258 dated Feb. 17, 2014, 4 pages.
English Translation of Office Action received for Korean Patent Application No. 10-2008-7011791 dated Jan. 15, 2014, 3 pages.
English Translation of Office Action received for Korean Patent Application No. 10-2013-7028338, dated Jan. 15, 2014, 3 pages.
English Translation of Second Office Action received for Chinese Patent Application No. 200980127166.7, dated Jun. 10, 2013, 1 page.
English Translation of the Third Office Action on Chinese Patent Application No. 200680045545.8 dated Feb. 15, 2015, 4 pages.
English Translation of Third Office Action on Japanese Patent Application No. 2009-553785 dated Apr. 22, 2014, 3 pages.
Esdar, C., et al., "Differentiation-associated apoptosis of neural stem cells is effected by Bcl-2 overexpression: impact on cell lineage determination," Eur. J. Cell Biol.,(2001), vol. 80, No. 8, pp. 539-553.
Examination Report for Indian Patent Application No. 3332/DELNP/2008 dated Aug. 23, 2013, 6 pages.
Examination Report issued on Australian Application 2013292330, dated Sep. 6, 2017.
Examination Report issued on Australian Application 2015205879, dated Mar. 15, 2016.
Examination Report issued on Australian Application 2016203892, dated Apr. 12, 2017.
Examination Report issued on EP Application 09747016.5, dated Jul. 26, 2016.
Examination Report issued on EP Application 15175802.6, dated Jan. 31, 2017.
Examination Report issued on Indian Application 2048/DELNP/2011, dated Sep. 15, 2016.
Examination Report issued on Indian Application 634/DELNP/2011, dated Jun. 8, 2017.
Examination Report issued on Indian Application 9033/DELNP/2010, dated May 19, 2017.
Examination Report No. 1 on Australian Application No. 2014202016 dated May 12, 2015, 3 pages.
Examination Report on Australian application 2009274172, dated Jul. 24, 2014, 3 pages.
Examination Report on Australian Patent Application No. 2012216462 dated Mar. 6, 2014, 3 pages.
Examination Report on Canadian Application 2,731,767, dated Sep. 5, 2014, 2 pages.
Examination Report on Canadian Application No. 2,735,522 dated Oct. 2, 2014, 2 pages.
Examination Report on European Application No. 09747016.5 dated Mar. 19, 2015, 5 pages.
Examiner's Report on Canadian Application No. 2680613 dated Nov. 28, 2014, 4 pages.
Examiner's Report on Canadian Application No. 2723114 dated Apr. 21, 2015, 4 pages.
Examiner's Report on European Application No. 1287097.6 dated Jan. 22, 2015, 6 pages.
Extended European Search report and Search Opinion received for Patent Application No. 12187097.6, dated Mar. 27, 2013, 8 pages.
Extended European Search Report for EP Patent Application No. 13188850.0, dated May 27, 2014, 8 pages.
Extended European Search Report received for European Patent Application No. 09810692.5, dated Jul. 11, 2011, 5 pages.
Extended European Search Report received for European Patent Application No. 06826025.6, dated Aug. 13, 2009, 8 pages.
Extended European Search Report received for European Patent Application No. 09747016.5, dated May 30, 2012, 8 pages.
Extended European Search Report received for European Patent Application No. 09800871. 7, dated Jun. 24, 2011, 5 pages.
Extended European Search Report received for European Patent Application No. 12187077.8, dated Mar. 25, 2013, 7 pages.
Extended Search Report issued on EP Application 13820331.0, dated Nov. 10, 2016.
Extended Search Report issued on European Application 14778538.0, dated Sep. 29, 2016.
Extended Search Report issued on European Application 14779483.8, dated Dec. 23, 2016.
Extended Search Report issued on European Patent Application 15175802.6, dated Dec. 14, 2015.
Fanidi et al., "Cooperative interaction between c-myc and bcl-2 proto-oncogenes," Nature, vol. 359, Oct. 8, 1992, pp. 554-556.
Felsher, et al., "Reversible Tumorigenesis by MYC in Hematopoietic Lineages", (1999), Molecular Cell, 4: 199-207.
Final Office Action on U.S. Appl. No. 12/467,957, dated Sep. 17, 2014, 9 pages.

(56) References Cited

OTHER PUBLICATIONS

Final Office Action on U.S. Appl. No. 12/506,894 dated Oct. 9, 2014, 15 pages.
Final Office Action on U.S. Appl. No. 13/797,648 dated Feb. 8, 2017.
Final Office Action on U.S. Appl. No. 14/461,105 dated Sep. 15, 2016.
Final Office Action on U.S. Appl. No. 14/509,870 dated Feb. 3, 2017.
Final Office Action on U.S. Appl. No. 12/701,383 dated Nov. 13, 2014, 18 pages.
Final Office Action on U.S. Appl. No. 13/795,659 dated Jul. 11, 2014, 16 pages.
Final Office Action on U.S. Appl. No. 13/795,659 dated Mar. 26, 2015, 18 pages.
Final Office Action on U.S. Appl. No. 13/797,648 dated Apr. 1, 2015, 12 pages.
Final Office Action on U.S. Appl. No. 11/583,970 dated Apr. 9, 2014, 20 pages.
Final Office Action received for Korean Patent Application No. 10-2009-7021320, dated May 29, 2013, 6 pages (3 pages of English Translation and 3 pages of Office Action).
Final Office Action received for U.S. Appl. No. 11/583,970, dated Nov. 17, 2011, 15 pages.
Final Office Action received for U.S. Appl. No. 12/701,383, dated Nov. 16, 2011, 13 paegs.
Final Office Action received for U.S. Appl. No. 11/583,970, dated Nov. 26, 2008, 13 pages.
Final Office Action received for U.S. Appl. No. 12/048,148, dated Feb. 15, 2013, 17 pages.
Final Office Action received for U.S. Appl. No. 12/467,957 dated Feb. 28, 2011, 8 pages.
Final Office Action received for U.S. Appl. No. 12/550,166, dated May 11, 2012, 12 pages.
Final Office Action received on U.S. Appl. No. 11/583,970, dated Nov. 4, 2009, 10 pages.
First Office Action issued on Chinese Application 201410479685.2, dated Nov. 17, 2015.
Gandarillas et al., "C-Myc promotes differentiation of human epidermal stem cells," Genes & Develoopment, vol. 11, 1997, pp. 2869-2882.
Gauss et al., "DEAE-Dextran Enhances Electroportation of Mammalian Cells", Nucleic Acids Research, vol. 20, No. 4, pp. 6739-6740 (1992).
Grumont et al., "The Mitogen-Induced Increase in T Cell Size Involves PKC and NFAT Activation of Rel/NF-kB-Dependent c-myc Expression," Immunity, 2004, vol. 21, p. 19-30.
Guzman et al., "Preferential induction of apoptosis for primary human leukemic stem cells," PNAS 99(25):16220-16225 (2002).
Habib et al., "Myc Stimulates B Lymphocyte Differentiation and Amplifies Calcium Signaling", J.Cell Biol., vol. 179, No. 4, 2007, pp. 717-731.
Hann et al., "Proteins Encoded by the Human C-Myc Oncogene: Differential Expression in Neoplastic Cells", Mol. Cell. Biol., vol. 4, No. 11, Nov. 1984, pp. 2486-2497.
Hiramatsu et al., "Complete Reconstitution of Human Lymphocytes from Cord Blood CD34 Cells Using the NOD/SCID/ycnull Mice Model", Blood, vol. 102, No. 3, 2003, pp. 873-880.
Ho, et al., "Synthetic Protein Transduction Domains: Enhanced Transduction Potential in Vitro and in Vivo", Cancer Research, (2001), vol. 61, pp. 474-477.
Hoffman, "Progress in the develoment of systems for in vitro expansion of human hematopoietic stem cells," Curr. Op. Hematology 6(3): 14 pages (1999).
Horton, S.J. et al., "Continuous MLL-ENL expression is necessary to establish a "Hox Code" and maintain immortalization of hematopoietic progenitor cells," Cancer Res. 65(20):9245-9252 (2005).
Hoshimaru, M. et al., "Differentiation of the immortalized adult neuronal progenitor cell line HC2S2 into neurons by regulatable suppression of the V-MYC oncogene," Proceedings of the National Acadamy of Sciences of USA 93(4):1518-1523 (1996).
Howard, M.J. et al., "Transplantation of apoptosis-resistant embryonic stem cells into the injured rat spinal cord," Somatosensory & Motor Research 22(1-2):37-44 (2005).
Huang et al., "Dynamic Regulation of C-Myc Proto-Oncogene Expression during Lymphocyte Development Revealed by a GFP-c-Myc Knock-In Mouse", Eur. J. Immunol., vol. 38, No. 2, 2008, pp. 342-349.
Huettner et al., "Reversibility of Acute B-Cell Leukaemia Induced by BCR-ABL 1," Nature Genetics, vol. 24, 2000, pp. 57-60.
International Preliminary Report and Written Opinion for International Application No. PCT/US2014/022971, dated Sep. 24, 2015.
International Preliminary Report on Patentability for International Application No. PCT/US2013/051384, dated Jan. 29, 2015, 12 pages.
International Preliminary Report on Patentability issued on PCT/US2014/022977, dated Sep. 15, 2015.
International Preliminary Report on Patentability received for PCT Patent Application No. PCT/US2006/040379, dated Apr. 23, 2008, 5 pages.
International Preliminary Report on Patentability received for PCT Patent Application No. PCT/US2008/056896, dated Sep. 15, 2009, 4 pages.
International Preliminary Report on Patentability received for PCT Patent Application No. PCT/US2008/082263, dated May 4, 2010, 6 pages.
International Preliminary Report on Patentability Received for PCT Patent Application No. PCT/US2009/003105, dated Nov. 17, 2010, 6 pages.
International Preliminary Report on Patentability received for PCT Patent Application No. PCT/US2009/051242, dated Jan. 25, 2011, 6 pages.
International Preliminary Report on Patentability received for PCT Patent Application No. PCT/US2009/055443, dated Mar. 1, 2011, 6 pages.
International Search Report and Written Opinion for International (PCT) Patent Application No. PCT/US06/040379, dated Sep. 24, 2007, 6 pages.
International Search Report and Written Opinion for International Application No. PCT/US2014/022971 dated Aug. 13, 2014, 12 pages.
International Search Report and Written Opinion on PCT/US2014/022977, dated Aug. 28, 2014, 13 pages.
International Search Report and Written Opinion received for PCT Patent Application No. PCT/US2008/056896 dated Aug. 14, 2008, 5 pages.
International Search Report and Written Opinion received for PCT Patent Application No. PCT/US2008/082263, dated Jun. 25, 2009, 8 pages.
International Search Report and Written Opinion received for PCT Patent Application No. PCT/US2009/003105, dated Jan. 15, 2010, 9 pages.
International Search Report and Written Opinion received for PCT Patent Application No. PCT/US2009/051242, dated Feb. 19, 2010, 9 pages.
International Search Report and Written Opinion received for PCT Patent Application No. PCT/US2009/055443, dated Jun. 30, 2010, 11 pages.
Iritani et al., "Modulation of T-lymphocyte development, growth and cell size by the Myc antagonist and transcriptional repressor Mad 1", The EMBO Journal, vol. 21, No. 18, pp. 4820-4830.
Iritani, et al., "c-Myc enhances protein synthesis and cell size during B lymphocyte development", PNAS, (1999), vol. 96, No. 23, pp. 13180-13185.
Jadlowsky, et al., "Dominant negative mutant Cyclin T1 proteins inhibit HIV transcription by specifically degrading Tat", Retrovirology, (2008), vol. 5, Article 63, 12 pages.
Jayapal et al., "Down-regulation of Myc is Essential for Terminal Erythroid Maturation" The Journal of Biological Chemistry, vol. 285, No. 51, pp. 40252-40265, Dec. 17, 2010.

(56) References Cited

OTHER PUBLICATIONS

Johnson, N.A. et al., "Lymphomas with concurrent BCL2 and MYC translocations: the critical factors associated with survival", Blood, 2009, vol. 114, No. 11, pp. 2273-2279.
Ju, et al., "Anti-Apoptotic Therapy with a Tat Fusion Protein Protects Against Excitotoxic Insults in Vitro and in Vivo", Experimental Neurology, vol. 210, 2008, pp. 602-607.
Karon et al., "Temporal sequence of major biochemical events during Blood Bank storage of packed red blood cells," Blood Transfus, vol. 10, 2012, pp. 453-461.
Kashio, et al., "A Protein Derived From the Fusion of TAT Peptide and FNK, a Bcl-xL Derivative, Prevents Cochlear Hair Cell Death From Aminoglycoside Ototoxicity In Vivo", Journal of Neuroscience Research, (2007), vol. 85, No. 7, pp. 1403-1412.
Kelso et al., "Survival of the Myeloid Progenitor Cell Line FDC-P1 is Prolonged by Interferon-y or Interleukin-4", Growth Factors, vol. 6, No. 3, 1992, pp. 233-242.
Kitada, et al., "Reversal of Chemoresistance of Lymphoma Cells by Antisense-Mediated Reduction of bcl-2 Gene Expression", Antisense Research and Development, (1994), vol. 4, pp. 71-79.
Korbling et al., "Allogenic Blood Stem Cell Transplantation: Peripheralization and Yield of Donor-Derived Primitive Hematopoietic Progenitor Cells (CD34+Thy-Idim) and Lymphoid Subsets, and Possible Predictors of Engraftment and Graft-Versus-Host Disease," Blood 86:2842-2848 (1995).
Krosl et al., "In vitro expansion of hematopoietic stem cells by recombinant TAT- HOXB4 protein," Nature Mediciine 9(11):1428-1432 (2003).
Lang et al., "Mechanisms and Significance of Eryptosis, the Suicidal Death of Erythorocytes," Blood Purification, Vole 33, 2012, pp. 125-130.
Levesque, J-P et al., "The endosteal 'osteoblastic' niche and its role in hematopoietic stem cell homing and mobilization", Leukemia, 2010, vol. 24, pp. 1979-1992.
Li et al., "Reconstitution of Functional Human B Lymphocytes in NOD/SCID Mice Engrafted with ex vivo Expanded CD34 Cord Blood Cells", Experimental Hematology, vol. 30, 2002, pp. 1036-1043.
Littlewood, et. al., "A modified oestrogen receptor ligand-binding domain as an improved switch for the regulation of heterologous proteins", Nucleic Acids Research, (1995), vol. 23, No. 10, pp. 1686-1690.
MacPherson, P. et al., "Activity-dependent gene regulation in conditionally- immortalized muscle precursor cell lines," J. Cell. Biol. 91(4):821-839 (2004).
McCarthy, "Underground movement", Nature Reviews Cancer, (2007), vol. 7, 1 page, published online Oct. 11, 2007.
Melkonyan et al., "Electroporation efficiency in mammalian cells is increased by dimethyl sulfoxide (DMSO)," Nucleic Acids Research 24:4356-4357 (1996).
Merino et al., "Developmental Regulation of the Bcl-2 Protein and Susceptibility to Cell Death in B Lymphocytes", The EMBO Journal, vol. 13, No. 3, 1994, pp. 683-691.
Miharada et al., "Efficient enucleation of erythroblasts differentiated in vitro from hematopoietic stem and progenitor cells", Nature Biotechnology, 24(10): 1255-1256, 2006.
Miller et al., "Expansion in vitro of adult murine hematopoietic stem cells with transplantable lympho-myeloid reconsituting ability," PNAS USA 94: 13648-13653 (1997).
Moore et al., "In Vitro Maintenance of Highly Purified, Transplantable hematopoietic Stem Cells," Blood 89(12):4337-4347 (1997).
Mooslehner et al., Retroviral Integration Sites in Transgenic Mov Mice Frequently Map in the Vicinity of Transcribed DNA Regions,: J. Virology 64:3056- 3058 (1990).
Muchmore et al., "X Ray and NMR Structure of Human Bcl-xL, an Inhibitor of Programmed Cell Death", Nature, vol. 381, May 23, 1996, pp. 335-341.
Non Final Office Action received for U.S. Appl. No. 11/583,970, dated May 9, 2011, 10 pages.
Non Final Office Action received for U.S. Appl. No. 12/048,148, dated Oct. 13, 2011, 9 pages.
Non Final Office Action received for U.S. Appl. No. 12/962,197, dated Aug. 26, 2011, 11 pages.
Non-Final Office Action on U.S. Appl. No. 14/461,105 dated Mar. 22, 2016.
Non-Final Office Action on U.S. Appl. No. 14/415,325 dated Dec. 23, 2016.
Non-Final Office Action on U.S. Appl. No. 14/509,870 dated Jul. 12, 2016.
Non-Final Office Action on U.S. Appl. No. 14/661,786, dated Aug. 27, 2015.
Non-Final Office Action on U.S. Appl. No. 14/873,296 dated Aug. 17, 2017.
Non-Final Office Action on U.S. Appl. No. 12/506,894 dated Apr. 3, 2015, 16 pages.
Non-Final Office Action on U.S. Appl. No. 13/795,659 dated Nov. 26, 2014, 13 pages.
Non-Final Office Action on U.S. Appl. No. 13/797,648 dated Jun. 17, 2016.
Non-Final Office Action on U.S. Appl. No. 11/583,970 dated Sep. 20, 2013, 19 pages.
Non-final Office Action on U.S. Appl. No. 12/467,957 dated Apr. 4, 2014, 14 pages.
Non-Final Office Action on U.S. Appl. No. 12/701,383 dated Jun. 13, 2014, 26 pages.
Non-final Office Action on U.S. Appl. No. 13/795,659 dated Mar. 10, 2014, 11 pages.
Non-final Office Action on U.S. Appl. No. 13/797,648 dated Apr. 3, 2014, 13 pages.
Non-Final Office Action received for U.S. Appl. No. 11/583,970, dated Mar. 12, 2008, 13 pages.
Non-Final Office Action received for U.S. Appl. No. 12/467,957 dated Oct. 13, 2010, 15 pages.
Non-Final Office Action received for U.S. Appl. No. 12/701,383, dated Apr. 28, 2011, 9 pages.
Non-Final Office Action received for U.S. Appl. No. 11/583,970, dated Mar. 23, 2009, 11 pages.
Non-Final Office Action received for U.S. Appl. No. 12/048,148 dated Jan. 19, 2011, 6 pages.
Non-Final Office Action received for U.S. Appl. No. 12/048,148, dated May 11, 2012, 9 pages.
Non-Final Office Action received for U.S. Appl. No. 12/506,894, dated Apr. 27, 2012, 13 pages.
Non-Final Office Action received for U.S. Appl. No. 12/550,166 dated Jan. 11, 2012, 7 pages.
Notice of Acceptance issued on Australian Application 2009274172, dated Aug. 3, 2015.
Notice of Acceptance of Australian Application No. 2009246876 dated Apr. 2, 2015, 3 pages.
Notice of Acceptance of Australian Application No. 2012216462, dated Apr. 10, 2015, 2 pages.
Notice of Allowance on U.S. Appl. No. 11/583,970, dated Aug. 29, 2014, 11 pages.
Notice of Allowance on U.S. Appl. No. 12/467,957, dated Nov. 26, 2014, 7 pages.
Notice of Allowance on U.S. Appl. No. 13/795,659 dated Mar. 1, 2016.
Notice of Allowance on U.S. Appl. No. 13/795,659, dated Sep. 29, 2015.
Notice of Allowance on U.S. Appl. No. 14/415,325 dated Jun. 9, 2017.
Notice of Allowance on U.S. Appl. No. 14/461,105 dated Jun. 2, 2017.
Notice of Allowance on U.S. Appl. No. 14/509,870 dated Jun. 22, 2017.
Notice of Allowance on U.S. Appl. No. 14/661,786 dated Apr. 25, 2016.
Notice of Allowance on U.S. Appl. No. 12/506,894 dated Jun. 16, 2015, 8 pages.
Notice of Allowance on U.S. Appl. No. 12/701,383 dated May 22, 2015, 9 pages.

(56) References Cited

OTHER PUBLICATIONS

Notice of Allowance on U.S. Appl. No. 13/777,967 dated Jul. 14, 2014.
Notice of Allowance on U.S. Appl. No. 12/550,166 dated Apr. 28, 2014, 4 pages.
Notice of Allowance received for U.S. Appl. No. 12/550,166, dated Nov. 26, 2012, 9 pages.
Notice of Reasons for Rejection (English translation) issued on Japanese application 2014-108137, dated Aug. 18, 2015.
Notice of Reasons for Rejection issued on Japanese Application 2015-075703, dated Dec. 8, 2016, English translation only.
Notice of Reasons for Rejection issued on Japanese application 2015-523297, dated Jul. 19, 2017, English Translation only.
Notice of Reasons for Rejection issued on Japanese Application 2016-027812, dated Mar. 1, 2017.
Notice of Reasons for Rejection issued on Japanese Application 2016-501117, dated Apr. 17, 2017.
Notice of Reasons for Rejectionissued on Japanese Application 2015-075703, dated May 11, 2016, English translation.
Notification of Defects issued on Israeli Application 208810, dated Sep. 18, 2017.
Notification prior to Allowance of Israeli Patent Application No. 209343 dated Apr. 7, 2014, 2 pages.
Notification Prior to Examination issued on Israeli Patent 241299, dated Dec. 15, 2015.
Notification Prior to Examination of Israeli Patent Application No. 232432 dated May 15, 2014, 3 pages.
Office Action issued Korean Application 10-2010-7028384, dated Apr. 28, 2017, English Translation.
Office Action issued on Australian Application 2014249202, dated Nov. 18, 2015.
Office Action issued on Canadian Appl. 2626525, dated Jun. 6, 2016.
Office Action issued on Canadian Application 2,626,525 dated Jun. 13, 2017.
Office Action issued on Canadian Application 2723114, dated Jul. 7, 2016.
Office Action issued on Canadian Application 2731767, dated Oct. 5, 2015.
Office Action issued on Canadian Application 2735522, dated Nov. 16, 2015.
Office Action issued on Chinese Application 201410168106.2, dated Jun. 22, 2017 English translation only.
Office Action issued on Chinese Application 201410479865.2, dated Jul. 5, 2016, English Translation only.
Office Action issued on Chinese Application 201480026147.6, dated Apr. 20, 2017, English translation.
Office Action issued on Japanese application 2015-523297, dated Apr. 3, 2017.
Office Action issued on Korean Appl. 10-2010-7028384, dated Aug. 18, 2016 English translation only.
Office Action on Canadian Application No. 2,626,525 dated Apr. 8, 2014, 4 pages.
Office Action on Canadian Application No. 2626525 dated May 8, 2015, 3 pages.
Office Action on Canadian Patent Application No. 2,680,613 dated Nov. 21, 2013, 3 pages.
Office Action received for Australian Patent Application No. 2006304392, dated Jul. 16, 2012, 3 pages.
Office Action received for Australian Patent Application No. 2009246876 dated Jan. 17, 2014, 6 pages.
Office Action received for Australian Patent Application No. 2009285547, dated Jul. 25, 2011, 2 pages.
Office Action received for Canadian Patent Application No. 2626525, dated Apr. 17, 2013, 4 pages.
Office Action received for Canadian Patent Application No. 2731767, dated Jul. 25, 2012, 3 pages.
Office Action received for Canadian Patent Application No. 2735522, dated Sep. 10, 2012, 3 pages.
Office Action received for Chinese Patent Application No. 200580031540.5, dated Jul. 3, 2012, English translation, 11 pages.
Office Action received for Chinese Patent Application No. 200680045545.8, dated Dec. 31, 2010, English translation, 8 pages.
Office Action received for Chinese Patent Application No. 200680045545.8, dated Sep. 15, 2011, English translation, 9 pages.
Office Action received for Chinese Patent Application No. 200880015602.7, dated Jan. 31, 2012, 16 pages (10 pages of English translation and 6 pages of Office Action).
Office Action received for Chinese Patent Application No. 200880015602.7, dated May 9, 2013, 13 pages (8 pages of English Translation and 5 pages of Official copy).
Office Action received for Chinese Patent Application No. 200880015602.7, dated Oct. 31, 2012, 10 pages (6 pages of English Translation and 4 pages of Chinese Office Action).
Office Action received for Chinese Patent Application No. 200980126312.4, dated Aug. 28, 2012, 12 pages (6 pages of English Translation and 6 pages of Office Action).
Office Action received for Chinese Patent Application No. 200980127166.7, dated Dec. 5, 2012, 4 pages (1 page of English Translation and 3 pages of Office Action).
Office Action received for Chinese Patent Application No. 200980126312.4, dated Jan. 30, 2012, 14 pages (7 pages of English translation and 7 pages of Office Action).
Office Action received for European Application No. 09810692.5 dated Feb. 25, 2014, 3 pages.
Office Action received for European Patent Application No. 06826025.6, dated Sep. 1, 2009, 3 pages.
Office Action received for European Patent Application No. 06826025.6, dated Sep. 22, 2009, 1 page.
Office Action received for European Patent Application No. 08743862.8, dated May 14, 2010, 6 pages.
Office Action received for European Patent Application No. 08743862.8, dated Sep. 23, 2010, 6 pages.
Office Action received for European Patent Application No. 09747016.5, dated Apr. 9, 2013, 6 pages.
Office Action received for European Patent Application No. 09810692.5, dated Mar. 28, 2012, 3 pages.
Office Action received for Indian Application No. 3332/DELNP/2008 dated Aug. 23, 2013, 3 pages.
Office Action received for Israel Patent Application No. 200919, dated Jan. 17, 2013, 4 pages (2 pages of English Translation and 2 pages of Official Copy).
Office Action received for Israel Patent Application No. 208810, dated Nov. 2, 2011, 3 pages of English Translation only.
Office Action received for Israel Patent Application No. 209343, dated Aug. 14, 2012, 3 pages (2 pages of English Translation and 1 page of Office Action).
Office Action received for Israel Patent Application No. 209968, dated Aug. 21, 2012, 4 pages (2 pages of English Translation and 2 pages of Office Action).
Office Action received for Israel Patent Application No. 200919, dated Dec. 5, 2011, 2 pages of English Translation only.
Office Action received for Israeli Patent Application No. 190946, dated Jul. 3, 2012, 1 page, (English Translation only).
Office Action received for Israeli Patent Application No. 208810, dated Jan. 2, 2013, 4 pages (English Translation only).
Office Action received for Japanese Application No. 2011-520133, dated Feb. 5, 2014, 4 pages (in Japanese).
Office Action received for Japanese Patent Application No. 2008-536713, dated Jul. 3, 2012, 2 pages (No English Translation Provided).
Office Action received for Japanese Patent Application No. 2009-553785, dated Jun. 19, 2012, 6 pages (2 pages of English Translation and 4 pages of Office Action).
Office Action received for Korean Patent Application No. 10-2008-7011791, dated May 28, 2013, English translation, 3 pages.
Office Action received for Korean Patent Application No. 10-2009-7021320, dated Jul. 29, 2011, 7 pages (3 pages of English Translation and 4 pages of Office Action).
Office Action received for Korean Patent Application No. 10-2009-7021320, dated Sep. 18, 2012, 11 pages (7 pages of English Translation and 4 pages of Office Action).

(56) References Cited

OTHER PUBLICATIONS

Official Action on European Application No. 09810692.5 dated Oct. 22, 2014, 3 pages.
Office Action issued on Chinese Application 201480026147.6, dated Sep. 28, 2017.
Oral Proceedings Summons received for European Patent Application No. 08743862.8, dated May 14, 2012, 6 pages.
Pan et al., "Reprogramming human fibroblasts using HIV-1 TAT recombinant proteins OCT4, SOX2, KLF4 and c-Myc," Mol. Biol Rep (2010) 37:2117-2124.
Partial Search Report issued on EP Appl. 14778538.0,dated Jul. 8, 2016.
Partial Supplementary European Search Report issued on EP Appl. 13820331.0, dated Jun. 30, 2016.
Pierelli et al., "Modulation of bcl-2 and p27 in human primitive proliferating hematopoietic progenitors by autocrine TGF-B 1 is a cell cycle-independent effect and influences their hematopoietic potential,"Blood 95:3001-3010 (2000).
Pinto et al., "Hematopoietic progenitor/stem cells immortalized by Lhx2 generate functional hematopoietic cells in vivo," Blood 99(11):3939-3946 (2002).
Podsypanina, K. et al., "Oncogene cooperation in tumor maintenance and tumor recurrence in mouse mammary tumors induced by MYC and mutant Kras," PNAS 105(13):5242-5247 (2008).
Polenakovic et al., "Is Erythropoietin a Survival Factor for Red Blood Cells," J. Am. Soc. Nephrol, vol. 7, 1996, pp. 1178-1182.
Pollock, K. et al., "A conditionally immortal clonal stem cell line from human cortical neuroepithelium for the treatment of ischemic stroke," Exp. Neurol., (2006), vol. 199, No. 1, pp. 143-155.
Pre-Appeal Examination Report on Japanese Application 2014-108137, dated Dec. 7, 2016, English translation only.
Prochownik et al., "Deregulated expression of c-myc by murine erythroleukaemia cells prevents differentiation," Nature, vol. 322, Aug. 28, 1986, pp. 848-850.
Qin et al., "Nuclear Factor KB Nuclear Translocation Upregulates c-Myc and p53 Expression during NMDA Receptor—Mediated Apoptosis in Rat Striatum", The Journal of Neuroscience, vol. 19, No. 10, May 15, 1999, pp. 4023-4033.
Rabbitts, et al., "Metabolism of c-myc gene products: c-myc mRNA and protein expression in the cell cycle", EMBO Journal, (1985), vol. 4, No. 8, pp. 2009-2015.
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.
Raymon, H.K. et al., "Immortalized human dorsal root ganglion cells differentiate into neurons with nociceptive properties," J. Neuroscience 19(13):5420-5428 (1999).
Re-Examination Report on Australian Patent No. 2009285547 dated Apr. 23, 2015, 3 pages.
Refaeli et al., "The protooncogene MYC can break B cell tolerance," PNAS, 102(11):4097-4102, (2005).
Refaeli, Y, "The B-Cell Antigen Receptor and Overexpression of MYC Can Cooperate in the Genesis of B-Cell Lymphomas", PLOS Biology, vol. 6, No. 6, e152, 2008, pp. 1208-1225.
Richter, et al., "Lhx.2 expression in hematopoietic progenitor/stem cells in vivo causes a chronic myeloproliferative disorder and altered globin expression," J. Hematol., (2003), 88(12):1336-1347.
Roh et al., "Transgenic Mice for Cre-Inducible Overexpression of the Oncogenes c-MYC and Pim-1 in Multiple Tissues", Genesis: The Journal of Genetics and Development, vol. 44 pp. 447-453, (2006).
Rosenwald, et al., "Increased Expression of Eukaryotic Translation Inhibition Factors eIF-4E and eIF-2alpha in Response to Growth Induction by C-MYC", Proc. Natl. Acad. Sci. USA, vol. 90, pp. 6175-6178, (1993).
Rudolph et al., "Expression of Mad1 in T cells leads to reduced thymic cellularity and impaired mitogen-induced proliferation", Oncogene, 2001, vol. 20, pp. 1164-1175.
Satoh et al, "Roles for c-Myc in Self-renewal of Hematopoietic Stem Cells," The Journal of Biological Chemistry, 2004, vol. 279, No. 24, p. 24986-24993.
Sauer, "Inducible Gene Targeting in Mice Using the Cre/lox System," Methods, (1998), vol. 14, No. 4, pp. 381-392.
Schiedlmeier et al., "High-level Ectopic HOXB4 Expression Confers a Profound in Vivo Competitive Growth Advantage on Human Cord Blood CD34 Cells, but Impairs Lymphomyeloid Differentiation", Blood, vol. 101, No. 5, Mar. 1, 2003, pp. 1759-1768.
Schmidt et al., "Transgenic Mice Bearing the Human c-myc Gene Activated by an Immunoglobulin Enhancer: A pre-B-cell Lymphoma Model", National Academy of Sciences, vol. 85, pp. 6047-6051 (1988).
Schroy, et al., "A Simple Method for Freezing and Thawing Cultured Cells," Methods in Cell Science (formerly known as TCA Manual), (1976), vol. 2, No. 1, pp. 309-310.
Schwarze et al., "Protein transduction: unrestricted delivery into all cells?" Trends Cell Biol. 10:290-295 (2000).
Seibutsugaku Jiten (Dictionary of Biology), Iwanami Shoten, 1997, The 4th edition, p. 1396, English translation not available.
Silva et al., "Erythropoietin Can Promote Erythroid Progenitor Survival by Repressing Apoptosis Through Bcl-xl, and Bcl-2," Blood, vol. 88, No. 5, Sep. 1, 1996, pp. 1576-1582.
Sipione, S. et al., "Modeling brain pathologies using neural stem cells," Methods Mol. Biol., (2002), vol. 198, pp. 245-262.
Snyder, et al., "Regulation of NMDA receptor trafficking by amyloid-3B2", Nature Neuroscience, (2005), vol. 8, No. 8, pp. 1051-1058.
Soane,L., et al., "TAT-mediated endocytotic delivery of the loop deletion Bcl-2 protein protects neurons against cell death", Journal of Neurochemistry, (2005), vol. 95, pp. 230-243.
Supplementary Search Report received for European Patent Application No. 08743862.8 dated Feb. 9, 2010, 1 page.
Taguchi et al., "Nuclear trafficking of macromolecules by an oligopeptide derived from Vpr of human immunodeficiency virus type-1" Biochem. Biophys. Res. Commun. 2004, 320(1) pp. 18-26.
Takahashi, et al., Induction of pluripotent stem cells from mouse embryonic and adult fibroblast cultures by defined factors, Cell, 126:663-676, 2006.
Theis, et al., "Expression of the myc/His-Tagged Human Peptide Transporter hPEPT1 in Yeast for Protein Purification and Functional Analysis", Protein Expression and Purification, (2001), vol. 22, pp. 436-442.
Thomas, et. al., "Progress and Problems with the Use of Viral Vectors for Gene Therapy", Nature, (May 2003), vol. 4, pp. 346-358.
Tsai et al., "Lymphohematopoietic progenitors immortalized by a retroviral vector harboring a dominant-negative retinoic acid receptor can recapitulate lymphoid, myeloid, and erythroid development," Genes & Dev. 8:2831-2841 (1994).
Varnum-Finney et al., "Pluripotent, cytokine-dependent, hematopoietic stem cells are immortalized by constitutive Notch1 signaling," Nature Medicine 6(11):1278-1281 (2000).
Vaux et al., "Bcl-2 gene promotes hemopoietic cell survival and cooperates with c- myc to immortalize pre-B cells," Nature 335:440-442 (1988).
Vaux, et al., "Immunologic competence of B cells subjected to constitutive c-myc oncogene expression in immunoglobulin heavy chain enhancer myc transgenic mice", J. Immunol., (1987), vol. 139, No. 11, pp. 3854-3860.
Wagner et al., "Myc-Mediated Apoptosis is Blocked by Ectopic Expression of Bcl-2," Molecular and Cellular Biology, Apr. 1993, pp. 2432-2440.
Wang et al., "Primitive Human Hematopoietic Cells Are Enriched in Cord Blood Compared with Adult Bone Marrow or Mobilized Peripheral Blood as Measured by the Quantitative in Vivo SCID-Repopulating Cell Assay," Blood 89:3919-3924 (1997).
Wechsler et al., "MXI1, a Putative Tumor Suppressor Gene, Suppresses Growth of Human Glioblastoma Cells", Cancer Research 57, pp. 4405-4912, (1997).
Wikipedia [online], "Stem Cell", 2008, [retrieved on Nov. 13, 2008]. Retrieved from the Internet: <URL: http//en.wikipedia.org/wiki/Stem_cell>, 11 pages.

(56) References Cited

OTHER PUBLICATIONS

Wilson, et al., "c-Myc controls the balance between hematopoietic stem cell self-renewal and differentiation", Genes and Development, 2004, vol. 18, pp. 2747-2763.
Wu et al., "Inhibition of c-myc Expression Induces Apoptosis of WEHI 231 Murine B Cells", Molecular and Cellular Biology, Sep. 1996, vol. 16, No. 9, pp. 5015-5025.
Wurm, et al., "Large-scale transient expression of mammalian cells for recombinant protein production," Curr. Op. Biotech., (1999), vol. 10, pp. 156-159.
Xi et al., "In Vitro Large Scale Production of Human Mature Red Blood Cells From Hematopoietic Stem Cells by Coculturing with Human Fetal Liver Stromal Cells," Biomed. Res. Int. Epub Jan. 30, 2013, 2013:807863.
Xu Zhixiang, et al, "The Development of the Study on the Anti-Tumor Effect of F1t3 Ligand," Chinese Journal of Tumor Biological Therapy, vol. 7, No. 3, Sep. 30, 2000.
Yagihashi, et al., "Detection of Anti-Survivin Antibody in Gastro-intestinal Cancer Patients", Clinical Chemistry, (2001), vol. 47, No. 9, pp. 1729-1731.
Yanai et al., "A novel stromal cell-dependent hematopoietic cell line established from temperature-sensitive SV40 T-antigen transgenic mice," Exp. Hematol., 27:1087-1096 (1999).
Young et al., "B-Cell Receptor Signaling in the Genesis and Maintenance of B-Cell Lymphoma", Future Oncology, vol. 4, No. 5, 2008, pp. 591-594.
Zhang et al., "Cytokines Regulating Hematopoietic Stem Cell Function", Current Opinion Hematology, vol. 15, No. 4, Jul. 2008, pp. 307-311.
Zhang et al., "Reprogramming of somatic cells via TAT-mediated protein transduction of recombinant factors," Biomaterials 33 (2012) 5047-5055.
Exam Report issued on European Application 14779483.8, dated Oct. 16, 2017.
Futaki, Chemistry and Biology (Kagaku to Seibutsu), vol. 43, No. 10, Oct. 1, 2005, p. 649-653 (English translation not available).
Office Action issued on Japanese Application 2016-501117, dated Nov. 15, 2017.
Pharmaceutics (Yakuzaigaku), 64(3), 2004, p. 164-167 (English translation not available).
Canadian Office Action, issued in corresponding CA Pat. App. No. 2879667, 4 pages (dated Jun. 18, 2019).
European Office Action, issued in corresponding EP Pat. App. No. 14779483.8, 4 pages (dated Jun. 28, 2019).
Final Office Action on U.S. Appl. No. 15/717,675 dated Jun. 27, 2019.
Japanese Office Action, issued in JP Pat. App. No. 2018-153567, 8 pages (dated Jul. 25, 2019).
Non-Final Office Action on U.S. Appl. No. 16/042,904 dated Jul. 12, 2019.
Notice of Allowance on U.S. Appl. No. 15/244,138 dated Jun. 5, 2019.
Final Office Action on U.S. Appl. No. 15/244,138 dated Jun. 4, 2018.
Non-Final Office Action on U.S. Appl. No. 15/785,000 dated Jun. 1, 2018.
Notice of Allowance on U.S. Appl. No. 15/179,735 dated May 29, 2018.
Office Action issued on Chinese Application 201510760532X, dated May 11, 2018.
European Office Action, issued in EP Pat. App. No. 13820331.0, 3 pages (dated Jul. 29, 2019).
Notice of Allowance on U.S. Appl. No. 15/717,675 dated Sep. 17, 2019.
Corrected Notice of Allowability on U.S. Appl. No. 16/042,904 dated Mar. 6, 2020.
Dudley, et al., "Adoptive Cell Transfer Therapy Following Non-Myeloablative but Lymphodepleting Chemotherapy for the Treatment of Patients with Refractory Metastatic Melanoma", Journal of Clinical Oncology 23(10): 2346-2357 (2005).
Final Office Action on U.S. Appl. No. 15/668,451 dated May 24, 2018.
Notice of Allowance on U.S. Appl. No. 16/042,904 dated Mar. 20, 2020.
Office Action on JP 2018-153567 dated Mar. 18, 2020.
Office Action on JP 2019-025374 dated Mar. 9, 2020.
Office Action on MX/a/2015/012168 dated Aug. 31, 2018.
Rubinstein, et al., "Ex Vivo Interleukin-12-Priming During CD8 T Cell Activation Dramatically Improves Adoptive T Cell Transfer Antitumor Efficacy in a Lymphodepleted Host", J. Am. Coll. Surg. 214(4): 700-707 (2002).
US Office Action on U.S. Appl. No. 15/668,451 dated Dec. 7, 2017.
Indian First Examination Report, issued in Indian Pat. App. No. 9205/DELNP/2015, 8 pages (dated Nov. 28, 2019).
European Office Action, issued in European Pat. App. No. 18154875.1, 4 pages (dated Sep. 6, 2019).
Indian First Examination Report, issued in Indian Pat. App. No. 9206/DELNP/2015, 6 pages (dated Dec. 26, 2019).
Non-Final Office Action on U.S. Appl. No. 14/461,105 dated Mar. 20, 2017.
A. Strasser, et al., "Novel primitive lymphoid tumours induced in transgenic mice by cooperation between myc and bcl-2", Letters to Nature 348: 331-333 (1990).
Chinese Office Action, issued in Chinese Pat. App. No. 201510760532.X, 14 pages (dated Jan. 10, 2020).
Notice of Allowance on U.S. Appl. No. 16/042,904 dated Jan. 29, 2020.
Final Office Action on U.S. Appl. No. 16/042,904 dated Nov. 1, 2019.
Altman, et al.,"Phenotypic Analysis of Antigen-Specific T Lymphocytes", Science 274: 94-96 (1996).
Andersen, et al.,"Parallel detection of antigen-specific T cell responses by combinatiorial encoding of MHC multimers", Nature Protocols 7(5): 891-902 (2012).
Bird et al., "Expansion of Human and Murine Hematopoietic Stem and progenitor Cells Ex Vivo without Genetic Modification Using MYC and Bcl-2 Fusion Proteins," PLoS One, Aug. 29, 2014, vol. 9, No. 8, pp. 1-20.
Canadian Office Action, issued in Canadian Pat. App. No. 2905285, 5 pages (dated Jan. 30, 2020).
Canadian Office Action, issued in Canadian Pat. App. No. 2905296, 4 pages (dated Jan. 31, 2020).
Canadian Office Action, issued in Canadian Pat. App. No. 3035209, 4 pages (dated Feb. 3, 2020).
Chang, et al., "Phenotypic expression in *E. coli* of a DNA sequence coding for mouse dihydrofolate reductase," Nature, vol. 275, Oct. 19, 1978, pp. 617-624.
Chang, et al.,"Phenotypic expression in *E. coli* of a DNA sequence coding for mouse dihydrotolate reductase", Nature 275: 617-624 (1978).
Chi, et al., "Physical Stability of Proteins in Aqueous Solution: Mechanism and Driving Forces in Nonnative Protein Aggregation," Pharm. Res., vol. 20, No. 9, Sep. 2003, pp. 1325-1336.
Cleland, et al., "The development of stable protein formulations: a close look at protein aggregation, deamidation, and oxidation," Crit. Rev. Ther. Drug Carrier Syst., vol. 70, No. 4, Jan. 1, 1993, pp. 307-377.
DeBoer, et al., "The tac promoter: A functional hybrid derived from the trp and lac promoters", Proc. Natl. Acad. Sci. USA 80: 21-25 (1983).
Deboer, et al., "The tac promoter: A functional hybrid derived from the trp and lac promoters," Proc. Natl. Acad. Sci. vol. 80, Jan. 1983, pp. 21-25.
Derossi, et al., "Trojan peptides: the penetratin system for intracellular delivery", Trends Cell Biol. 8: 84-87 (1998).
Derossi, et al., "Trojan peptides: the penetratin system for intracellular delivery," Cell Biology, vol. 8, Feb. 1998, pp. 84-87.
Elliot, et al., "Intercellular Trafficking and Protein Delivery by a Herpesvirus Structural Protein," Cell, vol. 88, Jan. 24, 1997, pp. 223-233.
Elliot, et al.,"Intercellular Trafficking and Protein Delivery by a Herpesvirus Structural Protein", Cell 88: 223-233 (1997).

(56) References Cited

OTHER PUBLICATIONS

EPO Communication under Rule 161 and 162, issued in EP Pat. App. No. 17876016.1, 3 pages (dated Jul. 9, 2019).
European Extended Search Report, issued in EP Pat. App. No. 17920607.3, 7 pages (dated Dec. 11, 2019).
European Office Action, issued in EP Pat. App. No. 14779483.8, 4 pages (dated Jan. 14, 2019).
First Office Action, issued in JP Pat. App. No. 2019-512193, 8 pages (dated Sep. 30, 2019).
Goeddel, et al. "Synthesis of human fibroblast interferon by *E. coli*", Nucleic Acids Res. 8: 4057-4074 (1980).
Goeddel, et al., "Direct expression in *Escherichia coli* of a DNA sequence coding for human growth hormone," Nature, vol. 281, Oct. 18, 1979, p. 544.
Goeddel, et al., "Synthesis of human fibroblast interferon by *E. coli*," Nucleic Acids Research, vol. 8, Aug. 12, 1980, p. 4057.
Goeddel, et al.,"Direct expression in *Escherichia coli* of a DNA sequence coding for human growth hormone", Nature 281: 544-548 (1979).
Heinkoff, et al., "Amino acid substitution matrices from protein blocks," Proc. Natl Acad. Sci. USA, vol. 89, Nov. 1992, pp. 10915-10919.
Henikoff. et al.,"Amino acid substitution matrices from protein blocks", Proc. Natl Acad. Sci. USA, 89: 10915-10919 (1992).
Huang, et al., "Negative Control of the Myc Protein by the Stress-Responsive Kinase Pak2," Molecular and Cellular Biology, vol. 24, No. 4, Feb. 2001, pp. 1582-1594.
International Preliminary Report on Patentability on PCT/US2017/045336 dated Feb. 13, 2020.
International Preliminary Report on Patentability, issued in Int'l. App. No. PCT/US2017/064206, 13 pages (dated Jun. 13, 2019).
International Preliminary Report on Patentability, issued in Int'l. App. No. PCT/US2018/044740, 9 pages (dated Feb. 13, 2020).
International Search Report and Written Opinion for PCT/US2017/064206, dated Mar. 19, 2018.
International Search Report and Written Opinion, dated Oct. 16, 2018, issued in International Application No. PCT/US2018/044740 (13 pages).
International Search Report and Written Opinion, issued in Int'l. App. No. PCT/US2019/062200, 13 pages (dated Jan. 16, 2020).
Kaptein, et al., "Anti-IgM-mediated Regulation of c-myc and Its Possible Relationship to Apoptosis," JBC, vol. 271, No. 31, Aug. 2, 1996, pp. 18875-18884.
Non-Final Office Action on U.S. Appl. No. 15/828,971 dated Jul. 8, 2019.
Non-Final Office Action on U.S. Appl. No. 16/184,086 dated Feb. 13, 2020.
Notice of Allowance on U.S. Appl. No. 15/668,451 dated Aug. 10, 2018.
Notice of Allowance on U.S. Appl. No. 15/828,971 dated Nov. 1, 2019.
Patel et al., "The c-MYC oncoprotein is a substrate of the acetyltransferases hGCN5/PCAF and TIP60," Molecular and Cellular Biology, Dec. 1, 2004, vol. 24, No. 24, pp. 10826-10834.
Schwarze, et al., "In vivo protein transduction: intracellular delivery of biologically active proteins, compounds and DNA," Trends Pharmacol Sci, vol. 21, Feb. 2000, pp. 45-48.
Schwarze, et al.,"In vivo protein transduction: intracellular delivery of biologically active proteins, compounds and DNA", Trends Pharmacol. Sci., 21: 45-48 (2000).
Siebenlist, et al., "*E. coli* RNA Polymerase Interacts Homologously with Two Different Promoters," Cell, vol. 20, Jun. 1980, pp. 269-281.
Siebenlist, et al.,"*E. coli* RNA Polymerase Interacts Homologously with Two Different Promoters", Cell 20: 269-281 (1980).
Stein et al., "TAT-MYC Recombinant Fusion Protein Enhances Hematopoietic Stem Cell Graft Performance and Immunne Cell Reconstitution after Transplantation," Blood, Dec. 7, 2017, vol. 130, Suppl. 1, p. 3175.
Wang, "Instability, stabilization, and formulation of liquid protein pharmaceuticals," Int. J. Pharm., vol. 185, Issue 2, Aug. 20, 1999, pp. 129-188.
Wang, "Lyophilization and development of solid protein pharmaceuticals," Int. J. Pharm., vol. 203, Issues 1-2, Aug. 2000, pp. 1-60.
Watt, et al., "Nucleotide sequence of cloned cDNA of human c-myc oncogene", Nature 303: 725-728 (1983).
Japanese Office Action on JP 2019-006759 dated Feb. 20, 2020.
Australian Examination Report, issued in Australian Pat. App. No. 2018247295, 2 pages (dated Dec. 6, 2019).
Notice of Allowance on U.S. Appl. No. 16/042,904 dated Dec. 11, 2019.
Notice of Allowance on U.S. Appl. No. 15/717,675 dated Nov. 6, 2019.
McNiece, et al, "Ex-vivo expansion of hematopoietic progenitor cells: preliminary results in breast cancer", Hematol. Cell Ther. 41(2): 82-86 (1999).
Non-Final Office Action on U.S. Appl. No. 16/261,207 dated May 13, 2020.
Office Action on JP 2019-512193 dated May 13, 2020.
Zhuang, et al., "C-MYC overexpression is required for continuous suppression of oncogene-induced senescence in melanoma cells", Oncogene 27: 6623-6634 (2008).
Office Action on JP 2019-006759 dated Aug. 6, 2020.
Office Action on JP 2019-529651 dated Jul. 15, 2020.

\* cited by examiner

Fig. 1A.
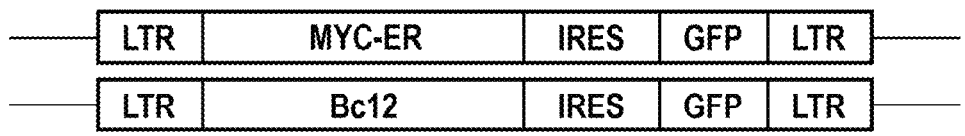
Fig. 1B.
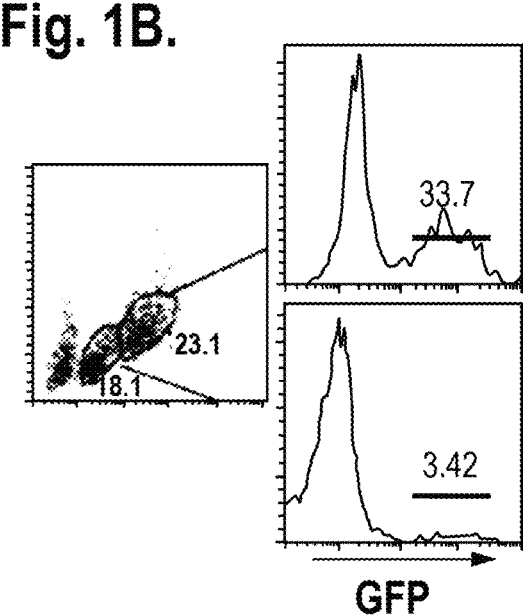
Fig. 1C.
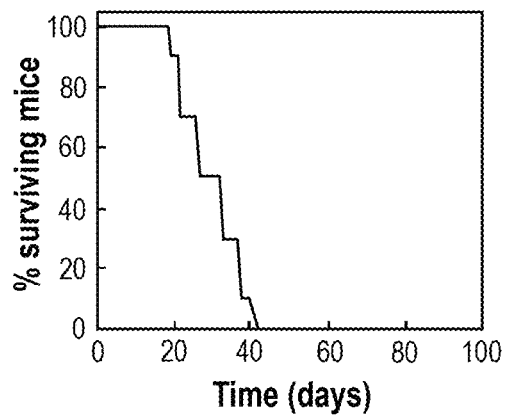
Fig. 1D. BL6 HSC (Early)
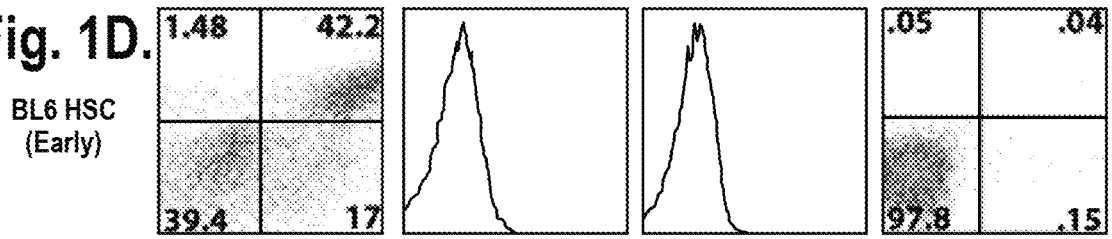
Fig. 1E. BL6 HSC (Established)
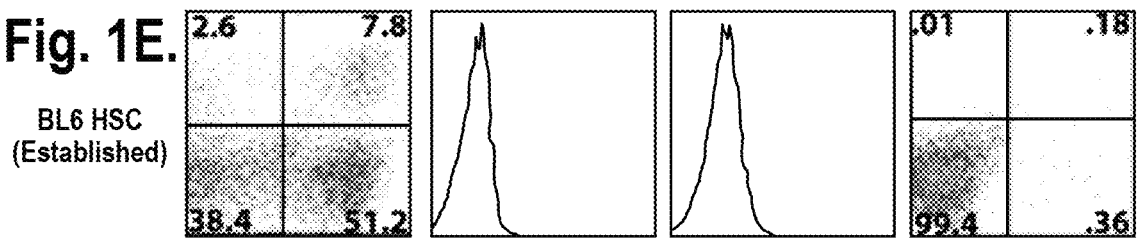
Fig. 1F. ex vivo LT-HSC
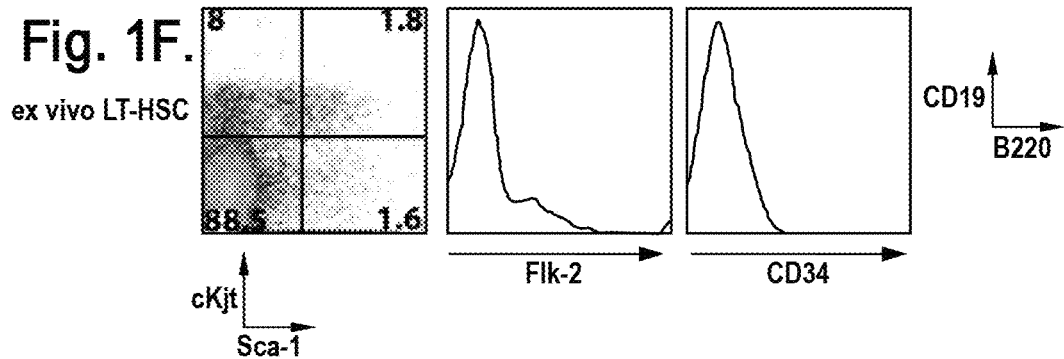

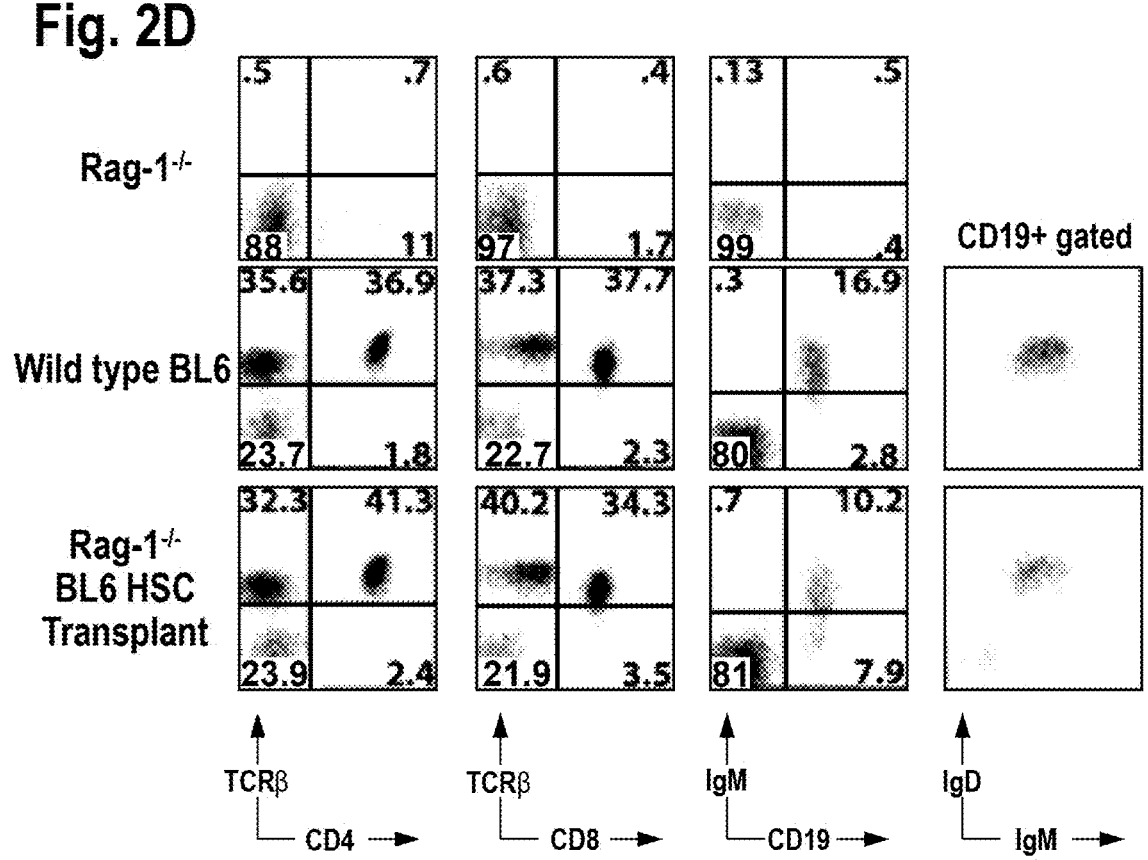

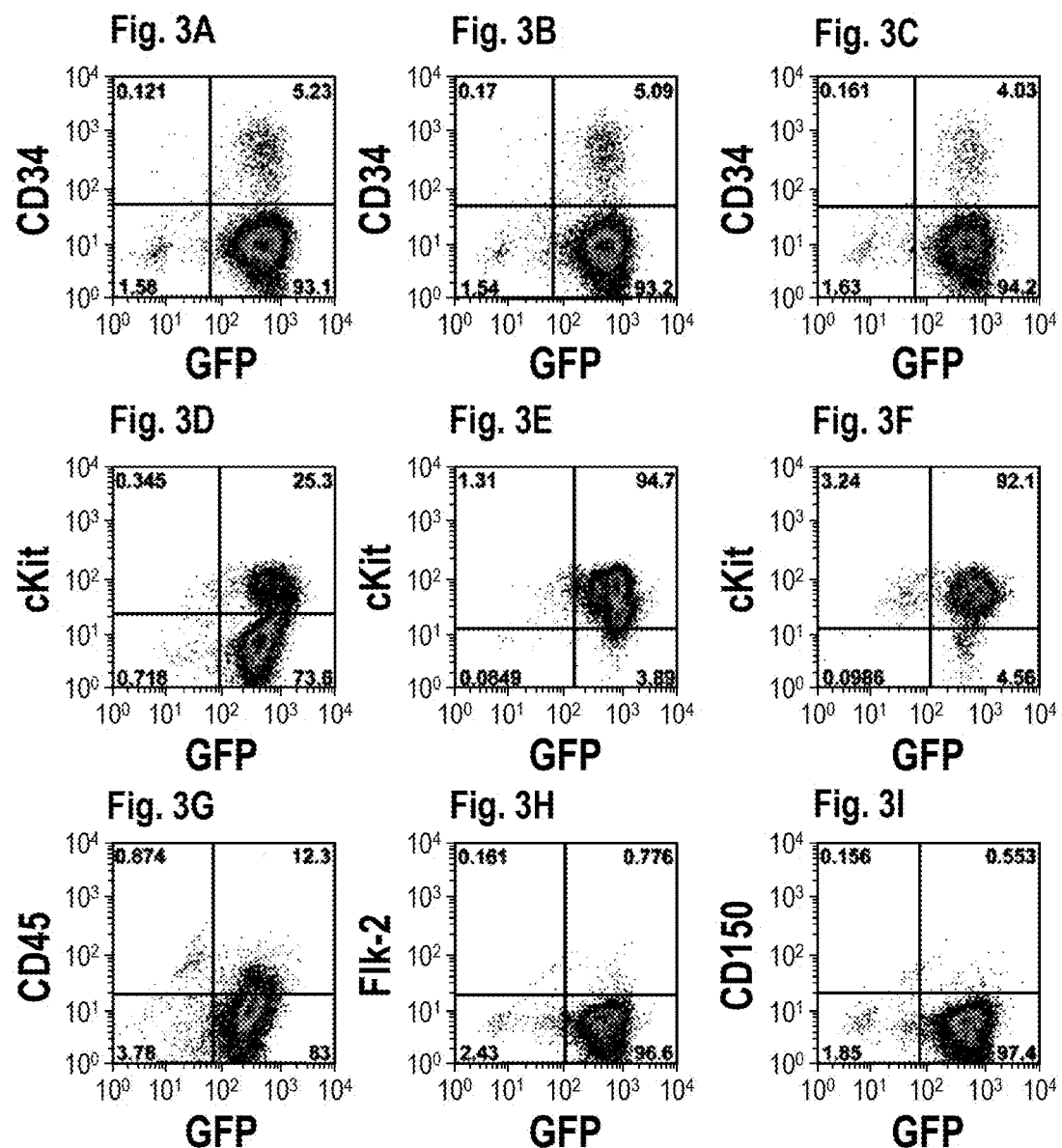

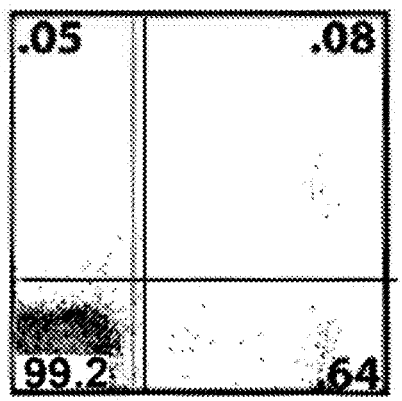
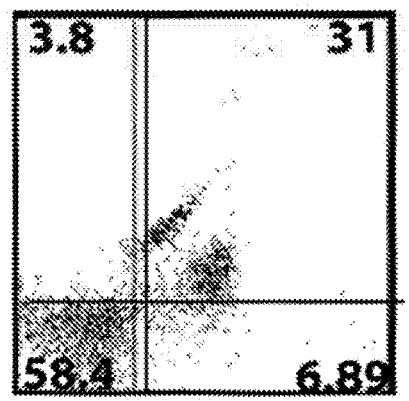
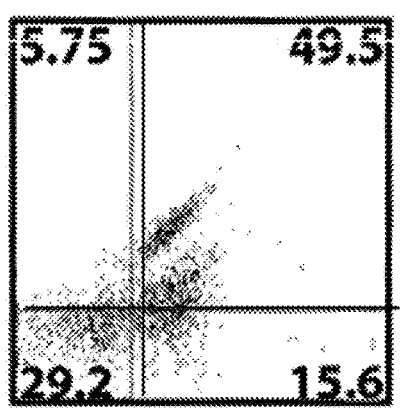

<br>

<br>

<br>

<br>

<br>

Tat-MYC →

Tat-Bcl2 →

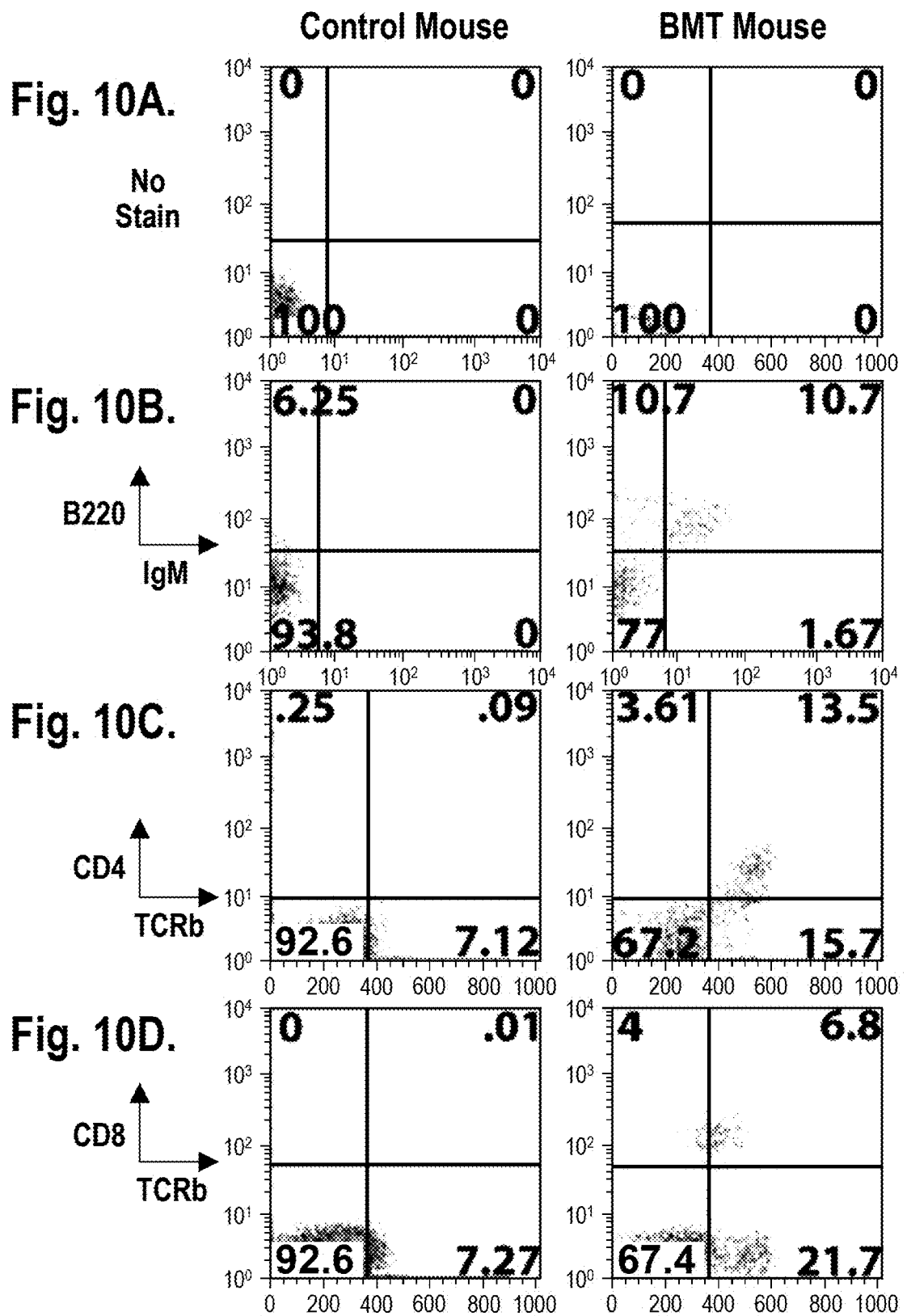

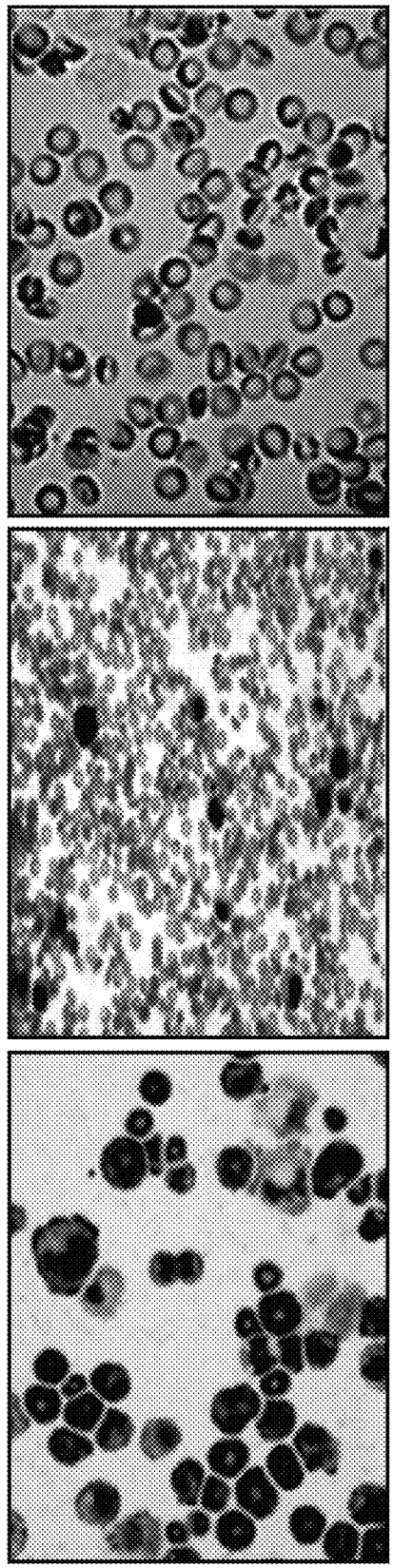
Fig. 11A. Control 40x
Fig. 11B. RBC 40x
Fig. 11C. RBC 100x

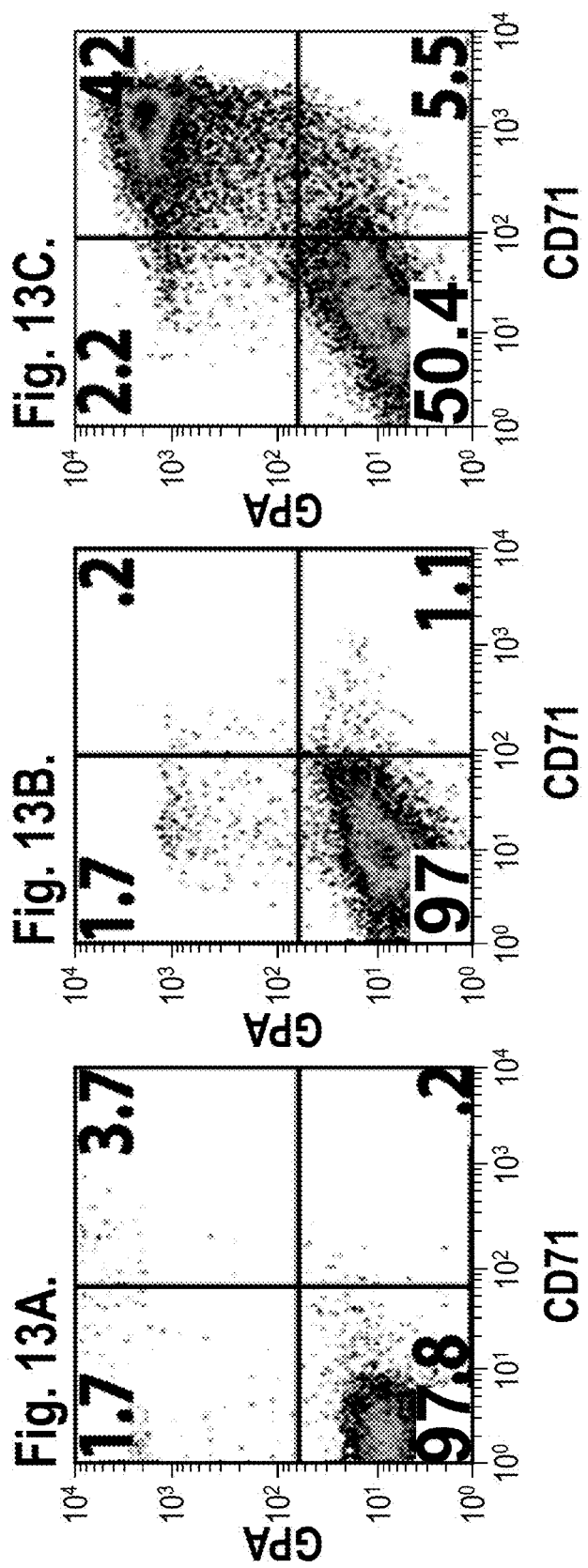

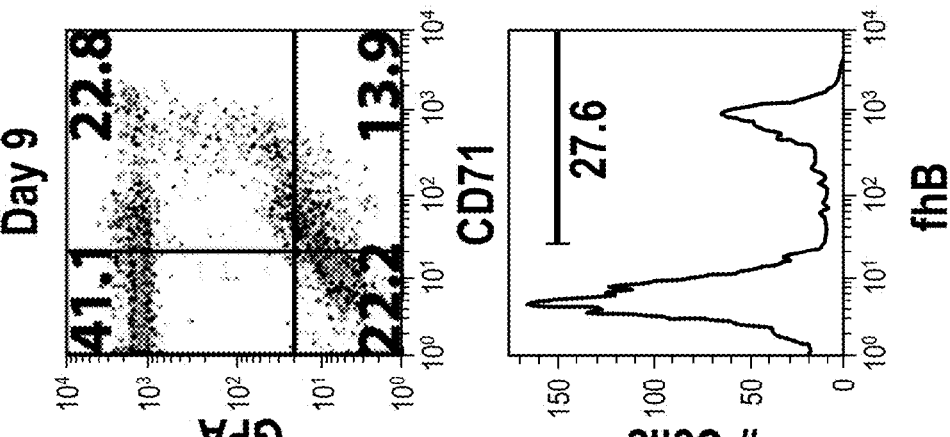
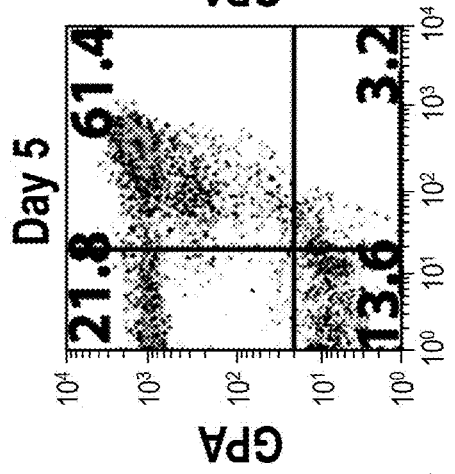
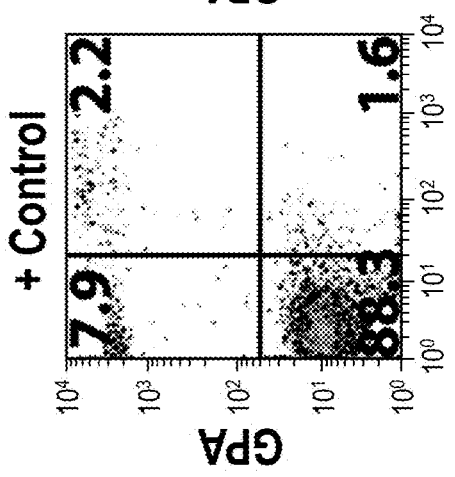

Fig. 15A. Day 3
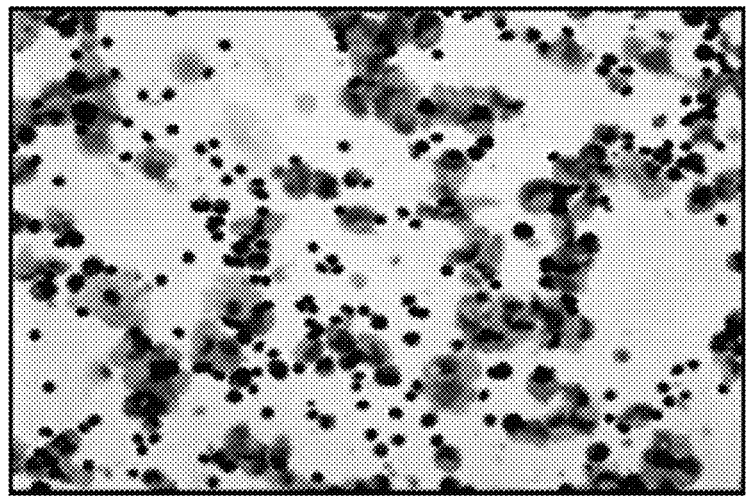
Fig. 15B. Day 7
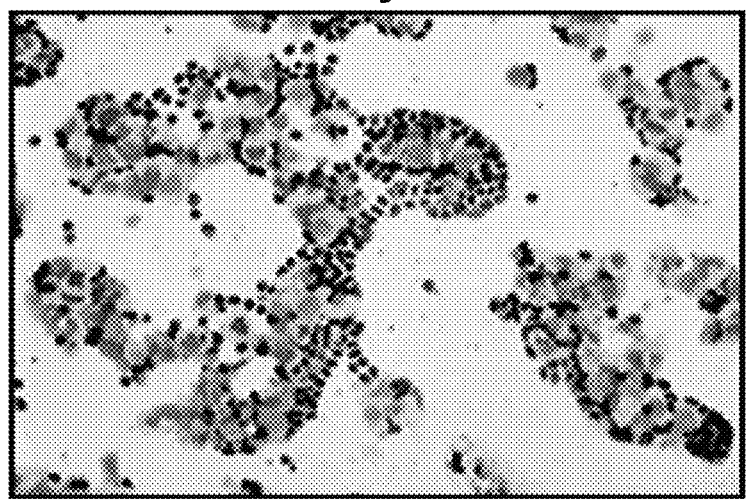

Fig. 18A.
| Tat | MYC | V5 | 6xHis |
| Tat | Bcl-2 | V5 | 6xHis |
Fig. 18B.
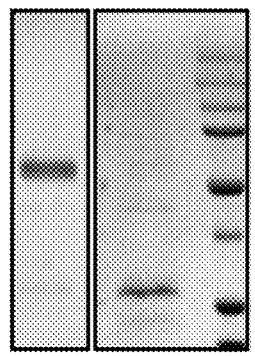
Fig. 18C.
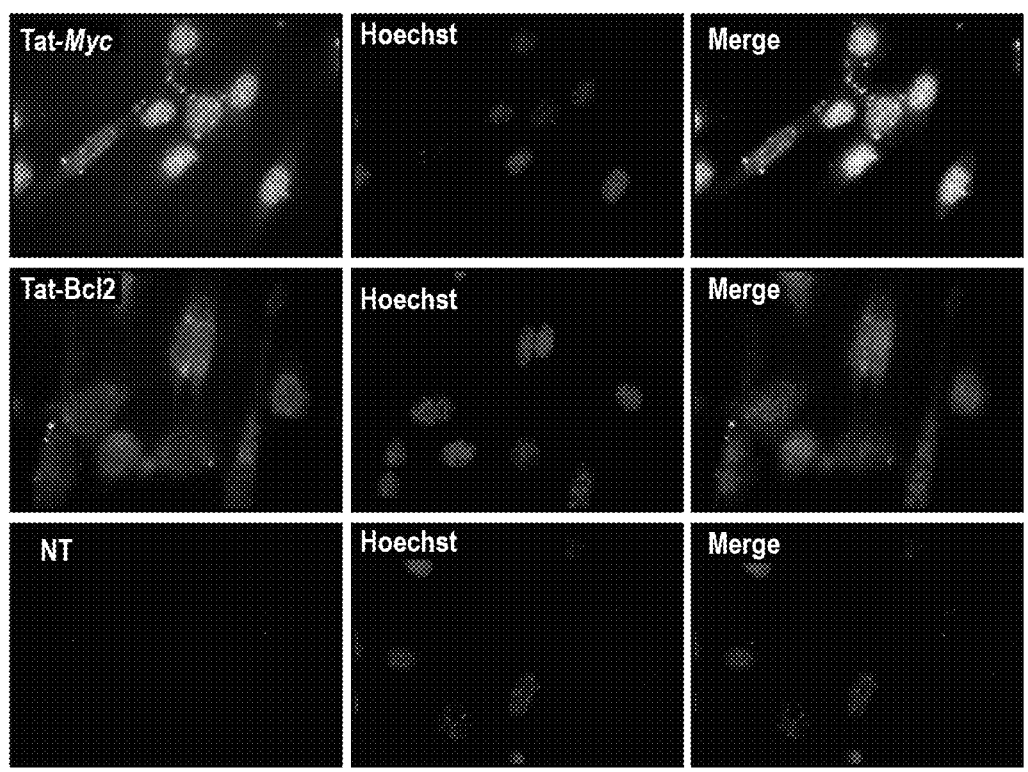

| Tat | MYC | | V5 | 6xHis |
|---|---|---|---|---|
| Tat | 3AMYC | | V5 | 6xHis |
| EPTD | MYC | | V5 | 6xHis |
| EPTD | 3AMYC | | V5 | 6xHis |
| VPR | MYC | | V5 | 6xHis |
| | MYC | VPR | V5 | 6xHis |

TAT-MYC Amino Acid sequence (SEQ ID NO: 1)

MRKKRRQRRRMPLNVSFTNRNYDLDYDSVQPYFYCDEEENFYQQQQQSELQPP
APSEDIWKKFELLPTPPLSPSRRSGLCSPSYVAVTPFSLRGDNDGGGSFSTADQL
EMVTELLGGDMVNQSFICDPDDETFIKNIIQDCMWSGFSAAAKLVSEKLASYQA
ARKDSGSPNPARGHSVCSTSSLYLQDLSAAASECIDPSVVFPYPLNDSSSPKSCAS
QDSSAFSPSSDSLLSSTESSPQGSPEPLVLHEETPPTTSSDSEEEQEDEEEIDVVSVE
KRQAPGKRSESGSPSAGGHSKPPHSPLVLKRCHVSTHQHNYAAPPSTRKDYPAA
KRVKLDSVRVLRQISNNRKCTSPRSSDTEENVKRRTHNVLERQRRNELKRSFFAL
RDQIPELENNEKAPKVVILKKATAYILSVQAEEQKLISEEDLLRKRREQLKHKLEQ
LRKGELNSKLEGKPIPNPLLGLDSTRTGHHHHHH

Amino acids 2-10 are the HIV Tat protein transduction domain
Amino acids 11-454 are c-Myc
Amino acids 455-468 are the 14 amino acid V5 epitope
Amino acids 472-477 are the 6 Histidine tag TAT-MYC Nucleotide sequence (SEQ ID NO: 2)

ATGAGGAAGAAGCGGAGACAGCGACGAAGAATGCCCCTCAACGTTAGCTTC
ACCAACAGGAACTATGACCTCGACTACGACTCGGTGCAGCCGTATTTCTACT
GCGACGAGGAGGAGAACTTCTACCAGCAGCAGCAGCAGAGCGAGCTGCAGC
CCCCGGCGCCCAGCGAGGATATCTGGAAGAAATTCGAGCTGCTGCCCACCCC
GCCCCTGTCCCCTAGCCGCCGCTCCGGGCTCTGCTCGCCCTCCTACGTTGCGG
TCACACCCTTCTCCCTTCGGGAGACAACGACGGCGGTGGCGGGAGCTTCTC
CACGGCCGACCAGCTGGAGATGGTGACCGAGCTGCTGGAGGAGACATGGT
GAACCAGAGTTTCATCTGCGACCCGGACGACGAGACCTTCATCAAAAACATC
ATCATCCAGGACTGTATGTGGAGCGGCTTCTCGGCCGCCGCCAAGCTCGTCTC
AGAGAAGCTGGCCTCCTACCAGGCTGCGCGCAAAGACAGCGGCAGCCCGAA
CCCCGCCCGCGGCCACAGCGTCTGCTCCACCTCCAGCTTGTACCTGCAGGATC
TGAGCGCCGCCGCCTCAGAGTGCATCGACCCCTCGGTGGTCTTCCCCTACCCT
CTCAACGACAGCAGCTCGCCCAAGTCCTGCGCCTCGCAAGACTCCAGCGCCT
TCTCTCCGTCCTCGGATTCTCTGCTCTCCTCGACGGAGTCCTCCCCGCAGGGC
AGCCCCGAGCCCCTGGTGCTCCATGAGGAGACACCGCCCACCACCAGCAGCG
ACTCTGAGGAGGAACAAGAAGATGAGGAAGAAATCGATGTTGTTTCTGTGGA
AAAGAGGCAGGCTCCTGGCAAAAGGTCAGAGTCTGGATCACCTTCTGCTGGA
GGCCACAGCAAACCTCCTCACAGCCCACTGGTCCTCAAGAGGTGCACGTCT
CCACACATCAGCACAACTACGCAGCGCCTCCCTCCACTCGGAAGGACTATCC
TGCTGCCAAGAGGGTCAAGTTGGACAGTGTCAGAGTCCTGAGACAGATCAGC
AACAACCGAAAATGCACCAGCCCCAGGTCCTCGGACACCGAGGAGAATGTC
AAGAGGCGAACACACAACGTCTTGGAGCGCCAGAGGAGGAACGAGCTAAAA
CGGAGCTTTTTTGCCCTGCGTGACCAGATCCCGGAGTTGGAAAACAATGAAA
AGGCCCCCAAGGTAGTTATCCTTAAAAAAGCCACAGCATACATCCTGTCCGT
CCAAGCAGAGGAGCAAAAGCTCATTTCTGAAGAGGACTTGTTGCGGAAACGA

Figure 24

TAT-Bcl2Δ Amino Acid sequence (SEQ ID NO: 3)

MRKKRRQRRRMAHAGRSGYDNREIVMKYIHYKLSQRATSGISIEAAGPALSPVP
PVVHLTLRQAGDDFSRRYRRDFAEMSSQLHLTPFTARGCFATVVEELFRDGVNW
GRIVAFFEFGGVMCVESVNREMSPLVDNIALWMTEYLNRHLHTWIQDNGGWDA
FVELYGPSMRPLFDFSWLSLKTLLSLALVGACITLGAYLSHKKGELNSKLEGKPIP
NPLLGLDSTRTGHHHHHH

Amino acids 2-10 are the HIV Tat protein transduction domain

Amino acids 11-212 are Bcl2Δ

Amino acids 213-226 are the 14 amino acid V5 epitope

Amino acids 230-235 are the 6 Histidine tag

TAT-Bcl2Δ Nucleotide sequence (SEQ ID NO: 4)

atgaggaagaagcggagacagcgacgaagaatggcgcacgctgggagaagtggttacgataaccgggagatagtgatgaa
gtacatccattataagctgtcgcagagggctacgagtgggatctcgatcgaggccgcggggcctgcgctcagcccggtgccac
ctgtggtccacctgaccctccgccaggccggcgacgacttctcccgccgctaccgccgcgacttcgccgagatgtccagccag
ctgcacctgacgcccttcaccgcgcggggatgctttgccacggtggtggaggagctcttcagggacggggtgaactgggggga
ggattgtggccttctttgagttcggtggggtcatgtgtgtggagagcgtcaaccgggagatgtcgcccctggtggacaacatcgc
cctgtggatgactgagtacctgaaccggcacctgcacacctggatccaggataacggaggctgggatgcctttgtggaactgta
cggccccagcatgcggcctctgtttgatttctcctggctgtctctgaagactctgctcagtttggccctggtgggagcttgcatcac
cctgggtgcctatctgagccacaagaagggcgagctcaattcgaagcttgaaggtaagcctatccctaaccctctcctcggtctc
gattctacgcgtaccggtcatcatcaccatcaccattga

Figure 25

SEQUENCE LISTING

<160> NUMBER OF SEQ ID NOS: 4

<210> SEQ ID NO 1
<211> LENGTH: 477
<212> TYPE: PRT
<213> ORGANISM: Artificial Sequence

```
<220> FEATURE:
<223> OTHER INFORMATION: Synthetic Construct

<400> SEQUENCE: 1

Met Arg Lys Lys Arg Gln Arg Arg Met Pro Leu Asn Val Ser
1               5                   10                  15

Phe Thr Asn Arg Asn Tyr Asp Leu Asp Tyr Asp Ser Val Gln Pro Tyr
                20                  25                  30

Phe Tyr Cys Asp Glu Glu Asn Phe Tyr Gln Gln Gln Gln Ser
            35                  40                  45

Glu Leu Gln Pro Pro Ala Pro Ser Glu Asp Ile Trp Lys Lys Phe Glu
    50                  55                  60

Leu Leu Pro Thr Pro Pro Leu Ser Pro Ser Arg Arg Ser Gly Leu Cys
65                  70                  75                  80

Ser Pro Ser Tyr Val Ala Val Thr Pro Phe Ser Leu Arg Gly Asp Asn
                85                  90                  95

Asp Gly Gly Gly Gly Ser Phe Ser Thr Ala Asp Gln Leu Glu Met Val
                100                 105                 110

Thr Glu Leu Leu Gly Gly Asp Met Val Asn Gln Ser Phe Ile Cys Asp
                115                 120                 125

Pro Asp Asp Glu Thr Phe Ile Lys Asn Ile Ile Gln Asp Cys Met
130                 135                 140

Trp Ser Gly Phe Ser Ala Ala Lys Leu Val Ser Glu Lys Leu Ala
145                 150                 155                 160

Ser Tyr Gln Ala Ala Arg Lys Asp Ser Gly Ser Pro Asn Pro Ala Arg
                165                 170                 175

Gly His Ser Val Cys Ser Thr Ser Ser Leu Tyr Leu Gln Asp Leu Ser
                180                 185                 190

Ala Ala Ala Ser Glu Cys Ile Asp Pro Ser Val Val Phe Pro Tyr Pro
                195                 200                 205

Leu Asn Asp Ser Ser Ser Pro Lys Ser Cys Ala Ser Gln Asp Ser Ser
210                 215                 220

Ala Phe Ser Pro Ser Ser Asp Ser Leu Leu Ser Ser Thr Glu Ser Ser
225                 230                 235                 240

Pro Gln Gly Ser Pro Glu Pro Leu Val Leu His Glu Glu Thr Pro Pro
                245                 250                 255

Thr Thr Ser Ser Asp Ser Glu Glu Glu Gln Glu Asp Glu Glu Ile
                260                 265                 270

Asp Val Val Ser Val Glu Lys Arg Gln Ala Pro Gly Lys Arg Ser Glu
                275                 280                 285

Ser Gly Ser Pro Ser Ala Gly Gly His Ser Lys Pro Pro His Ser Pro
                290                 295                 300

Leu Val Leu Lys Arg Cys His Val Ser Thr His Gln His Asn Tyr Ala
305                 310                 315                 320

Ala Pro Pro Ser Thr Arg Lys Asp Tyr Pro Ala Ala Lys Arg Val Lys
                325                 330                 335

Leu Asp Ser Val Arg Val Leu Arg Gln Ile Ser Asn Asn Arg Lys Cys
                340                 345                 350

Thr Ser Pro Arg Ser Ser Asp Thr Glu Glu Asn Val Lys Arg Arg Thr
                355                 360                 365

His Asn Val Leu Glu Arg Gln Arg Arg Asn Glu Leu Lys Arg Ser Phe
                370                 375                 380

Phe Ala Leu Arg Asp Gln Ile Pro Glu Leu Glu Asn Asn Glu Lys Ala
385                 390                 395                 400
```

Pro Lys Val Val Ile Leu Lys Lys Ala Thr Ala Tyr Ile Leu Ser Val
            405                 410                 415

Gln Ala Glu Glu Gln Lys Leu Ile Ser Glu Glu Asp Leu Leu Arg Lys
            420                 425                 430

Arg Arg Glu Gln Leu Lys His Lys Leu Glu Gln Leu Arg Lys Gly Glu
            435                 440                 445

Leu Asn Ser Lys Leu Glu Gly Lys Pro Ile Pro Asn Pro Leu Leu Gly
450                 455                 460

Leu Asp Ser Thr Arg Thr Gly His His His His His His
465                 470                 475

```
<210> SEQ ID NO 2
<211> LENGTH: 1434
<212> TYPE: DNA
<213> ORGANISM: Artificial Sequence
<220> FEATURE:
<223> OTHER INFORMATION: Synthetic Construct

<400> SEQUENCE: 2
atgaggaaga agcggagaca gcgacgaaga atgcccctca acgttagctt caccaacagg      60
aactatgacc tcgactacga ctcggtgcag ccgtatttct actgcgacga ggaggagaac     120
ttctaccagc agcagcagca gagcgagctg cagcccccgg cgcccagcga ggatatctgg     180
aagaaattcg agctgctgcc caccccgccc ctgtccccta gccgccgctc cgggctctgc     240
tcgccctcct acgttgcggt cacacccttc tcccttcggg agacaacga cggcggtggc      300 gggagcttct ccacgccga ccagctggag atggtgaccg agctgctggg aggagacatg      360
gtgaaccaga gtttcatctg cgacccggac gacgagacct tcatcaaaaa catcatcatc     420
caggactgta tgtggagcgg cttctcggcc gccgccaagc tcgtctcaga aagctggcc      480 tcctaccagg ctgcgcgcaa agacagcggc agcccgaacc ccgccgcgg ccacagcgtc      540 tgctccacct ccagcttgta cctgcaggat ctgagcgccg ccgcctcaga gtgcatcgac     600
ccctcggtgg tcttcccta ccctctcaac gacagcagct cgcccaagtc ctgcgcctcg     660
caagactcca gcgccttctc tccgtcctcg gattctctgc tctcctcgac ggagtcctcc     720
ccgcagggca gccccgagcc cctggtgctc catgaggaga caccgcccac caccagcagc     780
gactctgagg aggaacaaga agatgaggaa gaaatcgatg ttgtttctgt ggaaaagagg     840
caggctcctg gcaaaaggtc agagtctgga tcaccttctg ctggaggcca cagcaaacct     900
cctcacagcc cactggtcct caagaggtgc acgtctcca acatcagca aactacgca       960 gcgcctccct ccactcggaa ggactatcct gctgccaaga gggtcaagtt ggacagtgtc    1020
agagtcctga cacagatcag caacaaccga aaatgcacca gccccaggtc ctcggacacc    1080
gaggagaatg tcaagaggcg aacacacaac gtcttggagc gccagaggag gaacgagcta    1140
aaacggagct ttttgcccct gcgtgaccag atcccggagt tggaaaacaa tgaaaaggcc    1200
cccaaggtag ttatccttaa aaaagccaca gcatacatcc tgtccgtcca agcagaggag    1260
caaaagctca tttctgaaga ggacttgttg cggaaacgac gagaacagtt gaaacacaaa    1320
cttgaacagc tacggaaggg cgagctcaat tcgaagcttg aaggtaagcc tatccctaac    1380
cctctcctcg gtctcgattc tacgcgtacc ggtcatcatc accatcacca ttga          1434

<210> SEQ ID NO 3
<211> LENGTH: 235
<212> TYPE: PRT
<213> ORGANISM: Artificial Sequence
```

<220> FEATURE:
<223> OTHER INFORMATION: Synthetic Construct

<400> SEQUENCE: 3

Met Arg Lys Lys Arg Gln Arg Arg Met Ala His Ala Gly Arg
1               5                   10                  15

Ser Gly Tyr Asp Asn Arg Glu Ile Val Met Lys Tyr Ile His Tyr Lys
            20                  25                  30

Leu Ser Gln Arg Ala Thr Ser Gly Ile Ser Ile Glu Ala Ala Gly Pro
        35                  40                      45

Ala Leu Ser Pro Val Pro Val Val His Leu Thr Leu Arg Gln Ala
    50                  55                      60

Gly Asp Asp Phe Ser Arg Arg Tyr Arg Arg Asp Phe Ala Glu Met Ser
65                  70                  75                  80

Ser Gln Leu His Leu Thr Pro Phe Thr Ala Arg Gly Cys Phe Ala Thr
            85                  90                      95

Val Val Glu Glu Leu Phe Arg Asp Gly Val Asn Trp Gly Arg Ile Val
            100                 105                 110

Ala Phe Phe Glu Phe Gly Gly Val Met Cys Val Glu Ser Val Asn Arg
        115                 120                 125

Glu Met Ser Pro Leu Val Asp Asn Ile Ala Leu Trp Met Thr Glu Tyr
    130                 135                 140

Leu Asn Arg His Leu His Thr Trp Ile Gln Asp Asn Gly Gly Trp Asp
145                 150                 155                 160

Ala Phe Val Glu Leu Tyr Gly Pro Ser Met Arg Pro Leu Phe Asp Phe
                165                 170                 175

Ser Trp Leu Ser Leu Lys Thr Leu Leu Ser Leu Ala Leu Val Gly Ala
            180                 185                 190

Cys Ile Thr Leu Gly Ala Tyr Leu Ser His Lys Lys Gly Glu Leu Asn
        195                 200                 205

Ser Lys Leu Glu Gly Lys Pro Ile Pro Asn Pro Leu Leu Gly Leu Asp
    210                 215                 220

Ser Thr Arg Thr Gly His His His His His
225                 230                 235

<210> SEQ ID NO 4
<211> LENGTH: 708
<212> TYPE: DNA
<213> ORGANISM: Artificial Sequence
<220> FEATURE:
<223> OTHER INFORMATION: Synthetic Construct

<400> SEQUENCE: 4
atgaggaaga agcggagaca gcgacgaaga atggcgcacg ctgggagaag tggttacgat     60
aaccgggaga tagtgatgaa gtacatccat tataagctgt cgcagagggc tacgagtggg    120
atctcgatcg aggccgcggg gcctgcgctc agcccggtgc cacctgtggt ccacctgacc    180
ctccgccagg ccggcgacga cttctcccgc cgctaccgcc gcgacttcgc cgagatgtcc    240
agccagctgc acctgacgcc cttcaccgcg cggggatgct tgccacggt ggtggaggag    300 ctcttcaggg acggggtgaa ctgggggagg attgtgcct tctttgagtt cggtggggtc     360
atgtgtgtgg agagcgtcaa ccgggagatg tcgccctgg tggacaacat cgccctgtgg    420
atgactgagt acctgaaccg gcacctgcac acctggatcc aggataacgg aggctgggat    480
gcctttgtgg aactgtacgg ccccagcatg cggcctctgt tgatttctc ctggctgtct    540 ctgaagactc tgctcagttt ggccctggtg ggagcttgca tcaccctggg tgcctatctg    600

```
agccacaaga agggcgagct caattcgaag cttgaaggta agcctatccc taaccctctc    660
ctcggtctcg attctacgcg taccggtcat catcaccatc accattga                708
```

PRODUCTION AND USE OF RED BLOOD CELLS

CROSS-REFERENCE TO RELATED PATENT APPLICATIONS

This application is a divisional of U.S. application Ser. No. 13/797,648, filed Mar. 12, 2013, which claims the benefit of U.S. Provisional Application No. 61/776,732, filed Mar. 11, 2013, the disclosures of which are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 691772000900SeqList.txt, date recorded: Mar. 11, 2013, size: 9 KB)

FIELD

The present disclosure relates to new methods of producing mature red blood cells from hematopoietic stem cells in vitro, and their therapeutic and diagnostic use in vivo.

BACKGROUND

Transfusion of red blood cells (RBCs) is routinely used for many clinical and surgical applications. On average, 39,000 units of blood are needed every day, and data from 2004 indicate that 29 million units of blood were transfused in one year (American Association of Blood Banks website). This procedure has single-handedly saved many lives over the past 60 years. The demand for such transfusions continues to increase with advances in medical treatments and an aging population.

In addition to the traditional clinical settings that have benefited from the availability of red blood cell transfusion, such as surgery and treatment of trauma patients, there are a number of unique instances in which red blood cell transfusion would change the standard of care. For example, there are a number of rare phenotypes of RBCs in patients of Afro-Caribbean descent (Douay et al., *Transfusion Medicine Reviews* 21, 91-100, 2007). They are considered rare phenotypes, due to the lack of antigens such as H or ABO blood groups. Such patients can develop a neutralizing antibody response to ABO blood group antigens, rendering them ineligible for RBC transfusions. In fact, such patients must receive transfusions from an identical source to avoid a neutralizing antibody response, posing tremendous challenges in cases where repeated red blood cell transfusions are required (e.g., sickle cell patients, etc.).

Additionally, patients who suffer from a variety of antibody-based autoimmune diseases and experience autoimmune hemolytic anemia may also benefit from red blood cell transfusions. However, this presents a challenge in finding a donor, or limited set of donors whose RBCs are compatible with the patients' autoantibodies. In essence, these patients experience the same challenges as those with rare blood phenotypes.

Moreover, patients who suffer from hemoglobinopathies and thalassemias have congenic mutations that result in a shorter life span for their RBCs. While the idea of improving the life and health of these patients with blood transfusions is an old one, the frequency of transfusions required presents a major problem. The average lifespan of RBCs from a healthy donor is 28 days. The number of transfusions required for these patients is large, frequent, and poses a significantly increased risk of iatrogenic infection. The ability to generate RBCs in vitro and to provide transfusions of synchronized RBCs with a mean lifespan of 120 days would greatly reduce the number of transfusions required for these patients and truly improve their quality of life.

The issue of lifespan of RBCs collected from donors is also important in the context of traditional clinical use of RBCs for trauma and surgical procedures. The storage of RBC concentrates for up to one month may result in an RBC population that requires at least 24 hours to recover its ability to transport oxygen. In addition, a number of necrotic RBCs in those concentrates could trigger an inflammatory response in the recipient, along with the complications that arise from such an inflammatory response. The ability to generate a constant supply of RBCs in vitro would allow health professionals to anticipate and to meet the demands for fresh RBCs, and would also eliminate the need for long-term storage of RBC concentrates Another problem with red blood cell transfusions is the increasing difficulty in providing red blood cell transfusions. The reasons for this increasing difficulty include a steady drop in the supply of donated blood that is eligible for transfusion due to the increased number of infectious agents that have been shown to be transmitted through blood transfusions, the failure of hemoglobin and oxygen transporters (perflourocarbons) to show efficacy as RBC alternatives in the clinical setting, and recent complications associated with erythropoietin (EPO) usage. Ready access to a continuous supply of RBC progenitors that could generate a defined RBC product for transfusion would alter the practice in the clinic and render blood transfusion a safer and more extensively used procedure. However, such an approach must be able to provide a supply of RBCs that is safe, effective, and universal.

While some initial attempts have been made to derive RBCs in vitro from primary hematopoietic stem cells (derived from bone marrow, cord blood, or peripheral blood) or embryonic stem cells, to date they have been unsuccessful for a variety of reasons including one or more of expense, duration of protocol, multiple steps, use of feeder cells or serum, labor intensiveness, low yield, or failure to fully differentiate to mature, anucleated red blood cells. Attempts to generate RBCs in vitro include methods starting from primary hematopoietic stem cells (Neildez-Nguyen et al., *Nat Biotech* 20, 467-72, 2002), and embryonic stem cells (Lu et al., *Blood.* 2008 Dec. 1; 112(12):4475-84; Lu et al., *Regen Med* 3, 693-704, 2008. These approaches also don't generally allow for a defined and continuous source of RBC progenitors.

Citation of the above documents and studies is not intended as an admission that any of the foregoing is pertinent prior art. All statements as to the contents of these documents are based on the information available to the applicants and do not constitute any admission as to the correctness of the contents of these documents.

BRIEF SUMMARY

Accordingly, there is a need for improved approaches for in vitro production of fully mature human red blood cells. The present disclosure provides novel methods of producing a red blood cell (RBC) population by culturing hematopoietic stem cells (HSCs) in the presence of one or more recombinant protein, such as an exogenous protein, that induces one or more of cell survival or proliferation, EPO, and optionally, IL-3. Advantageously, these methods produce mature anucleated red blood cells in about 10 days that exhibit an adult red blood cell phenotype that includes, without limitation, expression of Glycophrin A (GPA), increased levels of adult hemoglobin, decreased levels of CD71 (transferrin receptor), and decreased levels of fetal hemoglobin. Moreover, production of the RBCs from conditionally immortalized human long-term HSCs that can be passaged indefinitely in vitro, cryopreserved, and recovered, allows for the continuous production of fully differentiated red blood cells from a defined, well-characterized, source. Additionally, RBCs produced by the novel methods of the present disclosure may also contain and/or express one or more recombinant protein of interest that can be used to treat a subject in need thereof.

Accordingly, certain aspects of the present disclosure relate to a method for producing a population of mature red blood cells from hematopoietic stem cells, by: culturing the hematopoietic stem cells in the presence of EPO and one or more first recombinant protein, or biologically active fragment thereof, that promotes cell survival and/or proliferation; under conditions that induce differentiation of the hematopoietic stem cells to mature red bloods cells, thereby producing a population of mature red blood cells. In some embodiments, the hematopoietic stem cells are conditionally immortalized hematopoietic stem cells. In some embodiments that may be combined with any of the preceding embodiments, the hematopoietic stem cells are protein transduced hematopoietic stem cells, and the one or more first recombinant protein, or biologically active fragment thereof, is an exogenous protein. In some embodiments that may be combined with any of the preceding embodiments, the hematopoietic stem cells are transgenic hematopoietic stem cells. In some embodiments that may be combined with any of the preceding embodiments, the one or more first recombinant protein, or biologically active fragment thereof, is one or more polypeptide selected from a MYC polypeptide, an ICN-1 polypeptide, homologues thereof, and biologically active fragments thereof. In some embodiments that may be combined with any of the preceding embodiments, the MYC polypeptide is one or more MYC polypeptide selected from n-Myc, c-Myc, 1-Myc, v-Myc, and s-Myc. In some embodiments that may be combined with any of the preceding embodiments, one or more of the one or more first recombinant protein, or biologically active fragment thereof, contains a protein transduction domain. In some embodiments that may be combined with any of the preceding embodiments, the protein transduction domain is one or more protein transduction domain selected from TAT, VPR, and EPTD. In some embodiments that may be combined with any of the preceding embodiments, the one or more first recombinant protein, or biologically active fragment thereof, is TAT-MYC. In some embodiments that may be combined with any of the preceding embodiments, the one or more first recombinant protein, or biologically active fragment thereof, is provided as a bolus. In some embodiments that may be combined with any of the preceding embodiments, the one or more first recombinant protein is provided as a bolus about every 24 hours, about every 48 hours, or about every 72 hours. In some embodiments that may be combined with any of the preceding embodiments, the method further includes culturing the hematopoietic stem cells in the presence of IL-3. In some embodiments that may be combined with any of the preceding embodiments, the method further includes culturing the hematopoietic stem cells in the absence of feeder cells and serum. In some embodiments that may be combined with any of the preceding embodiments, the method further includes culturing the population of mature red blood cells in the presence of one or more second recombinant protein, or biologically active fragment thereof, that inhibits apoptosis. In some embodiments that may be combined with any of the preceding embodiments, the one or more second recombinant protein, or biologically active fragment thereof, contains one or more Bcl-2 homology domains. In some embodiments that may be combined with any of the preceding embodiments, the one or more Bcl-2 homology domains are one or more Bcl-2 homology domains selected from BH1, BH2, BH3, and BH4. In some embodiments that may be combined with any of the preceding embodiments, the one or more second recombinant protein is one or more of Bcl-2, Bcl-w, Bcl-X, Bcl-XL, or Mcl-1. In some embodiments that may be combined with any of the preceding embodiments, the one or more second recombinant protein, or biologically active fragment thereof, is Bcl-2. In some embodiments that may be combined with any of the preceding embodiments, one or more of the one or more second recombinant protein, or biologically active fragment thereof, contains a protein transduction domain. In some embodiments that may be combined with any of the preceding embodiments, the protein transduction domain is one or more protein transduction domains selected from TAT, VPR, and EPTD. In some embodiments that may be combined with any of the preceding embodiments, the one or more second recombinant protein, or biologically active fragment thereof, is TAT-Bcl-2. In some embodiments that may be combined with any of the preceding embodiments, the hematopoietic stem cells further contain one or more recombinant protein of interest, or biologically active fragment thereof. In some embodiments that may be combined with any of the preceding embodiments, the one or more recombinant protein of interest, or biologically active fragment thereof, is an exogenous protein, or biologically active fragment thereof. In some embodiments that may be combined with any of the preceding embodiments, the hematopoietic stem cells contain one or more transgenes that encode one or more proteins selected from the one or more first recombinant protein, or biologically active fragment thereof; the one or more second recombinant protein, or biologically active fragment thereof; and one or more recombinant protein of interest, or biologically active fragment thereof. In some embodiments that may be combined with any of the preceding embodiments, the expression or function of one or more of the one or more first recombinant protein, or biologically active fragment thereof; the one or more second recombinant protein, or biologically active fragment thereof; or one or more recombinant protein of interest, or biologically active fragment thereof is controllable. In some embodiments that may be combined with any of the preceding embodiments, the expression or function of one or more of the one or more first recombinant protein, or biologically active fragment thereof; the one or more second recombinant protein, or biologically active fragment thereof; or one or more recombinant protein of interest, or biologically active fragment thereof is inducible. In some embodiments that may be combined with any of the preceding embodiments, one or more of the one or more transgenes encode an antibiotic responsive element or a hormone responsive element. In some embodiments that may be combined with any of the preceding embodiments, the antibiotic responsive element or the hormone responsive element is one or more responsive element selected from an estrogen response element, a gonadotropin response element, or a tetracycline response element, and a glucocorticoid response element. In some embodiments that may be combined with any of the preceding embodiments, the one or more transgenes over-express one or more one or more proteins selected from the one or more first recombinant protein, or biologically active fragment thereof; the one or more second recombinant protein, or biologically active fragment thereof; and one or more recombinant protein of interest, or biologically active fragment thereof. In some embodiments that may be combined with any of the preceding embodiments, the production of the population of mature red blood cells is accelerated by at least 45% compared to production of a population of red blood cells from a primary stem cell cultured in the presence of IL-3 and EPO for eight days, then in the presence of feeder cells and EPO for three days, and finally in the presence of feeder cells alone for 10 days. In some embodiments that may be combined with any of the preceding embodiments, the population of mature red blood cells is produced in about 7 to 14 days. In some embodiments that may be combined with any of the preceding embodiments, the population of mature red blood cells exhibits one or more characteristics selected from a population of mature red blood cells, where about 40% to about 100% of the cells are anucleated; a population of mature red blood cells, where about 40% to about 100% of the cells express GPA; a population of mature red blood cells, where about 40% to about 100% of the cells express adult hemoglobin; a population of mature red blood cells, where about 40% to about 100% of the cells exhibit decreased levels of CD71 expression; a population of mature red blood cells, where about 40% to about 100% of the cells exhibit decreased levels of fetal hemoglobin expression. In some embodiments that may be combined with any of the preceding embodiments, the hematopoietic stem cells are human hematopoietic stem cells. In some embodiments that may be combined with any of the preceding embodiments, the hematopoietic stem cells were isolated from a patient with a rare blood type. In some embodiments that may be combined with any of the preceding embodiments, the patient has an autoimmune condition. In some embodiments that may be combined with any of the preceding embodiments, the hematopoietic stem cells were produced from embryonic stem cells or induced pluripotent stem cells. In some embodiments that may be combined with any of the preceding embodiments, the population of mature red blood cells is a population of human cells. In some embodiments that may be combined with any of the preceding embodiments, the population of mature red blood cells has one or more blood types selected from A$^+$, A$^-$, B$^+$, B$^-$, AB$^+$, AB$^-$, O$^+$, and O$^-$. In some embodiments that may be combined with any of the preceding embodiments, the population of mature red blood cells is a rare blood type. In some embodiments that may be combined with any of the preceding embodiments, the population of mature red blood cells is a population of non-human animal cells.

Other aspects of the present disclosure relate to a population of in vitro differentiated mature red blood cells, containing anucleated red blood cells expressing GPA, expressing adult hemoglobin, exhibiting decreased levels of CD71 expression, and exhibiting decreased levels of fetal hemoglobin expression, where: about 40% to about 100% of the red blood cells in the population are anucleated; about 40% to about 100% of the red blood cells in the population express GPA; about 40% to about 100% of the red blood cells in the population express adult hemoglobin; about 40% to about 100% of the red blood cells in the population exhibit decreased levels of CD71 expression; and about 40% to about 100% of the red blood cells in the population exhibit decreased levels of fetal hemoglobin expression. In some embodiments that may be combined with any of the preceding embodiments, the red blood cells contain one or more recombinant protein of interest. In some embodiments that may be combined with any of the preceding embodiments, the red blood cells have a rare blood type. In some embodiments that may be combined with any of the preceding embodiments, the red blood cells are human red blood cells. In some embodiments that may be combined with any of the preceding embodiments, the red blood cells are non-human animal red blood cells. In some embodiments that may be combined with any of the preceding embodiments, the population of in vitro differentiated mature red blood cells is produced by any methods of producing a population of mature red blood cells from hematopoietic stem cells of any of the preceding embodiments.

Other aspects of the present disclosure relate to a pharmaceutical composition containing: a population of in vitro differentiated mature red blood cells, where about 40% to about 100% of the red blood cells in the population are anucleated, about 40% to about 100% of the red blood cells in the population express GPA, about 40% to about 100% of the red blood cells in the population express adult hemoglobin, about 40% to about 100% of the red blood cells in the population exhibit decreased levels of CD71 expression, and about 40% to about 100% of the red blood cells in the population exhibit decreased levels of fetal hemoglobin expression; and one or more pharmaceutically acceptable excipients. In some embodiments that may be combined with any of the preceding embodiments, where the composition further contains one or more recombinant protein of interest, or biologically active fragment thereof. In some embodiments that may be combined with any of the preceding embodiments, the population of red blood cells contains one or more recombinant protein of interest, or biologically active fragment thereof. In some embodiments that may be combined with any of the preceding embodiments, the one or more recombinant protein of interest, or biologically active fragment thereof, is an exogenous protein. In some embodiments that may be combined with any of the preceding embodiments, the red blood cells have a rare blood type. In some embodiments that may be combined with any of the preceding embodiments, the red blood cells are human red blood cells. In some embodiments that may be combined with any of the preceding embodiments, the red blood cells are non-human animal red blood cells. In some embodiments that may be combined with any of the preceding embodiments, the population of in vitro differentiated mature red blood cells is produced by any methods of producing a population of mature red blood cells from hematopoietic stem cells of any of the preceding embodiments.

Other aspects of the present disclosure relate to a method of treatment, prevention, or diagnosis of a disease or disorder characterized by a deficiency of anucleated red blood cells by: providing to a subject in need thereof a population of in vitro differentiated mature red blood cells, where about 40% to about 100% of the red blood cells in the population are anucleated, about 40% to about 100% of the red blood cells in the population express GPA, about 40% to about 100% of the red blood cells in the population express adult hemoglobin, about 40% to about 100% of the red blood cells in the population exhibit decreased levels of CD71 expression, and about 40% to about 100% of the red blood cells in the population exhibit decreased levels of fetal hemoglobin expression. In some embodiments that may be combined with any of the preceding embodiments, the subject is a human. In some embodiments that may be combined with any of the preceding embodiments, the subject is a non-human animal. In some embodiments that may be combined with any of the preceding embodiments, the population of red blood cells contains one or more recombinant protein of interest, or a biologically active fragment thereof. In some embodiments that may be combined with any of the preceding embodiments, the one or more recombinant protein of interest, or biologically active fragment thereof, is an exogenous protein. In some embodiments that may be combined with any of the preceding embodiments, the population of in vitro differentiated mature red blood cells are produced by any methods of producing a population of mature red blood cells from hematopoietic stem cells of any of the preceding embodiments.

Other aspects of the present disclosure relate to a method for extending the half-life of a population of mature red blood cells in vitro by: maintaining the population of red blood cells in a media containing one or more exogenous polypeptide, homologues thereof or biologically active fragments thereof, that inhibit apoptosis. In some embodiments that may be combined with any of the preceding embodiments, the one or more exogenous polypeptide, homologues thereof or biologically active fragments thereof, contains one or more Bcl2 homology domains. In some embodiments that may be combined with any of the preceding embodiments, the one or more Bcl-2 homology domains are one or more Bcl-2 homology domains selected from BH1, BH2, BH3, and BH4. In some embodiments that may be combined with any of the preceding embodiments, the one or more exogenous polypeptide, homologues thereof or biologically active fragments thereof, is one or more of Bcl-2, Bcl-w, Bcl-X, Bcl-XL, or Mcl-1. In some embodiments that may be combined with any of the preceding embodiments, the one or more exogenous polypeptide, homologues thereof or biologically active fragments thereof, is Bcl-2. In some embodiments that may be combined with any of the preceding embodiments, one or more of the one or more exogenous polypeptide, homologues thereof or biologically active fragments thereof, contains a protein transduction domain. In some embodiments that may be combined with any of the preceding embodiments, the protein transduction domain is one or more protein transduction domains selected from TAT, VPR, and EPTD. In some embodiments that may be combined with any of the preceding embodiments, the one or more exogenous polypeptide, homologues thereof or biologically active fragments thereof, is TAT-Bcl-2. In some embodiments that may be combined with any of the preceding embodiments, the population of mature red blood cells is produced by any methods of producing a population of mature red blood cells from hematopoietic stem cells of any of the preceding embodiments.

BRIEF DESCRIPTION OF THE DRAWINGS

FIGS. 1A-1F depict a general approach for the generation of ctlt-HSC cell lines. FIG. 1A depicts a schematic representation of retroviral constructs used to transduce primary murine HSC cells with MYC-ER and Bcl-2. FIG. 1B depicts flow cytometric analyses of HSCs obtained from 5-fluorouracil treated donors following transduction with pMIG-MYC-ER and pMIG-Bcl-2. FIG. 1C depicts kinetics of leukemogenesis in mice transplanted with the transduced HSCs shown in FIG. 1B. FIG. 1D depicts FACS analysis of a ctlt-HSC soon after recovery from the bone marrow of leukemic mice. FIG. 1E depicts FACS analysis of a ctlt-HSC cell line that has been established. FIG. 1F depicts FACS analysis of stem cell markers in normal, unmanipulated Lt-HSCs from the bone marrow of wild type C57/BL6 mice.

FIGS. 2A-27D depict the characterization of mature immune cells that arise following transplantation of ctlt-HSCs. FIG. 2A depicts the frequency of cells derived from ctlt-HSCs in lymphoid tissues after transplantation. FIG. 2D depicts the analysis of peripheral, mature lymphocytes in transplant recipient mice following the second serial passage of ctlt-HSCs.

FIGS. 3A-3I depict the surface phenotype of three human ctlt-HSC cell lines. FIG. 3A, FIG. 3B, and FIG. 3C show the CD34$^+$ fraction of transduced (i.e., GFP$^+$) HSCs from three established human ctlt-HSC cell lines. FIG. 3D, FIG. 3E, and FIG. 3F show the c-kit$^+$ fraction of transduced (i.e., GFP$^+$) HSCs from three established human ctlt-HSC cell lines. FIG. 3G depicts that the transduced (i.e., GFP$^+$) HSCs from the established human ctlt-HSC cell lines do not express CD45. FIG. 3H depicts that the transduced (i.e., GFP$^+$) HSCs from the established human ctlt-HSC cell lines do not express Flk-2. FIG. 3I depicts that the transduced (i.e., GFP$^+$) HSCs from the established human ctlt-HSC cell lines do not express CD150.

FIGS. 4A-4D depict the differentiation of human ctlt-HSC cells lines into mature lymphoid cells in NOD/SCID/ β2M$^{-/-}$ mice. FIG. 4A depicts data obtained from a control mouse (no transplant). FIG. 4B, FIG. 4C, and FIG. 4D show data obtained from a transplant recipient mouse that presented mature human lymphoid cells in the peripheral blood.

FIG. 5A depicts H and E staining of mouse peripheral blood. FIG. 5B depicts H and E staining of primary human fetal cord blood. FIG. 5C, FIG. 5D, and FIG. 5E show H and E staining of three conditionally transformed fetal cord blood cell lines that were treated for 12 days with IL-3 and EPO. FIG. 5F shows a magnified view of the cells from FIG. 5E to show red blood cell morphology.

FIG. 6 depicts that in vitro generated human RBCs can rescue mice from chemically induced lethal anemia.

FIG. 7 depicts that in vitro generated human RBCs can rescue mice from hemorrhagic shock.

FIG. 8A depicts the TAT-MYC. FIG. 8B depicts TAT-Bcl2.

FIG. 9A depicts unstained cells. FIG. 9B depicts staining with antibodies to Sca1 and c-Kit. FIG. 9C depicts staining with antibodies to B220 and CD3. FIG. 9D depicts the surface phenotype of the resulting ptlt-HSC line.

FIGS. 10A-10D depict FACS analysis showing reconstitution of lymphoid compartment in Rag-1$^{-/-}$ mice by a murine ptlt-HSC cell line. FIG. 10A depicts unstained cells. FIG. 10B depicts staining for B cell markers B220 and IgM. FIG. 10C depicts staining for T cell markers CD4 and TCRβ. FIG. 10D depicts staining for T cell markers CD8 and TCRβ.

FIGS. 11A-11C depict the development of mature murine red blood cells from ptlt-HSCs in vitro. FIG. 11A depicts H and E staining of undifferentiated murine ptlt-HSCs under a 40× objective. FIG. 11B depicts H and E staining of red blood cells derived from murine ptlt-HSCs under a 40× objective. FIG. 11C depicts H and E staining of red blood cells derived from murine ptlt-HSCs under a 100× objective.

FIG. 12A depicts staining with antibodies to CD38 and CD34 after culturing the HSCs for 3 days in medium containing TAT-MYC and TAT-Bcl-2. FIG. 12B depicts staining with antibodies to CD38 and CD34 after culturing the HSCs for 14 days in medium containing TAT-MYC and TAT-Bcl-2.

FIGS. 13A-13C depict the induction of red blood cell differentiation in vitro. FIG. 13A depicts unstained HSC cells from FIG. 12 after 4 days of culturing in medium containing IL-3 and EPO. FIG. 13B depicts staining with antibodies to GPA and CD71 after culturing the HSC cells from FIG. 12 for 4 days in neutral medium. FIG. 13C depicts staining with antibodies to GPA and CD71 after culturing the HSC cells from FIG. 12 for 4 days in medium containing IL-3 and EPO.

FIGS. 14A-14C depict dynamic analysis of red blood cell differentiation markers in vitro. FIG. 14A depicts staining with antibodies to GPA, CD71, and fetal hemoglobin of mature human RBC cells (+Control). FIG. 14B depicts staining with antibodies to GPA, CD71, and fetal hemoglobin after 5 days of culturing the HSC cells from FIG. 12 in medium containing IL-3 and EPO. FIG. 14C depicts staining with antibodies to GPA, CD71, and fetal hemoglobin after 9 days of culturing the HSC cells from FIG. 12 in medium containing IL-3 and EPO.

FIGS. 15A and 15B depict histological analysis of enucleation in culture. FIG. 15A depicts H and E staining of cells from FIG. 12 after 3 days of culturing in medium containing IL-3 and EPO. FIG. 15B depicts H and E staining of cells from FIG. 12 after 7 days of culturing in medium containing IL-3 and EPO.

FIG. 16A depicts red blood cells differentiated from conditionally immortalized ptlt-HSCs after culturing in medium containing IL-3 and EPO for 4 days. FIG. 16B depicts H and E staining of red blood cells, showing maturation and enucleation of the red blood cells.

FIG. 17A depicts H and E staining of untreated (control) mouse hematopoietic stem cells from bone marrow. FIG. 17B depicts H and E staining of mouse hematopoietic stem cells from bone marrow treated with IL3 and EPO, but not Tat-Myc or Tat-Bcl-2. FIG. 17C depicts H and E staining of mouse hematopoietic stem cells from bone marrow treated with IL3, EPO and Tat-Myc, but not Tat-Bcl-2. FIG. 17D depicts H and E staining of mouse hematopoietic stem cells from bone marrow treated with IL3, EPO, and Tat-Bcl-2, but not Tat-Myc. FIG. 17E depicts H and E staining of mouse hematopoietic stem cells from bone marrow treated with IL3, EPO, Tat-Bcl-2, and Tat-Myc.

FIGS. 18A-18E depict the generation and in vitro characterization of Tat fusion proteins. FIG. 18A depicts a graphical representation of Tat-Myc and Tat-Bcl-2 fusion proteins including the location of the in frame protein transduction domain of HIV-1 Tat and the V5 and 6× His tags. FIG. 18B depicts recombinant proteins following purification from E. coli, separation by SDS-PAGE, and staining with Coomassie. FIG. 18C depicts a lawn of confluent 3T3 cells exposed to purified recombinant Tat-Myc, Tat-Bcl-2, or left untreated (NT) for two hours, and then fixed and stained with a monoclonal antibody to V5 and with a Hoechst 9934 nuclear stain. The Tat-Myc protein largely localized to the nuclear region in this timeframe, whereas the Tat-Bcl-2 remained in the cytoplasmic and perinuclear space. FIG. 18D depicts an SDS-PAGE and western blot analysis (monoclonal antibodies to V5 and (β-actin) of human cord blood derived HSCs pulsed with a single exposure of Tat-Myc for 1 hours, washed, and then lysed (at the indicated time points) to separate the plasma membrane and cytoplasmic fraction from the nuclear fraction. FIG. 18E depicts a SDS-PAGE and western blot analysis (monoclonal antibodies to V5 and (β-actin) of the nuclear fraction of human cord blood derived HSCs pulsed with a single exposure of Tat-Myc for 2 hours, washed, and then lysed (at the indicated time points) to separate the plasma membrane and cytoplasmic fraction from the nuclear fraction. The bulk of the protein is lost between 24 and 48 hours. There is no detectable protein left at any point after 72 hours.

FIG. 19A depicts a graphical representation of a FACS analysis of the surface phenotype of the human cord blood cells expanded in vitro for 14 days (Top panels cytokine cocktail only; Bottom panels cytokine cocktail supplemented with Tat-Myc and Tat-Bcl-2). FIG. 19B depicts a graphical representation of the kinetics of CD34+ cells expansion in vitro under both sets of conditions. FIG. 19C depicts the images of three different colony types developed in methylcellulose assays under conditions that support myeloerythroid differentiation, derived from human ptlt-HSCs. FIG. 19D depicts a graphical representation of the quantification of each colony type that was observed in methylcellulose cultures seeded with either $10^3$ cord blood cells cultured with a cytokine cocktail (black bars), $10^3$ cord blood cells cultured with a cytokine cocktail supplemented with Tat-Myc and Tat-Bcl-2 (dark grey bars), or $10^4$ fresh un-manipulated cord blood cells (light grey bars). FIG. 19E depicts a graphical representation of the quantification of the number of colonies observed in methylcellulose cultures upon replating of the cells shown in FIG. 19D.

FIG. 20A depicts a graphical representation of a FACS analysis of the bone marrow of cohorts of sublethally irradiated NSG mice given transplants of $10^6$ cord blood cells expanded in vitro in a cocktail of cytokines (first panel; FCB), or expanded in a cocktail of cytokines supplemented with Tat-Myc and Tat-Bcl-2 (second panel; FCB TMTB), or 5×$10^6$ fresh un-manipulated cord blood cells (third panel; Fresh FCB). FIG. 20B depicts a graphical representation of a FACS analysis of bone marrow, spleen and thymus cells from the xenochimaeric mice. All cells were stained for human CD45. Gating on CD45+ cells showed human CD34+ $CD38^{lo}$ cells in the bone marrow (first panel; BM); human $CD19^+$ and human CD3+ lymphocytes in the spleen (second panel; spleen); and human CD3+ cells in the thymus (third panel; thymus). FIG. 20C depicts a graphical representation of a FACS analysis of human splenic B-cells labeled with CFSE and cultured in the presence of monoclonal antibodies to human CD40 and IgM. Human B-cells that developed in NSG xenochimaeric mice underwent proliferation following stimulation of their antigen receptor. FIG. 20D depicts a graphical representation of the quantification of myeloerythroid colonies from human CD34+ $CD38^{lo}$ cells obtained from the bone marrow of NSG xenochimaeric mice and plated on methycellulose. FIG. 20E depicts a graphical representation of the quantification of the development of myeloerythroid colonies following replating. FIG. 20F depict a graphical representation of the quantification of myeloid and lymphoid cell differentiation (CD11b, CD33, CD3, and CD19 expression) in the CD45 positive population of bone marrow cells expanded in vitro in a cocktail of cytokines (open circles) or a cocktail of cytokines supplemented with Tat-Myc and Tat-Bcl-2 (black squares). FIG. 20G depicts a graphical representation of the quantification of myeloid and lymphoid cell differentiation (CD11b, CD33, CD3, and CD19 expression) in the CD45 positive population of spleen cells expanded in vitro in a cocktail of cytokines (open circles) or a cocktail of cytokines supplemented with Tat-Myc and Tat-Bcl-2 (black squares).

FIG. 21A depicts a graphical representation of the surface phenotype of human CD45+ cells showing an enrichment of the human CD34+ and CD38+ fraction. FIG. 21B depicts a graphical representation of the kinetics of cell expansion in vitro over 18 days in culture in the presence of Tat-Myc and Tat Bcl-2. FIG. 21C depicts a graphical representation showing that $5 \times 10^3$ human adult G-CSF HSCs, expanded in vitro with Tat-Myc and Tat-Bcl-2, gave rise to 4 morphologically distinct colony types in methylcellulose. FIG. 21D depicts a graphical representation of FACS analysis showing that human adult G-CSF HSCs expanded in vitro with Tat-Myc and Tat-Bcl-2 gave rise to human hematopoietic lineages in xenochimaeric NSG mice. Bone marrow was from NSG mice transplanted ptlt-HSCs expanded with a cytokine cocktail supplemented with Tat-Myc and Tat-Bcl-2 (first panel; G-CSF+TMTB) or with fresh un-manipulated cord blood cells (second panel; Fresh FCB). FIG. 21E depicts a graphical representation of FACS analysis of cells from bone marrow, spleen, and thymus. Bone marrow cells included human CD45 cells that were also human CD34+ and CD38+ (first panel), spleen cells included human CD45 cells that also stained for human CD3 (second panel), and thymus cells included human CD45 cells as well as CD3 (third panel). FIG. 21F and FIG. 21G depict a graphical representation of a cohort of xenochimaeric mice engrafted with $10^6$ G-CSF mobilized cells expanded in vitro in a cocktail of cytokines supplemented with Tat-Myc and Tat-Bcl-2 (black squares) were assessed for myeloid and lymphoid cell differentiation. The CD45 positive population of bone marrow cells (FIG. 21F) and spleen cells (FIG. 21G) were analyzed for CD11b, CD33, CD3, and CD19 expression.

FIG. 22A depicts a diagrammatic alignment of some representative Myc fusion protein constructs. FIG. 22B depicts a graphical representation of the percent live T cells 48 hours after treatment with representative Myc fusion protein constructs.

FIG. 23A depicts a graphical representation of the live gate from FACS analysis (forward X side scatter) for untreated cells (No treatment). FIG. 23B depicts a graphical representation of the live gate from FACS analysis (forward X side scatter) for Tat-Cre treated cells (Tat-Cre Control). FIG. 23C depicts a graphical representation of the live gate from FACS analysis (forward X side scatter) for Tat-Bcl2 treated cells (Tat-Bcl2). FIG. 23D depicts a graphical representation of the live gate from FACS analysis (forward X side scatter) for Tat-Myc treated cells (Tat-Myc).

FIG. 24 depicts the amino acid (SEQ ID NO: 1) and nucleic acid (SEQ ID NO: 2) sequences for some embodiments of the Tat-Myc polypeptide.

FIG. 25 depicts the amino acid (SEQ ID NO: 3) and nucleic acid (SEQ ID NO: 4) sequences for some embodiments of the Bcl-2 domain polypeptide.

FIG. 26A depicts that on days 6 and 11, cells were assessed for GPAxCD71 erythroid surface markers; and on day 11, the cells were also assessed for adult and fetal hemoglobin expression by flow cytometry. FIG. 26B depicts that on day 10, a sample from the differentiation culture was cytospun on to a coverslip for H&E staining. Images are 10 and 20× magnification.

DETAILED DESCRIPTION

Figure 2A:
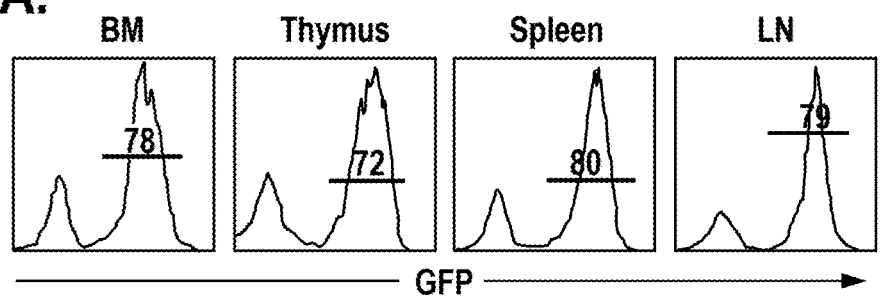

The present disclosure relates, among other things, to the in vitro production of red blood cells from hematopoietic stem cells (HSCs) by culturing HSCs with erythropoietin (EPO), optionally IL-3, and one or more recombinant protein, or biologically active fragment thereof, that promotes one or more of cell survival or proliferation. The differentiation process described herein does not require feeder cells (e.g., fibroblasts) and/or serum, and results in the production of mature anucleated red blood cells in about 7 to 14 days.

The methods of producing mature red blood cells described herein can be used with HSCs from any source, including but not limited to, bone marrow, peripheral blood, mobilized peripheral blood, cord blood, and placenta, as well as HSCs produced from embryonic stem cells and induced pluripotent stem cells. HSCs isolated from any source may be used to produce, without limitation, universal donor red blood cells, red blood cells of a rare blood type, red blood cells for personalized medicine (e.g., autologous transfusion, optionally with pay-loading or genetic engineering), and red blood cells engineered to include one or more proteins of interest.

Production of mature red blood cells from HSCs in vitro, using the methods of the present disclosure, can be enhanced by using conditionally immortalized HSCs. Enhancement may include, but is not limited to, one or more of increased numbers of mature red blood cells per starting HSC, improvement of one or more characteristics of the population of mature red blood cells, or decreased numbers of days to generate mature red blood cells. Conditionally immortalized HSCs may be produced by exposing HSCs to a first protein that promotes cell proliferation and/or cell survival and a second protein that inhibits apoptosis, using one or more of any transgenic approach and/or protein transduction approach known in the art.

The present disclosure also relates, among other things, to populations of mature red blood cells produced by one or more of the methods of the present disclosure. Populations of mature red blood cells may be characterized by one or more characteristics, including but not limited to, at least about 40%, at least about 50%, at least about 55%, at least about 60%, at least about 65%, at least about 70%, at least about 75%, at least about 80%, at least about 85%, at least about 90%, at least about 95%, at least about 99%, or 100% of the cells in the population being anucleated cells, expressing increased levels of GPA, increased levels of adult hemoglobin (second decade or higher by FACS), decreased levels of CD71 (e.g. GPA$^+$/CD71$^-$) expression, and decreased levels of fetal hemoglobin (first decade; 0-10 by FACS). Populations of mature red blood cells may also include one or more recombinant proteins of interest. These proteins of interest may be useful in prevention, treatment, or diagnosis of one or more diseases or disorders.

The present disclosure also relates, among other things, to pharmaceutical compositions including populations of mature red blood cells produced by one or more of the methods described herein. These pharmaceutical compositions may also include one or more exogenous proteins of interest useful in prevention, treatment, or diagnosis of one or more diseases or disorders.

The present disclosure also relates, among other things, to methods of treating, preventing, or diagnosing a disease or a disorder characterized by a deficiency of red blood cells by providing to a subject in need thereof a population of mature red blood cells of the present disclosure. The present disclosure also relates, among other things, to methods of treating or preventing a disease or a disorder by administering one or more population of red blood cells or pharmaceutical composition of the present disclosure that includes one or more proteins of interest to a subject, where the one or more proteins of interest are useful in treating or preventing the disease or disorder.

The present disclosure also relates, among other things, to methods for extending the life or half-life of red blood cells or population of red blood cells in vitro. Extension of the red blood cell half life in vitro expands the ability of blood banks to store and supply blood for patients (e.g., civilian and armed forces) in need. As described herein, maintenance of red blood cells in media containing one or more exogenous polypeptide that inhibits apoptosis increases the half-life of population of red blood cells in vitro.

Proteins of the Present Disclosure

Certain aspects of the present disclosure relate to the in vitro production of a population of red blood cells from hematopoietic stem cells (HSCs), maintenance of a population of red blood cells, by culturing the HSCs and/or red blood cells in the presence of media containing one or more recombinant proteins (such as exogenous proteins), or biologically active fragment thereof, that promote cell survival and/or proliferation and/or inhibit apoptosis. Further aspects of the present disclosure relate to HSCs and/or red blood cells of the present disclosure that contain, include, and/or express one or more proteins of interest.

As used herein, a protein that "promotes cells survival and/or proliferation" refers to a protein whose biological activity either directly or indirectly activates, induces, enhances, stimulates, allows, or increases cell survival and/ or cell proliferation. As used herein, a "biologically active fragment" of a protein of the present disclosure, such as a protein that promotes cell survival and/or proliferation or a protein that inhibits apoptosis, is a fragment of a full-length protein of the present disclosure that retains at least one activity and/or function of the full-length protein.

As used herein, the terms "polypeptide", "peptide" and "protein" are used interchangeably and refer to a polymer of amino acid residues. The terms apply to naturally occurring amino acid polymers as well as amino acid polymers in which one or more amino acid residues is a non-naturally occurring amino acid, e.g., an amino acid analogue. As used herein, the terms encompass amino acid chains of any length, including full length proteins, where the amino acid residues are linked by covalent peptide bonds Recombinant Proteins that Promote Cell Survival and/or Cell Proliferation Certain aspects of the present disclosure relate to the in vitro production of a population of red blood cells from hematopoietic stem cells (HSCs) by culturing the HSCs in the presence of media containing one or more recombinant protein, or biologically active fragment thereof, that promotes cell survival and/or proliferation.

Any suitable protein known in the art that promotes cell survival and/or proliferation may be used. In some embodiments, the one or more recombinant protein that promotes cell survival and/or proliferation is an onco-peptide (e.g., a polypeptide encoded by a proto-oncogene and/or oncogene). Suitable onco-peptides may be of any suitable class that induces cell immortality. Examples of suitable onco-peptides that that promotes cell survival and/or proliferation include, without limitation, growth factors and/or mitogens (e.g., PDGF-derived growth factors such as c-Sis); receptor tyrosine kinases, particularly constitutively active receptor tyrosine kinases (e.g., epidermal growth factor receptor (EGFR), thrombocyte-derived growth factor receptor (PDGFR), vascular endothelial growth factor receptor (VEGFR), and HER2/neu); cytoplasmic tyrosine kinases (e.g., Src-family, Syk-ZAP-70 family, and BTK family of tyrosine kinases); cytoplasmic serine/threonine kinases and their regulatory subunits (e.g., Raf kinases, cyclin-dependent kinases, members of the Akt family); regulatory GTPases (e.g., Ras protein); transcription factors (e.g., MYC and HIF-la); telomerase reverse transcriptases (e.g., TERT or hTERT); and/or factors that activate other onco-peptides (e.g., cyclins, including cyclins A, B, D, and/or E, such as cyclin D1 and D3).

In certain embodiments, a protein that promotes cell survival and/or proliferation is, by way of non-limiting example, MYC, mTOR, cyclin D1, cyclin D3, STAT3, STAT5, AML-ETO, AKT, ICN-1, hTERT, PDK-1, MLL-ENL, IL3 receptor .beta. chain, .beta.-catenin, Hedgehog family (Shh, Ihh, Dhh), Bmi-1, c-Jun, Wnt, Bcl-2, Bcl-6, Bcl-10, epidermal growth factor receptor (EGFR, ErbB-1, HER1), ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family; platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family; TRK receptor family; ephrin (EPH) receptor family; AXL receptor family; leukocyte tyrosine kinase (LTK) receptor family; TIE receptor family, angiopoietin 1,2; receptor tyrosine kinase-like orphan receptor (ROR) receptor family; discoidin domain receptor (DDR) family; RET receptor family; KLG receptor family; RYK receptor family; MuSK receptor family; Transforming growth factor .beta. (TGF-.beta.) receptors, TGF-.beta.; Cytokine receptors, Class I (hematopoietin family) and Class II (interferon/IL-10 family) receptors, tumor necrosis factor (TNF) receptor superfamily (TNFRSF), death receptor family; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), .beta.-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: .beta.-Dgalactose 2-a-Lfucosyltransferase (LDLR/FUT) fusion protein, HLA-A2. arginine to isoleucine exchange at residue 170 of the .alpha.-helix of the .alpha.2-domain in the HLA-A2 gene (HLA-A*201-R170I), HLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class I, NFYC, OGT, OS-9, pml-RARalpha fusion protein, PRDX5, PTPRK, K-ras (KRAS2), N-ras (NRAS), HRAS, RBAF600, SIRT2, SNRPD1, SYT-SSX1 or -SSX2 fusion protein, Triosephosphate Isomerase, BAGE, BAGE-1, BAGE-2, 3, 4, 5, GAGE-1, 2, 3, 4, 5, 6, 7, 8, GnT-V (aberrant N-acetyl glucosaminyl transferase V, MGAT5), HERV-K-MEL, KK-LC, KM-HN-1, LAGE, LAGE-1, CTL-recognized antigen on melanoma (CAMEL), MAGE-A 1 (MAGE-1), MAGE-A2, MAGE-A3, MAGE-A4, MAGE-A5, MAGE-A6, MAGE-A8, MAGE-A9, MAGE-A10, MAGE-A11, MAGE-A12, MAGE-3, MAGE-B1, MAGE-B2, MAGE-B5, MAGE-B6, MAGE-C1, MAGE-C2, mucin 1 (MUC1), MART-1/Melan-A (MLANA), gp100, gp100/Pmell7 (SILV), tyrosinase (TYR), TRP-1, HAGE, NA-88, NY-ESO-1, NY-ESO-1/LAGE-2, SAGE, Sp17, SSX-1,2,3,4, TRP2-INT2, carcino-embryonic antigen (CEA), Kallikrein 4, mammaglobin-A, OA1, prostate specific antigen (PSA), TRP-1/gp75, TRP-2, adipophilin, interferon inducible protein absent in melanoma 2 (AIM-2), BING-4, CPSF, cyclin D1, epithelial cell adhesion molecule (Ep-CAM), EphA3, fibroblast growth factor-5 (FGF-5), glycoprotein 250 (gp250), EGFR (ERBB1), HER-2/neu (ERBB2), interleukin 13 receptor .alpha.2 chain (ILI 3Ralpha2), IL-6 receptor, intestinal carboxyl esterase (iCE), alpha-feto protein (AFP), M-CSF, mdm-2, MUC1, p53 (TP53), PBF, PRAME, PSMA, RAGE-1, RNF43, RU2AS, SOX10, STEAP1, survivin (BIRC5), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA661, LDHC, MORC, SGY-1, SPO11, TPX1, NY-SAR-35, FTHL17, NXF2, TDRD1, TEX15, FATE, TPTE, immunoglobulin idiotypes, Bence-Jones protein, estrogen receptors (ER), androgen receptors (AR), CD40, CD30, CD20, CD19, CD33, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), β-human chorionic gonadotropin, squamous cell carcinoma antigen, neuron-specific enolase, heat shock protein gp96, GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), simian virus 40 (SV40) derived transforming genes and proteins, Human papilloma virus (HPV) proteins (HPV-E6, HPV-E7, major or minor capsid antigens, others), Epstein-Ban virus (EBV) proteins (EBV latent membrane proteins—LMP1, LMP2; others), Hepatitis B or C virus proteins, Human immunodeficiency virus (HIV) proteins, functional homologues, functional analogues, or biologically active fragments thereof.

In some embodiments, a protein that promotes cell survival and/or proliferation is a protein that inhibits an endogenous antagonist (e.g., protein and/or gene) of cell survival and/or proliferation. For example, the protein may be an inhibitor of a transcriptional repressor that suppresses expression of a gene that promotes cell survival and/or proliferation. In certain embodiments, the transcriptional repressor may antagonize an onco-peptide of the present disclosure that regulates expression of a gene that promotes cell survival and/or proliferation, such as MYC. For example, in some embodiments, the protein inhibits at least one member of the MAD family of transcriptional repressors, e.g., MAD-1; or cyclin-dependent kinase inhibitors (e.g., p16, p19, p21, or p27).

In other embodiments, cell survival and/or proliferation is promoted by an agent that inhibits an endogenous antagonist (e.g., protein and/or gene) of cell survival and/or proliferation. For example, the agent may be a genetic inhibitor or a small molecule inhibitor (such as, an antagonist). In some embodiments, the agent may include an inhibitor of a transcriptional repressor that suppresses expression of a gene that promotes cell survival and/or proliferation. In certain embodiments, the transcriptional repressor antagonizes an onco-peptide of the present disclosure that regulates expression of a gene that promotes cell survival and/or proliferation, e.g., MYC. For example, in some embodiments, the agent that inhibits at least one member of the MAD family of transcriptional repressors, e.g., MAD-1. In certain other embodiments, the agent is an inhibitor of cyclin-dependent kinase inhibitors (e.g., p16, p19, p21, or p27).

Any agent that inhibits an endogenous antagonist of a protein that promotes cell survival and/or proliferation relative to a wild-type cell of the same type is suitable for use in the methods of the present disclosure. An agent that is an inhibitor of an endogenous antagonist of a protein that promotes cell survival and/or proliferation reduces, inhibits, or decreases the activity or level of the antagonist at any stage or by any mechanism. For example, in some instances, such an agent interferes with expression of an agent that antagonizes the activity of a protein that promotes cell survival and/or proliferation, e.g., at the translational level or at the transcriptional level. In certain embodiments, an agent that interferes with expression of an agent that antagonizes the activity of a protein that promotes cell survival and/or proliferation is an agent capable of RNA interference (an RNAi molecule). In some embodiments, an RNAi molecule is generated by cleavage of or binding to mRNA encoding a polypeptide. An RNAi molecule is generated by any suitable means, including by small interfering RNA (siRNA), microRNA (miRNA), double stranded RNA (dsRNA), or small hairpin RNA (shRNA). In certain embodiments, an agent that interferes with expression of an agent that antagonizes the activity of a protein that promotes cell survival and/or proliferation is a small molecule, e.g., a small organic molecule.

In other embodiments, the agent inhibits the activity or level of a protein that anatgonizes cell survival and/or proliferation. In some embodiments, the agent acts directly on the protein that anatgonizes cell survival and/or proliferation. For example, the agent may bind to and inhibit the activity of the protein that anatgonizes cell survival and/or proliferation. Accordingly, in certain embodiments the agent is an antibody or small molecule that binds to and disrupts the natural function of a protein that anatgonizes cell survival and/or proliferation.

In other embodiments, the protein that promotes cell survival and/or proliferation further includes a protein transduction domain (PTD).

In some embodiments, protein that promotes cell survival and/or proliferation is provided as a bolus. As used herein, a "bolus" refers to an amount or concentration of a protein that is given to a subject the increase the concentration of the protein in the blood of the subject to an effective level. A bolus may be administered by any suitable method known in the art. In some embodiments, the bolus is provided about every 12 hours, about every 24 hours, about every 36 hours, about every 48 hours, about every 60 hours, or about every 72 hours.

In some embodiments, the one or more recombinant protein that promotes cell survival and/or cell proliferation is a MYC polypeptide, a homologue thereof or a biologically active fragment thereof. In some embodiments, the one or more recombinant protein that promotes cell survival and/or cell proliferation is an ICN-1 polypeptide, a homologue thereof or a biologically active fragment thereof. In certain embodiments, the one or more recombinant protein that promotes cell survival and/or cell proliferation is a PTD-MYC fusion protein. In certain embodiments, the one or more recombinant protein that promotes cell survival and/or cell proliferation is a PTD-ICN-1 fusion protein.

MYC

A MYC polypeptide of the present disclosure includes, without limitation, any polypeptide, or fragment thereof, having the activity of a MYC protein.

As used herein, "MYC" and "MYC protein" are used interchangeably and refer to a protein that is a member of the MYC family of bHLH (basic helix-loop-helix) transcription factors. MYC proteins of the present disclosure are transcription factors that regulate expression of MYC responsive genes, and as such enter the nucleus of a cell to function. MYC activity can activate expression of certain MYC responsive genes, while repressing expression of other MYC responsive genes. MYC activity can regulate various cellular functions including, without limitation, cell proliferation, cell growth, cell survival, and apoptosis.

As described herein, transient expression of MYC, provided from an exogenous or endogenous source, during red blood cell production from HSCs can increase the yield of mature red blood cells, can decrease the length of time for the production of mature red blood cells, can increase the percent of mature red blood cells in a population, and/or can increase the rate of production of mature red blood cells as compared to production in the absence of MYC. Without wishing to be bound by theory, it is believed that it is the transient expression of low levels of MYC that promote HSC differentiation to mature red blood cells, as it has been shown that prolonged expression of MYC in embryonic stem cells promotes self-renewal by inhibiting differentiation (e.g., Cartwright et al., *Development.* 2005 March; 132(5):885-96). Moreover, the ability of transient expression of MYC at low levels to enhance the production of mature red blood cells from HSCs is surprising given the recent finding that ectopic high levels of MYC expression inhibited differentiation of erythroid progenitor cells to anucleated red blood cells (Jayapal et al., *J Biol Chem.* 2010 Dec. 17; 285(51):40252-65).

PTD-MYC fusion proteins of the present disclosure allow for an increase in MYC activity in HSCs by the exogenous addition of MYC, without the need for overexpressing endogenous MYC in the HSCs or recombinantly expressing MYC via genetic manipulation of the HSCs.

MYC polypeptides of the present disclosure include, without limitation, full length MYC proteins, fragments that retain the activity of a full-length MYC protein, homologues thereof, and analogues thereof. MYC polypeptides of the present disclosure may be produced by any suitable method known in the art. For example, a MYC polypeptide may be purified from a native source, may be recombinantly expressed, or may be chemically synthesized.

MYC Proteins

Examples of full length MYC proteins suitable for use in any of the methods of the present disclosure include, without limitation, c-Myc, N-Myc, L-Myc, v-MYC, and S-Myc.

In certain preferred embodiments, the MYC polypeptide is a full-length c-Myc polypeptide. The c-Myc polypeptide may have one or more of the following features: the polypeptide may be a polymer of 439 amino acids, the polypeptide may have a molecular weight of 48.804 kDa, the polypeptide may contain a basic Helix-Loop-Helix Leucine Zip-per (bHLH/LZ) domain, or the polypeptide may bind to a sequence containing CACGTG (i.e., an E-box sequence). Preferably, the c-Myc polypeptide is the human c-Myc polypeptide having NCBI Accession Number NP_002458.2. Moreover, a c-Myc polypeptide of the present disclosure may be a c-Myc polypeptide that has not undergone any post-translational modifications. Alternatively, a c-Myc polypeptide of the present disclosure may be a c-Myc polypeptide that has undergone post-translational modifications.

Biologically Active MYC Fragments

In other embodiments, a MYC polypeptide of the present disclosure is a biologically active fragment of a full-length MYC protein that retains at least one activity of a full-length MYC protein. The MYC polypeptide may be a fragment of c-Myc, N-Myc, L-Myc, or S-Myc.

A MYC fragment of the present disclosure may contain at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 150, at least 200, at least 250, at least 300, at least 350, at least 400, or more consecutive amino acid residues of the amino acid sequence of a MYC protein.

MYC Homologues and Analogues

In other embodiments, a MYC polypeptide of the present disclosure is a homologue or analogue of a MYC protein, or a fragment thereof, that retains at least one activity of a full-length MYC protein.

For example, a MYC polypeptide of the present disclosure may include an amino acid sequence that is at least 40% to 100% identical, e.g., at least 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to a MYC protein or fragments thereof. In certain embodiments, the MYC polypeptide is a homologue or an analogue of c-Myc, N-Myc, L-Myc, S-Myc, or fragments thereof.

MYC polypeptides of the present disclosure also include functional homologues or analogues of the human c-Myc polypeptide having NCBI Accession Number NP_002458.2, or a fragment thereof. In certain embodiments, the c-Myc homologue or analogue contains an amino acid sequence that is at least 40% to 100% identical, e.g., at least 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the c-Myc polypeptide sequence of NCBI Accession Number NP_002458.2 or fragment thereof.

In other embodiments, the c-Myc homologue or analogue contains a polypeptide sequence of at least 10 amino acids, at least 20 amino acids, at least 30 amino acids, at least 40 amino acids, at least 50 amino acids, at least 60 amino acids, at least 70 amino acids, at least 80 amino acids, at least 90 amino acids, at least 100 amino acids, at least 150 amino acids, at least 200 amino acids, at least 250 amino acids, at least 300 amino acids, at least 350 amino acids, at least 400 amino acids, or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the c-Myc polypeptide sequence of NCBI Accession Number NP_002458.2 or fragment thereof.

As used herein, a "homologue" refers to a protein or polypeptide having amino acid sequence similarity between a reference sequence and at least a fragment of a second sequence. Homologues may be identified by any method known in the art, preferably, by using the BLAST tool to compare a reference sequence to a single second sequence or fragment of a sequence or to a database of sequences. As described below, BLAST will compare sequences based upon percent identity and similarity.

The terms "identical" or percent "identity," in the context of two or more sequences (e.g., amino acid sequences), refer to two or more sequences or subsequences that are the same. Two sequences are substantially identical if two sequences have a specified percentage of amino acid residues or nucleotides that are the same (i.e., 29% identity, optionally 30%, 40%, 45%, 50%, 55%, 60%, 65%, 70%, 75%, 80%, 85%, 90%, 95%, 99% or 100% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 10 amino acids in length, or more preferably over a region that is 20, 50, 200, or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastp, the default parameters are Gap opening penalty=11 and Gap extension penalty=1. For blastn, the default parameters are Gap opening penalty=5 and Gap extension penalty=2.

As used herein, a "comparison window" includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1981), by the homology alignment algorithm of Needleman and Wunsch (1970) J Mol Biol 48(3):443-453, by the search for similarity method of Pearson and Lipman (1988) Proc Natl Acad Sci USA 85(8): 2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection [see, e.g., Brent et al., (2003) Current Protocols in Molecular Biology, John Wiley & Sons, Inc. (Ringbou Ed)].

Two examples of algorithms that are suitable for determining percent sequence identity and sequence similarity are the BLAST and BLAST 2.0 algorithms, which are described in Altschul et al. (1997) Nucleic Acids Res 25(17): 3389-3402 and Altschul et al. (1990) J. Mol Biol 215(3)-403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a wordlength of 3, and expectation (E) of 10, and the BLOSUM62 scoring matrix [see Henikoff and Henikoff, (1992) Proc Natl Acad Sci USA 89(22):10915-10919] alignments (B) of 50, expectation (E) of 10, M=5, N=-4, and a comparison of both strands. For nucleotide sequences, the BLASTN program uses as defaults a wordlength (W) of 11, an expectation (E) or 10, M=5, N=-4, and a comparison of both strands.

The BLAST algorithm also performs a statistical analysis of the similarity between two sequences (see, e.g., Karlin and Altschul, (1993) *Proc Natl Acad Sci USA* 90(12):5873-5877). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two polypeptides are substantially identical is that the first polypeptide is immunologically cross-reactive with antibodies raised against the second polypeptide. Thus, a polypeptide is typically substantially identical to a second polypeptide, for example, where the two peptides differ only by conservative substitutions.

As disclosed herein, suitable MYC polypeptides also include conservatively modified variants of MYC polypeptides of the present disclosure. "Conservatively modified variants" as used herein include individual substitutions, deletions, or additions to an encoded amino acid sequence which result in the substitution of an amino acid with a chemically similar amino acid. Conservative substitution tables providing functionally similar amino acids are well known in the art. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Proteins Downstream of MYC

In other embodiments, a suitable protein of the present disclosure that promotes cell survival and/or proliferation is a protein that promotes cell survival and/or proliferation and that is downstream of MYC in a MYC pathway. Any protein downstream known in the art is suitable for use with the methods of the present disclosure. Examples of suitable proteins that promote cell survival and/or proliferation and that are downstream of MYC include, without limitation, AKT and AKT-related proteins, such as PDK-1, mTORC2, PI3K-delta. The protein downstream of MYC that promotes cell survival and/or proliferation may further be a PTD-fusion protein. Accordingly, in certain embodiments, the protein downstream of MYC that promotes cell survival and/or proliferation is an AKT-PTD fusion protein, a PTD-PDK-1 fusion protein, a PTD-mTORC2 fusion protein, or a PTD-PI3K-delta fusion protein.

In other embodiments, cell survival and/or proliferation is promoted in HSCs of the present disclosure by inhibiting a protein that antagonize cell survival and/or proliferation and that is downstream of MYC in a MYC pathway. Examples of proteins that antagonize cell survival and/or proliferation and that are downstream of MYC include, without limitation, of pTEN, PP2A, PHLPP, CTMP. Accordingly, in certain embodiments, cell survival and/or proliferation is promoted in HSCs of the present disclosure by inhibiting pTEN, PP2A, PHLPP, and/or CTMP. Any method known in the art for inhibiting protein and/or gene expression, activity, and/or function may be used, including without limitation the methods disclosed herein. Non-limiting examples include genetic inhibitors, small molecule inhibitors, RNA interference, and antibodies.

Activities of Full-Length MYC Proteins

In other embodiments, a MYC protein or PTD-MYC fusion protein of the present disclosure contains a full-length MYC polypeptide having at least one MYC activity, a fragment of a MYC protein that retains at least one activity of a full-length MYC protein, a homologue of a MYC protein that retains at least one activity of a full-length MYC protein, or an analogue of a MYC protein that retains at least one activity of a full-length MYC protein.

Full-length MYC proteins of the present disclosure have numerous activities. Examples of such activities include, without limitation, transcription factor activity, protein binding activity, nucleic acid binding activity, cell proliferation regulation activity, cell growth regulation activity, apoptosis regulation activity, morphogenesis regulation activity, development regulation activity, and enhanced hematopoietic compartment reconstitution activity.

In some embodiments, a MYC protein or PTD-MYC fusion protein of the present disclosure has a MYC activity that together with EPO and, optionally, IL-3 produce mature red blood cells from HSCs. In other embodiments, a MYC protein or PTD-MYC fusion protein of the present disclosure has a MYC activity that conditionally immortalizes HSCs. Advantageously, administering MYC in the form of a PTD-MYC fusion protein results in transient MYC activity in HSCs. In some embodiments, the level of transient MYC activity is sufficient to enhance HSC differentiation to mature red blood cells. Additionally, a PTD-MYC fusion protein of the present disclosure can increase the intracellular levels of MYC in HSCs, which results in an expansion of the HSCs. This transient MYC activity avoids the potentially negative effects of prolonged MYC activity in the cells, such as uncontrolled cell growth and oncogenic transformation. Moreover, the use of a PTD-MYC fusion protein allows for the induction of MYC activity in the HSCs without genetically modifying the cells.

Exogenous Proteins that Inhibit Apoptosis

Certain aspects of the present disclosure relate to the in vitro maintenance of red blood cells or a population of red blood cells of the present disclosure by culturing the red blood cells or population of red blood cells in the presence of media including one or more recombinant protein (such as an exogenous protein) that inhibits apoptosis. Other aspects of the present disclosure also relate to further culturing HSCs of the present disclosure in the presence of media including one or more exogenous protein that inhibits apoptosis. As used herein a protein or polypeptide that "inhibits apoptosis" refers to a protein or polypeptide whose function either directly or indirectly reduces, prevents, or decreases a process associated with apoptosis (i.e., programmed cell death).

Any suitable protein known in the art that inhibits apoptosis may be used. In some embodiments, the protein that inhibits apoptosis is a protein that contains one or more Bcl-2 homology domains. Examples of proteins that contain one or more Bcl-2 homology domains include, without limitation, Bcl-2, Bcl-x, Bcl-XL, Mcl1, CED-9, Al, Bfl-1, and Bcl-w.

In some embodiments, a protein that inhibits apoptosis is a protein that inhibits any endogenous protein and/or gene known in the art that promotes apoptosis. Examples of proteins that promote apoptosis include, without limitation, Bcl-2 family members, caspases, and proteins of the TNF family of receptors.

In other embodiments, inhibition of apoptosis is achieved by an agent that inhibits an endogenous protein and/or gene known in the art that promotes apoptosis. For example, the agent may be a genetic inhibitor or a small molecule inhibitor (such as, an antagonist). Any genetic inhibitor or small molecule inhibitor known in the art for inhibiting apoptosis may be used. In some embodiments, the agent interferes with expression of a protein that promotes apoptosis. For example, the agent may interfere with expression a protein that promotes apoptosis at the translational level or at the transcriptional level. In some embodiments, RNA interference is used to interfere with the expression of a protein that promotes apoptosis. In other embodiments, the agent inhibits the activity or level of a protein that promote apoptosis. In some embodiments, the agent acts directly on the protein that promotes apoptosis. For example, the agent may bind to and inhibit the activity of a protein that promotes apoptosis. Accordingly, in certain embodiments the agent is an antibody or small molecule that binds to and disrupts the natural function of a protein that inhibits apoptosis.

In some embodiments, the one or more exogenous protein that inhibits apoptosis is one or more protein that contains one or more Bcl-2 homology domains. In some embodiments, the one or more exogenous protein that inhibits apoptosis further includes a protein transduction domain (PTD). In some embodiments, the one or more exogenous protein that inhibits apoptosis is a PTD-Bcl-2 fusion protein.

Bcl-2

A Bcl-2 polypeptide of the present disclosure includes, without limitation, any polypeptide, or fragment thereof, having the activity of a Bcl-2 protein.

As used herein, "Bcl-2," "Bcl-2 polypeptide," and "Bcl-2 protein" are used interchangeably and refer to a protein that is a member of the Bcl-2 protein family that has one or more and/or all Bcl-2 homology (BH) domains, such as but not limited to, BH1, BH2, BH3, and BH4. Members of the bcl-2 protein family typically form heterodimer or homodimers, and function as regulators of apoptosis. In certain preferred embodiments, Bcl-2 polypeptides of the present disclosure have anti-apoptotic activity and/or an activity useful in the process of conditional immortalization of HSCs.

As described herein, the addition of exogenous Bcl-2 to a population of red blood cells can increase the length of time the red blood cells remain viable in vitro, can increase the percentage of red blood cells that remain viable over time, and/or can delay and/or reduce the loss of one or more red blood cell functional characteristics over time in vitro, as compared with a corresponding population of red blood cells that is maintained in the absence of Bcl-2. In some embodiments, the addition of exogenous Bcl-2 is to red blood cell storage media. The one or more functional characteristics may include, but are not limited to, one or more of oxygen carrying capacity, amount of hemoglobin, type of hemoglobin expressed (adult vs. fetal), level of transferrin receptor expressed on the surface, or one or more mature red blood cell markers.

In another embodiment, transient up-regulation of Bcl-2, provided from an exogenous or endogenous source during the final stages of red blood cell production from HSCs, may increase the length of time the red blood cells remain viable in vitro, may increase the percentage of red blood cells that remain viable over time, and/or may delay and/or reduce the loss of one or more red blood cell functional characteristics over time in vitro, as compared with maintenance in the absence of Bcl-2. In some embodiments, the transient up-regulation of Bcl-2, provided from an exogenous or endogenous source during the final stages of red blood cell production from HSCs, is designed to enhance RBC maintenance in red blood cell storage media.

In another embodiment, the present disclosure is drawn to red blood cell storage media containing Bcl-2.

PTD-Bcl-2 fusion proteins of the present disclosure allow for an increase in Bcl-2 activity in HSCs by the exogenous addition of Bcl-2, without the need for overexpressing endogenous Bcl-2 in the HSCs or recombinantly expressing Bcl-2 via genetic manipulation of the HSCs.

Bcl-2 polypeptides of the present disclosure include, without limitation, full length Bcl-2 proteins, fragments that retain the activity of a full-length Bcl-2 protein, homologues thereof, and analogues thereof. In some embodiments, Bcl-2 fragments that retain the activity of a full-length Bcl-2 protein include a truncated form of Bcl-2 that has been deleted for the unstructured loop domain (Anderson, M., et al. (1999). Refolding, purification and characterization of a loop deletion mutant of human Bcl-2 from bacterial inclusion bodies. Prot Expr. Purif. 15, 162-70). Bcl-2 polypeptides of the present disclosure may be produced by any suitable method known in the art. For example, a Bcl-2 polypeptide may be purified from a native source, may be recombinantly expressed, or may be chemically synthesized.

Bcl-2 Proteins

Examples of full length Bcl-2 proteins suitable for use in any of the methods of the present disclosure include, without limitation, Bcl-2, Bcl-x, Bcl-XL, Mcl-1, CED-9, Bcl-2 related protein Al, Bfl-1, and Bcl-w.

In certain preferred embodiments, the Bcl-2 polypeptide is a full-length human Bcl-2 polypeptide that has been deleted for the unstructured loop domain. The human Bcl-2 polypeptide may have one or more of the following features: the polypeptide may be a polymer of 239 amino acids, the polypeptide may have a molecular weight of approximately 26.3 kDa, or the polypeptide may contain at least one Bcl-2 homology (BH) domain, such as BH1, BH2, BH3, and BH4. Preferably, the human Bcl-2 polypeptide is the Bcl-2 polypeptide having NCBI Accession Number NP_000624.2. Moreover, a Bcl-2 polypeptide of the present disclosure may be a Bcl-2 polypeptide that has not undergone any post-translational modifications. Alternatively, a Bcl-2 polypeptide of the present disclosure may be a Bcl-2 polypeptide that has undergone post-translational modifications.

Biologically Active Bcl-2 Fragments

In other embodiments, a Bcl-2 polypeptide of the present disclosure is a biologically active fragment of a full-length Bcl-2 protein that retains at least one activity of a full-length Bcl-2 protein. The Bcl-2 polypeptide may be a fragment of Bcl-2, Bcl-x, Bcl-XL, Mcl-1, CED-9, Bcl-2 related protein Al, Bfl-1, or Bcl-w.

A Bcl-2 fragment of the present disclosure may contain at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, or more consecutive amino acid residues of the amino acid sequence of a Bcl-2 protein.

Bcl-2 Homologues and Analogues

In other embodiments, a Bcl-2 polypeptide of the present disclosure is a homologue or analogue of a Bcl-2 protein or fragment thereof. For example, a Bcl-2 polypeptide of the present disclosure may include an amino acid sequence that is at least 40% to 100% identical, e.g., at least 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to a Bcl-2 protein or fragments thereof. In certain embodiments, the Bcl-2 polypeptide is a homologue or analogue of Bcl-2, Bcl-x, Bcl-XL, Mcl-1, CED-9, Bcl-2 related protein Al, Bfl-1, Bcl-w, or fragments thereof.

Bcl-2 polypeptides of the present disclosure also include functional homologues or analogues of the human Bcl-2 polypeptide having NCBI Accession Number NP_00624.2, or a fragment thereof. In certain embodiments, the Bcl-2 homologue or analogue contains an amino acid sequence that is at least 40% to 100% identical, e.g., at least 40%, 45%, 50%, 55%, 60%, 65%, 70%, 75%, 80%, 85%, 86%, 87%, 88%, 90%, 91%, 92%, 94%, 95%, 96%, 97%, 98%, or any other percent from about 40% to about 100% identical to the Bcl-2 polypeptide sequence of NCBI Accession Number NP_00624.2 or fragment thereof.

In other embodiments, the Bcl-2 homologue or analogue contains a polypeptide sequence of at least 10 amino acids, at least 20 amino acids, at least 30 amino acids, at least 40 amino acids, at least 50 amino acids, at least 60 amino acids, at least 70 amino acids, at least 80 amino acids, at least 90 amino acids, at least 100 amino acids, at least 110 amino acids, at least 120 amino acids, at least 130 amino acids, at least 140 amino acids, at least 150 amino acids, at least 160 amino acids, at least 170 amino acids, at least 180 amino acids, at least 190 amino acids, at least 200 amino acids, at least 210 amino acids, at least 220 amino acids, at least 230 amino acids, or more in length that is at least 50% to 100% identical, e.g., at least 50%, 55%, 60%, 65%, 70%, 75%, 80%, 85%, 86%, 87%, 88%, 90%, 91%, 92%, 94%, 95%, 96%, 97%, 98%, or any other percent from about 50% to about 100% identical to the Bcl-2 polypeptide sequence of NCBI Accession Number NP_00624.2 or fragment thereof.

As disclosed herein, suitable Bcl-2 polypeptides also include conservatively modified variants of Bcl-2 polypeptides of the present disclosure.

Bcl-2 Homologues that Promote Apoptosis

In some embodiments, apoptosis is inhibited by inhibiting a protein that contains one or more BH domains and that promotes apoptosis. Examples of BH domain-containing proteins that promote apoptosis include, without limitation, Bcl-Xs, BIM, PUMA, NOXA, NOXA-2, DIVA, BAK, BAX, BIK, BAD, BID, and EGL-1. Accordingly, in certain embodiments, apoptosis is inhibited by inhibiting Bcl-Xs, BIM, PUMA, NOXA, NOXA-2, DIVA, BAK, BAX, BIK, BAD, BID, and/or EGL-1. Any method known in the art for inhibiting protein and/or gene expression, activity, and/or function may be used, including without limitation the methods disclosed herein. Non-limiting examples include genetic inhibitors, small molecule inhibitors, RNA interference, and antibodies.

Activities of Full-Length Bcl-2 Proteins

In other embodiments, a Bcl-2 protein or a PTD-Bcl-2 fusion protein of the present disclosure contains a full-length Bcl-2 polypeptide having at least one Bcl-2 activity, a fragment of a Bcl-2 protein that retains at least one activity of a full-length Bcl-2 protein, a homologue of a Bcl-2 protein that retains at least one activity of a full-length Bcl-2 protein, or an analogue of a Bcl-2 protein that retains at least one activity of a full-length Bcl-2 protein.

Full-length Bcl-2 proteins of the present disclosure have numerous activities. Examples of such activities include, without limitation, apoptosis regulation activity, cell survival regulation activity, protein binding activity, mitochondrial membrane permeability regulation activity, caspase regulation activity, voltage-dependent anion channel regulation activity, G2 checkpoint regulation activity, outer mitochondrial membrane channel (VDAC) regulation activity, mitochondrial membrane potential regulation activity, protein channel activity, and cytochrome C regulation activity.

In some embodiments, a Bcl-2 protein or a PTD-Bcl-2 fusion protein of the present disclosure has a Bcl-2 activity that aids in the production of mature red blood cells from HSCs, in the maintenance of red blood cells or a population of red blood cells, and/or in the immortalization of HSCs. Advantageously, administering Bcl-2 in the form of a PTD-Bcl-2 fusion protein results in transient Bcl-2 activity in HSCs. This transient Bcl-2 activity avoids any potentially negative effects of prolonged Bcl-2 activity in the cells. Moreover, the use of a PTD-Bcl-2 fusion protein allows for the induction of Bcl-2 activity in the red blood cells and/or HSCs without genetically modifying the cells, and allows for maintenance of anucleated mature red blood cells in vitro.

Proteins of Interest

Certain aspects of the present disclosure relate to the in vitro production of a population of red blood cells from HSCs; the in vitro maintenance of red blood cells or a population of red blood cells, and/or the administration of red blood cells to a subject in nned thereos, where the red blood cells or population of red blood cells includes one or more proteins of interest. Aspects of the present disclosure also include population of red blood cells including one or more proteins of interest, and pharmaceutical compositions including such population of red blood cells. In some embodiments, the one or more protein of interest further includes a protein transduction domain (PTD). In some embodiments, the protein of interest is a PTD-protein of interest fusion protein.

The proteins of interest may include, but are not limited to, one or more growth factors, hormones, or other polypeptides useful for prevention, diagnosis and/or treatment of one or more diseases or disorders. Use of red blood cells or populations of red blood cells of the present disclosure containing one or more proteins of interest is advantageous for a variety of reasons, including but not limited to, one or more of the transient nature of the red blood cells and encoded proteins they will deliver; the lack of genetic material in the fully mature, anucleated cells; and the use of a "self" vessel that is tolerated by the lymphoid compartment from ontogeny.

In some embodiments, proteins of interest are associated with red blood cell membranes in vitro prior to administration, for example by transfusion, into a subject. In some embodiments, such association is mediated by a covalent or non-covalent bond. Non-limiting examples of such associations may include sulfhydryl bonds and antibody-epitope binding, among others.

In some embodiments, proteins of interest are configured for administration through incorporation into the outer surface membrane of in vitro-produced red blood cells. In some embodiments, the HSC used in the process of producing the red blood cell is engineered to express and/or over-express one or more protein of interest. Optionally, the protein of interest may be engineered with one or more of an export sequence, a plasma membrane retention element, or a protease cleavage site.

In some embodiments, proteins of interest are configured for administration through incorporation into a red blood cell or HSC of the present disclosure using a fusion protein including a protein transduction domain. Methods of making and using such PTD-protein of interest fusion proteins are known in the art and described herein, and include methods similar to those used for Myc and Bcl-2, among others.

In some embodiments, the HSCs are conditionally immortalized HSCs. In some embodiments, the conditionally immortalized HSCs are protein transduced HSCs, are conditionally immortalized through the use of inducible transgenes, and/or are immortalized by the transient overexpression of one or more endogenous and/or exogenous genes that promote immortalization. Genes that promote immortalization are well known in the art (e.g., U.S. Patent Application Publication No. US 2007/0116691).

In some embodiments, the conditionally immortalized HSCs are universal donor HSCs. In some embodiments, the conditionally immortalized HSCs are from a rare blood type, or from an individual in need of treatment. In some embodiments, the individual may suffer from a rare disease, have a rare blood phenotype, or a blood phenotype for which it is difficult to find an allotype match.

Construction of Vectors Encoding Proteins of Interest

In some aspects of the present disclosure, the proteins of interest are incorporated into HSCs of the present disclosure using any suitable method of transgenically modifying HSCs known in the art (e.g., Riviere et al., Blood. 2012 Feb. 2; 119(5):1107-16), including without limitaiton, those disclosed herein. For example, one or more proteins of interest can be incorporated into HSCs utilizing methods similar to those described herein to generate transgenic conditionally immortalized HSCs (e.g., see "HSC cell line" section and Examples below).

In some embodiments, the proteins of interest will be encoded for by a cDNA in the context of a vector, such as a viral vector. Methods for incorporating cDNA encoding proteins of interest into a viral vector are known in the art and include, without limitation, those disclosed herein.

In some embodiments, a population of red blood cells of the present disclosure includes one or more proteins of interest designed to be released from the surface of the red blood cells following transfusion in vivo. In some embodiments, the vector will also include one or more of an export sequence, a plasma membrane retention element, or a protease cleavage site linked and/or fused with the protein of interest.

Protein export sequences are well known in the art. In some embodiments, the protein of interest will further include an endoplasmic reticulum signal sequence, optionally at the N-terminal. In some embodiments, the protein of interest is Bcl-2.

Plasma membrane retention elements are well known in the art, and include, without limitation, one or more of the cytoplasmic region of a GPI-linked protein, or optionally one or more red blood cell transmembrane protein such as CD40, CD25, igG, FcRN, CD8 and/or CD16.

Protease cleavage sites are well known in the art. In some embodiments, a plasma retention element may include transmembrane portions of IgG linked to the protein of interest, where the IgG transmembrane and/or linker portion includes one or more IgG cleavage sites, optionally recognized by mammalian proteases. The protease cleavage site may be selected for ease of release of the protein of interest in vivo, optionally through selection of a substrate of normal (endogenous) serum proteases.

In some embodiments, the population of red blood cells includes one or more proteins of interest designed to be maintained on the surface of the red blood cell following transfusion in vivo. Accordingly, in some embodiments the vector includes one or more of an export sequence and a plasma membrane retention element. In some embodiments, the cytoplasmic and/or transmembrane portions of the fusion protein may be derived from a source such as, but not limited to, cDNA encoding one or more red blood cell transmembrane protein such as but not limited to CD40, CD25, igG, FcRN, CD8 and/or CD16, among others.

In some embodiments, the population of red blood cells includes one or more proteins of interest designed to be maintained on the surface of the red blood cell and configured to bind proteins or other compounds during payloading prior to transfusion in vivo. This allows more flexibility as far as payload options for the red blood cell, including avoiding potential toxicity issues, and/or difficulties with genetic engineering of HSCs used for producing the red blood cells. In some embodiments, the vector will also include one or more of an export sequence, a plasma membrane retention element, or a binding site or linkage moiety. In some embodiments, binding sites or linkage moieties may include not are not limited to, sulfhydryl moieties, one portion of a biotin-avidin linkage, as well as reversible and non-reversible crosslinking agents (e.g., DSS, DSST, PEG, etc.).

In some embodiments, it is explicitly contemplated to include one or more proteins of interest in red blood cell or populations of red blood cells of the present disclosure. For example, HSCs may be modified to incorporate targeting molecules, decoy receptors, and/or protein payloads, among others.

Exemplary Proteins of Interest

Although not intending to be limiting, a variety of examples of proteins of interest and their use are provided. In some embodiments, the red blood cell-associated proteins of interest allow for the transient delivery of hematopoietic growth factors and differentiation factors including, but not limited to, EPO, TPO, and GM-CSF; or factors that may be utilized to mobilize HSCs, such as G-CSF. In some embodiments, proteins of interest with targets in the hematopoietic compartment may be incorporated into red blood cells using transgenic methods that result in the maintenance of the protein of interest on the surface of the red blood cell, thereby limiting uptake of the protein of interest into other tissue compartments, and allowing more rapid clearance from the system.

In some embodiments, the red blood cell-associated proteins of interest allow for the delivery of decoy receptors that affect inflammatory pathways in patients with acute inflammatory conditions, including, but not limited to, IL-R-Fc, IL6R-Fc, TNFaR-FC, IFNaR-Fc, and BAFFR-Fc. The red blood cells may be designed with one or more of these receptors incorporated into their plasma membranes. Although not intending to bound by any theory, the receptors may be able to bind their cognate ligands and remove the ligands from circulation, thereby decreasing these circulating inflammatory mediators and ameliorating the acute inflammatory condition. In some embodiments, a similar decoy receptor approach may be used to remove other moieties from the blood, including for example, viral particles.

In some embodiments, the red blood cell-associated proteins of interest allow for the delivery of decoy ligands that can competitively bind to receptors associated with cytokine storms, including, but not limited to,IL-R-Fc, IL6R-Fc, TNFaR-FC, IFNaR-Fc, and BAFFR-Fc, and alleviate the clinical signs associated with a cytokine storm using a similar approach.

In some embodiments, the red blood cell-associated proteins of interest allow for the delivery of protein-encoded toxins, including, but not limited to, cholera toxin, shigella toxin, ricin, and diphteria toxin. Such toxic payloads may be designed for the treatment of cancers, such as solid tumors that are highly vascularized. In some embodiments, the proteins of interest can be engineered to be expressed on these red blood cells. In some embodiments, HSCs are engineered to express transmembrane proteins having an external portion configured with a covalent or non-covalent binding site. For example, the external portion may have sulfhydryl moieties designed to form disulfide bonds, avidin-biotin linkages, or any other linkage that allows the later association of the desired payload (e.g., protein-encoded toxins, and optionally other desired payloads). For example, the red blood cells may also be engineered using one or more of these approaches to deliver membrane-bound angiogenic inhibitors to the sites of the tumors.

In some embodiments, the red blood cell-associated proteins of interest allow for the targeting of the red blood cells to tissues and/or cells of interest. For example, targeting may be useful in bringing red blood cells to tumors or to tumor cells, among other uses. In some embodiments, targeting may be achieved through a variety of methods including, but not limited to, expression of markers, receptors, ligands, and antibodies on the surface of the red blood cells, or through linkage of one or more of these moieties onto the surface of the red blood cells.

In some embodiments, the red blood cell associated proteins of interest allow for the delivery of proangiogenic and/or lymphangiogenic factors to tissues affected by vascular dysregulation such as but not limited to frost bite, cancer-related vasoconstriction, or rheumatic joints, etc.

In some embodiments, the red blood cell-associated proteins of interest allow for the delivery of vasodilatory peptides in acute cases involving vassal constriction, including, but not limited to, vessal constriction during acute cardiac infarctions, obstetrical uses during child delivery, and acute and/or persistent migraine headaches, among others.

In some embodiments, the red blood cell-associated proteins of interest allow for the delivery of antigens for boosting life-long immunity. The antigen may be delviered via a genetically modified red blood cell designed to present the antigen of interest (protein) along with a TLR ligand on the red blood cell.

In some embodiments, the red blood cell-associated proteins of interest allow for the delivery of one or more proteins of interest to alleviate clot formation in patients at high risk of having clots. In some embodiments, a blood transfusion to a patient at high risk of having clots may include red blood cells having membrane-bound proteases that are specific to fibrotic tissues in embolitic masses, and optionally having targeting molecules to such locations. A similar approach may be useful for patients at elevated risk for pulmonary embolisms.

In some embodiments, the proteins of interest do not include Myc or Bcl-2.

Protein Transduction Domains

As used herein, the terms "peptide transduction domain," "protein transduction domain," and "PTD" are used interchangeably and refer to a peptide sequence or domain of a protein that promotes penetration of protein into a mammalian cell and/or compartment(s) within a mammalian cell. In one non-limiting example, a PTD promotes penetration of a coupled peptide and/or protein into the nucleus of a cell.

PTDs of the present disclosure may be isolated from a PTD-containing protein by any method of isolating a protein domain known in the art, such as standard molecular biology and biochemical techniques. Alternatively, PTDs of the present disclosure may be synthesized. Suitable PTDs of the present disclosure may be about 8 to about 30 amino acid residues in length, and enriched in basic amino acid residues, such as argentine (Arg) and lysine (Lys). In some embodiments, PTDs may have a short peptide sequence enriched in basic amino acids (arginine and lysine), optionally arranged in an alpha-helical structure.

As disclosed herein, PTDs of the present disclosure are coupled (e.g., fused, conjugated, cross-linked, etc.) to a peptide and/or protein in order to facilitate the penetration of the peptide and/or protein into a mammalian cell and/or compartment within a mammalian cell. For example, in certain embodiments a PTD of the present disclosure is coupled to a MYC protein and/or a Bcl-2 protein and/or a protein of interest.

Protein transduction domains suitable for use in any of the methods of the present disclosure include any PTD known in the art (e.g., U.S. Patent Application Publication Nos. US 2007/0116691 and US 2010/0055129). For example, suitable PTDs may be obtained or derived from proteins that include, without limitation, lentiviral TAT (Trans-Activator of Transcription) proteins, lentiviral VPR proteins, herpesviral VP22 proteins, and homeoproteins.

Examples of suitable PTDs obtained or derived from lentiviral TAT proteins include, without limitation, the PTD from a TAT protein of a TAT protein-containing virus, the PTD from a TAT protein of a TAT protein-containing lentivirus, the PTD from the HIV-1 TAT protein, the PTD from the HIV-2 TAT protein, the PTD from the SIV TAT protein, the PTD from a primate lentivirus TAT protein, the PTD from an ovine lentivirus TAT protein, the PTD from a bovine lentivirus TAT protein, the PTD from an equine lentivirus TAT protein, the PTD from a feline lentivirus TAT protein, a PTD from the TAT protein of a subvariant of HIV, SIV, primate lentivirus, ovine lentivirus, bovine lentivirus, equine lentivirus, or feline lentivirus, and homologues thereof. In certain embodiments, the PTD is amino acid residues 48-57 of the HIV TAT protein ($TAT_{[48-57]}$). In other embodiments, the PTD is amino acid residues 57-48 of the HIV TAT protein ($TAT_{[57-48]}$).

Examples of suitable PTDs that may obtained or derived from lentiviral VPR proteins include, without limitation, the PTD from a VPR protein of a VPR protein-containing virus, the PTD from a VPR protein of a VPR protein-containing lentivirus, the PTD from the HIV-1 VPR protein, the PTD from the HIV-2 VPR protein, the PTD from the SIV VPR protein, the PTD from a primate lentivirus VPR protein, the PTD from an ovine lentivirus VPR protein, the PTD from a bovine lentivirus VPR protein, the PTD from an equine lentivirus VPR protein, the PTD from a feline lentivirus VPR protein, a PTD from the VPR protein of a subvariant of HIV, SIV, primate lentivirus, ovine lentivirus, bovine lentivirus, equine lentivirus, or feline lentivirus, and homologues thereof.

Examples of suitable PTDs that may obtained or derived from herpesviral VP22 proteins include, without limitation, the PTD from the human herpesvirus 1(HSV-1) VP22 protein, the PTD from the human herpesvirus 2 (HSV-2) VP22 protein, the PTD from the BHV-1 VP22 protein, the PTD from the Psittacid herpesvirus 1VP22 protein, the PTD from the Equine herpesvirus 1 VP22 protein, the PTD from the Equine herpesvirus 4 VP22 protein, the PTD from the Gallid herpesvirus 2 VP22 protein, the PTD from the Varicella-zoster virus VP22 protein, and homologues thereof.

Examples of suitable PTDs that may be obtained or derived from homeodomain transcription factors include, without limitation, the homeodomain (HD) from the *Drosophila* Antennapedia (Antp) protein, the HD from the *Drosophila* Fushi tarazu (Ftz) protein, the HD from the *Drosophila* Engrailed (En) protein, the HD from the chick Engrailed-2 protein, the HD from mammalian homeoproteins, the HD from human homeoproteins, the HD from human Hox-A5 homeoprotein, the HD from human Hox-A4 homeoprotein, the HD from human Hox-B5 homeoprotein, the HD from human Hox-B6 homeoprotein, the HD from human Hox-B7 homeoprotein, the HD from human HOX-D3 homeoprotein, the HD from human GOX homeoprotein, the HD from human MOX-2 homeoprotein, the HD from human Hoxc-8 homeoprotein, the HD from human Islet-1 (Isl-1) homeoprotein, and homologues thereof.

Additionally, suitable PTDs include, without limitation, the PTD derived from Kaposi-FGF (K-FGF or FGF-4), the PTD derived from FGF-2, the PTD derived from FGF-1, and the PTD from other members of the FGF-family of proteins.

Other suitable PTDs include synthetic PTDs (e.g., Beerens, AMJ et al. *Curr Gene Ther.* 2003 October; 3(5):486-94). In some embodiments, a synthetic PTD may include EPTD, an optimized protein transduction domain (YARAAAR-QARA) (Ho, A. et al., *Cancer Res.* (2001) 61:474-477).

Further suitable PTDs include, without limitation, a CHARIOT™ peptide (Active Motif, Carlsbad, Calif.).

In some embodiments, PTDs of the present disclosure are produced recombinantly, while in others the PTDs are produced synthetically or are purified from a native source.

PTD Fusion Protein Modifications

In some embodiments, PTD fusion proteins of the present disclosure contain one or more molecules that link the PTD to a polypeptide, such as a recombinant protein of the present disclosure that promotes cell survival and/or proliferation, an exogenous protein of the present disclosure that inhibits apoptosis, or a protein of interest of the present disclosure. In further embodiments, the one or more linker molecules are amino acid peptides.

PTD fusion proteins of the present disclosure may further contain at least one amino acid sequence that facilitates purification of the fusion proteins. For example, the PTD fusion proteins may contain a protein tag, such as a polyhistidine tag. Alternatively, or in addition, the PTD-MYC fusion proteins may contain an epitope tag, such as a V5 epitope tag.

Accordingly, in certain embodiments, PTD fusion proteins of the present disclosure further contain a polyhistidine tag. In some embodiments, the polyhistidine tag is a 6-histidine tag. In some embodiments, the histidine tag contains the sequence HHHHHH. Additionally, the histidine tag may be added to a PTD fusion protein of the present disclosure by any suitable method known in the art. For example, a PTD fusion protein sequence may be cloned into an expression vector encoding a polyhistidine tag. Alternatively, a polyhistidine tag may be added by PCR (i.e., the PCR primers contain a polyhistidine sequence).

Moreover, a PTD fusion protein of the present disclosure may also contain at least one protein tag. In some embodiments, the at least one protein tag is an epitope tag. Preferably, the epitope tag is a V5 epitope tag. In some embodiments, the V5 epitope tag contains the amino acid sequence: GKPIPNPLLGLDST, while in other embodiments the V5 epitope tag contains the amino acid sequence: IPNPLLGLD. The amino acids may be either in the D formation, or in the L formation. In some embodiments, a first plurality of amino acids is in the D formation and a second plurality is in the L formation. Additionally, a V5 epitope tag of the present disclosure may be added to a PTD fusion protein of the present disclosure by any suitable method known in the art. For example, a PTD fusion protein sequence may be cloned into an expression vector encoding a V5 epitope tag. Alternatively, aV5 epitope tag may be added by PCR (i.e., the PCR primers contain a V5 epitope sequence).

In certain preferred embodiments, a PTD fusion protein of the present disclosure further contains a polyhistidine tag and an epitope tag. Preferably, the PTD fusion protein contains a 6-histidine tag and a V5 epitope tag.

Construction of PTD Fusion Proteins

In some embodiments, a PTD fusion protein of the present disclosure may be constructed by any suitable method known in the art (e.g., U.S. Patent Application Publication No. US 2010/0055129).

In one non-limiting example, a nucleic acid sequence encoding a PTD-recombinant protein that promotes cell survival and/or proliferation of the present disclosure (e.g., a PTD-MYC fusion protein, a PTD-ICN-1 fusion protein, etc.) may be generated by PCR. In certain embodiments, nucleic acid sequence encoding a PTD-MYC fusion protein is generated by PCR. This may be accomplished by designing a forward primer for a MYC sequence that contains an in frame PTD sequence, such as the RKKRRQRRR 9-amino-acid sequence of TAT, and a reverse primer for the MYC sequence that is designed to remove the stop codon. The PCR product from a PCR reaction using such primers may then be cloned into any suitable expression vector known in the art.

In one non-limiting example, a nucleic acid sequence encoding a PTD-exogenous protein that inhibits apoptosis of the present disclosure (e.g., a PTD-Bcl-2 fusion protein, a PTD-Bcl-w fusion protein, a PTD-Bcl-X fusion protein, a PTD-Bcl-X1 fusion protein, a PTD-Mcl-1 fusion protein, etc) may be generated by PCR. In certain embodiments, nucleic acid sequence encoding a PTD-Bcl-2 fusion protein is generated by PCR. This may be accomplished by designing a forward primer for a Bcl-2 sequence that contains an in frame PTD sequence, such as the RKKRRQRRR 9-amino-acid sequence of TAT, and a reverse primer for the Bcl-2 sequence that is designed to remove the stop codon. The PCR product from a PCR reaction using such primers may then be cloned into any suitable expression vector known in the art. The Bcl-2 unstructured loop may be removed from the BCL-2 coding sequence using a site directed mutagenesis kit.

In one non-limiting example, a nucleic acid sequence encoding a PTD-protein of interest fusion protein of the present disclosure may be generated by PCR. This may be accomplished by designing a forward primer for a protein of interest sequence that contains an in frame PTD sequence, such as the RKKRRQRRR 9-amino-acid sequence of TAT, and a reverse primer for the protein of interest sequence that is designed to remove the stop codon. The PCR product from a PCR reaction using such primers may then be cloned into any suitable expression vector known in the art.

Hematopoietic Stem Cells

Other aspects of the present disclosure relate to the in vitro production of a population of red blood cells by culturing hematopoietic stem cells (HSCs), optionally conditionally immortalized and/or genetically engineered to include one or more protein of interest, with EPO, and optionally IL-3, and one or more recombinant protein, or biologically active fragment thereof, that promotes cell survival and/or proliferation. This process may be performed in the presence or the absence of feeder cells and serum. In certain preferred embodiments, the process is performed in the absence of feeder cells and/or serum.

HSCs suitable for use with the methods of the present disclosure may be produced from embryonic stem (ES) cells and/or induced pluripotent stem (iPS) cells. Any method of producing HSCs from ES cells and/or iPS cells known in the art may be used (e.g., Keller, G. *Genes Dev.* 2005 19: 1129-1155; and Papapetrou Sadelain, *F1000 Med Rep.* 2010 Jun. 16; 2). For example, HSCs may be produced from ES cells by patterning the hematopoietic development of ES cell culuure on the hematopoietic commitment in the early embryo (e.g., Keller, G. *Genes Dev.* 2005 19: 1129-1155).

Additionally, HSCs suitable for use with the methods of the present disclosure may be obtained by any suitable technique known in the art. For example, HSCs may be found in the bone marrow of a donor, which includes femurs, hip, ribs, sternum, and other bones. Any method known in the art for extracting or harvesting bone marrow cells may be used. In one non-limiting example, HSCs may be obtained directly from the marrow cavity of the hip using a needle and syringe to aspirate cells from the marrow cavity. Rich marrow may be obtained from the hip by performing multiple small aspirations.

Alternatively, suitable HSCs may be obtained from peripheral blood cells found in the blood of a donor, optionally following pre-treatment with cytokines, such as G-CSF (granulocyte colony-stimulating factors), that induce HSCs to be released from the bone marrow compartment of the donor. HSCs may also be obtained from peripheral blood that has undergone an apheresis procedure to enrich for HSCs. Any apheresis procedure known in the art may be used. In certain embodiments, the apheresis procedure is a leukapheresis procedure.

Additionally, suitable HSCs may be obtained from umbilical cord blood, placenta, and mobilized peripheral blood. For experimental purposes, fetal liver, fetal spleen, and AGM (Aorta-gonad-mesonephros) of animals are also useful sources of HSCs. Additionally, HSCs may be procured from a source that obtained HSCs from the bone marrow, peripheral blood, umbilical cord, or fetal tissue of a donor.

In some embodiments, HSCs are obtained from a human umbilical cord or placenta. Another source of HSCs that may be utilized is the developing blood-producing tissues of fetal animals. In humans, HSCs may be found in the circulating blood of a human fetus by about 12 to 18 weeks. In some embodiments, human HSCs are obtained from any source, e.g., the bone marrow, umbilical cord, peripheral blood, or fetal tissue of blood, of type A+, A−, B+, B−, O+, O−, AB+, and AB− donors. In other embodiments, human HSCs are obtained from any source, e.g., the bone marrow, umbilical cord, peripheral blood, or fetal tissue of blood, of universal donors or donors having a rare blood type. Rare blood types are know in the art and include, without limitation, Oh, CDE/CDE, CdE/CdE, $C^WD-/C^WD-$, −D−/−D−, Rh:−51, LW(a−b+), LW(a−b−), S−s−U−, S−s−U(+), pp, Pk, Lu(a+b−), Lu(a−b−), Kp(a+b−), Kp(a−b−), Js(a+b−), Ko, K:−11, Fy(a−b−), Jk(a−b−), Di(b−), I−, Yt(a−), Sc:−1, Co(a−), Co(a−b−), Do(a−), Vel−, Ge−, Lan−, Lan(+), Gy(a−), Hy−, At(a−), Jr(a−), In(b−), Tc(a−), Cr(a−), Er(a−), Ok(a−), JMH−, and En(a−).

In other embodiments, human HSCs are obtained from any source, e.g., the bone marrow, umbilical cord, peripheral blood, or fetal tissue of blood, of donors having an auto-immune disorder, immune defficiency, or any other disease or disorder that would benefit from a transplantation of HSCs and/or transfusion of blood. Such donors may also be the recipients. Advantageously, HSCs obtained from such donor may be used for personalized HSC and/or blood therapy.

In one non-limiting example, human HSCs may be obtained by anesthetizing the stem cell donor, puncturing the posterior superior iliac crest with a needle, and performing aspiration of bone marrow cells with a syringe. In another non-limiting example, HSCs may be obtained from the peripheral blood of a donor, where a few days prior to harvesting the stem cells form the peripheral blood, the donor is injected with G-CSF in order to mobilize the stem cells to the peripheral blood.

Accordingly, in some embodiments, HSCs are obtained from an autologous donor, that is the donor will also be the recipient of the HSCs and/or red blood cells derived from such HSCs. Any methods known in the art and described herein may be used to obtain HSCs from the autologous donor. The HSCs and/or any therapeutic products derived or produced therefrom, such as red blood cells, are then transplanted, administered, and or transfused back to the original donor. Similarly, HSCs may be obtained from an allogenic donor, such as a sibling, parent, or other relative of a subject in need of an HSC transplantation and/or blood transfusion.

In one non-limiting example, allogenic HSCs are obtained by collecting HSCs from different blood groups or major histocompatibility complex (MHC) or human leukocyte antigen (HLA) matching sources. Autologous and/or allogenic HSC transplantation and/or blood transfusion may occur at any time after the donation, such as days later, months later, or even years later. Autologous donation may be particularly useful in cases where the subject in need of HSCs and/or blood transplantation and/or transfusion would have a negative, deleterious, or toxic reaction to transplantation and/or transfusion of HSCs and/or blood from any other donor, including allogenic and/or universal donors. Examples of patients that may benefit from autologous and/or allogenic donation are well known in the art and include, without limitation, those suffering from an autoimmune disorder, blood disease or disorder, immune disease or disorder, or other related diseases or conditions.

Cells obtained from, for example, bone marrow, peripheral blood, or cord blood, are typically processed after extraction or harvest. Any method known in the art for processing extracted or harvested cells may be used. Examples of processing steps include, without limitation, filtration, centrifugation, screening for hematopathologies, screening for viral and/or microbial infection, erythrocyte depletion, T-cell depletion to reduce incidence of graft-versus-host disease in allogenic stem cell transplant recipients, volume reduction, cell separation, resuspension of cells in culture medium or a buffer suitable for subsequent processing, separation of stem cells from non-stem cells (e.g., stem cell enrichment), ex vivo or in vitro stem cell expansion with growth factors, cytokines, and/or hormones, and cryopreservation.

Any suitable method for stem cell enrichment known in the art may be used. Examples of stem cell enrichment methods include, without limitation, fluorescence activated cell sorting (FACS) and magnetic activated cell sorting (MACS).

Accordingly, in certain embodiments, HSCs suitable for use in the methods of the present disclosure are human HSCs.

HSCs obtained from a donor may be identified and/or enriched by any suitable method of stem cell identification and enrichment known in the art, such as by utilizing certain phenotypic or genotypic markers. For example, in some embodiments, identification of HSCs includes using cell surface markers associated with HSCs or specifically associated with terminally differentiated cells of the system. Suitable surface markers may include, without limitation, one or more of c-kit, Sca-1, CD4, CD34, CD38, Thy 1, CD2, CD3, CD4, CD5, CD8, CD43, CD45, CD59, CD90, CD105, CD133, CD135, ABCG2, NK1.1, B220, Ter-119, Flk-2, CDCP1, Endomucin, Gr-1, CD46, Mac-1, Thy 1.1, and the signaling lymphocyte activation molecule (SLAM) family of receptors. Examples of SLAM receptors include, without limitation, CD150, CD48, and CD244.

Additionally, HSCs obtained from a donor may be separated from non-stem cells by any suitable method known in the art including, without limitation, fluorescence activated cell sorting (FACS) and magnetic activated cell sorting (MACS).

In one non-limiting example, human peripheral blood cells are incubated with antibodies recognizing c-kit, Sca-1, CD34, CD38, Thy 1, CD2, CD3, CD4, CD5, CD8, CD43, CD45, CD59, CD90, CD105, CD133, ABCG2, NK1.1, B220, Ter-119, Flk-2, CDCP1, Endomucin, or Gr-1. Antibodies for CD2, CD3, CD4, CD5, CD8, NK1.1, B220, Ter-119, and Gr-1 are conjugated with magnetic beads. The cells expressing CD2, CD3, CD4, CD5, CD8, NK1.1, B220, Ter-119, or Gr-1 are retained in the column equipped to trap magnetic beads and cells attached to magnetic bead conjugated antibodies. The cells that are not captured by the MACS column are subjected to FACS analysis. Antibodies for c-kit, Sca-1, CD34, CD38, Thy 1, are conjugated with fluorescent materials known in the art. The cells that are $CD34^+$, $CD38^{low/-}$, $c\text{-}kit^{-/low}$, $Thy\ 1^+$ are separated from the rest of sample by virtue of the types of fluorescent antibodies associated with the cells. These cells are provided as human long-term HSCs suitable for use with any of the methods of the present disclosure.

In another non-limiting example, cells obtained from a subject are labeled with the same set of magnetic bead conjugated antibodies as described above (antibodies against one or more of CD2, CD3, CD4, CD5, CD8, NK1.1, B220, Ter-119, or Gr-1) and fluorescent conjugated CD 150, CD244 and/or CD48 antibodies. After removing cells captured by the magnetic bead conjugated antibodies from the sample, the sample is analyzed by FACS and $CD150^+$, $CD244^-$ and $CD48^-$ cells are retained as long-term HSCs.

In some embodiments, HSCs utilized in the methods of the present disclosure contain one or more of the markers: $c\text{-}kit^-$, $Sca\text{-}1^+$, $CD34^{low/-}$, $CD38^+$, $Thy\ 1^{+/low}$, $CD34^+$, $CD38^{low/-}$, $c\text{-}kit^{-/low}$, and/or $Thy\ 1^+$. In some embodiments, the HSCs utilized in the methods of the present disclosure lack one or more of the markers: CD2, CD3, CD4, CD5, CD8, NK1.1, B220, Ter-119, and/or Gr-1. In certain embodiments, the HSCs utilized in the methods of the present disclosure are of an A+, A−, B+, B−, O+, O−, AB+, or AB− type.

Alternatively, suitable HSCs may be obtained from a non-human source. Suitable non-human HSCs may be isolated from, femurs, hip, ribs, sternum, and other bones of a non-human animal, including, without limitation, laboratory/research animals, rodents, pets, livestock, farm animals, work animals, pack animals, rare or endangered species, racing animals, and zoo animals. Further examples of suitable non-human animals include, without limitation, monkeys, primates, mice, rats, guinea pigs, hamsters, dogs, cats, horses, cows, pigs, sheep, goats, and chickens. For example, HSCs may be obtained from murine bone marrow cells, by incubating the bone marrow cells with antibodies recognizing cell surface molecules such as one or more of c-kit, Sca-1, CD34, CD38, Thy 1, CD2, CD3, CD4, CD5, CD8, CD43, CD45, CD59, CD90, CD105, CD133, ABCG2, NK1.1, B220, Ter-119, Flk-2, CDCP1, Endomucin, or Gr-1. Antibodies for CD2, CD3, CD4, CD5, CDS, NK1.I, B220, Ter-119, and Gr-1 are conjugated with magnetic beads. In MACS equipment, the cells harboring CD2, CD3, CD4, CD5, CD8, NK1.1, B220, Ter-119, or Gr-1 on their surface are retained in the column equipped to trap magnetic beads and the cells attached to magnetic bead conjugated antibodies. The cells that are not captured by MACS column are subjected to FACS analysis. For FACS analysis, Antibodies for surface molecules such as c-kit, Sca-1, CD34, CD38, Thy 1, are conjugated with fluorescent materials. The cells that are $c\text{-}kit^+$, $Sca\text{-}1^+$, $CD34^{low/-}$, $CD38^+$, $Thy\ 1^{+/low}$ are separated from the rest of the sample by virtue of the types of fluorescent antibodies associated with the cells. These cells are provided as murine long-term HSCs suitable for use with any of the methods of the present disclosure. In other embodiments, different sets of marker are used to separate murine long-term HSCs from cells of bone marrow, umbilical cord blood, fetal tissue, and peripheral blood.

In some embodiments, obtaining HSCs from bone marrow includes first injecting the HSC donor, such as a mouse or other non-human animal, with 5-fluorouracil (5-FU) to induce the HSCs to proliferate in order to enrich for HSCs in the bone marrow of the donor.

Moreover, HSCs suitable for use with any of the methods of the present disclosure, whether obtained from, or present in, cord blood, bone marrow, peripheral blood, or other source, may be grown or expanded in any suitable, commercially available or custom defined medium (e.g., Hartshorn et al., *Cell Technology for Cell Products*, pages 221-224, R. Smith, Editor; Springer Netherlands, 2007). For example, serum free medium may utilize albumin and/or transferrin, which have been shown to be useful for the growth and expansion of $CD34^+$ cells in serum free medium. Also, cytokines may be included, such as Flt-3 ligand, stem cell factor (SCF), and thrombopoietin (TPO), among others. HSCs may also be grown in vessels such as bioreactors (e.g., Liu et al., *Journal of Biotechnology* 124:592-601, 2006). A suitable medium for ex vivo expansion of HSCs may also contain HSC supporting cells, such as stromal cells (e.g., lymphoreticular stromal cells), which can be derived, for example, from the disaggregation of lymphoid tissue, and which have been shown to support the in vitro, ex vivo, and in vivo maintenance, growth, and differentiation of HSCs, as well as their progeny.

HSC growth or expansion may be measured in vitro or in vivo according to routine techniques known in the art. For example, WO 2008/073748, describes methods for measuring in vivo and in vitro expansion of HSCs, and for distinguishing between the growth/expansion of HSCs and the growth/expansion of other cells in a potentially heterogeneous population (e.g., bone marrow), including for example intermediate progenitor cells.

HSC Cell Lines

In other embodiments, HSCs suitable for use in any of the methods of the present disclosure may also be derived from an HSC cell line. Suitable HSC cell lines include any cultured hematopoietic stem cell line known in the art. Non-limiting examples include the conditionally immortalized long-term stem cell lines described in U.S. Patent Application Publication Nos. US 2007/0116691 and US 2010/0047217.

In certain embodiments, HSCs suitable for use in the methods of the present disclosure are conditionally immortalized before being differentiated into red blood cells. In some embodiments, HSCs suitable for use in the methods of the present disclosure may also be modified to include one or more proteins of interest before being differentiated into red blood cells. In some embodiments, conditional immortalization and/or inclusion of one or more proteins of interest may be achieved through any method known in the art and described herein, such as one or more of a transgenic approach, a protein-transduction approach, or an approach enhancing the expression of endogenous proteins.

Proteins Useful for Conditionally Immortalizing HSCs

In some embodiments, HSCs used in the methods of the present disclosure for the production of red blood cells were conditionally immortalized by contacting the HSCs with a composition containing one or more recombinant protein that promotes cell survival and/or cell proliferation and, optionally, one or more exogenous protein that inhibits apoptosis. In some embodiments, the one or more recombinant protein that promotes cell survival and/or proliferation also optionally inhibits apoptosis. In some embodiments, the one or more recombinant protein that promotes cell survival and/or proliferation is a MYC polypeptide, a biologically active fragment thereof or homologue thereof, of the present disclosure. In some embodiments, the one or more recombinant protein that promotes cell survival and/or proliferation further includes a protein transduction domain (PTD). In some embodiments, the one or more recombinant protein that promotes cell survival and/or proliferation is a PTD-MYC fusion protein. In some embodiments, the one or more exogenous protein that inhibits apoptosis is a protein that includes a Bcl-2 homology domain. In some embodiments, the one or more of exogenous protein that inhibits apoptosis further include a protein transduction domain (PTD). In some embodiments, the one or more of exogenous protein that inhibits apoptosis is a PTD-Bcl-2 fusion protein.

PTD-MYC and PTD-Bcl-2 fusion proteins of the present disclosure allow for an increase in MYC and Bcl-2 activity in HSCs by the exogenous addition of MYC and Bcl-2, without the need for overexpressing the endogenous genes encoding MYC and Bcl-2, or recombinantly expressing MYC and Bcl-2 via genetic manipulation. However, manipulation of HSCs to induce overexpression of such endogenous genes, optionally, through the creation of transgenic HSCs as well as other techniques to create conditionally immortalized stem cells are expressly envisioned herein.

In some embodiments, the HSCs to be differentiated into red blood cells (and/or the red blood cells) are further transduced with one or more disclosed proteins of interest. In some embodiments, these one or more proteins of interest are other than Myc or Bcl-2. In some embodiments, the proteins of interest are fusion proteins including a PTD domain of the present disclosure. In some embodiments, the PTD domain is TAT.

Transgenic Approach

In some embodiments, conditionally immortalized HSCs for use in the methods of the present invention are established using any transgenic approach known in the art (e.g., U.S. Patent Application Publication Nos. US 2007/0116691 and US 2010/0047217. For example, HSCs may be immortalized by obtaining an expanded population of HSCs, transfecting (transducing) the HSCs with a vector that encodes a recombinant protein that promotes cell survival and/or proliferation that is regulatable (e.g., inducible and/or controllable), transfecting (transducing) the HSCs with a vector encoding a recombinant protein that inhibits apoptosis, and expanding the transfected HSCs in the presence of a combination of stem cell growth factors under conditions where the recombinant protein that promotes cell survival and/or proliferation is induced and/or active.

The recombinant protein that promotes cell survival and/or proliferation is regulatable (e.g., inducible or controllable), so that the precombinant protein can be activated and deactivated (i.e., turned on or turned off) as desired to either maintain the HSCs in an immortalized state or to allow it to differentiate into a desired cell type, such as a red blood cell. The recombinant protein that promotes cell survival and/or proliferation may be any protein of the present disclosure that promotes cell survival and/or proliferation. In certain preferred embodiments, the protein that promotes cell survival and/or proliferation is MYC. Similarly, the recombinant protein that inhibits apoptosis may be any protein of the present disclosure that inhibits apoptosis. In certain preferred embodiments, the protein that inhibits apoptosis is Bcl-2.

In some embodiments, the recombinant protein that promotes cell survival and/or proliferation and/or the recombinant protein that inhibits apoptosis has been modified such that activity is inducible or repressible. For example, the recombinant proteins may further contain an inducible receptor. In certain embodiments, the recombinant proteins contain an estrogen receptor (ER). In certain embodiments, the recombinant protein that promotes cell survival and/or proliferation and that contains an estrogen receptor is a MYC-ER polypeptide. In certain embodiments, the recombinant protein that inhibits apoptosis and that contains an estrogen receptor is a Bcl-2-ER polypeptide. In certain embodiments, the recombinant proteins containing an estrogen receptor are induced by 4-hydroxytamoxifen (4-OHT). Alternatively, the recombinant proteins may contain a glucocorticoid receptor (GR), e.g., a glucocorticoid receptor that is sensitive to mifepristone (MIFEPREX). In certain embodiments, the recombinant protein that promotes cell survival and/or proliferation and that contains a glucocorticoid receptor is a MYC-GR polypeptide. In certain embodiments, the recombinant protein that inhibits apoptosis and that contains a glucocorticoid receptor is a Bcl-2-GR polypeptide.

Any method known in the art for obtaining an expanded population of HSCs known in the art may be used. For example, HSCs may be cultured with one or more growth factor that promotes cell proliferation and/or cell division.

Preferably, the vectors are an integrating vector, which has the ability to integrate into the genome of a cell (e.g., a retroviral vector). The HSCs can be transfected and/or transduec with the vectors using any suitable method of transfecting cells, and particularly mammalian cells, including by using combinations of techniques. Examples of suitable vectors, include without limitation, retroviral vectors, lentivirus vectors, parvovirus vectors, vaccinia virus vectors, coronavirus vectors, calicivirus vectors, papilloma virus vectors, flavivirus vectors, orthomixovirus vectors, togavirus vectors, picornavirus vectors, adenoviral vectors, and modified and attenuated herpesviruses vectors. Any such virus vector can further be modified with specific surface expressed molecules that target these to HSCs, such as membrane bound SCF, or other stem-cell specific growth factor ligands. Other methods of transfection of mammalian cells include, but are not limited to, direct electroporation of mammalian expression vectors, such as by using NUCLEOFECTOR™ technology (AMAXA Biosystems). This technology is a highly efficient non-viral gene transfer method for most primary cells and for hard-to-transfect cell lines, which is an improvement on the long-known method of electroporation, based on the use of cell-type specific combinations of electrical current and solutions to transfer polyanionic macromolecules directly into the nucleus. Additionally, suitable methods of transfection can include any bacterial, yeast, or other artificial methods of gene delivery that are known in the art.

In some embodiments, one or more of the proteins of interest are incorporated into one or more HSCs suitable for use in the methods of the present disclosure (e.g., primary cell lines or conditionally immortalized cell lines) using approaches similar to those described for the production of conditionally immortalized HSCs.

Enhancement of Endogenous Expression

In some embodiments, conditionally immortalized HSCs for use in the methods of the present disclosure may be established by enhancing the expression of endogenous proteins that promote cell survival and/or proliferation, including, without limitation, any protein of the present disclosure that promote cell survival and/or proliferation. For example, expression of an endogenous onco-peptide of the present disclosure, MYC polypeptide, ICN-1 polpeptide, homologue thereof, and/or analogue thereof may be enhanced. Additionally, conditionally immortalized HSCs for use in the methods of the present disclosure may be established by also enhancing the expression of endogenous proteins that inhibit apoptosis, including, without limitation, any protein of the present disclosure that inhibits apoptosis. For example, expression of an endogenous protein of the present disclosure that contains one or more Bcl-2 homology domain of the present disclosure, Bcl-2 polypeptide, Bcl-x polypeptide, Bcl-XL polypeptide, Mcl-1 polypeptide, CED-9 polypeptide, Bcl-2 related protein Al polypeptide, Bfl-1 polypeptide, Bcl-w polypeptide, homologue thereof, and/or analogue thereof may be enhanced.

In some embodiments, the expression of one or more of the proteins of interest is increased in one or more HSCs suitable for use in the methods of the present disclosure (e.g., primary cell lines or conditionally immortalized cell lines) using approaches similar to those described for the enhanced production of, for example, MYC and/or Bcl-2.

Protein Transduction Approach

In some embodiments, HSCs obtained and/or produced by any method disclosed herein may be treated with a gene product that promotes cell survival and/or proliferation, including, but not limited to any recombinant protein of the present disclosure that promotes cell survival and/or proliferation (e.g., onco-peptide, MYC, ICN-1, homologues thereof, analogues thereof, and biologically active fragments thereof) and/or with a protein of the present disclosure that inhibits apoptosis of the HSCs (e.g., proteins containing one or more Bcl-2 homology domains, Bcl-2, Bcl-x, Bcl-XL, Mcl-1, CED-9, Bcl-2 related protein Al, Bfl-1, Bcl-w, homologues thereof, analogues thereof, and biologically active fragments thereof) (e.g., U.S. Patent Application Publication No. US 2007/0116691). In some embodiments, the protein that promotes cell survival and/or proliferation is a fusion protein containing a PTD. In some embodiments, the protein that inhibits apoptosis is a fusion protein containing a PTD. In some embodiments, HSCs obtained and/or produced by any method disclosed herein may be treated with one or more compound (optionally an exogenous protein) that enables the transient upregulation of at least one function of a recombinant protein of the present disclosure that promotes cell survival and/or proliferation in a cell. In some embodiments, the recombinant protein that promotes cell survival and/or proliferation protein is a PTD-MYC and/or ICN-1 fusion protein. In certain embodiments, the PTD-MYC fusion protein is a TAT-MYC and/or ICN-1 fusion protein.

In some embodiments, HSCs obtained by any method disclosed herein may be treated with one or more compound (optionally an exogenous protein) that enables the transient upregulation of at least one function of a recombinant protein of the present disclosure that inhibits apoptosis in a cell. In some embodiments, the exogenous protein that inhibits apoptosis of the HSCs is a PTD-Bcl-2 fusion protein. In some embodiments, the PTD-Bcl-2 fusion protein is a TAT-Bcl-2 fusion protein.

In some embodiments, one or more of the proteins of interest are incorporated into one or more HSCs suitable for use in the methods of the present disclosure (e.g., primary cell lines or conditionally immortalized cell lines) using approaches similar to those described for the production of conditionally immortalized HSCs using PTD-fusion proteins.

In other embodiments, HSCs suitable for use in any of the methods of the present disclosure are contacted with a composition containing a fusion protein containing a protein of the present disclosure that promotes cell survival and/or proliferation fused to a PTD (e.g., a PTD-MYC and/or PTD-ICN-1 fusion protein). In further embodiments, the composition further contains a fusion protein containing a protein of the present disclosure that inhibits apoptosis fused to a PTD (e.g., a PTD-Bcl-2 fusion protein). In some embodiments, the HSCs are contacted with a composition containing a PTD-MYC and/or PTD-ICN-1 fusion protein, and a second composition containing a PTD-Bcl-2 fusion protein.

In other embodiments, HSCs suitable for use in any of the methods of the present disclosure are expanded in the presence of a fusion protein containing a protein of the present disclosure that promotes cell survival and/or proliferation fused to a PTD (e.g., a TAT-MYC protein and/or TAT-ICN-1 protein fusion) prior to being differentiated into red blood cells. In further embodiments, the HSCs are also expanded in the presence of a fusion protein containing a protein of the present disclosure that inhibits apoptosis fused to a PTD (e.g., a TAT-Bcl-2 fusion protein). For example, HSCs may be expanded by culturing the cells in the presence of a PTD-MYC and/or PTD-ICN-1 fusion protein, and optionally in the presence of a PTD-Bcl-2 fusion protein and additional cytokines and/or growth factors, for at least one day, at least two days, at least three days, at least four days, at least five days, at least six days, at least seven days, at least eight days, at least nine days, at least 10 days, at least 11 days, at least 12 days, at least 13 days, at least 14 days, or more.

Accordingly, HSCs suitable for use in any of the methods of the present disclosure may be obtained from embryonic stem cells (ES cells), fetal stem cells, induced pluripotent stem cells (iPS cells), bone marrow, from an apheresis procedure, from peripheral blood cells, from peripheral blood cells that have undergone leukapheresis, from umbilical cord blood, from amniotic fluid, from placenta, from cultured HSC cells, from an immortalized HSC cell line, or from a conditionally immortalized HSC cell line.

Production of Red Blood Cells

Certain aspects of the present disclosure relate to methods for producing a population of mature red blood cells from HSCs, by culturing the HSCs in the presence of EPO, optionally IL-3, and one or more recombinant protein of the present disclosure that promotes cell survival and/or proliferation under conditions that induce differentiation of the HSCs to mature red bloods cells, thereby producing the population of mature red blood cells. The recombinant protein may be exogenously provided or provided through transgenic manipulation of the HSCs. Alternatively the protein that promotes cell survival and/or proliferation may be an endogenous protein that is induced to be overexpressed. In some embodiments, the recombinant, induced, and/or exogenous protein is an onco-peptide of the present disclosure, MYC, ICN-1, homologues thereof, analogues thereof, and/or biologically active fragments thereof. Optionally the protein that promotes cell survival and/or proliferation may form part of a fusion protein. In some embodiments, the fusion protein includes one or more of a PTD, an epitope tag, or a protein purification tag. In some embodiments, the HSCs are modified to include one or more proteins of interest before being differentiated into red blood cells. In some embodiments, conditional immortalization and/or inclusion of one or more proteins of interest may be achieved through any method known in the art and described herein, such as one or more of a transgenic approach, a protein-transduction approach, or an approach enhancing the expression of endogenous proteins In some embodiments of the methods of the present disclosure, a composition containing a fusion protein containing a protein of the present disclosure that promotes cell survival and/or proliferation fused to a PTD (e.g., a PTD-MYC protein and/or PTD-ICN-1 protein fusion) is administered during the step of culturing the conditionally immortalized HSCs in the presence of EPO, and optionally IL-3 and other components. In some embodiments, the HSCs are cultured in the presence or in the absence of feeder cells and/or serum. In certain preferred embodiments, the HSCs are cultured in the absence of feeder cells and/or serum.

In some embodiments, the HSCs are cultured in the presence of at least 0.5 µ/ml, at least 0.6 µ/ml, at least 0.7 µ/ml, at least 0.8 µml, at least 0.9 µ/ml, at least 1 µ/ml, at least 2 µ/ml, at least 3 µ/ml, at least 4 µ/ml, at least 5 µ/ml, at least 6 µ/ml, at least 7 µ/ml, at least 8 µ/ml, at least 9 µ/ml, at least 10 µ/ml, at least 15 µ/ml, at least 20 µ/ml, at least 25 µ/ml, at least 30 µ/ml, at least 35 µ/ml, at least 40 µ/ml, at least 45 µ/ml, at least 50 µ/ml, at least 55 µ/ml, at least 60 µ/ml, at least 65 µ/ml, at least 70 µ/ml, at least 75 µ/ml, at least 80 µ/ml, at least 85 µ/ml, at least 90 µ/ml, at least 95 µ/ml, or at least 100 µ/ml of recombinant protein that promotes cell survival and/or proliferation (e.g., MYC, ICN-1, homologues thereof, analogues thereof, and/or biologically active fragments thereof).

In some embodiments, the HSCs are cultured in the presence of at least 0.5 µ/ml, at least 0.6 µ/ml, at least 0.7 µ/ml, at least 0.8 µ/ml, at least 0.9 µ/ml, at least 1 µ/ml, at least 2 µ/ml, at least 3 µ/ml, at least 4 µ/ml, at least 5 µ/ml, at least 6 µ/ml, at least 7 µ/ml, at least 8 µ/ml, at least 9 µ/ml, at least 10 µ/ml, at least 15 µ/ml, at least 20 µ/ml, at least 25 µ/ml, at least 30 µ/ml, at least 35 µ/ml, at least 40 µ/ml, at least 45 µ/ml, at least 50 µ/ml, at least 55 µ/ml, at least 60 µ/ml, at least 65 µ/ml, at least 70 µ/ml, at least 75 µ/ml, at least 80 µ/ml, at least 85 µ/ml, at least 90 µ/ml, at least 95 µ/ml, or at least 100 µ/ml MYC.

In certain embodiments, the HSCs, optionally conditionally immortalized HSCs, are cultured in the presence of at least 0.5 µ/ml, at least 0.6 µ/ml, at least 0.7 µ/ml, at least 0.8 µ/ml, at least 0.9 µ/ml, at least 1 µ/ml, at least 2 µ/ml, at least 3 µ/ml, at least 4 µ/ml, at least 5 µ/ml, at least 6 µ/ml, at least 7 µ/ml, at least 8 µ/ml, at least 9 µ/ml, at least 10 µ/ml, at least 15 µ/ml, at least 20 µ/ml, at least 25 µ/ml, at least 30 µ/ml, at least 35 µ/ml, at least 40 µ/ml, at least 45 µ/ml, at least 50 µ/ml, at least 55 µ/ml, at least 60 µ/ml, at least 65 µ/ml, at least 70 µ/ml, at least 75 µ/ml, at least 80 µ/ml, at least 85 µ/ml, at least 90 µ/ml, at least 95 µ/ml, or at least 100 µ/ml ICN-1.

In certain embodiments, the HSCs, optionally conditionally immortalized HSCs, are cultured in the presence of at least 1.0 unit/ml EPO, at least 1.2 units/ml EPO, at least 1.4 units/ml EPO, at least 1.6 units/ml EPO, at least 1.8 units/ml EPO, at least 2.0 units/ml EPO, at least 2.2 units/ml EPO, at least 2.4 units/ml EPO, at least 2.6 units/ml EPO, at least 2.8 units/ml EPO, at least 3.0 units/ml EPO, at least 3.2 units/ml EPO, at least 3.4 units/ml EPO, at least 3.6 units/ml EPO, at least 3.8 units/ml EPO, at least 4.0 units/ml EPO, or more EPO.

In certain embodiments, the HSCs, optionally conditionally immortalized HSCs, are further cultured in the presence of at least 1 ng/ml IL-3, at least 2 ng/ml IL-3, at least 3 ng/ml IL-3, at least 4 ng/ml IL-3, at least 5 ng/ml IL-3, at least 6 ng/ml IL-3, at least 7 ng/ml IL-3, at least 8 ng/ml IL-3, at least 9 ng/ml IL-3, at least 10 ng/ml IL-3, at least 11 ng/ml IL-3, at least 12 ng/ml IL-3, at least 13 ng/ml IL-3, at least 14 ng/ml IL-3, at least 15 ng/ml IL-3, at least 16 ng/ml IL-3, at least 17 ng/ml IL-3, at least 18 ng/ml IL-3, at least 19 ng/ml IL-3, at least 20 ng/ml IL-3, at least 21 ng/ml IL-3, at least 22 ng/ml IL-3, at least 23 ng/ml IL-3, at least 24 ng/ml IL-3, at least 25 ng/ml IL-3, or more IL-3.

In certain embodiments, the HSCs, optionally conditionally immortalized HSCs, are are cultured in the presence of at least 1 ng/ml IL-3, at least 2 ng/ml IL-3, at least 3 ng/ml IL-3, at least 4 ng/ml IL-3, at least 5 ng/ml IL-3, at least 6 ng/ml IL-3, at least 7 ng/ml IL-3, at least 8 ng/ml IL-3, at least 9 ng/ml IL-3, at least 10 ng/ml IL-3, at least 11 ng/ml IL-3, at least 12 ng/ml IL-3, at least 13 ng/ml IL-3, at least 14 ng/ml IL-3, at least 15 ng/ml IL-3, at least 16 ng/ml IL-3, at least 17 ng/ml IL-3, at least 18 ng/ml IL-3, at least 19 ng/ml IL-3, at least 20 ng/ml IL-3, at least 21 ng/ml IL-3, at least 22 ng/ml IL-3, at least 23 ng/ml IL-3, at least 24 ng/ml IL-3, at least 25 ng/ml IL-3, or more IL-3; and at least 1.0 unit/ml EPO, at least 1.2 units/ml EPO, at least 1.4 units/ml EPO, at least 1.6 units/ml EPO, at least 1.8 units/ml EPO, at least 2.0 units/ml EPO, at least 2.2 units/ml EPO, at least 2.4 units/ml EPO, at least 2.6 units/ml EPO, at least 2.8 units/ml EPO, at least 3.0 units/ml EPO, at least 3.2 units/ml EPO, at least 3.4 units/ml EPO, at least 3.6 units/ml EPO, at least 3.8 units/ml EPO, at least 4.0 units/ml EPO, or more EPO.

In further embodiments, the HSCs, optionally conditionally immortalized HSCs, are cultured in the presence of EPO, and optionally IL-3, for at least one day, at least two days, at least three days, at least four days, at least five days, at least six days, at least seven days, at least eight days, at least nine days, at least 10 days, or longer.

In further embodiments, the HSCs, optionally conditionally immortalized HSCs, are further cultured in the presence of about 1-500 ng/ml FLT-3, about 1-500 ng/ml SCF, about 1-500 ng/ml GM-CSF, and/or about 1-500 ng/ml TPO. The HSCs, optionally conditionally immortalized HSCs, may be further cultured in the presence of FLT-3, SCF, GM-CSF, and/or TPO for at least one day, at least two days, at least three days, at least four days, at least five days, at least six days, at least seven days, at least eight days, at least nine days, at least 10 days, or longer. The FLT-3, SCF, GM-CSF, and/or TPO may be added to the culture media at any point during the period of time when the HSCs are differentiating into mature red blood cells, and/or after the mature red blood cells have been produced.

In further embodiments, the HSCs, optionally conditionally immortalized HSCs, are further cultured in the presence of at least 1 ng/ml FLT-3, at least 2 ng/ml FLT-3, at least 3 ng/ml FLT-3, at least 4 ng/ml FLT-3, at least 5 ng/ml FLT-3, at least 6 ng/ml FLT-3, at least 7 ng/ml FLT-3, at least 8 ng/ml FLT-3, at least 9 ng/ml FLT-3, at least 10 ng/ml FLT-3, at least 15 ng/ml FLT-3, at least 20 ng/ml FLT-3, at least 25 ng/ml FLT-3, at least 30 ng/ml FLT-3, at least 35 ng/ml FLT-3, at least 40 ng/ml FLT-3, at least 45 ng/ml FLT-3, at least 50 ng/ml FLT-3, at least 55 ng/ml FLT-3, at least 60 ng/ml FLT-3, at least 65 ng/ml FLT-3, at least 70 ng/ml FLT-3, at least 75 ng/ml FLT-3, at least 80 ng/ml FLT-3, at least 85 ng/ml FLT-3, at least 90 ng/ml FLT-3, at least 95 ng/ml FLT-3, at least 100 ng/ml FLT-3, at least 150 ng/ml FLT-3, at least 200 ng/ml FLT-3, at least 250 ng/ml FLT-3, at least 300 ng/ml FLT-3, at least 350 ng/ml FLT-3, at least 400 ng/ml FLT-3, at least 450 ng/ml FLT-3, at least 500 ng/ml FLT-3, or more of FLT-3.

In further embodiments, the HSCs, optionally conditionally immortalized HSCs, are further cultured in the presence of at least 1 ng/ml SCF, at least 2 ng/ml SCF, at least 3 ng/ml SCF, at least 4 ng/ml SCF, at least 5 ng/ml SCF, at least 6 ng/ml SCF, at least 7 ng/ml SCF, at least 8 ng/ml SCF, at least 9 ng/ml SCF, at least 10 ng/ml SCF, at least 15 ng/ml SCF, at least 20 ng/ml SCF, at least 25 ng/ml SCF, at least 30 ng/ml SCF, at least 35 ng/ml SCF, at least 40 ng/ml SCF, at least 45 ng/ml SCF, at least 50 ng/ml SCF, at least 55 ng/ml SCF, at least 60 ng/ml SCF, at least 65 ng/ml SCF, at least 70 ng/ml SCF, at least 75 ng/ml SCF, at least 80 ng/ml SCF, at least 85 ng/ml SCF, at least 90 ng/ml SCF, at least 95 ng/ml SCF, at least 100 ng/ml SCF, at least 150 ng/ml SCF, at least 200 ng/ml SCF, at least 250 ng/ml SCF, at least 300 ng/ml SCF, at least 350 ng/ml SCF, at least 400 ng/ml SCF, at least 450 ng/ml SCF, at least 500 ng/ml SCF, or more of SCF.

In further embodiments, the HSCs, optionally conditionally immortalized HSCs, are further cultured in the presence of at least 1 ng/ml GM-CSF, at least 2 ng/ml GM-CSF, at least 3 ng/ml GM-CSF, at least 4 ng/ml GM-CSF, at least 5 ng/ml GM-CSF, at least 6 ng/ml GM-CSF, at least 7 ng/ml GM-CSF, at least 8 ng/ml GM-CSF, at least 9 ng/ml GM-CSF, at least 10 ng/ml GM-CSF, at least 15 ng/ml GM-CSF, at least 20 ng/ml GM-CSF, at least 25 ng/ml GM-CSF, at least 30 ng/ml GM-CSF, at least 35 ng/ml GM-CSF, at least 40 ng/ml GM-CSF, at least 45 ng/ml GM-CSF, at least 50 ng/ml GM-CSF, at least 55 ng/ml GM-CSF, at least 60 ng/ml GM-CSF, at least 65 ng/ml GM-CSF, at least 70 ng/ml GM-CSF, at least 75 ng/ml GM-CSF, at least 80 ng/ml GM-CSF, at least 85 ng/ml GM-CSF, at least 90 ng/ml GM-CSF, at least 95 ng/ml GM-CSF, at least 100 ng/ml GM-CSF, at least 150 ng/ml GM-CSF, at least 200 ng/ml GM-CSF, at least 250 ng/ml GM-CSF, at least 300 ng/ml GM-CSF, at least 350 ng/ml GM-CSF, at least 400 ng/ml GM-CSF, at least 450 ng/ml GM-CSF, at least 500 ng/ml GM-CSF, or more of GM-CSF.

In further embodiments, the HSCs, optionally conditionally immortalized HSCs, are further cultured in the presence of at least 1 ng/ml TPO, at least 2 ng/ml TPO, at least 3 ng/ml TPO, at least 4 ng/ml TPO, at least 5 ng/ml TPO, at least 6 ng/ml TPO, at least 7 ng/ml TPO, at least 8 ng/ml TPO, at least 9 ng/ml TPO, at least 10 ng/ml TPO, at least 15 ng/ml TPO, at least 20 ng/ml TPO, at least 25 ng/ml TPO, at least 30 ng/ml TPO, at least 35 ng/ml TPO, at least 40 ng/ml TPO, at least 45 ng/ml TPO, at least 50 ng/ml TPO, at least 55 ng/ml TPO, at least 60 ng/ml TPO, at least 65 ng/ml TPO, at least 70 ng/ml TPO, at least 75 ng/ml TPO, at least 80 ng/ml TPO, at least 85 ng/ml TPO, at least 90 ng/ml TPO, at least 95 ng/ml TPO, at least 100 ng/ml TPO, at least 150 ng/ml TPO, at least 200 ng/ml TPO, at least 250 ng/ml TPO, at least 300 ng/ml TPO, at least 350 ng/ml TPO, at least 400 ng/ml TPO, at least 450 ng/ml TPO, at least 500 ng/ml TPO, or more of TPO.

Current methods of producing red blood cells from primary HSCs, for example see Giarratana et al., (2005) *Nat Biotech* 23, 69-74, require at least three weeks (21 days) to produce red blood cells. However, the methods of the present disclosure for producing a population of red blood cells from conditionally immortalized HSCs produce red blood cells in about 10 days. As compared to the at least 21 days of the current methods, the 10 days of the presently disclosed methods represents an acceleration of approximately 52%. Thus, in some embodiments, the production of the population of mature red blood cells is accelerated by at least 45%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 75%, at least 80%, at least 85%, at least 90%, at least 95%, or more compared to production of a population of red blood cells from a primary stem cell cultured in the presence of IL-3 and EPO for eight days, then in the presence of feeder cells and EPO for three days, and finally in the presence of feeder cells alone for 10 days (see, Giarratana et al., (2005) *Nat Biotech* 23, 69-74).

In other embodiments, the population of mature red blood cells is produced in about 7 to 14 days. In other embodiments, the population of mature red blood cells is produced in about 3 days, about 4, about 5 days, about 6 days, about 7 days, about 8 days, about 9 days, about 10 days, about 11 days, about 12 days, about 13 days, or about 14 days.

In other embodiments of the methods of the present disclosure, the produced population of red blood cells is a population of fully mature red blood cells. In still other embodiments, at least 40%, at least 45%, at least 50%, at least 55%, at least 60%, at least 65%, at least 70%, at least 75%, at least 80%, at least 85%, at least 90%, at least 95%, or at least 100% of the cells in the population of mature red blood cells are anucleated. In yet other embodiments, the population of mature red blood cells is continually produced from conditionally immortalized HSCs.

In other embodiments of the methods of the present disclosure, at least 40%, at least 45%, at least 50%, at least 55%, at least 60%, at least 65%, at least 70%, at least 75%, at least 80%, at least 85%, at least 90%, at least 95%, or at least 100% of the cells in the population of mature red blood cells express Glycophrin A (GPA). In further embodiments, at least 40%, at least 45%, at least 50%, at least 55%, at least 60%, at least 65%, at least 70%, at least 75%, at least 80%, at least 85%, at least 90%, at least 95%, or at least 100% of the cells in the population of mature red blood cells exhibit decreased levels of CD71 (transferrin receptor) expression. In further embodiments, at least 40%, at least 45%, at least 50%, at least 55%, at least 60%, at least 65%, at least 70%, at least 75%, at least 80%, at least 85%, at least 90%, at least 95%, or at least 100% of the cells in the population of mature red blood cells exhibit decreased levels of fetal hemoglobin expression. In further embodiments, at least 40%, at least 45%, at least 50%, at least 55%, at least 60%, at least 65%, at least 70%, at least 75%, at least 80%, at least 85%, at least 90%, at least 95%, or at least 100% of the cells in the population of mature red blood cells express adult hemoglobin.

In other embodiments, the produced population of mature red blood cells is a population of human cells. In further embodiments, the produced population of mature red blood cells is a population of non-human animal cells, including, wihtout limitation, a population of cells from laboratory/research animals, rodents, pets, livestock, farm animals, work animals, pack animals, rare or endagerred species, racing animals, zoo animals, monkies, primates, mice, rats, guinea pigs, hamsters, dogs, cats, horses, cows, pigs, sheep, goats, and chickens.

The methods of the present disclosure may also utilize HSCs, optionally conditionally immortalized HSCs, derived from human HSCs obtained from donors having a blood of type A+, A−, B+, B−, O+, O−, AB+, or AB−. Accordingly, the red blood cells produced from the HSCs will be of blood type A+, A−, B+, B−, O+, O−, AB+, or AB−.

Additionally, the methods of the present disclosure may also utilize HSCs, optionally conditionally immortalized HSCs derived from human HSCs obtained from donors having a rare blood type including, without limitation, Oh, CDE/CDE, CdE/CdE, $C^WD$−/$C^WD$−. −D−/−D−, $Rh_{null}$, Rh:−51, LW(a−b+), LW(a−b−), S−s−U−, S−s−U(+), pp, Pk, Lu(a+b−), Lu(a−b−), Kp(a+b−), Kp(a−b−), Js(a+b−), Ko, K:−11, Fy(a−b−), Jk(a−b−), Di(b−), I−, Yt(a−), Sc:−1, Co(a−), Co(a−b−), Do(a−), Vel−, Ge−, Lan−, Lan(+), Gy(a−), Hy−, At(a−), Jr(a−), In(b−), Tc(a−), Cr(a−), Er(a−), Ok(a−), JMH−, and En(a−). Accordingly, in some embodiments, the population of red blood cells produced from the HSCs will be of a rare blood type including, without limitation, Oh, CDE/CDE, CdE/CdE, $C^WD$-/$C^WD$-, -D-/-D-, h $R_{null}$, Rh:-51, LW(a+b+), LW(a-b-), S-s-U-, S-s-U(+), pp, Pk, Lu(a+b-), Lu(a-b-), Kp(a+b-), Kp(a-b-), Js(a+b-), Ko, K:-11, Fy(a-b-), Jk(a-b-), Di(b-), I-, Yt(a-), Sc:-1, Co(a-), Co(a-b-), Do(a-), Vel-, Ge-, Lan-, Lan(+), Gy(a-), Hy-, At(a-), Jr(a-), In(b-), Tc(a-), Cr(a-), Er(a-), Ok(a-), JMH-, and En(a-).

Additionally, the methods of the present disclosure may also utilize HSCs, optionally conditionally immortalized HSCs derived from donors having an auto-immune disorder, immune deficiency, or any other disease or disorder that would benefit from a transplantation of HSCs and/or transfusion of blood to produce a population of mature red blood cells that can be used for personalized therapies. For example, the population of mature red blood cells may be produced from HSCs obtained from an autologous or allogenic donor. Advantageously, autologous red blood cells may be particularly useful in cases where the subject in need of a blood transfusion and/or treatment with red blood cells would have a negative, deleterious, or toxic reaction to treatment with red blood cells derived or obtained from any other donor, including allogenic and/or universal donors. Examples of patients that may benefit from treatment with red blood cells produced from HSCs derived from autologous and/or allogenic donors are well known in the art and include, wihtout limitaiton, those suffering from an autoimmune disorder, blood disease or disorder, immune disease or disorder, or other related diseases or conditions.

In certain embodiments the population of red blood cells is produced from conditionally immortalized HSCs that can be passaged indefinitely in vitro, cryopreserved, and recovered. Accordingly, such conditionally immortalized HSCs allow for the continuous production of fully differentiated red blood cells from a defined, well-characterized, source.

The methods of the present disclosure may utilize HSCs from any source, including but not limited to, primary hematopoietic stem cells from cord blood, placenta, peripheral blood, bone marrow, or mobilized blood. Hematopoietic stem cells derived from embryonic stem cells, fetal blood cells or induced pluripotent stem cells, as well as conditionally immortalized hematopoietic stem cells such as transgenic and protein transduced conditionally immortalized cells are expressly contemplated.

Populations of Red Blood Cells

Certain aspects of the present disclosure relate to populations of red blood cells, such as mature red blood cells, optionally produced by one or more methods of the present disclosure. Populations of red blood cells may also include one or more proteins of interest of the present disclosure. These proteins of interest may be useful in prevention, treatment, and/or diagnosis of one or more diseases or disorders as disclosed herein.

In some aspects, populations of red blood cell may be characterized by one or more characteristics, including but not limited to, at least about 40%, at elast 45%, at least about 50%, at least about 55%, at least about 60%, at least about 65%, at least about 70%, at least about 75%, at least about 80%, at least about 85%, at least about 90%, at least about 95%, at least about 99%, or about 100% of the cells in the population are anucleated, express GPA, express adult hemoglobin (second decade or higher by FACS), exhibit decreased levels of CD71 expression (e.g. GPA$^+$/CD71$^-$), and/or exhibit decreased levels of fetal hemoglobin (first decade; 0-10 by FACS). Populations of red blood cells may also include one or more recombinant proteins of interest. These proteins of interest may be useful in prevention, treatment, and/or diagnosis of one or more diseases or disorders as disclosed herein.

In some embodiments, a population of red blood cells may further include an exogenous protein of the present disclosure that inhibits apoptosis, such as a protein containing a Bcl-2 homology domain. The exogenous protein may also be a fusion protein that contains a PTD. In some embodiments, the exogenous protein is Bcl-2, a homologue thereof, an anlogue thereof, and/or a biologically active fragment thereof. In certain embodiments, the exgenous protein is Bcl-2, optionally PTD-Bcl-2. In some embodiments, the population of red blood cells are maintained in storage media that includes an protein of the present disclosure that inhibits apoptosis, such as a protein containing a Bcl-2 homology domain. In some embodiments, the exogenous protein in the storage media is Bcl-2, a homologue thereof, an anlogue thereof, and/or a biologically active fragment thereof. In certain embodiments, the exgenous protein in the storage medias is Bcl-2, optionally PTD-Bcl-2 Bcl-2.

Pharmaceutical Compositions

Certain aspects of the present disclosure relate to pharmaceutical compositions including one or more populations of red blood cells of the present disclosure and one or more pharmaceutically acceptable excipients. Any pharmaceutically acceptable excipient known in the art that is suitable for use with red blood cells may be used. In one non-limiting example, the pharmaceutically acceptable excipient is a pH-balanced saline solution.

In some embodiments, the composition further includes one or more proteins of interest of the present disclosure.

The populations of red bloods are optionally produced by one or more methods of the present disclosure and/or exhibit one or more of characteristics of the present disclosure, including without limitation, about 40% to about 100% of the red blood cells in the population are anucleated, about 40% to about 100% of the red blood cells in the population express adult hemoglobin, about 40% to about 100% of the red blood cells in the population exhibit increased expression of adult hemoglobin, about 40% to about 100% of the red blood cells in the population exhibit decreased levels of CD71 expression, and about 40% to about 100% of the red blood cells in the population exhibit decreased levels of fetal hemoglobin expression. Additionally, the population of red blood cells may have a rare blood type. In some embodiments, the red blood cells are human red blood cells. Alternatively, the red blood cells are non-human red blood cells derived from any non-human animal of the present disclosure.

The populations of red blood cells may also include one or more protein of interest of the present disclosure. In some embodiments, the one or more proteins of interest are associated on the surface of the red blood cells.

Pharmaceutical compositions of the present disclosure containing a one or more populations of red blood cells of the present disclosure and one or more pharmaceutically acceptable excipients, where the red blood cells optionally contain one or more proteins of interest of the present disclosure may be formulated for in vivo administration, such as through transfusion. Any formulation known in the art for in vivo administration of a pharmaceutical composition containing a population of red blood cells may be used.

Therapeutic Uses

Red blood cells described herein and/or produced according to any of the methods of the present disclosure for producing a population of mature red blood cells from HSCs, optionally conditionally immortalized HSCs also find use in therapeutic applications.

The use of red blood cell transfusions for patients in need of such treatment for a variety of reasons and disorders is well known in the art, and approaches are standard medical practice. The red blood cells described herein and/or produced according to the methods of the present disclosure can be used to treat patients using the same approaches and conditions currently used for blood transfusions.

In certain embodiments, the present disclosure relates to methods of treatment, prevention, or diagnosis of a disease or disorder characterized by a deficiency of red blood cells by administering a population of red blood cells of the present disclosure, or prepared according to any of the methods of the present disclosure, to a subject having a disorder characterized by a deficiency of red blood cells. In some embodiments, about 40% to about 100% of the red blood cells in the population are anucleated, about 40% to about 100% of the red blood cells in the population express adult hemoglobin, about 40% to about 100% of the red blood cells in the population exhibit increased expression of adult hemoglobin, about 40% to about 100% of the red blood cells in the population exhibit decreased levels of CD71 expression, and about 40% to about 100% of the red blood cells in the population exhibit decreased levels of fetal hemoglobin expression.

As used herein, a "deficiency of red blood cells," refers to a subject that has an amount of red blood cells that is from about 20% to about 900% lower than the amount of red blood cells in a subject having a normal amount of red blood cells; or has an amount of red blood cells that is from about 10 times to about 1,000 times lower than the amount of red blood cells in a subject having a normal amount of red blood cells.

Disorders characterized by a deficiency of red blood cells may include, without limitation, anemia (e.g., congenital anemia, aplastic anemia, pernicious anemia, iron deficiency anemia, sickle cell anemia, spherocytosis, hemolytic anemia, Aceruloplasminemia, Adenosine deaminase increased activity -ADA-, Adenylate kinase deficiency, Aldolase deficiency, Alpha-thalassaemia-trait or carrier, Atransferrinemia, Autosomal dominant sideroblastic anemia, Autosomal recessive sideroblastic anemia, Beta-thalassaemia-trait or carrier, Beta-thalassaemia major (and intermedia), CDA with thrombocytopenia (GATA I mutation), Compound heterozygous sickling disorders, Congenital acanthocytosis, Congenital dyserythropoietic anaemia type I, Congenital dyserythropoietic anaemia type II, Congenital dyserythropoietic anaemia type III, Delta Beta-thalassaemia, Diamond-Blackfan-Anemia, DMT1-deficiency anaemia, Familial hypoplastic anaemia, Fanconi anaemia, Gamma-glutamylcysteine synthetase deficiency, GLRX5-related Sideroblastic anaemia, Glucose phosphate isomerase deficiency, Glucose-6-phosphate dehydrogenase deficiency, Glutathione reductase deficiency, Glutathione synthetase deficiency, Haemoglobin C disease, Haemoglobin D disease, Haemoglobin E disease, Haemoglobin H disease, Haemoglobin Lepore, Haemoglobin M with anaemia, Hereditary Elliptocytosis, Hereditary persistance of fetal haemoglobin, Hereditary Spherocytosis, Hereditary Stomatocytosis, Hexokinase deficiency, Hydrops fetalis, Imerslund-Grasbeck-Syndrom, Iron—refractory iron deficiency anemia, Kearns-Sayre syndrome, Lecithin cholesterol acyltransferase deficiency, Mitochondrial myopathy sideroblastic anemia, thalassaemias, congenitale dyserythropoetic anemia, Pancytopenia with malformations, Paroxysmal nocturnal hemoglobinuria, Pearson's Syndrome, Phosphofructokinase deficiency, Phosphoglycerate kinase deficiency, Pyrimidine 5 nucleotidase deficiency, Pyruvate kinase deficiency, Sickle cell anemia, Sickle cell trait, Sideroblastic anemia associated with ataxia, SLC25A38-related Sideroblastic anemia, Thiamine-responsive megaloblastic anemia, Triose phosphate isomerase deficiency, Unstable haemoglobin, Wolfram Syndrome, and X-linked sideroblastic anemia), Gaucher's disease, hemolysis, neutropenia, thrombocytopenia, granulocytopenia, hemophilia, Hodgkin's lymphoma, Non-Hodgkin's lymphoma, B cell chronic lymphoma, Burkitt's lymphoma, Follicular-like lymphoma, diffused large B-cell lymphoma, multiple myeloma, acute myeloid leukemia, pre-B acute lymphocytic leukemia, pre-T acute lymphocytic leukemia, acute promyelocytic leukemia, refractory leukemia, or combinations thereof.

In certain instances, the disorder characterized by a deficiency of red blood cells results from (partially or fully) one or more of chemotherapy, chemical exposure, radiation therapy, and/or radiation exposure. In some embodiments, a population of red blood cells produced by any method of the present disclosure is co-administered with chemotherapy and/or radiation therapy or one or more protein of interest.

In some embodiments, a population of red blood cells of the present disclosure, and/or produced according to any method of the present disclosure is administered to or transfused into a s cells subject in need thereof, e.g., suffering from a loss of blood. A loss of blood may be the result of for example, internal or external bleeding, hemorrhage, trauma, or surgery, among others.

Treatment with one or more of the population of red blood cells of the present disclosure may also be useful for some infectious diseases associated with hemorrhage, such as but not limited to, families of RNA viruses (Arenaviridae, Bunyaviridae, Filoviridae, and Flaviviridae) that are linked to viral hemorrhagic fever. Examples of viral hemorrhagic fevers including but are not limited to, Lassa fever, Ebola, Marburg, Rift Valley fever, dengue, and yellow fever.

In embodiments where an immediate transfusion is needed, large quantities of red blood cells described herein and/or prepared according to any method of the present disclosure are administered to an individual. In other embodiments, sustained transfusion of the produced population of red blood cells is administered to the individual.

For treatment of some diseases, disorders, and/or conditions it is useful to administer red blood cells adapted to be a delivery system for one or more proteins of interest of the present disclosure. Any methods of adapting red blood cells to be a delivery system for proteis known in the art and disclosed herein may be used. Any disease disorder and/or condition known in the art and disclosed herein that would benefit from treatment with a disclosed protein of interest may be treated with the methods of the present disclosure, including, without limitation, subjects in need of hematopoietic growth factors, acute inflammatory conditions, cytokine storm conditions, clinical signs associate with cytokine storms, cancer, vascular dysregulation (e.g., frost bite, cancer-related vasoconstriction, or rheumatic joints, etc), acute cardiac infarctions, obstetrical uses during child delivery, acute and/or persistent migraine headaches, subjects in need of an immunity booster, subjects at high risk of having clots, subjects at elevated risk for pulmonary embolisms, cardiovascular diseases, immune diseases and/or disorder, and autoimmune diseases and/or disorders.

A "subject", "patient", or "host" to be treated by any of the methods of the present disclosure may be any human or non-human animal, such as any of the non-human animal disclosed herein, in need of such treatment. For example, the subject may have a deficiency of red blood cells, has an autoimmune deficiency, an anemia, cancer, or any other disease, disorder, or condition known in the art and disclosed herein that may be treated by red blood cells of the present disclosure and/or one or more proteins of interest of the present disclosure.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following Examples are merely illustrative and are not meant to limit any aspects of the present disclosure in any way.

EXAMPLES

The following examples describe the results of differentiating murine and human conditionally transformed long-term hematopoietic stem cell lines (clt-HSC) and protein transduced long-term hematopoietic stem cells (ptlt-HSC) to red blood cells (RBCs) in vitro.

The described approach facilitates the rapid production of populations of mature enucleated red blood cells that are optionally payloaded with one or more proteins of interest. In addition, generation of conditionally immortalized HSCs as the starting material allows for production and maintenance of universal donor blood, or a variety of major blood types as well as rare blood types and even personalized blood to resolve the problem of continuous blood shortage that patients with rare blood types have encountered over the years. Further, this technology can be used provide a constant, predictable supply of RBCs for transfusions that are derived from a defined source that can be certified to be pathogen-free and have an extended shelf life that will allow the establishment of a sufficient stock supply of RBCs.

Example 1: Generation of Conditionally Transformed Long-Term Reconstituting Hematopoietic Stem Cell Lines HSC-enriched bone marrow (BM) cells were prepared by treatment of mice with 5-fluorouracil (5FU) to ablate proliferating cells. Ex vivo BM cells from treated mice were further enriched for HSCs by culturing in medium containing IL-3, IL-6, and SCF, as previously described (Van Parijs et al., *Immunity* 11, 763-770, 1999). Cells were then subjected to three rounds of spin infection with pMIG-MYC-ER and pMIG-Bcl-2 viruses encoding oncoproteins as well as green fluorescent protein (FIG. 1A) (Refaeli et al., *J. Exp. Med.* 196, 999-1005, 2002). Variants of the pMSCV backbone were generated to encode the cDNAs for human MYC-ER or Bcl-2 as well as an IRES element and a reporter gene (EGFP). The resulting viruses generated bi-cistronic transcripts such that the level of reporter gene expression correlated with the level of expression of the first cDNA.

This treatment yielded a rate of retroviral transduction of approximately 33.7%, as determined by the frequency of green fluorescent protein (GFP) expressing cells 96 hours after the initial cultures were established (FIG. 1B). $10^5$ transduced HSCs were transplanted into cohorts of young, lethally irradiated, male C57/BL6 mice, and these mice were given weekly injections of 4-hydroxytamoxifen (4-OHT) in an amount of 1 mg/mouse/week, beginning 10 days after transplantation. Leukemias developed in over 90% of these mice with a consistent latency period of four weeks (FIG. 1C). The curve in FIG. 1C represents the percentage of surviving mice at a given point in time after the 4-OHT injections began (day 0 in the graph). All of the mice died uniformly from an AML-like leukemia after about 40 days (FIG. 1C). The data shown in FIG. 1 were from one experiment representative of 4 independent experiments. Development of leukemias required the continuous administration of 4-OHT.

Although the specific example provided is directed to the conditional immortalization of HSCs using Myc and Bcl-2, a similar approach would be used to incorporate other proteins of interest into HSCs, and optionally to control the expression of the proteins of interest. In some embodiments, the HSCs would include conditionally immortalized HSCs or protein transduced HSCs.

Example 2: Conditionally Transformed HSC Cell Lines Exhibiting a Lt-HSC Surface Phenotype To assess the phenotype and homogeneity of the cell lines developed in Example 1, the cellular expression of a variety of surface markers was analyzed. Cells were stained with antibodies to c-kit, Sca-1, CD34, and Flk-2. Additionally, the cells were stained for specific lineages: CD19 and B220 for B-lineage cells, Thy 1.2 for T-lineage cells, Mac-1 for myeloid cells, Gr-1 for neutrophils, and Ter-119 for red blood cell progenitors. As shown in FIGS. 1D-1F, the phenotype consistently observed was lineage negative (CD19-, B220-), but Sca-1$^+$, c-kit$^+$, CD34$^-$, and Flk-2$^-$. This pattern of marker expression is consistent with that previously reported for murine primary Lt-HSCs (Cheshier et al., *Proc. Natl Acad. Sci. USA* 96, 3120-3125, 1999). It was also noted that when ctlt-HSC cell lines were maintained in culture for extended periods of time, cellular c-kit expression decreased (FIG. 1E). This change is not associated with detectable changes in in vivo or in vitro function. Moreover, it was also found that c-Kit levels were restored when cells were cultured overnight without SCF, suggesting that SCF drives modulation of its receptor.

In particular, FIG. 1D shows ctlt-HSCs obtained from the bone marrow of leukemic mice soon after recovery. In these samples, approximately 42.2% of the cells were Sca-1$^+$ and c-kit$^+$; approximately 100% of the cells were CD34$^-$ and Flk-2$^-$; and approximately 99.8% of the cells were B220$^-$ and CD19$^-$ (FIG. 1D).

FIG. 1E shows ctlt-HSC cell lines that were maintained in culture for extended periods of time. In these samples, approximately 7.79% of the cells were Sca-1$^+$ and c-kit$^+$; approximately 51.2% of the cells were Sca-1$^+$ but c-kit$^-$; approximately 100% of the cells were CD34$^-$ and Flk-2$^-$; and approximately 99.4% of the cells were B220$^-$ and CD19$^-$ (FIG. 1E).

FIG. 1F shows normal, unmanipulated Lt-HSCs obtained from the bone marrow of wild type C57/BL6 mice. In these samples, only approximately 1.84% of the cells were Sca-1$^+$ and c-kit$^+$, approximately 8.03% of the cells were Sca-1$^-$ and c-kit$^-$, while the majority of the cells (approximately 88.5%) were negative for both Sca-1 and c-kit (FIG. 1F). Additionally, while approximately 100% of the cells were CD34$^-$, not all of the cells were Flk-2$^-$ (FIG. 1F).

Moreover, as shown in FIG. 1D, at an early stage of the process of establishing a ctlt-HSC cell line, the cells predominantly express high levels of c-kit and Sca-1, and do not express Flk-2, CD34, or lineage markers such as CD19 and B220. FACS analysis of an established ctlt-HSC cell line shows that once the ctlt-HSC cell line was expanded and cryopreserved, it retained a stable surface phenotype. These cells expressed high levels of Sca-1, but had reduced surface levels of c-Kit, and remained negative for Flk-2, CD34, B220, CD 19, and other lineage markers (FIG. 1E). The reduction of c-kit levels from the surface appears to be a result of continuous signaling, since they require SCF to retain their HSC-like phenotype. The results of the ctlt-HSC cell line were compared to normal, unmanipulated long-term HSCs from the bone marrow of wild-type C57/BL6 mice. As shown in FIG. 1F, the cells were stained with antibodies to c-kit, sca-1, Flk-2, and CD34, in order to compare the expression levels of the marker proteins from normal HSCs and from the ctlt-HSC cell lines.

Example 3: Rescue of Mice from Lethal Irradiation by Transplantation of ctlt-HSCs This example demonstrates that ability of ctlt-HSC cell lines to give rise to differentiated red blood cells (RBCs). This ability, as well as competence to maintain an active HSC compartment for extended periods of time, is critical to establish the identity of ctlt-HSC as Lt-HSC. The ability of the ctlt-HSC cell lines to reconstitute the hematopoietic compartment of lethal irradiated animals was examined in two ways. First, $10^3$ ctlt-HSC cells along were transferred with $3 \times 10^5$ whole bone marrow cells from Rag-$1^{-/-}$ mice into lethally irradiated young C57/BL6 mice. The addition of the "carrier" Rag-$1^{-/-}$ cells ensured that recipients could produce red blood cells during the period of time required for transferred HSCs to re-establish erythropoiesis. Supplementation with whole "carrier" bone marrow cells is generally used in conjunction with HSC reconstitution in order to allow transplant recipients to survive the loss of existing red blood cells that follows irradiation (Uchida et al., *J. Exp. Med.* 175, 175-184, 1992). Thus, the experiments were designed so that the only possible source of mature lymphoid cells was the transplanted ctlt-HSC cells. In a variation of this approach $10^3$ ctlt-HSC cells were transplanted into sublethally irradiated Rag-$1^{-/-}$ mice without carrier bone marrow. Mice receiving ctlt-HSC were euthanized 6 or 12 weeks after transplantation and lymph node, spleen, thymus, and bone marrow tissues were harvested for analysis of reconstitution. The resulting cell suspensions were stained with lineage specific antibodies to ascertain the extent of the reconstitution. The cells that developed from ctlt-HSCs were traced in vivo by virtue of the retrovirally encoded reporter gene, GFP.

The ctlt-HSC cell lines gave rise to bone marrow, thymus, spleen, and lymph node tissue with a high frequency of GFP$^+$ cells (70-80% of viable recovered cells) in bone marrow, thymus, spleen, and lymph nodes (FIG. 2A). These histograms were derived from the organs in one mouse exemplary of each within a cohort of five. In particular, approximately 78% of bone marrow cells were GFP+, approximately 72% of thymus cells were GFP+, approximately 80% of spleen cells were GFP+, and approximately 79% of lymph node (LN) cells were GFP+ (FIG. 2A).

Figure 2B:
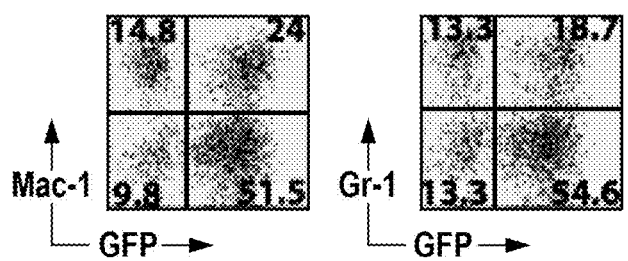
FIG. 2B depicts the detection of GFP$^+$ myeloid lineage cells in the bone marrow.

As shown in FIG. 2B, cells obtained from bone marrow were stained for Mac-1 and Gr-1. While not all of the myeloid cells found in the bone marrow expressed GFP, a significant portion was GFP$^+$ and hence was derived from the ctlt-HSCs. In particular, approximately 14.8% of the cells were Mac-1$^+$, with approximately 24% of the cells being both GFP$^+$ and Mac-1$^+$. Thus, approximately 61.8% of Mac-1$^+$ cells were derived from ctlt-HSCs (FIG. 2B). Additionally, approximately 32% of the cells were Gr-1$^+$, with approximately 18.7% of the cells being both GFP$^+$ and Gr-1$^+$. Thus, approximately 58.4% of Mac-1$^+$ cells were derived from ctlt-HSCs (FIG. 2B).

Figure 2C:
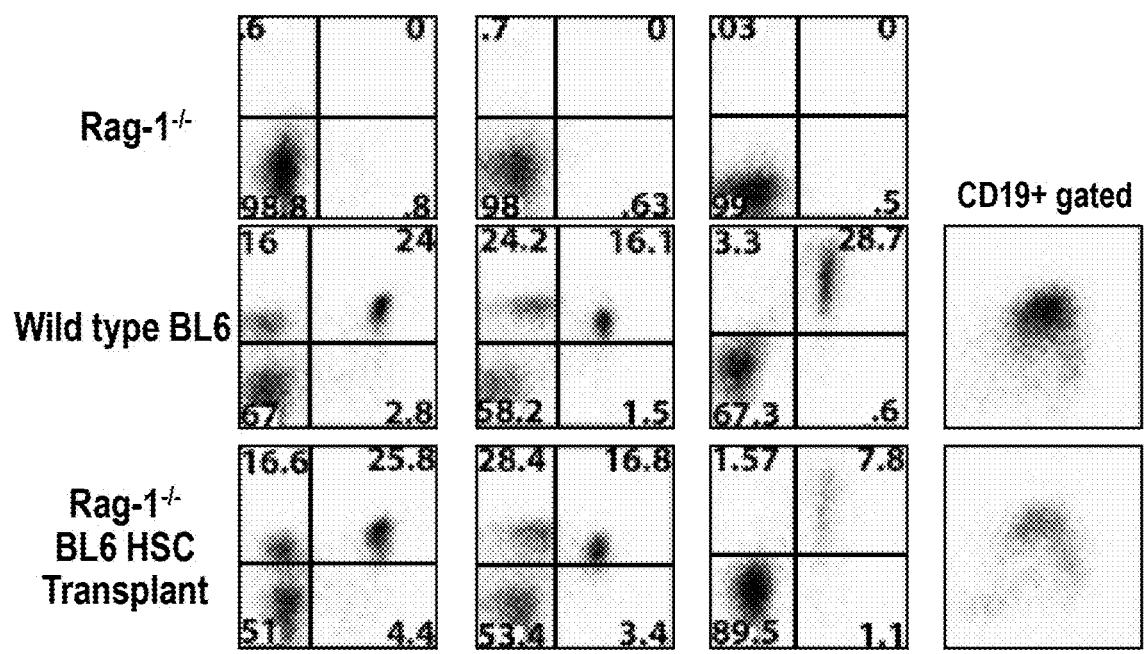
FIG. 2C depicts the analysis of peripheral, mature lymphocytes in the spleen.

As shown in FIG. 2C, cells obtained from spleen tissue of chimeric Rag-$1^{-/-}$ mice were analyzed by flow cytometry for the presence of mature T and B cells. Rag-$1^{-/-}$ mice and wild type mice were used as controls. The cells were stained for the presence of TCRαβ T cells that were either CD4 or CD8 single positive. In addition, cells were stained for the presence of CD 19$^+$ B cells that expressed IgM and IgD on their surface.

In particular, spleen cell samples from the chimeric Rag-$1^{-/-}$ mice had approximately 25.8% TCRαβ$^+$ and CD4$^+$ cells, approximately 16.8% TCRαβ$^+$ and CD8$^+$ cells, and approximately 7.8% IgM$^-$ and CD19$^+$ cells (FIG. 2C). This is compared to spleen cell samples from control Rag-$1^{-/-}$ mice that had no TCRαβ$^+$ and CD4$^+$ cells, TCRαβ$^+$ and CD8$^-$ cells, or IgM$^+$ and CD 19$^+$ cells; and spleen cell samples from wild type mice that had approximately 24% TCRαβ$^+$ and CD4$^+$ cells, approximately 16.1% TCRαβ$^+$ and CD8$^+$ cells, and approximately 28.7% IgM$^+$ and CD19$^+$ cells (FIG. 2C).

As can be seen in FIG. 2C, while the frequency of mature T-cells in the spleen was comparable to what can be found in wild-type, unmanipulated C57/BL6 mice, the development of B-cells was delayed.

It was then determined whether the ctlt-HSCs were capable of self-renewal following transplantation. Bone marrow cells obtained from the first set of ctlt-HSC transplant recipient mice were serially transplanted into a second cohort of lethally irradiated Rag-$1^{-/-}$ mice. Reconstitution was analyzed 6 or 12 weeks later.

As shown in FIG. 2D, the secondary transplantation was also able to give rise to mature lineages. Spleens were collected from the cohort of the chimeric mice, and single cell suspensions were prepared and used for FACS analysis. The frequency of mature T and B cells found in recipients, control Rag-$1^{-/-}$ mice, and control wild-type C57/BL6 mice were compared. The analysis showed the presence of mature CD4 and CD8 single positive TCRαβ T cells in the spleens at a frequency similar to that of the wild-type mice. CD19$^+$, IgM$^+$, and IgD$^+$ B cells were also present, albeit at a lower frequency than in the wild-type mice.

In particular, spleen cell samples from the secondary transplant recipient Rag-$1^{-/-}$ mice had approximately 41.3% TCRαβ$^+$ and CD4$^+$ cells, approximately 34.3% TCRαβ$^+$ and CD8$^+$ cells, and approximately 10.2% IgM$^+$ and CD19$^+$ cells (FIG. 2D). This is compared to spleen cell samples from control Rag-$1^{-/-}$ mice that had approximately 0.7% TCRαβ$^+$ and CD4$^+$ cells, approximately 0.4% TCRαβ$^+$ and CD8$^+$ cells, and 0.5% IgM$^+$ and CD19$^+$ cells; and spleen cell samples from wild type mice that had approximately 36.9% TCRαβ$^+$ and CD4$^+$ cells, approximately 37.7% TCRαβ$^+$ and CD8$^+$ cells, and approximately 16.9% IgM$^+$ and CD19$^+$ cells (FIG. 2D).

Seven successive serial transplants were subsequently performed and reconstitution of mature lineages from the initial $10^3$ ctlt-HSCs was observed with no evidence of tumor formation (Table 1). For this experiment, one million whole bone marrow cells were transplanted into lethally irradiated Rag-$1^{-/-}$ mice. Transplantation into Rag$1^{-/-}$ mice (Jackson Laboratory) was carried out as described for NSG mice except Rag$1^{-/-}$ mice received two subsequent doses (2-3 hours apart) of 450 rads of radiation just prior to injection the BM cells via the tail vein.

TABLE 1

| Transplant | # repeat mice | PB Avg T % | Std Dev | PB Avg B % | Std Dev |
|---|---|---|---|---|---|
| 1 | 8 | 29.300 | 14.106 | 15.190 | 12.834 |
| 2 | 9 | 48.910 | 17.396 | 15.230 | 16.619 |
| 3 | 4 | 36.900 | 7.230 | 6.955 | 5.206 |
| 4 | 3 | 21.560 | 9.415 | 7.683 | 4.657 |
| 5 | 4 | 32.930 | 13.968 | 7.140 | 1.373 |
| 6 | 7 | 16.051 | 5.582 | 0.7629 | 0.472 |
| 7 | 5 | 15.174 | 8.99 | 0.239 | 0.156 |
| 8 | 6 | 0.8 | 0.341 | 0.044 | 0.044 |

Example 4: Development of Human Ctlt-HSC Cell Lines and Chimeric Mice Bearing a Human Hematopoietic Compartment A method for conditionally immortalizing murine long-term HSCs has been previously developed. This approach was extended to conditionally immortalize human long-term HSCs so as to determine whether the mechanisms responsible for conditionally immortalizing murine HSCs are universally applicable to any HSCs or whether they are specific only to murine cells. In order to test this notion, the CD34$^+$ fraction of human adult bone marrow, or cord blood were obtained (initially from Stem Cell Technologies, Vancouver, BC, and then from the UCHSC cord blood bank). The cells were cultured in a specialized medium developed for human HSCs (Stemline II medium, Sigma, St. Louis, Mo.) supplemented with human recombinant IL-3, IL-6, and SCF. The human HSCs were then transduced with retroviruses encoding MYC-ER or Bcl-2, along with a GFP reporter. The retroviruses were the same pMSCV variants used in Example 1. However, these retroviruses were modified to be packaged with an amphotropic envelope in order to enable transduction into human cells. The transduced human HSCs were either transplanted into sublethally irradiated NOD/SCID/β2M$^{-/-}$ mice, or maintained in long-term cultures in vitro in the presence of the IL-3, IL-6, and SCF cytokine cocktail and 4-OHT. The two different approaches resulted in human ctlt-HSC cell lines. A set of human ctlt-HSC cell lines generated completely in vitro have been maintained in continuous culture for 14 months. The initial surface phenotypes of three retrovirally transduced cell lines showed a significant enrichment of the CD34$^+$ fraction. The cells had over a 10,000-fold enrichment of the CD34$^+$ fraction over initial frequencies of HSCs (FIGS. 3A-3C)

FACS analysis of was performed to determine the surface phenotype of three established human ctlt-HSC cell lines. As shown in FIG. 3, the expanded and cryopreserved human ctlt-HSC cell lines retained a stable surface phenotype that is represented. The transduced (i.e., GFP$^+$) cells were shown to express high levels of CD34 (FIGS. 3A-3C). In particular, the 3 different ctlt-HCS lines 5.23%, 5.09% and 4.03% GFP×CD34 double positive cells. These 3 ctlt-HSC lines were also 25.3%, 94.7, and 92.1 cKit×GFP double positive (FIGS. 3D-3F). These same 3 ctlt-HSC lines also remained very low for lineage markers CD45, Flk-2, and CD150. Shown is the flow cytometry characterization of 1 of the ctlt-HSC lines having 12.3% CD45×GFP double positive cells (FIG. 3G), 0.77% Flk-2×GFP double positive cells (FIG. 3H), and 0.55% CD150×GFP double positive cells (FIG. 3I); as well as B220, CD19, and other lineage markers (thy 1.2, Gr-1, Mac-1, and Ter-119). While there may be some heterogeneity in terms of surface marker expression levels among the three established different human ctlt-HSC cell lines, it is believed that the heterogeneity is the result of the previously reported inherent heterogeneity in the adult HSC compartment (McKenzie et al., Nat Immunol 7, 1225-33, 2006).

In order to examine the pluripotency of the established human ctlt-HSC cell lines, a known xenotransplant model was used (Dick et al., Stem Cells 15 Suppl 1, 199-203, 1997). This model involves the irradiation of NOD/SCID/β2M$^{-/-}$ mice, and the transplantation of ctlt-HSC into the irradiated mice. Cohorts of NOD/SCID/β2M$^{-/-}$ mice were sublethally irradiated (300 Rads) and 10$^4$ CD34$^+$ human ctlt-HSC cells were transplanted into the mice. The cells were maintained in culture for 10 weeks prior to transplantation. The mice were bled at either 6 or 12 weeks after transplantation. Lymphocytes present in the peripheral blood of the humanized chimeric NOD/SCID/β2M$^{-/-}$ mice were stained with antibodies specific to human leukocyte antigens. Specifically, the samples were stained with antibodies to CD19, CD20 and CD3.

As shown in FIG. 4, human B cells (hIgM$^+$ cells) and human CD45$^+$ T cells were detected in the peripheral blood of the chimeric NOD/SCID/β2M$^{-/-}$ mice, as compared to a control mouse that did not receive a stem cell transplant. In particular, peripheral blood of the control mouse had 0.075% hIgM$^+$/hCD45$^+$ cells (FIG. 4A), peripheral blood of a first chimeric mouse had 31% hIgM$^+$/hCD45$^+$ cells (FIG. 4B), peripheral blood of a second chimeric mouse had 77.1% hIgM$^+$/hCD45$^+$ cells (FIG. 4C), and peripheral blood of a third chimeric mouse had 49.5% hIgM$^+$/hCD45$^+$ cells (FIG. 4B).

Example 5: In Vitro Generation of Mature RBCs from Human Ctlt-HSCs

The ability of human ctlt-HSCs to generate mature RBCs in vitro was shown using the well-established surface markers of the erythroid lineage. Human ctlt-HSCs were incubated in liquid medium (Stemline II medium), and treated with EPO and IL-3 for 12 days. As shown in FIG. 5, H and E staining analysis 10 days after seeding the cultures with EPO and IL-3 showed a large number of enucleated cells in culture. Examination of enucleated cell populations by flow cytometry showed a population of cells expressing erythroid cell surface markers Glycophorin A, CD71, and CD41. Additionally, these cells lacked CD45 expression or expression of other non-erythroid lineage markers.

Figure 5C:
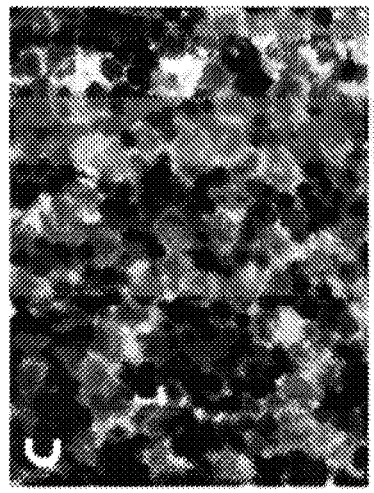
FIGS. 5A-5F depict human red blood cells generated in vitro using human ctlt-HSCs as the source.
Figure 5B:
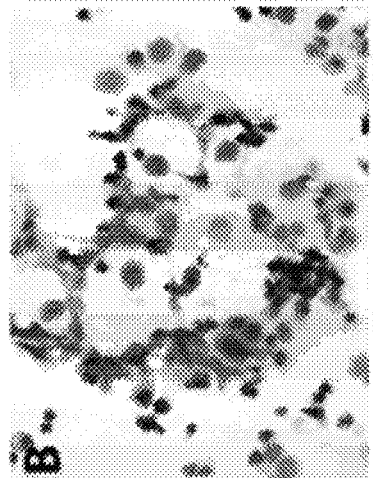
Figure 5A:
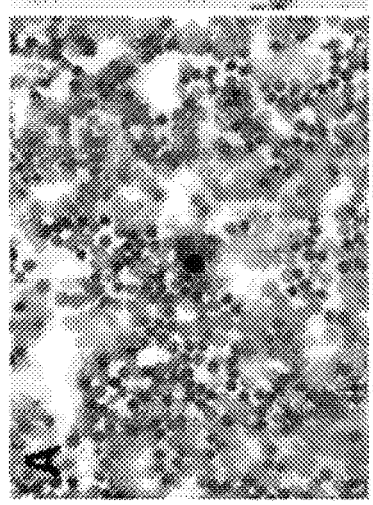
Figure 5F:
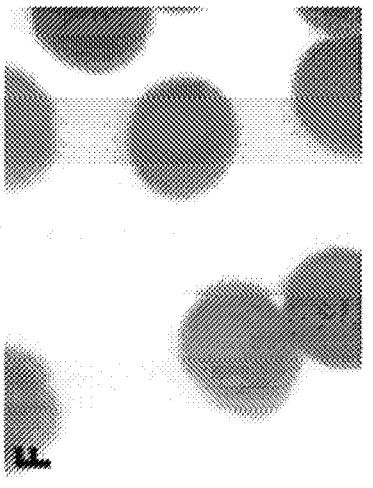
Figure 5E:
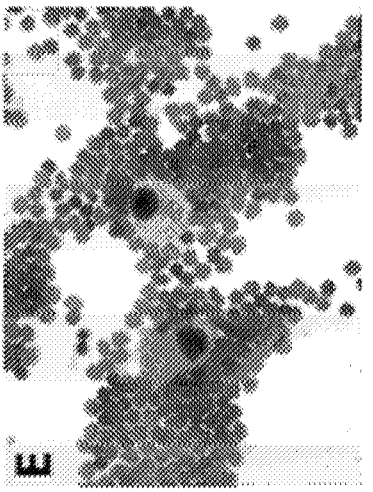
Figure 5D:
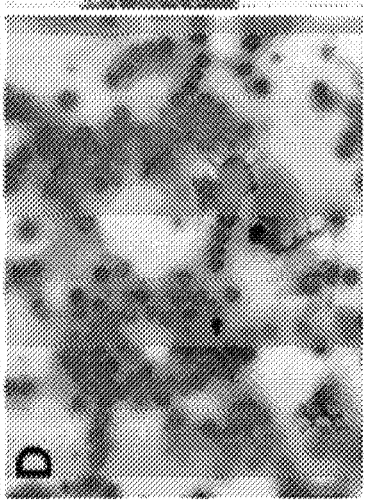

In particular, FIG. 5A shows H and E staining of control mouse peripheral blood. FIG. 5B shows H and E staining of primary human fetal cord blood. FIGS. 5C, 5D, and 5E show H and E staining of three conditionally transformed fetal cord blood cell lines that were treated for 12 days with IL-3 and EPO; and FIG. 5F shows a magnified view of the cells from FIG. 5E to show red blood cell morphology.

Example 6: In Vivo Functional Characterization of Ctlt-HSC-Derived Human RBCs The functionality of RBCs generated in vitro from ctlt-HSCs was determined by testing for their ability to rescue mice from lethal anemias. As human RBCs were being used, the mice chosen for these experiments were immunocompromised mice. Two different strains of immunocompromised mice were used for these studies. These two mice strains are generally used for such studies (Hogan et al., Biol Blood Marrow Transplant 3, 236-46, 1997). The two strains are NOD/SCID mice and Rag-1$^{-/-}$/γc$^{-/-}$ mice. The operating principle for the in vivo functional studies was to induce some form of anemia that would otherwise be lethal in the mice, unless they are provided with a functional RBC population.

One protocol that was used was adapted from Hiroyama (see, Hiroyama, *PloS One* 2, e1544, 2008). This protocol uses phenylhydrazine to induce anemia by hemolysis in vivo. The treated mice are then either given RBCs the following day, or no further treatment. A second injection of the drug follows 4 days later. If no functional RBCs are provided after the first round of chemically-induced hemolysis, the animals die soon after the second round and lethal challenge. If functional RBCs are provided, the mice are rescued from the lethal anemic challenge.

Ten days after initial seeding, $10^7$ human RBCs were derived in vitro from populations of human ctlt-HSCs using methods described herein. A cohort of NOD/SCID mice were obtained and treated with 80 mg/kg of phenylhydrazine on day 0. On day 1, the $10^7$ human RBCs were transferred by tail vein injection into half the cohort of treated mice. The second phenylhydrazine challenge was performed on day 6. The mice were then observed for survival for 9 days following the second phenylhydrazine challenge.

Figure 6:
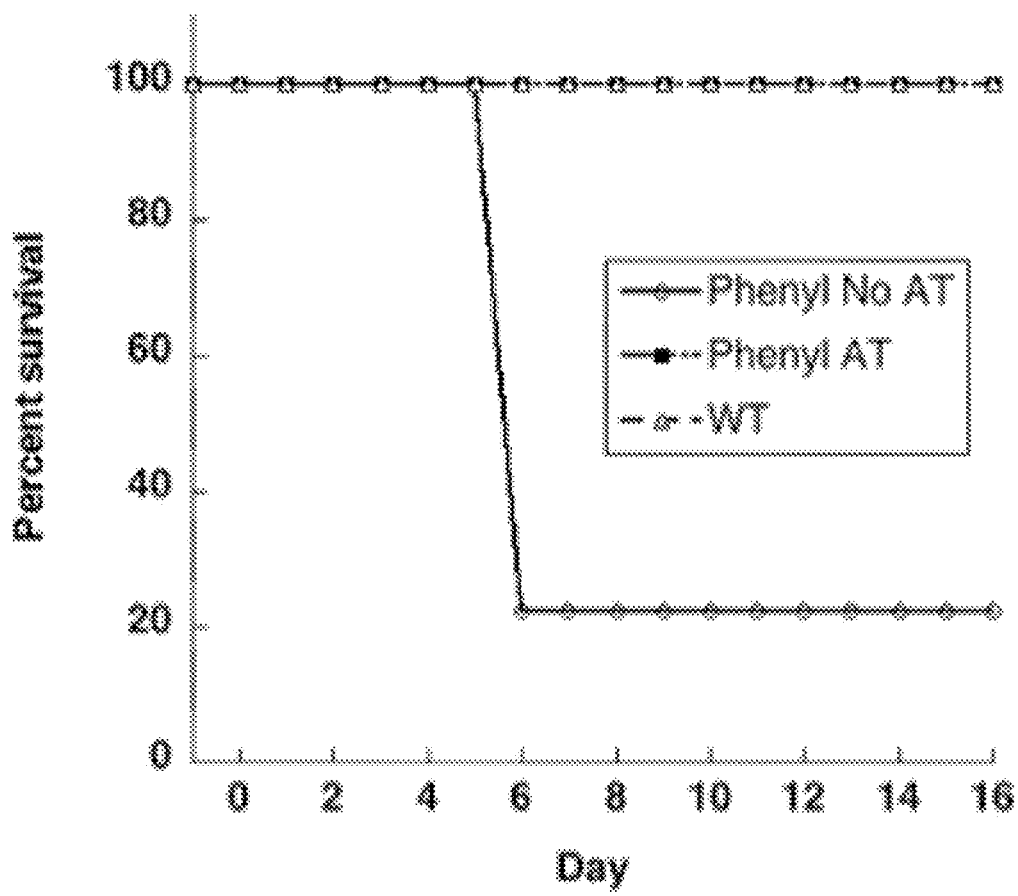

As shown in FIG. 6, the ctlt-HSC-derived human RBCs were able to rescue the mice from a chemically induced lethal anemia. In particular, only approximately 20% of the mice treated with phenylhydrazine (Phenyl) but not with human ctlt-HSCs-derived RBCs (No AT) survived, while 100% of the mice treated with both phenylhydrazine (Phenyl) and human ctlt-HSCs-derived RBCs (AT) survived (FIG. 6). This was comparable to wild type mice that were not treated with phenylhydrazine (WT).

Another method that was used to test the in vivo functionality of the ctlt-HSC-derived human RBCs included a protocol that is normally used to assess RBC homeostasis. In this instance, mice were bled extensively (5000, or about 17% total blood volume), and then left in the vivarium for observation. However, it was discovered that normal mice recovered from this injury without further intervention. It was thus reasoned that in order to delay the recovery of the RBC compartment from hemorrhagic shock, the erythroid progenitors would need to incapacitated.

Figure 7:
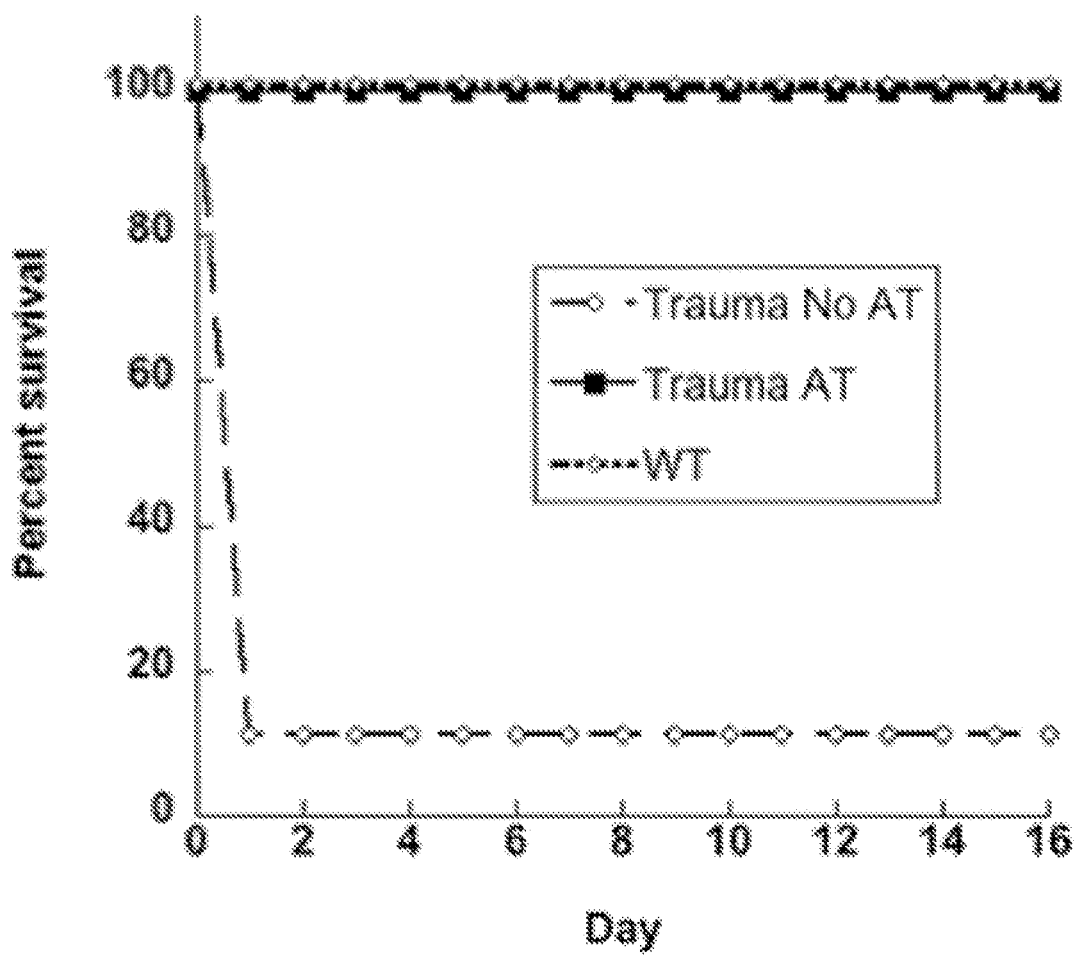

Accordingly, in order to affect the rate of RBC recovery, immunocompromised mice were sublethally irradiated with 450 Rads prior to 400 µl tail bleedings. In this instance, the mice died within 48 hours unless a transfusion of $1 \times 10^7$ erythroid cells was provided via tail vein injection. This form of lethal anemia was induced in a cohort of Rag-1$^{-/-}$/γc$^{-/-}$ mice, with half the cohort receiving $1 \times 10^7$ erythroid cells derived in vitro from populations of human ctlt-HSCs using methods described herein. The mice were monitored for survival for 9 days following induction of the acute anemia and erythroid cell transplantation. As shown in FIG. 7, in vitro ctlt-HSC-derived human RBCs were able to rescue the Rag-1$^{-/-}$/γc$^{-/-}$ mice from the combined injury-induced lethal anemia. In particular, only approximately 10% of the Rag-1$^{-/-}$/γc$^{-/-}$ mice survived the combined injury-induced lethal anemia (Trauma No AT), while 100% of the mice rescued with human ctlt-HSCs-derived RBCs (Trauma AT) survived (FIG. 7). This was comparable to wild type mice that were not subjected to the combined injury-induced lethal anemia (WT).

Example 7: Direct Protein Transduction of TAT-MYC and TAT-Bcl-2 Fusion Proteins into HSCs One of the risks associated with the approach of utilizing MYC-ER and/or Bcl-2-ER to generate ctlt-HSC cell lines is the random integration of viral sequences into the genome of the host cells. This is a concern, as the persistence of any nucleated ctlt-HSCs in the RBC preparations for transfusion may pose an unwanted risk for patients receiving those cells. The experiments described in this example demonstrate an alternative approach for generating ctlt-HSC cell lines without introducing viral sequences into the genome of host cells.

Figure 8A:
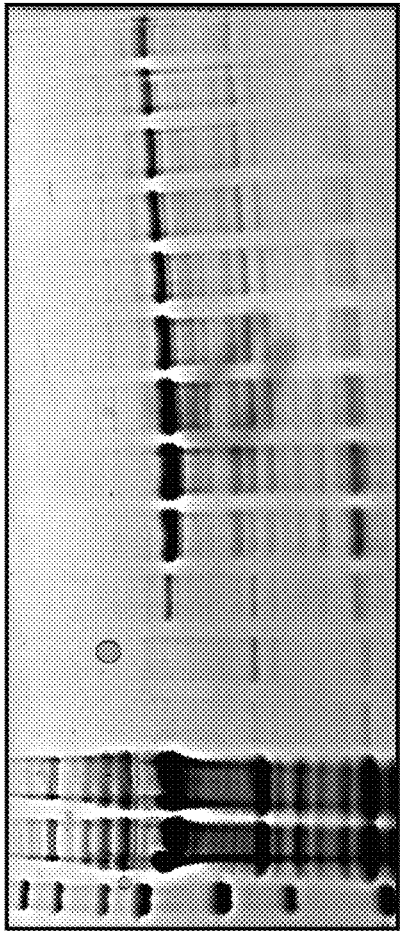
FIGS. 8A and 8B depict the expression and purification of recombinant TAT-MYC and TAT-Bcl2 protein for direct transduction of protein into cells.
Figure 8B:
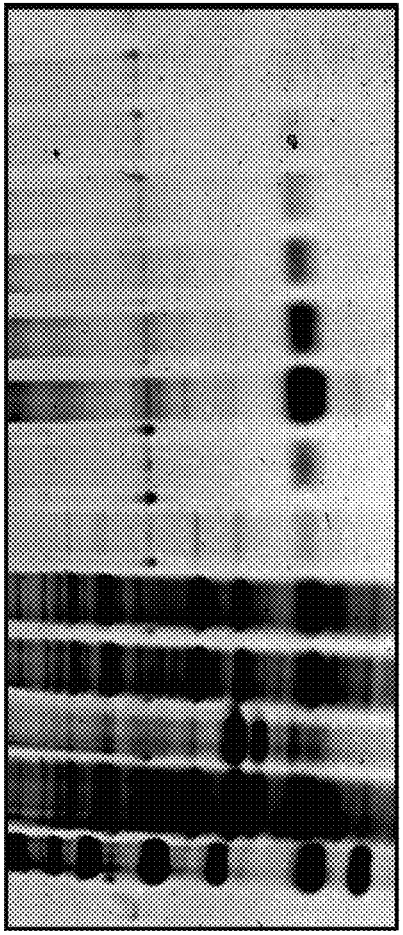

To introduce proteins into cells without genetic manipulation (i.e., viral transduction), this alternative approach relies on the ability of the HIV-1 TAT (TAT) protein to cross biological membranes and deliver a protein cargo into cells (Schwarze et al., *Trend Pharmacol Sci* 21, 45-8, 2000). A number of plasmids were generated that encode TAT fragments fused to either MYC or Bcl-2. The plasmids were then transformed into bacterial cells, and the cells were induced with IPTG during log-phase growth. The induced cells were collected 3 hours later and the proteins were purified on a Nickel column. Fractions were then analyzed by a Bradford assay for protein content, and run on an SDS-PAGE gel that was stained with Commassie Blue (FIG. 8). As shown in FIG. 8A, fractions E2-E11 contained TAT-MYC, with fraction E3-E5 containing the most TAT-MYC. As shown in FIG. 8B, fractions E1-E6 contained TAT-Bcl-2, with fraction E2 containing the most TAT-Bcl-2.

Figure 9A:
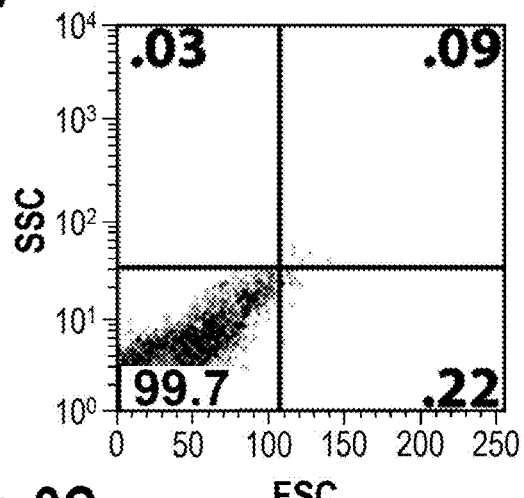
FIGS. 9A-9D depict FACS analysis showing the development of murine protein transduced long-term HSC cell lines (ptlt-HSCs).
Figure 9B:
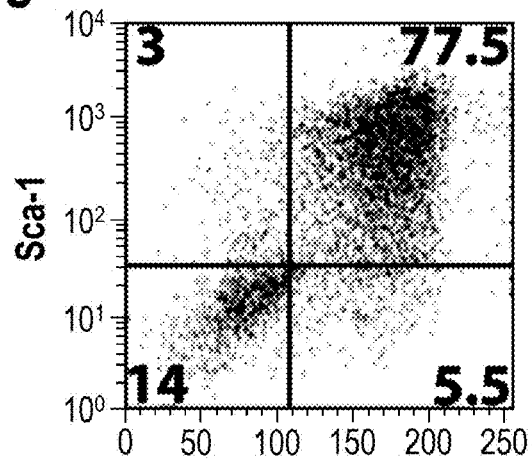
Figure 9C:
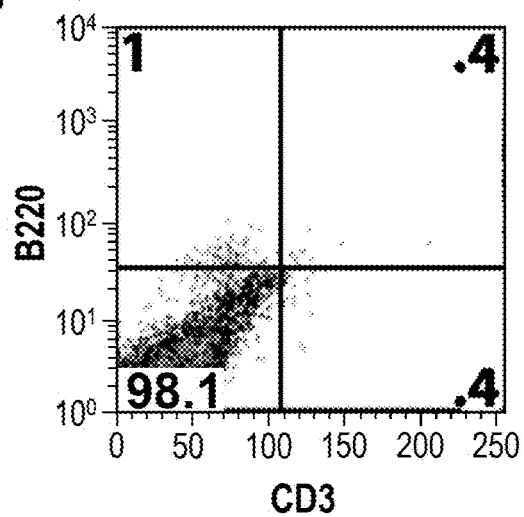
Figure 9D:
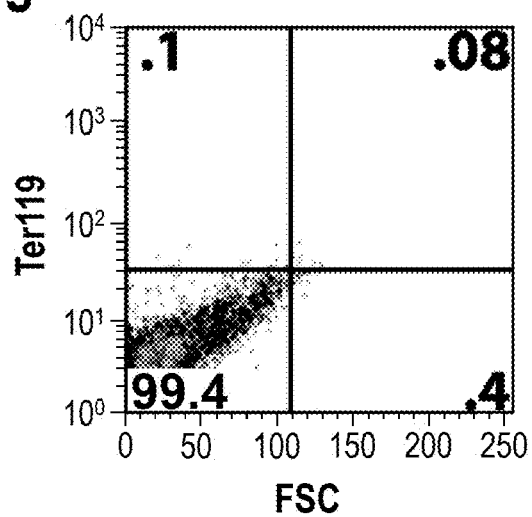

The notion of using TAT-MYC and TAT-Bcl-2 to directly transduce murine Lt-HSCs was tested in order to generate ptlt-HSC cell lines without retroviral gene transduction of MYC-ER and Bcl-2. 5FU-enriched HSCs were collected from the bone marrow of C57/BL6 mice and incubated in medium that was supplemented with recombinant IL-3, IL-6, and SCF. Additionally, the cells were incubated with purified recombinant 5 ug/ml TAT-MYC and 10 ug/ml TAT-Bcl-2 proteins that were prepared under low endotoxin conditions. The medium and TAT-Fusion proteins were replaced every 48 hours and the cells were maintained in culture for 21 days. An aliquot of the ptlt-HSC cell line was then used to characterize the phenotype of the murine ptlt-HSC cell line by flow cytometry. The cells were stained with antibodies against stem cell markers c-kit and sca-1, as well as lineage markers CD3, B220, and Ter119. As shown in FIG. 9, the c-kit$^+$, sca-1$^+$, lin$^-$ cell population in these cultures was preferentially expanded. This is a similar phenotype to what is seen in primary murine Lt-HSCs (Cheshier et al., *Proc. Natl Acad. Sci. USA* 96, 3120-3125, 1999). In particular, 77.5% of the cells were c-kit$^+$ and sca-1$^+$ (FIG. 9B), while 98.1% were CD3$^-$ and B220$^-$ (FIG. 9C) and 99.4% of the cells were Ter119$^-$ (FIG. 9D).

In order to characterize the in vivo pluripotency of the TAT-MYC and TAT-Bcl-2 derived ptlt-HSC cell line, $10^4$ cells were transplanted into sublethally irradiated Rag-1$^{-/-}$ mice. Four weeks post transplant, peripheral blood was collected from the recipient mice by venipuncture. The PBMCs were then assessed by flow cytometry for B cell markers B220 and IgM, and T cell markers CD4, CD8, and TCRβ. The stained cells were compared to unstained cells. As shown in FIG. 10, transplantation of the murine ptlt-HSC cell line into the sublethally irradiated Rag-1$^{-/-}$ mice resulted in reconstitution of the lymphoid compartment. In particular, approximately 10.7% of PBMCs were B220$^+$ and IgM$^+$ as compared to 0% in the control Rag-1$^{-/-}$ mouse (FIG. 10B); approximately 13.5% of PBMCs were CD4$^-$ and TCRβ$^+$ as compared to approximately 0.09% in the control Rag-1$^{-/-}$ mouse (FIG. 10C); and approximately 6.8% of PBMCs were CD8$^+$ and TCRβ$^+$ as compared to approximately 0.011% in the control Rag-1$^{-/-}$ mouse (FIG. 10D).

Example 8: Development of RBCs from Murine ptlt-HSCs Transduced with TAT-MYC and TAT-Bcl-2 Fusion Proteins Mature, anucleated RBCs were also derived from murine ptlt-HSC cell lines generated by transduction with TAT-MYC and TAT-Bcl-2 fusion proteins, similar to what was observed with human ctlt-HSCs (FIG. 5). In this experiment, murine ptlt-HSCs were cultured both in the presence and absence of IL-3, EPO, and TAT-MYC. After 10 days in culture, cell differentiation was assessed by H and E staining (FIG. 11). It was found that murine ptlt-HSCs treated with IL-3, EPO, and TAT-MYC resulted in a large frequency of fully enucleated murine RBCs (FIGS. 11B and 11C), while control cells did not differentiate into RBCs (FIG. 11A). In addition, the murine RBCs were characterized by flow cytometry and found to express increased levels of Glycophorin A and decreased levels of CD71.

Example 9: Generation of Human ptlt-HSC-Derived Red Blood Cells

The following example describes the in vitro production and characterization of human mature, enucleated red blood cells from a human protein transduced long-term HSC (ptlt-HSC) cell line. Advantageously, human red blood cells can be reliably produced in 10 days under culture conditions that do not require the use of genetically modified HSCs, animal serum, or animal feeder cells. Additionally, the produced red blood cells are fully differentiated and mature human red blood cells that are enucleated, express Glycophrin A (GPA), and decreased levels of CD71 and fetal hemoglobin. The CD71 marker is the transferrin receptor, which is normally expressed at high levels in erythrocyte (i.e., red blood cell) progenitor cells, but is down-regulated in mature erythrocytes. The GPA marker is commonly expressed at high levels in mature erythrocytes as a sign of membrane maturation.

In Vitro Production and Expansion of ptlt-HSC Cell Line

Transgenic and protein-transduced conditionally immortalized hematopoietic stem cells have been described previously (references). In this experiment, ptlt-HSC cell lines were produced using protein transduction with TAT-MYC and TAT-Bcl-2 fusion proteins as described previously. These fusion proteins contain a TAT peptide derived from the HIV-1 TAT (TAT) protein.

A unit of human cord blood was obtained from a local cord blood bank. The nucleated cell population from the cord blood was then isolated by diluting the cells 1:1 with phosphate buffered saline (PBS). 20 ml of diluted cord blood cells are gently overlaid onto 20 ml Ficoll-Paque Plus (Amersham Biosciences). The cells were then spun at 900× gravity for 60 minutes. After the spin, the buffy coat was removed with a glass pipette and washed twice with PBS. The cells were then resuspended and cultured in Iscove's Modified Dulbecco's Medium supplemented with 15% human plasma, 100 units per ml Penn/Strep, 20 ng/ml IL-3, 50 ng/ml IL-6, 50 ng/ml Stem Cell Factor, 20 ng/ml GM-CSF, 20 ng/ml TPO, 20 ng/ml Flt3-L, 5 μg/ml TAT-MYC and 5 μg/ml TAT-Bcl2.

Figure 12A:
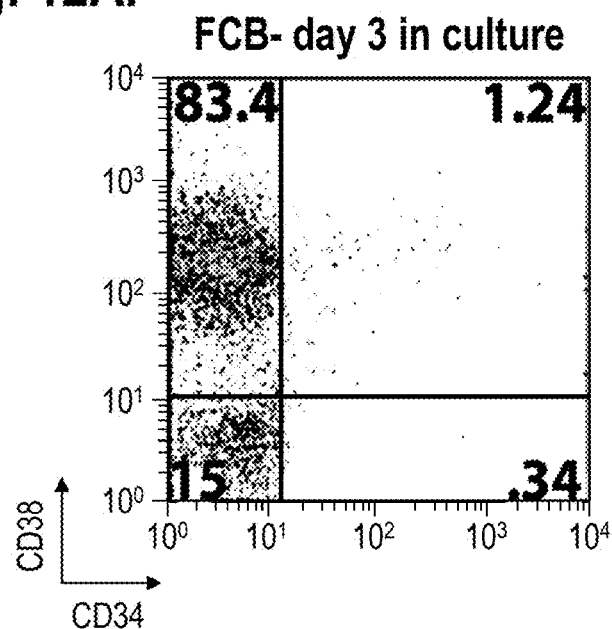
FIGS. 12A and 12B depict cord blood-derived HSC expansion in vitro.
Figure 12B:
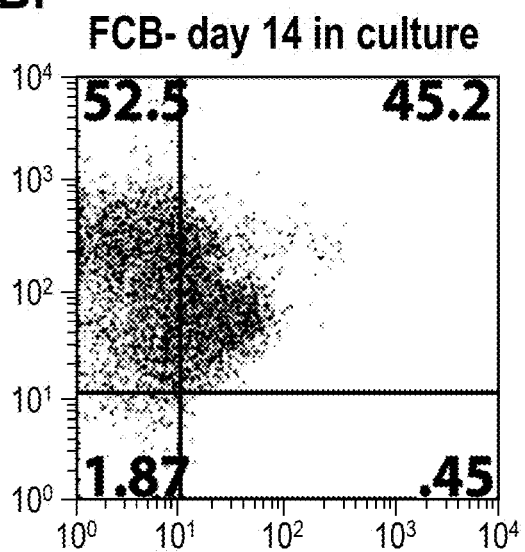

The initial cell population (Day 0) was 0.12% $CD34^+/CD38^{lo}$. After 3 days in culture, the frequency of $CD34^+/CD38^{lo}$ cells had risen to 1.24% (FIG. 12A). After 14 days in culture, 45.2% of the cell population was $CD34^+/CD38^{lo}$ (FIG. 12B). Moreover, there was a net increase in the total number of cells after 14 days in culture. The HSCs formed a cell line after being expanded in culture for 21 days in the presence of TAT-MYC and TAT-Bcl-2. This cell line was designated as a protein transduced long-term HSC (ptlt-HSC) cell line. This cell line was then used as the source of cells for red blood cell (RBC) differentiation and characterization.

In Vitro Production of ptlt-HSC-Derived RBCs

The in vitro produced human ptlt-HSCs were then used to produce human enucleated and mature RBCs. These ptlt-HSC-derived human RBCs were then characterized. FACS analysis was used to measure the expression levels and patterns of human Glycophrin A (GPA), human CD71 (transferrin receptor), and human fetal hemoglobin.

Red blood cell differentiation is induced by culturing the cord blood-derived ptlt-HSCs in DMEM medium supplemented with 3.2 ng/ml IL-3 and 100 units/ml EPO, as well as 15% human Plasma and 100 units per ml Penn/Strep. The cells were then cultured for at least 9 days.

As shown in FIG. 13, upon transfer of the ptlt-HSC culture to RBC differentiation conditions (IL-3 and EPO), the cells began to express GPA and CD71 at high levels after 4 days. Cells maintained in medium containing TAT-MYC and TAT-Bcl2, but lacking IL-3 and EPO, did not show these changes (FIG. 12). A sample of the culture was used for FACS analysis of cell surface expression of Glycophrin A (GPA) and CD71 (transferrin receptor). As shown in FIG. 13, ptlt-HSCs induced into the RBC differentiation program by culturing in the presence of IL-3 and EPO were stained for GPA and CD71 expression, and compared to unstained cells and ptlt-HSCs cultured in a neutral medium containing TAT-MYC and TAT-Bcl2, but lacking IL-3 and EPO. The results show that by day 4 of culturing with IL-3 and EPO, approximately 42% of cells were $CD71^+/GPA^+$ (FIG. 13C), as compared to the approximately 0.366% of $CD71^+/GPA^+$ cells in the unstained control (FIG. 13A) and the approximately 0.222% of $CD71^+/GPA^+$ cells that were cultured for 4 days in the neutral media (FIG. 13B).

Additionally, 9 days after transitioning the ptlt-HSCs into differentiation culture, the developing RBCs began to reduce their expression of the transferrin receptor (CD71), while retaining high levels of GPA on their surface (FIG. 14). This shift in the expression of CD71 was concurrent with an increase in the frequency of enucleated human RBCs in the culture (FIGS. 14 and 15). The cells were also stained for fetal hemoglobin.

FIG. 14 shows that as the developing RBCs transition from GPA/CD71 double positive to $GPA^-/CD71^{lo}$, they also switch from expressing high levels of human fetal hemoglobin to low levels of fetal hemoglobin. Without wishing to be bound by theory, it is believed that the $GPA^+/CD71^{lo}$ cells having low levels of fetal hemoglobin have correspondingly high levels of adult hemoglobin.

FACS analysis of cells from the RBC differentiation cultures was performed at three time points after induction (day 7, day 12 and day 22). The FACS analysis measured cell surface expression of GPA and CD71. The cells were also monitored for expression of fetal and adult hemoglobin. Primary human RBC obtained from peripheral blood were used as a positive control (FIG. 14; Control top row). The results show that on day 7, there were many GPA/CD71 double positive cells (FIG. 14; 1st panel top). The results also show that by day 12, the cells had mostly shifted to $GPA^+/CD71^{lo}$ (FIG. 14; 2nd panel top). The cells from day 12 also expressed high levels of fetal hemoglobin (FIG. 14; 2nd panel bottom). By day 22 in differentiation media the cells remained $GPA^+/CD71^{lo}$ but had downregulated expression levels of fetal hemoglobin and increase expression of adult hemoglobin (FIG. 14; 3rd panel top and bottom).

These dynamic changes of maturation marker expression were consistent with changes observed in bone marrow during normal RBC differentiation in humans and mice. In particular, after 7 days of culturing the ptlt-HSC cells in induction culture (IL-3 and EPO), approximately 60.9% of cells were GPA$^+$/CD71$^+$, approximately 1% of cells were GPA$^+$/CD71$^-$, and 71.4% of cells expressed fetal hemoglobin (FIG. 14B). After 22 days of culturing the ptlt-HSC cells in induction culture (IL-3 and EPO), the GPA$^+$/CD71$^+$ had transitioned to GPA$^+$/CD71$^-$. Similar to the control blood, 76% of the GPA positive cells expressed adult hemoglobin and only 20.3% of cells expressed fetal hemoglobin (FIG. 14; 2nd and 3rd panel bottom row).

Additionally, histological analysis of anucleation in culture was performed by staining day 3 and day 7 RBC differentiation culture samples with H and E (FIG. 15). Cells were laid on a slide using a cytospin apparatus. The slides were then stained with H and E, and photographs were obtained using an inverted microscope and light photography. The appearance of small, enucleated cells is observed as early as day 3 (FIG. 15A), with increased numbers seen by day 7 (FIG. 15B).

Example 10: Scale-up Production of ptlt-HSC-Derived Red Blood Cells

The following example describes scaling up the in vitro production of human ptlt-HSC-derived RBCs to clinically relevant levels of production.

Production of ptlt-HSC-Derived RBCs in Gas Permeable Bag

A gas-permeable bag was also used to scale up production of human ptlt-HSC-derived RBCs in vitro (FIG. 16).

Figure 16A:
FIGS. 16A and 16B depict human red blood cell production in a gas-permeable bag.
Figure 16B:
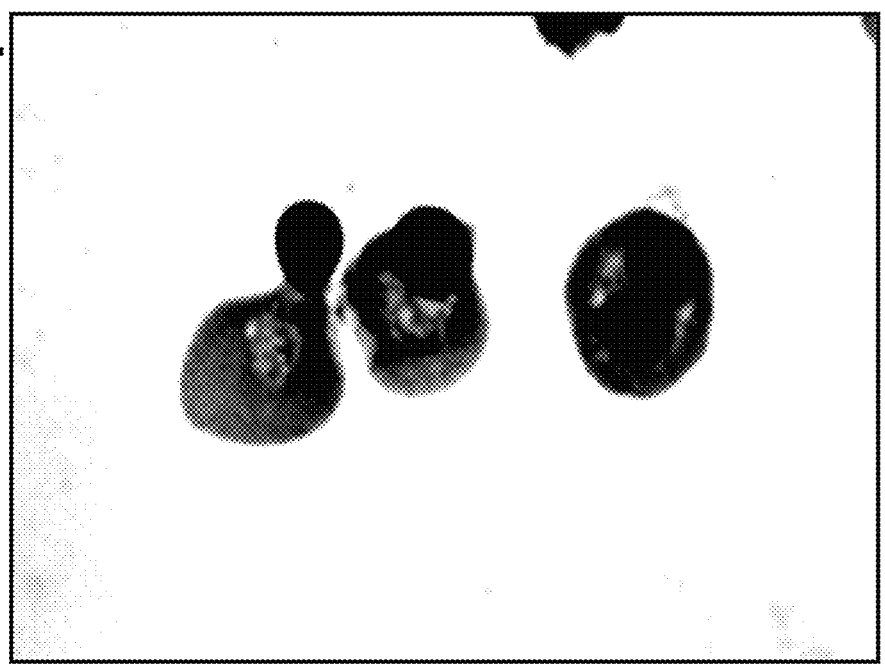

A gas-permeable bag having a Teflon-based coating on the cell contact side was optimized for the in vitro production of the ptlt-HSC-derived RBCs (FIG. 16A). The culture was started with human ptlt-HSCs that were incubated in neutral conditions, with TAT-MYC and TAT-Bcl-2, for 5 days in a gas-permeable bag (Origene). The culture was then switched into medium containing IL-3 and EPO in order to induce RBC differentiation. The photo shown in FIG. 16A was taken after 4 days of incubation in the RBC differentiation medium. FIG. 16B shows RBC maturation and anucleation in the gas-permeable culture bags. Cells were sampled from the bag shown in FIG. 16A, and fixed to a glass slide with a cytospin apparatus. The slide was then stained with H and E, and a photograph obtained using an inverted microscope and light photography.

Serial Passage of In Vitro ptlt-HSC Differentiation Culture

This example describes the length of time ptlt-HSCs cultured in RBC differentiation medium can continue to produce RBCs in vitro. This is an important factor in the development of a process for producing a clinically relevant amount of RBCs for human transfusion ($10^{11}$ cells/unit).

The first set of experiments involves the serial passage of ptlt-HSCs under erythroid differentiation conditions (i.e., cultured with IL-3 and EPO) in vitro. Ctlt-HSCs are plated at densities of $3\times10^6$, $10^6$, $3\times10^5$, and $10^5$ in a 6 well plate. The cells are cultured in Iscove's Modified Dulbecco's Medium supplemented with 10% human plasma, 100 units per ml Penn/Strep, 20 ng/ml IL-3, 50 ng/ml IL-6, 50 ng/ml Stem Cell Factor, 20 ng/ml GM-CSF, 20 ng/ml TPO, and 20 ng/ml Flt3-L. The starting ptlt-HSC population is then stained for human HSC and erythroid markers (GPA, CD71 and fetal hemoglobin). The cultures are monitored visually and by FACS analysis for the development of mature RBCs. An aliquot of the cells is removed 10 days after the initial cultures are set up, and spun through a Ficoll gradient in order to separate the nucleated live cells from the RBCs. Both fractions of cells are analyzed by FACS for expression of cell surface markers of HSC and erythroid lineages. A similar approach is also used for analysis of the cultures at the end of each 10-day cycle.

The nucleated cells present in the interphase of the Ficoll gradient are washed in fresh PBS and medium, and plated again under the same conditions. It was shown that at least one ctlt-HSC cell line was able to generate mature RBCs after three serial passages, starting with a single concentration of ctlt-HSCs. In some embodiments, ctlt-HSC lines are expanded and then exposed to red blood cell differentiation media in the presence of PTD-Myc. After red blood cells are separated in approximately 9 to 28 days, the remaining non-red blood cells are again placed in differentiation media, and red blood cells are separated in approximately 9 to 28 days. This process can be repeated at least 3 times, and is expected to continue indefinitely The results suggest that ptlt-HSC-derived erythroid progenitors can continue to produce RBCs for 2-4 passages.

Large-Scale Production of ptlt-HSC-Derived RBCs in a Culture Bioreactor System

This example describes testing four different systems for the large-scale in vitro production of mature, enucleated human RBCs from ptlt-HSCs.

Two systems were initially tested (a flexible plastic container designed for cell culture and a gas-permeable bag). The results with these systems showed that large-scale human RBC production can be optimized by making design changes in the tissue culture vessels and alterations to the culture conditions.

In order to consider more efficient approaches for the generation of large numbers of RBCs, the one step protocol described above for producing RBCs in vitro from human ptlt-HSCs is adapted to spinner flask bioreactors (e.g., Ambr micro bioreactor from TAP Biosystems, and Integrity PadReactor from ATMI), gas-permeable bags (Origene system), gas-permeable tissue culture flasks (Wilson Wolf G-rex Oxygen permeable flasks), or flexible plastic containers designed for cell culture (GE Wave system). These experiments determine the feasibility of large-scale production of human RBCs in vitro from ptlt-HSCs.

The basic protocol used to generate RBCs in vitro from human ptlt-HSCs begins with obtaining cord blood-derived HSCs. The nucleated cell population from umbilical cord blood is isolated by diluting the cells 1:1 with phosphate buffered saline (PBS). 20 ml of diluted cord blood cells are gently overlaid onto 20 ml Ficoll-Paque Plus (Amersham Biosciences). The cells are then spun at 900×gravity for 60 minutes. After the spin, the buffy coat is removed with a glass pipette and washed twice with PBS. The cells are then resuspended in Iscove's Modified Dulbecco's Medium supplemented with 10% human albumin, 100 units per ml Penn/Strep, 20 ng/ml IL-3, 50 ng/ml IL-6, 50 ng/ml Stem Cell Factor, 20 ng/ml GM-CSF, 20 ng/ml TPO, 20 ng/ml Flt3-L, 5 µg/ml TAT-MYC and 5 µg/ml TAT-Bcl2. The cells are maintained under these culture conditions for 12-30 days, depending on the degree of enrichment for the CD34+/CD38-population desired, as well as the total cell number required. Red blood cell differentiation is induced when the medium is changed to DMEM supplemented with 15% human albumin, 100 units per ml Penn/Strep, 20 ng/ml IL-3, and 3.2 units/ml EPO. Cells are cultured for an additional 11 days. Cells are then monitored for RBC differentiation by FACS using antibodies against GPA, CD71, and fetal hemoglobin. Histology staining for H and E is also performed.

The in vitro RBC production protocol is adapted for large-scale production in a spinner flask-based bioreactor that was previously used to grow large numbers of human hematopoietic cells derived from cord blood units. This system involves the use of two different spinner flask bioreactor systems. First, the Ambr micro bioreactor system (TAP Biosystems) is used. This is an apparatus that carries 10-15 ml cultures under spinner flasks conditions that mimic the characteristics of classical bioreactors, on a small scale. This instrument uses disposable micro reactor chambers and is controlled in an automated manner. One of the key advantages is that it allows for the simultaneous culture of 24 different conditions (*Genetic Engineering and Biotechnology News*, Nov. 1, 2010, Vol. 30, N. 19). This approach enables the quick optimization and adaptation of the in vivo conditions for RBC development to a bioreactor based format. Once the conditions are optimized, the process is transitioned to a large scale system (Integrity PadReactor, ATMI). The PadReactor system is a single use bioreactor that is composed of a drive unit, which allows the user to simultaneously grow cells in bags of different volumes, a mobile tank, that supports the bag in which the cells grow and is able to move into modular manufacturing spaces, as well as the bioreactor vessel, which is a single use cell bag that contains a paddle and allows for non-invasive mixing as the paddle rotates inside the bag. This system provides improved mixing with reduce shear forces, is amenable to suspension cells, and can grow the cells in a low volume.

Gas Permeable Bags

As described above, a basic gas-permeable bag (Origene) was used to produce RBCs in vitro. These bags have an interior Teflon coating that is also able to exchange gas from the entire surface area of the vessel. However, the system can be optimized to continuously provide medium changes once the cells reach a critical density. Accordingly, a new system can be designed that enables continuous flow of medium in a two-chamber gas-permeable bag system. In addition to minimizing cell loss, the system is also able to provide for a continuous flow system where medium and waste are perfused through the outer chamber. This system also allows the switching of ptlt-HSC cultures from HSC growth conditions to RBC differentiation conditions.

The ptlt-HSC are tested to determine whether the cells are able to propagate in the dual bag system. The bag is seeded with $10^7$ human ptlt-HSCs and maintained in Iscove's Modified Dulbecco's Medium supplemented with 10% human albumin, 100 units per ml Penn/Strep, 20 ng/ml IL-3, 50 ng/ml IL-6, 50 ng/ml Stem Cell Factor, 20 ng/ml GM-CSF, 20 ng/ml TPO, and 20 ng/ml Flt3-L along with TAT-MYC and TAT-Bcl-2. These are neutral conditions that allow the ptlt-HSC cells to propagate and retain their pluripotency. The initiating ptlt-HSCs are then stained with antibodies for human stem cell surface markers 10 days later and the magnitude of the expansion of the ptlt-HSCs is determined under these conditions.

Once the dual bag is tested in the context of supporting the expansion of ptlt-HSC under neutral conditions, a dual bag system will be seeded with ptlt-HSCs for RBC production. The pore size used is in the order of a SkDa cutoff, to prevent the RBCs from being flushed during the cycling of the medium. The dual bag system will be seeded with $10^7$ ctlt-HSCs and the cells will be cultured with Iscove's Modified Dulbecco's Medium supplemented with 10% human albumin, 100 units per ml Penn/Strep, 20 ng/ml IL-3, 50 ng/ml IL-6, 50 ng/ml Stem Cell Factor, 20 ng/ml GM-CSF, 20 ng/ml TPO, and 20 ng/ml Flt3-L along with TAT-MYC and TAT-Bcl-2. After 3 days in culture, the medium is switched to Iscove's Modified Dulbecco's Medium supplemented with 10% human albumin, 100 units per ml Penn/Strep, 20 ng/ml IL-3, and 50 ng/ml EPO. Samples are collected from the bioreactor every 3 days. This time frame is a result of the need to replenish some of the medium with cytokine containing medium. The collected cells are then analyzed by counting as well as by FACS and microscopy as described in the Examples above. The total output of RBCs is determined over the period of time (10-12 days) that the dual bag system is reported to support cell expansion. In addition, the fate of the ptlt-HSCs that were used to inoculate the cartridge on day 1 is also determined. Ideally, the ptlt-HSCs remain active for 2-4 rounds of culture in the dual bag system such that the RBCs can be harvested and the remaining ptlt-HSCs can be re-seeded in fresh medium in order to generate additional RBCs. Continuous centrifugation methods currently used for RBC separation from peripheral blood obtained from patients is used for the collection of the RBCs generated in the dual bag system.

Flexible Plastic Bag Containers

As described above, a flexible plastic bag container designed for cell culture (GE Wave) was also used to produce RBCs in vitro. However, the system can be optimized to reduce the premature and uncontrolled differentiation of the starting ptlt-HSC population.

A large number of ptlt-HSCs obtained from static cultures in standard vented tissue culture flasks is transferred into RBC differentiation medium when placed into the flexible plastic bag container. The rates of anucleation and kinetics of RBC maturation are examined by using FACS analysis to measure expression levels of CD71, GPA, and fetal hemoglobin. Histological analysis is also used to verify the state of maturation. The interior of the flexible plastic container is then coated with a small number of ptlt-HSCs that are expanded and switched to RBC differentiation medium in the same vessel.

Gas Permeable Tissue Culture Flask

In addition to experimenting with two different bag-based bioreactor systems, and a spinner flask apparatus, a gas-permeable tissue culture flask is tested for scaling up production of ptlt-HSCs and RBCs.

A gas-permeable flask (Wilson Wolf) is tested for both scaled production of a small number of ptlt-HSCs into a clinically relevant number of cells, and regulated differentiation of ptlt-HSCs into RBCs. The entire procedure is performed in a single flask. The flask provides cells with far better access to oxygen and nutrients than existing devices. Furthermore, the flask is much easier to use. The flask functions in a standard incubator and uses standard laboratory equipment. The bottom of the flask is made of a unique di-methyl silicone gas-permeable membrane that provides better oxygen permeability than any existing gas-permeable device (Lapteva and ad Ver, *Stem Cells Int*, Epub 2011, Se. 11). Cells gravitate to this gas-permeable membrane, where they are submerged under far greater medium depth than existing devices can allow. Under these conditions, the cells receive oxygen and nutrients on demand without being subjected to frequent feeding or any disturbances from medium mixing equipment.

Example 11: In Vitro and In Vivo Characterization of Human ptlt-HSC Cell Lines

The following example describes the characterization of the surface phenotypes, and in vitro and in vivo pluripotency of the human ptlt-HSC cell lines produced in Example 9. The experiments described in this section determine the lineage potential in vitro using standard methycellulose differentiation assays, and in vivo using xenotransplant mouse models.

A minimum of 4 human ptlt-HSC cell lines are used for the studies discussed in this example. The human ptlt-HSC cell lines selected are chosen based on the following four criteria. First, the cell lines have a surface phenotype that resembles primary human Lt-HSCs (CD34$^+$, CD133$^+$, CD48$^+$, CD150$^+$, lin$^-$). Second, the human ptlt-HSCs propagate vigorously in culture under the conditions described in Example 9, and retain a dependency on exogenously added TAT-MYC for proliferation in vitro. Third, the human ptlt-HSCs are able to recover from cryopreservation in a prompt manner while retaining their surface phenotype and growth characteristics. Fourth, one cell line is selected from each of the following genotypes: A rh–, B rh–, AB rh–, 0 rh– in order to generate a panel of human ptlt-HSCs that give rise to the major forms of RBCs that are used clinically.

Ten, $10^2$, or $10^3$ human ptlt-HSC cell lines are seeded in methycellulose differentiation medium as previously described (Dick et al., *Stem Cells* 15 Suppl 1, 199-203, 1997). Medium that is supplemented with cytokines intended to push HSC differentiation toward the myeloid lineages (Dick et al., *Stem Cells* 15 Suppl 1, 199-203, 1997), myeloid-erythroid lineages, or pre-B-cell lineage (Cheshier et al., *Proc. Natl Acad. Sci. USA* 96, 3120-3125, 1999; and Hogan et al., *Biol Blood Marrow Transplant* 3, 236-46, 1997) is specifically used. The plates are then evaluated for colony formation in terms of number of colonies, morphology, and kinetics of colony development as a measurement of precursor frequency. ptlt-HSC cell lines that are pluripotent, as defined by their ability to give rise to specific colonies in each of the different conditions tested, are then identified.

Once it has been demonstrated that the ptlt-HSC cell lines in question are competent in their ability to give rise to multiple hematopoietic lineages in vitro, their pluripotency is examined in vivo. These ptlt-HSC cells are then used for transplantation into cohorts of 10 sublethally irradiated NOD/SCID mice, as previously done with primary human Lt-HSCs (Dick et al., *Stem Cells* 15 Suppl 1, 199-203, 1997; and Hogan et al., *Biol Blood Marrow Transplant* 3, 236-46, 1997). The irradiated mice are given transplants of $10^4$ ptlt-HSCs that have been maintained in the culture conditions described in Example 9. The mice are then bled by venipuncture in order to collect peripheral blood samples for analysis. The red blood cells are lysed, and the PBMCs are stained for human CD3 and CD19. Once human lymphoid cells are detected in the peripheral blood, the mice are euthanized by $CO_2$ asphyxia and cervical dislocation. Lymph nodes, spleen, thymus, and bone marrow are then harvested from the mice. Single cell suspensions are generated from the organs and the cells are stained with antibodies specific for human CD3, CD19, CD4, CD8, Mac-1, Gr-1, and Ter-119. The detection of multiple lineages of human hematopoietic cells confirms the pluripotency of the human ptlt-HSC cell lines. Two controls are included. For the negative control, non-manipulated mice, or mice that are sublethally irradiated and not given a transplant of human ptlt-HSC cells are used. As a positive control, a cohort of mice that are sublethally irradiated and transplanted with the human ctlt-HSC cell line generated in Example 4 are used.

Example 12: Analysis of Hemoglobin Types Expressed in Ctlt-HSC-Derived Human RBCs The following example describes the differentiation state (e.g., the extent of differentiation into the erythroid lineage, and the developmental state) of the human red blood cells (RBCs) produced in Example 9, by determining the specific kind of hemoglobin (fetal, adult, etc.) of the RBCs.

The nature of the hemoglobins expressed in the human RBCs generated in Example 11 using methods described herein is determined by two parallel approaches. First, mRNA is obtained from the RBC precursors present in the cultures used to generate human RBCs. In addition, primary human RBCs obtained from a healthy, anonymous volunteer are also used as a positive control. Human ctlt-HSCs are incubated in Stemline II medium supplemented with IL-3 and EPO, as described in Example 7. Fractions of cells are collected every 48 hours for 10 days. A fraction of the cells are used for flow cytometric analysis for cell surface phenotype and erythroid differentiation markers. The cells are stained for human CD71 and GPA. The remainder of the cells in the sample is used to obtain mRNA in order to generate cDNA. The resulting cDNAs are used as templates for semiquantitative RT-PCR (Q-PCR) for three globin genes (hemoglobin α, β, and γ), and two housekeeping genes ((β-actin and GAPDH). Sets of primers are used to amplify hemoglobin transcripts that are normally expressed in fetal RBCs. mRNA from the positive control is also isolated. It is expected that the human RBCs and their progenitor cells generated in vitro from ctlt-HSCs express adult globin genes. The mRNA results are confirmed by using monoclonal antibodies and FACS analysis.

The presence of hemoglobin proteins in the ctlt-HSC-derived humans RBCs are confirmed by perfusion chromatography and HPLC, as previously described (Honig et al., *J Biol Chem* 265, 126-32, 1990). The RBCs obtained from in vitro cultures described above are collected and washed 3 times in 0.9% NaCl, then suspended in 9 volumes of water, lysed with saponin and clarified by centrifugation at 600×g. Globin mass spectra is obtained using a MALDI-TOF (matrix assisted laser desorption/ionization time-of-flight) mass spectrometer (Bruker Omniflex), as described previously (Honig et al., *Am. J. Hematol* 34, 199-203, 1990). ZipTips is purchased from Millipore and packed with C18 and C4 resins to prepare the solutions for MS analysis of peptide and protein, respectively. Cyano-4-hydroxycinnamic acid (CHCA) and sinapinic acid (SA) are used as the matrix for peptide and protein, respectively. Aliquots (1.3 ml) of the matrix solution (3-10 mg CHCA or SA in 1 ml aqueous solution of 50% acetonitrile containing 0.1% TFA) are used to elute the peptide/protein from ZipTips and spotted onto MALDI-TOF target. A LC/MS/MS system (Agilent series 1200 HPLC modules, Agilent HPLC Chip interface, Agilent 6510 Quadrupole Time-of-Flight mass spectrometer) equipped with a 337 nm pulsed nitrogen laser is used to analyze the samples. External mass calibration is performed using the peaks of a mixture of pigeon cyctochrome c at m/z 12362, apomyoglobin at m/z 16952 and adolase (rabbit muscle) at m/z 39212.

The mRNA levels for globin genes that are normally expressed in fetal RBCs are also examined to compare against the globin genes expressed in the ctlt-HSC-derived humans RBCs.

Example 13: Analysis of Oxygen-Binding Characteristics of Ctlt-HSC-Derived Human RBCs The following example describes the functional nature of the hemoglobin proteins expressed in the human red blood cells (RBCs) produced in Example 9, by measuring the Oxygen equilibrium curves in the RBCs.

Oxygen equilibrium curves as are measured as previously described (Honig et al., *Am. Hematol* 34, 199-203, 1990; Maurer et al., Nature 227, 388-90, 1970; and Lee et al., *Rapid Commun Mass Spectrom* 19, 2629-35, 2005). The method that is used is a continuous method using a double-wavelength spectrophotometer (Hemox analyzed, TCS). The RBCs are suspended in 50 mM bis-Tris buffer containing 140 mM NaCl at 37° C. and pH 7.4. The binding properties of hemoglobin are studied by flash photolysis of solutions in 1-mm optical cuvettes. Briefly, the kinetics of the rebinding of CO to intracellular hemoglobin tetramers is analyzed at 436 nm after photolysis with a 10-ns pulse at 532 nm, as previously described (Honig et al., *Am. J. Hematol* 34, 199-203, 1990; Maurer et al., Nature 227, 388-90, 1970; and Lee et al., *Rapid Commun Mass Spectrom* 19, 2629-35, 2005).

Oxygen binding characteristics of the ctlt-HSC-derived human RBCs is also analyzed.

Example 14: Analysis of Cell Shape and Flexibility of ctlt-HSC-Derived Human RBCs The following example describes the determination of whether the human red blood cells (RBCs) produced in Example 9 can elongate and function in the context of the microvasculature in vivo by measuring the flexibility of the RBCs.

The deformability of the ctlt-HSC-derived human RBCs and primary RBCs obtained from peripheral blood is examined as previously described (Kaul et al., *Am J Physiol Heart Circ Physiol* 295, 2008). Briefly, RBCs preparations are obtained from the in vitro ctlt-HSC cultures described in Example 9, and from peripheral blood from a healthy adult are passed through a deleukocyting filter (Leucolab LCG2, Macopharma). The enucleated cells are then examined by ekacytometry. The RBCs are suspended in 4% polyvinylpyrrolidine solution and then exposed to an increasing osmotic gradient in the ektocytometer (Technicon, Bayer) (from 60 to 450 mosM). The change in the laser diffraction of the RBCs in this setting is recorded. The photometric measurement produces a signal termed the deformability index (DI). Analysis of the DI curves provides a measure of dynamic deformability of the cell membrane as a function of osmolarity at a constant applied shear stress of 170 dynes/cm2. The DI max is related to the mean surface area of the cells.

Example 15: Analysis of Lifespan of Ctlt-HSC-Derived Human RBCs

The following example describes the average lesion-free lifespan of the human red blood cells (RBCs) produced in Example 9 in order to ascertain if they are equivalent to primary human RBCs. The average lifespan of a primary human RBC is estimated at 120 days. The shelf life of RBC concentrates for clinical use is generally 28 days, due to the variation of ages of the RBCs collected from peripheral blood. It is believed that the ability to synchronize production of RBCs in vitro enables a significant increase in the shelf life of RBC concentrates for clinical use.

In some embodiments, red blood cells are produced using the methods described herein over 7 to 30 days. In some embodiments, red blood cells produced using the methods described herein are collected on or about the same day, for example, on or about Day 9, Day 10, Day 11, Day 12, Day 13, Day 14, Day 15, Day 16, Day 17, Day 18, Day 19, Day 20, Day 21, Day 22, Day 23, Day 24, Day 25, Day 26, Day 27, or Day 28. The red blood cells are then assessed for viability over time using known methods, including those described herein.

In some embodiments, red blood cells would be maintained in red blood cell storage media. In some embodiments, the red cell storage media further includes Bcl-2, optionally PTD-Bcl-2. Bcl-2 (optionally PTD-Bcl-2 may be provided as an initial bolus, may be provided continually, or provided at intervals (e.g. every 24 hours, 48 hours, 72 hours, 96 hours, etc.). Concentrations of Bcl-2 provided may include 0.5 ug/ml to 100 ug/ml or more. In some embodiments, 1 ug/ml, 5 ug/ml, 10 ug/ml, 25 ug/ml, or 50 ug/ml of Bcl-2 (optionally TAT-Bcl-2) may be provided to the storage media. The red blood cells are then assessed for viability over time using known methods, including those described herein.

In order to determine the average lesion-free lifespan of ctlt-HSC-derived human RBCs, three criteria are used that can be quantified and measured by flow cytometry. First, the number of viable RBCs present in a culture is counted over a period of time, in order to measure the attrition rate from a known starting number. Second, the levels of CD47 on the surface of the ctlt-HSC-derived human RBCs are measured. Third, the levels of phosphatidylserine (PS) exposed on the surface of the ctlt-HSC-derived human RBCs are measured. All three criteria are measured using a flow cytometric approach. The forward and side scatter characteristics are used in combination with a vital-dye (LDS-751) in order to ascertain the number of viable, enucleated RBCs present in a culture at a particular point in time. The levels of CD47 present on the surface of RBCs are measured using a monoclonal antibody that is conjugated to the fluorochrome APC. The levels of PS exposed on the surface of the RBCs are measured with Annexin V-FITC, as previously described (Holovati et al., *Transfusion* 48, 1658-68, 2008).

Cultures of ctlt-HSCs are set up in the presence of IL-3 and EPO, as described in Example 9. The RBCs appear first on days 8-10 of the culture. RBCs from the ctlt-HSCs cultures are collected and passed through a deleukocyting filter (Leucolab LCG2, Macopharma). Primary human RBCs are obtained from a healthy anonymous donor. Both sets of cells are set up in culture in Stemline II medium, and the cultures are maintained at 37° C. Aliquots of cells are also stored at 4° C. in a citrate buffer that is normally used to store RBC concentrates (Lagerberg et al., Transfusion 47, 2242-9, 2007). Each set of conditions are established with $10^{10}$ cells.

In order to determine the lesion-free survival of the RBCs from either source, an aliquot is removed every 4 days and the cells are stained with the vital dye (LDS-751), anti-human CD47-APC, and Annexin V FITC. The cells are then analyzed using a BD FACSCalibur Flow cytometer. Aliquots are continuously analyzed until there are no more viable cells left in the specific condition, or for 120 days, whichever comes first. The RBC cultures maintained in Stemline II medium at 37° C. have their medium replenished every 7 days.

Example 16: Comparison of Methods for RBC Differentiation from 5-FU Treated Bone Marrow The following example describes the production of red blood cells from bone marrow of mice.

C57BL/6 (Jackson labs #003548) mice are intravenously injected with 5 mg 5-fluorouracil (Genera Medix Cat # NDC 10139-063-11) in 200 ul Dulbecco's PBS. Five days later, bone marrow cells are harvested from the tibia and femur of the C57BL/6 mice.

Pellet harvested bone marrow cells, and resuspend in 5 ml sterile TAC buffer (135 mM $NH_4CL$, 17 mM Tris Ph 7.65) to lyse the red blood cells. Allow cells to sit in TAC buffer for 1-2 min and then spin cells down at 1200 RPM for 5 min. Wash the cells with 25 ml of D10 media. Resuspend cell pellet in 10 ml of BM Medium (500 ml bottle DMEM containing 90 ml heat inactivated FBS, 6 ml Penn/Strep (Gibco Cat #15140), 6 ml MEM NEAA (Gibco Cat #11140), 6 ml L-glutamine (Gibco Cat #25030), 6 ml Hepes (Gibco Cat #15630), and 60 ml of cytokine cocktail (IL3, IL6, and SCF).

These resuspended cells are counted and seeded in wells of a 24 well cluster dish at a density of $1\times10^6$ cells per well in 1 ml of medium. Note: if 5FU treatment works each mouse should yield $1$-$1.2\times10^6$ BM cells compared to $10\times10^6$ in an untreated mouse.

Each well containing 1 ml of media is treated with 5 units of TAT-MYC and 5 units of TAT-Bcl2 diluted in 20 ul human serum albumin (Grifols NDC 68516-5216-2). Media is changed every 2 days to refresh cytokines and TAT-fusion proteins. Sca-1×cKit population will begin to dominate the culture beginning around days 14-17.

Seed $2\times10^5$ of the Sca-1 xcKit cells per well of a 6 well plate. Replace the BM media with RBC differentiation media #1 (IMDM supplemented to 15% heat inactivated FBS, 10% IL3 containing media, and 100 units per ml EPO, 100 mM dexamethasone and 25 ug/ml Holo-Tranferrin). To separate test wells, add the following test fusion proteins: 5 units per/ml of TAT-MYC, 5 units per/ml of TAT-Bcl-2, or both 5 units per/ml of TAT-MYC and 5 units per/ml of TAT-Bcl-2.

The RBC differentiation media #1 and fusion proteins are refreshed every 2 days for the first 6 days. RBC media #1 is then replaced with RBC media #2 (IMDM supplemented to 15% heat inactivated FBS, 10% IL3 containing media, and 100 units per ml EPO and 25 ug/ml Holo-Tranferrin). Continue to refresh RBC media #2 and fusion proteins every 2 days until RBCs appear, about 9-12 days.

Figure 17A:
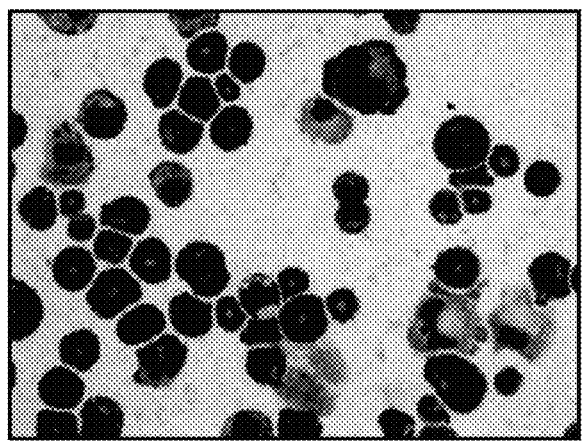
FIGS. 17A-17E depict mouse red blood cell production from bone marrow cells.
Figure 17B:
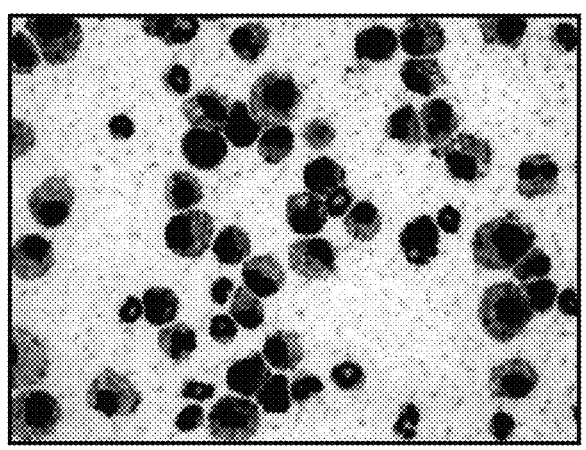
Figure 17C:
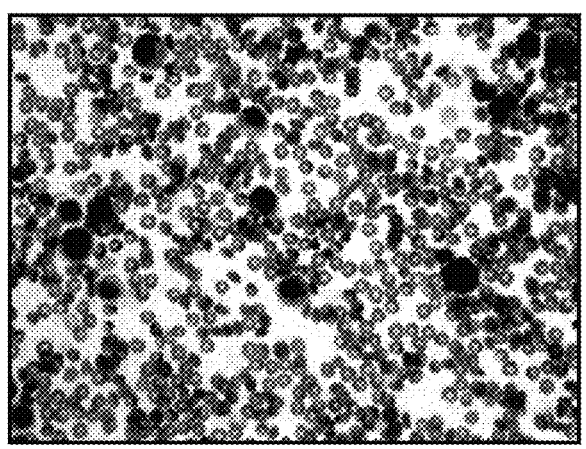
Figure 17D:
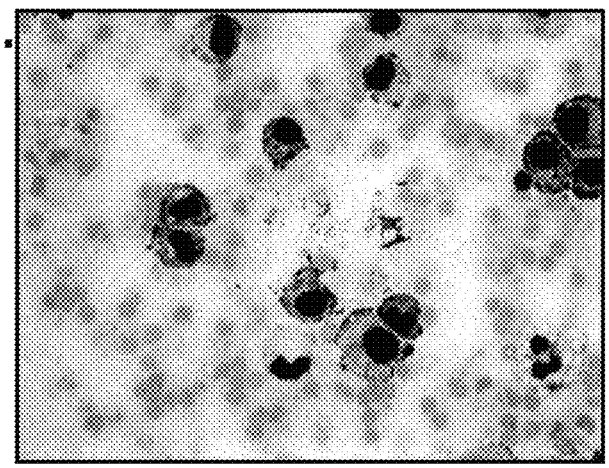
Figure 17E:
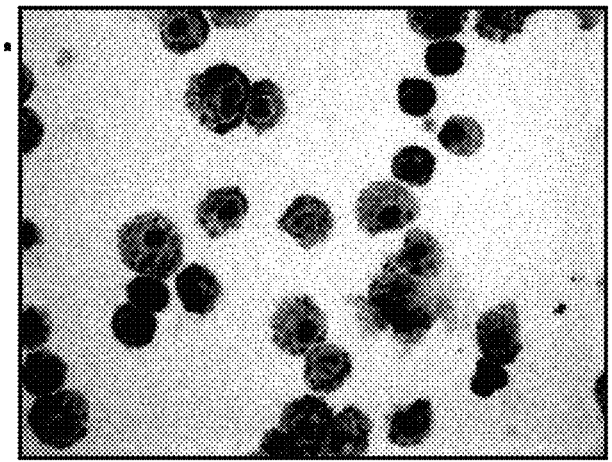

As shown in FIG. 17, the addition of TAT-Myc (FIG. 17C) during red blood cell differentiation leads to increased numbers and percent of red blood cell production compared with untreated controls (FIG. 17A), differentiation in IL3 and EPO alone (FIG. 17B), or IL3 and EPO with the addition of TAT-Bcl-2 (FIG. 17D) or the combination of TAT-Bcl-2 and TAT-Myc (FIG. 17E).

Example 17: Payloading Murine Red Blood Cells

5FU enriched bone marrow derived HSCs are collected as described previously. The cells are collected 5 days after 5 FU treatment of mice, placed in culture with IL-3, IL-6, SCF and TAT-MYC and TAT-Bcl-2. The cells are retrovirally transduced for the first 2 days of culture with one or more of pMSCV-hCD122-IRES-GFP or pMSCV-IRES-GFP. Following transduction, the cells are expanded in media containing IL-3, IL-6, SCF, TAT-MYC and TAT-Bcl-2 for another 14 days.

The cells are characterized by FACS for surface levels of c-kit, sca-1, lineage markers (B220, CD3, ter-119, Mac-1, Gr-1), as well as GFP expression and surface hCD122. The expanded murine LSK population that also expresses GFP and hCD122 will then be switched to the RBC differentiation conditions using media containing IL-3, EPO and low concentrations of TAT-MYC as described previously. 14-28 days later, the cultures will be continuously monitored and characterized for expression of CD71, GPA, adult and fetal hemoglobin, as well as GFP and hCD 122, as described previously.

Example 18: Generation of Biologically Active TAT-Myc and TAT-Bcl-2 Fusion Proteins Fusion proteins having the HIV-1 TAT protein transduction domain (PTD) and either the ORF for human Myc, or a truncated form of human Bcl-2, that has been deleted for the unstructured loop domain (Anderson, M., et al. (1999). *Prot Expr. Purif.* 15, 162-70), were generated. The recombinant proteins also encoded a V5 peptide tag and a 6– His tag, to facilitate detection and purification (FIG. 18A). The amino acid sequence and nucleotide sequence of the TAT-MYC fusion protein are depicted in FIG. 24. The amino acid sequence and nucleotide sequence of the TAT-Bcl-2A fusion protein are depicted in FIG. 25.

pTAT-Myc-V5-6× His ($Amp^R$) and pTAT-Bcl2Δ-V5-6× His($Amp^R$): plasmid were generated by PCR amplification of a cDNA encoding human cMyc or human Bcl2 using a forward primer encoding an in frame TAT protein transduction domain of HIV (RKKRRQRRR). The PCR products were cloned into pET101/D-Topo (Invitrogen) vector. The unstructured loop (A.A. #27-80) was removed from the BCL-2 coding sequence using a Quick Change site directed mutagenesis kit (Stratagene #200521-5).

The proteins were synthesized in *E. coli* and purified to homogeneity. SDS-PAGE electrophoresis and Coomassie Staining revealed the level of purity of the final product used for our studies (FIG. 18B). pTAT-Myc-V5-6× His was transformed into BL21-STAR(DE3) cells (Invitrogen) and protein was induced with 0.5 mM IPTG at 37° C. for 3 hrs. The cells were lysed in lysis buffer (8 M urea, 100 mM NaH2PO4, 10 mM Tris pH to 7.0, 10 mM imidazole, pH 7.2). The lysate was diluted to 6M urea and brought to 450 mM NaCl, 50 mM $NaH_2PO_4$, 5 mM Tris pH 7.0. The lysate was treated with Benzonase (500 units) at room temp for 1 hour, clarified by centrifugation at 12,000 RPM for 60 min and filtered through a 0.22 μM filter. Myc-V5-6× His was purified on a nickel affinity column (GE) using a GE AKTA purifier 10 FPLC. Myc-V5-6× His was refolded by dialyzing into dialysis buffer (450 mM NaCl, 50 mM $NaH_2PO_4$, 5 mM Tris pH 7.0, 5% glycerol, 1 mM DTT). Endotoxin was reduced by passing the purified protein over an Acticlean Etox colum (Sterogen).

Bcl2Δ-V5-6× His protein was induced as described above. The cells were lysed in 50 mL of lysis buffer (200 mM NaCl, 200 mM KCL, 50 mM $NaH_2PO_4$, 5 mM Tris pH 7.0, 5% glycerol, 1 mM DTT) supplemented with 500 units Benzonase, 1 mM PMSF, 2 ug/ml Leupeptin, 0.015 units/ml Aprotinin, 5 uM Hen Egg Lysozyme (HEL) per 1 L of induced protein, and immediately placed on ice for 1 hour. The cells were sonicated on ice (Duty cycle=50%, Output=5) for 2 sets of 2 minutes. The lysate was cleared by centrifugation at 12,000 RPM for 60 min and was filtered through a 0.22 μM filter. Bcl2Δ-V5-6× His was purified on a nickel affinity column (GE) and endotoxin was removed as described above.

Example 19: Confirmation of Appropriate Localization of TAT-Fusion Proteins

The fusion proteins localized to the appropriate intracellular compartment (FIG. 18C). NIH 3T3 cells were seeded onto glass cover slips in six-well plates and grown to 30 to 40% confluence. Each well was transduced with 10 µg/ml of TAT-Myc or TAT-Bcl-2 or no treatment as a negative control. The cells were fixed in 4% paraformaldehyde-PBS for 10 minutes at room temperature (RT) 2 hours following the protein transduction. Cells were permeabilized in PBS supplemented with 1% bovine serum albumin (BSA) and 0.1% Triton X-100 at RT for 3 minutes. Cells were incubated for 45 minutes with V5 mouse monoclonal antiserum (Invitrogen) diluted in PBS-1% BSA (1:1,000). Cells were washed and incubated for 30 minutes with Goat anti-mouse Alexa 488 secondary antibodies (Invitrogen A21121). Cover slips were mounted onto glass slides with a 10 µl drop of 50% glycerol with Hoechst at 1 µg/ml. Images were obtained on a Zeiss Imager Z1 Fluorescence microscope.

Figure 18D:
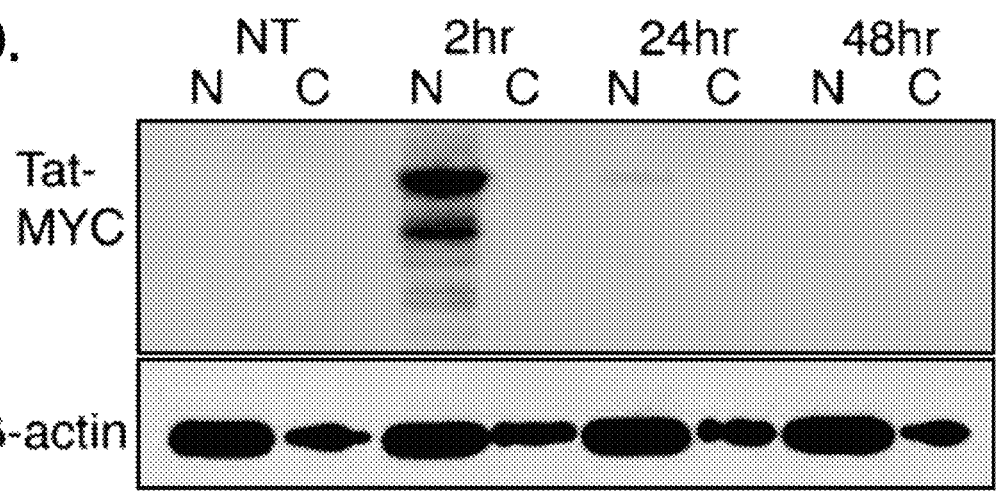
Figure 18E:
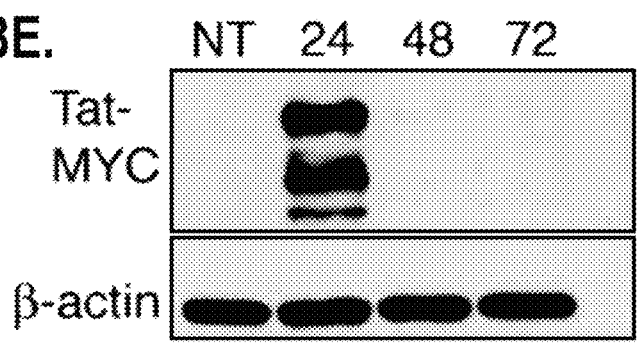

TAT-Myc rapidly localized to the nucleus in primary human HSCs (FIG. 18D). TAT-fusion proteins are fully degraded after 72 hours in HSCs (FIG. 18E). Fetal cord blood cells were transduced with TAT-Myc and TAT-Bcl2Δ for 1 hour followed by 3 PBS washes. Two hours post-transduction $5 \times 10^6$ cells were harvested and the nuclear and cytoplasmic fractions were isolated. Cells ($5 \times 10^6$) were harvested every 24 hours for the next 5 days. Nuclear and cytoplasmic proteins were prepared by lysing cells in 10 mM HEPES (pH 7.6), 10 mM $NaCl_2$, 3 mM $CaCl_2$, and 0.5% NP40. Nuclei were pelleted, and the cytoplasmic-containing supernatant fraction was precipitated with trichloroacetic acid (TCA). Following SDS-PAGE, Western blots were probed with anti-V5 antibody (Invitrogen), anti-human (β-actin (abcam), and goat anti-rabbit IgG-HRP or goat anti-mouse IgG-HRP (Santa Cruz Biotechnology).

Example 20: Expansion of Human Cord Blood-Derived HSCs with TAT-Myc and TAT-Bcl-2

Fresh cord blood cells were obtained from samples that were discarded from a local cord blood bank. All human cells were de-identified and exempt from IRB oversight. Cord blood included O+, O−, A+, A−, B+, B−, and AB+ all of which showed approximately the same expansion profiles.

The total cord volume was split into 20 ml aliquots and diluted 1:1 in PBS. Diluted cord blood (20 ml) was gently overlaid on 20 mls of Ficoll-Paque Plus (Amersham Biosciences Cat #17-1440-03). The cells were spun at 900× gravity for 60 min. The buffy coat was removed with a glass pipette and was washed twice with PBS. The cells were resuspended in FCB media (Iscove's (Gibco) supplemented with 10% human plasma, 100 units per ml Penn/Strep, 30 ml of media containing SCF, IL3 and IL6 and 30 mls of media containing TPO, FLT3-L, and GM-CSF described above. FCB media was further supplemented with 5 µg/ml recombinant TAT-Myc, and 10 µg/ml recombinant TAT-Bcl-2 just prior to addition to the fetal cord blood (FCB) cells. The medium was replaced every 3 days over the course of the expansion.

Figure 19A:
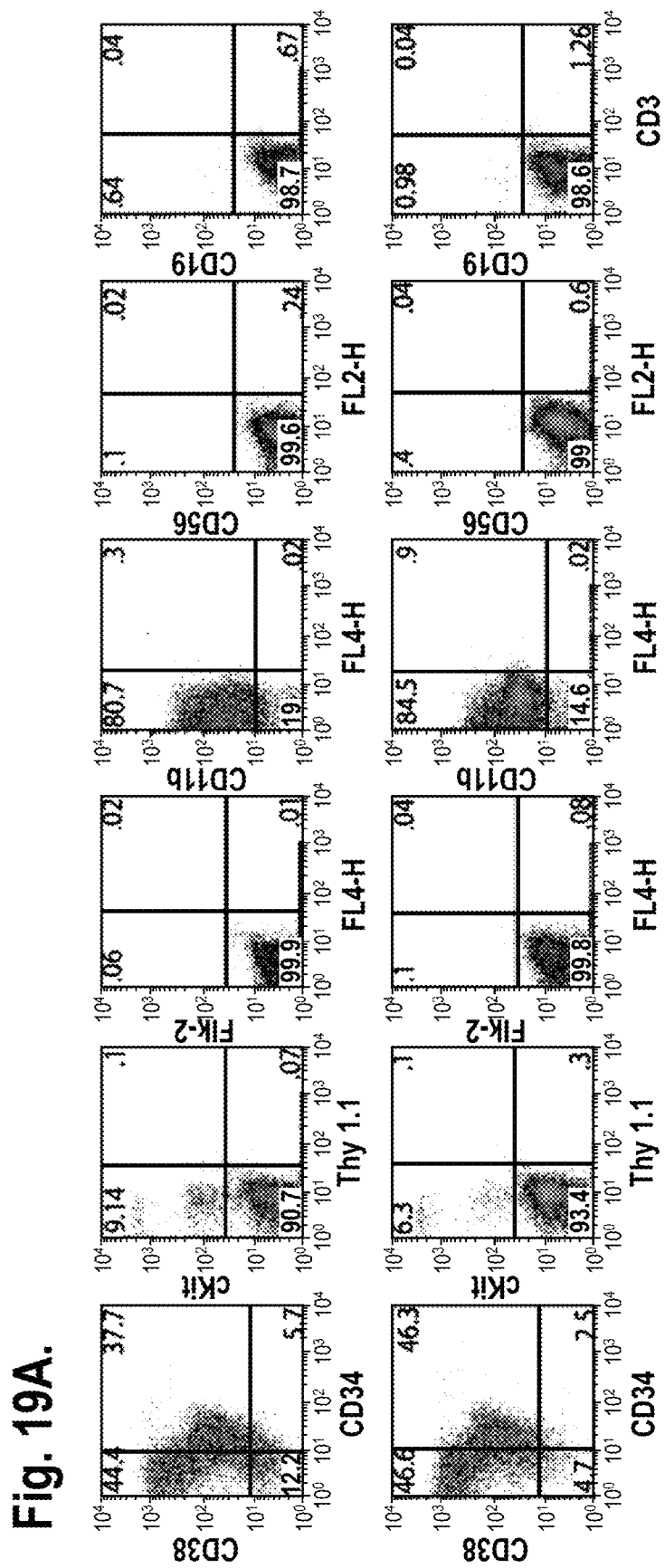
FIGS. 19A-19E depict a graphical representation of the expansion of human cord blood cell-derived HSCs with Tat-Myc and Tat-Bcl-2.
Figure 19B:
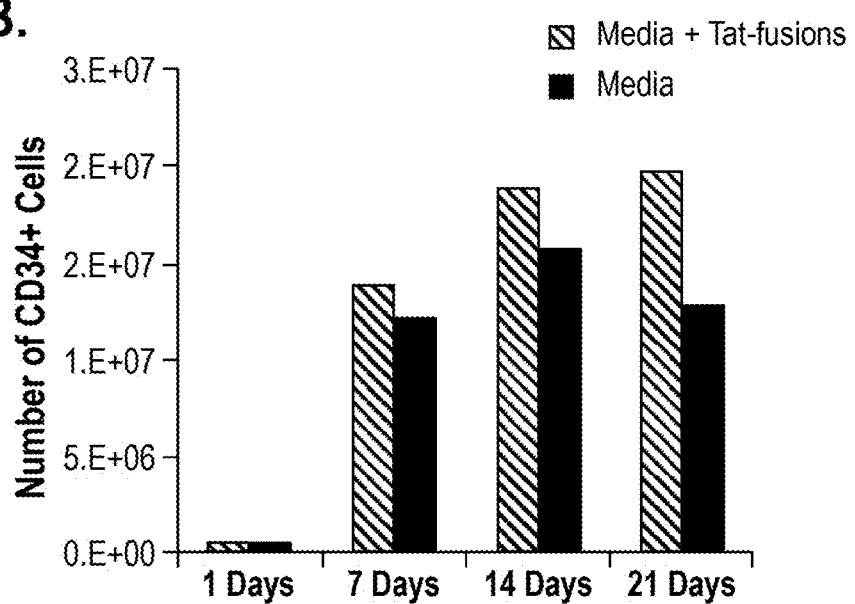

The cytokine cocktail contained IL3, IL6, TPO, Flt3-L, SCF, and GM-CSF which differs from previously reported media in the combination of these six cytokines (Suzuki, T., et al. (2006). Stem Cells 24, 2456-65.), as well as by the addition of recombinant TAT-Myc and TAT-Bcl-2. Evaluation of the surface phenotype of the in vitro expanded human HSCs showed that the human HSCs retain their surface characteristics after extended culture in the presence of TAT-Myc and TAT-Bcl-2 (FIG. 19A). This set of conditions resulted in 86.4 fold increase in the number of CD34+ cells in 14 days of culture, and 103.8 fold increase in the number of human CD34+ cells derived from unfractionated cord blood in 21 days of culture (FIG. 19B).

Figure 19C:
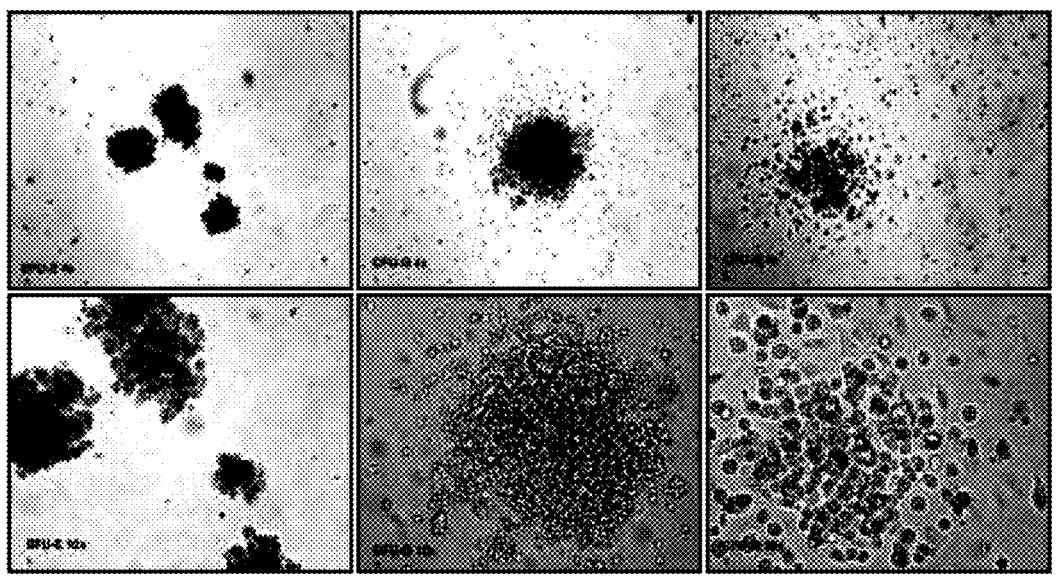
Figure 19D:
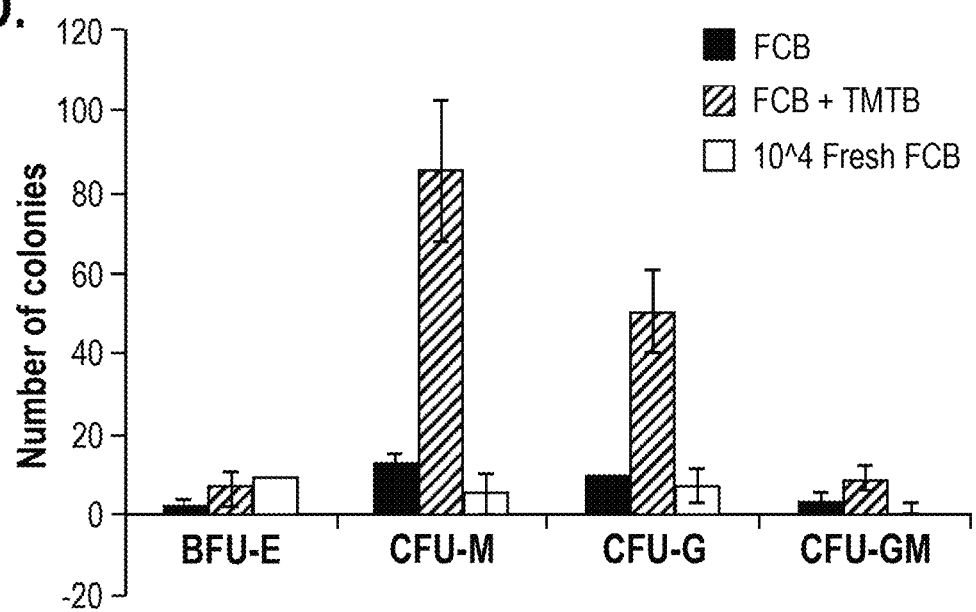
Figure 19E:
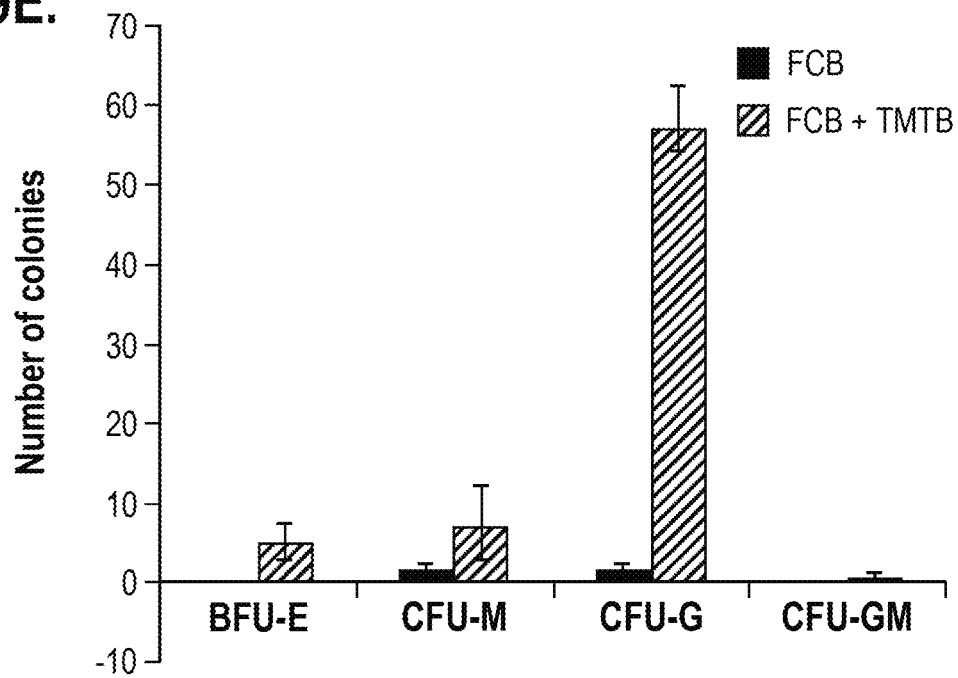

Example 21: TAT-Myc and TAT-Bcl-2 Expanded Human CB HSCs are Biologically Active In Vitro and In Vivo The in vitro expanded human HSCs were plated on MethoCult Optimum (StemCell Technologies), and were examined for their ability to give rise to specific colony types. The in vitro expanded human HSCs are able to give rise to CFU-G, CFU-M, CFU-GM and BFU-E colonies (FIGS. 19C and 19D). In addition, while the surface phenotype of the HSCs expanded in the presence of TAT-Myc and TAT-Bcl-2 was preserved in culture, their colony-forming unit content was significantly enriched under these conditions (FIG. 19D). The CD34+ cells expanded in the presence of TAT-Myc and TAT-Bcl-2 were also able to give rise to new BFU-E, CFU-M, CFU-G and CFU-GM colonies, whereas the CD34+ cells cultured in media alone did not generate new colonies (FIG. 19E).

NOD/SCID/gc−/− mice (NSG) mice were used as recipients for experiments to test the ability of the human CD34+ cells expanded in vitro to give rise to mature human hematopoietic lineages in vivo. This is a documented mouse model useful for this purpose (Tanaka, S., et al. (2012). Development of mature and functional human myeloid subsets in hematopoietic stem cell-engrafted NOD/SCID/IL2rgKO mice. J Immunol 188, 6145-55.).

Fetal cord blood cells (FCBs) were injected into NOD/SCID/gc−/− mice (NSG) mice (Jackson Laboratory) that received 180 rads of radiation just prior to injection. Expanded FCBs were washed 3 times in PBS and injected via the tail vein in 200p1 PBS. Eight weeks post-transplant, the mice were bled via the tail vein to assess reconstitution by flow cytometry using the following antibodies: anti-human CD3 (hCD3) (Biolegend Cat #300312), anti-human CD19 (hCD19) (Biolegend Cat #302208) and anti-human CD45 (hCD45) (Biolegend Cat #304028).

Figure 20A:
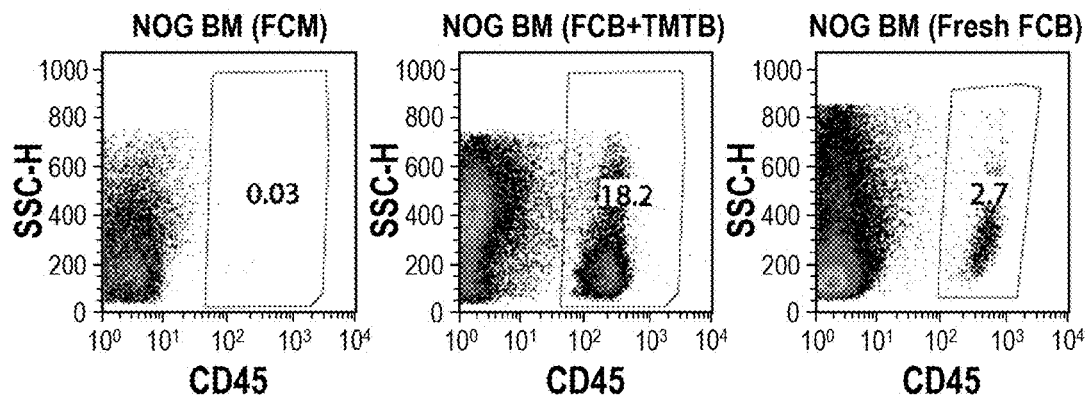
FIGS. 20A-20G depict a graphical representation of the functional analysis of human cord blood derived protein-transduced long term (ptlt)-HSC in vivo.
Figure 20B:
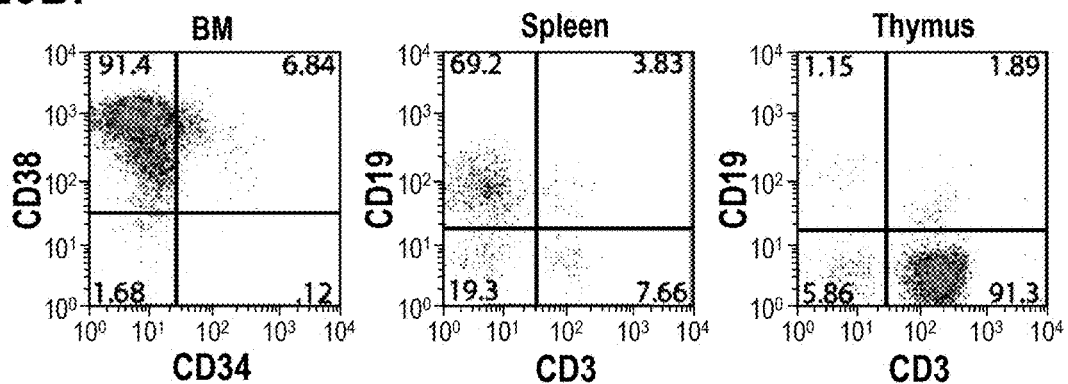

Short term development of human CD45+ expressing T and B cells in NSG chimeric mice generated with 1×107 unfractionated cord blood cells was observed. However, the introduction of 1×106 protein-transduced long-term (ptlt)-HSC generated in vitro by culture with TAT-Myc and TAT-Bcl-2 for 14 days resulted in a higher frequency of human CD45+ cells in xenochimeric NSG mice. In addition, human CD45+ cells could be observed in the peripheral blood of the mice for up to 20 weeks post transplant (FIG. 20A). Human CD45+, CD34+ CD38lo HSCs were found in the bone marrow (FIG. 20B), human CD45+/CD3+ and human CD45+/CD19+ lymphoid cells were found in the spleen, and human CD45+, CD3+ lymphoid cells were found in the thymus of xenochimeric mice.

Figure 20C:
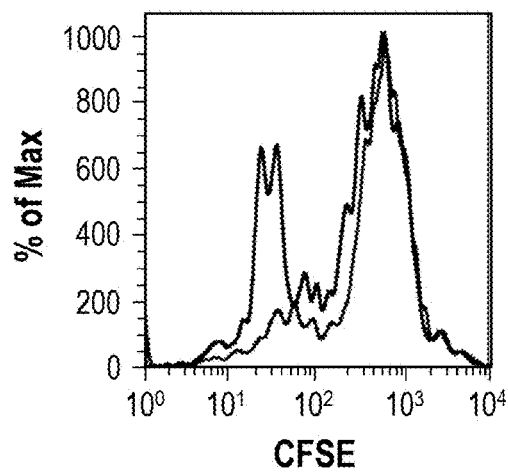

Human CD45+ CD19+ cells from the spleens of xenochimeric NSG mice were labeled with CFSE, and were activated with monoclonal antibodies to human CD40 and IgM. The cells were analyzed at 72 hours by flow cytometry for dilution of CFSE. FIG. 20C shows the proliferation profile of the human B-cells that developed in vivo in xenochimeric NSG mice.

Figure 20D:
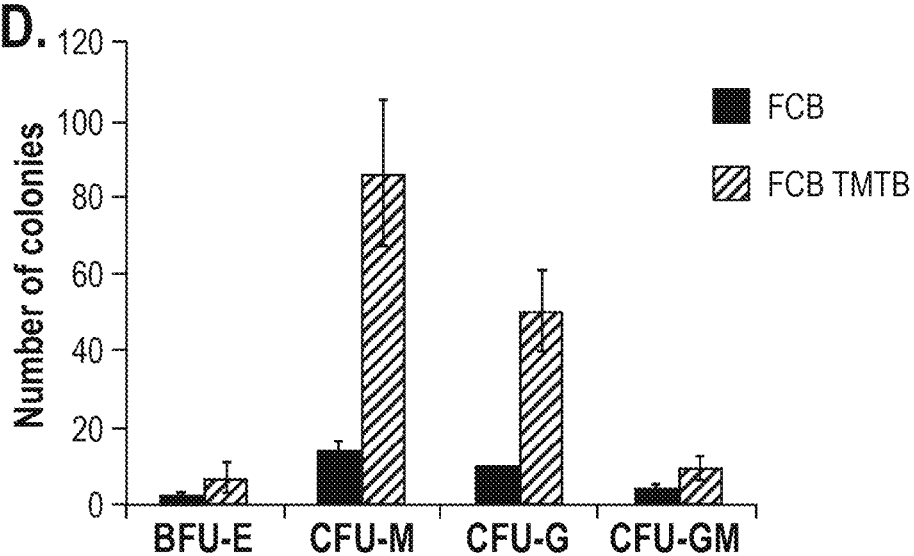
Figure 20E:
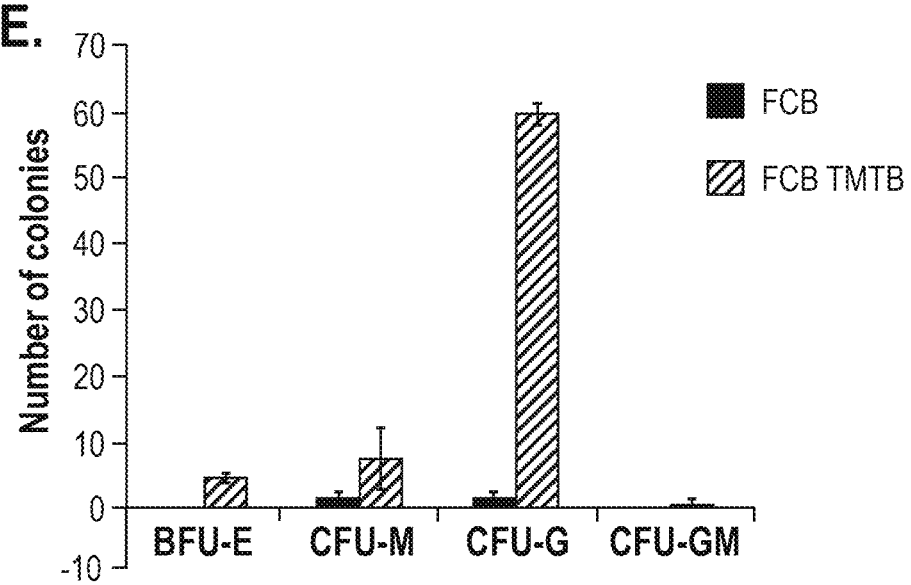

Human CD45+, CD34+ CD38lo HSCs from the bone marrow of xenochimeric NSG mice were used to seed in MethoCult Optimum. These cells gave rise to colonies in MethoCult plates (FIG. 20D), and some of the colonies could still be observed following serial replating (FIG. 20E). The number of colonies in both instances was significantly higher for NSG mice reconstituted with human cord blood cells cultured for 14 days with TAT-Myc and TAT-Bcl-2 than for cells obtained from NSG mice reconstituted with fresh, un-manipulated human cord blood cells.

Figure 20F:
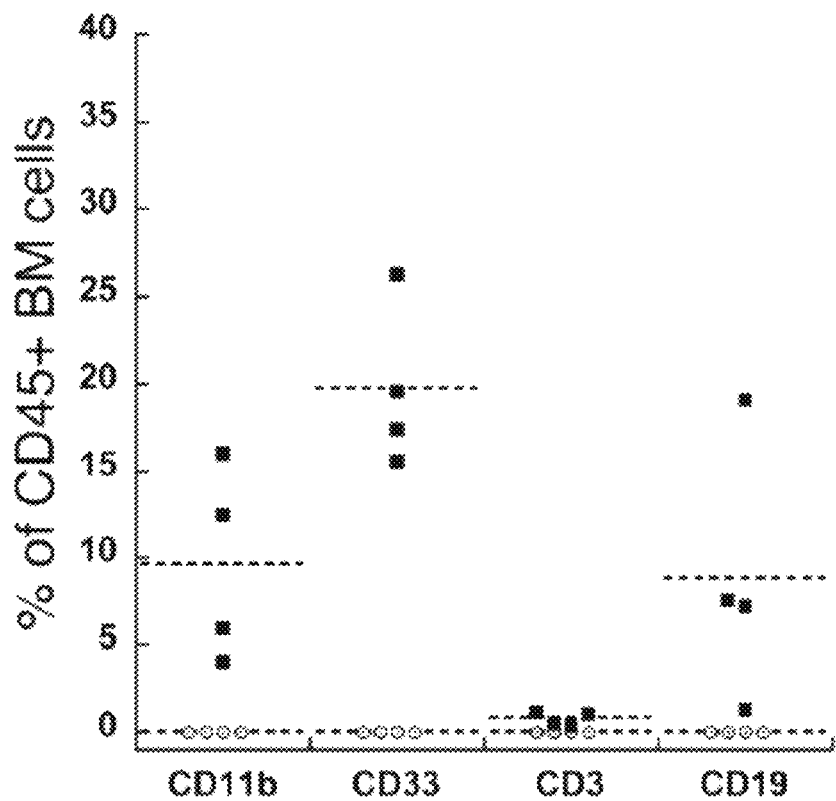
Figure 20G:
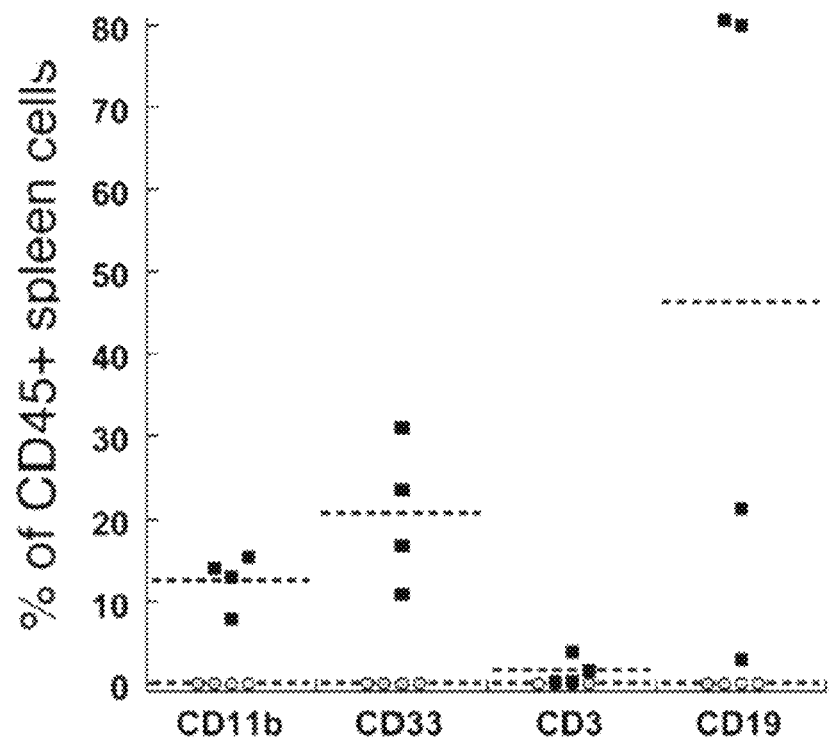

In addition, a cohort of xenochimeric mice, engrafted with 10⁶ cord blood cells previously expanded in vitro in a cocktail of cytokines supplemented with TAT-Myc and TAT-Bcl-2 (black squares), were assessed for myeloid and lymphoid cell differentiation. The CD45 positive population of bone marrow cells (FIG. 20F) and spleen cells (FIG. 20G) were analyzed for CD11b, CD33, CD3, and CD19 expression. Both myeloid and lymphoid cell differentiation was observed in the bone marrow and spleen of these xenochimeric mice.

Example 22: Expansion of Human G-CSF Mobilized Peripheral Blood HSCs with TAT-Myc and TAT-Bcl-2

G-CSF mobilized cells were received in a 1 ml volume of elutriated blood from 5 patients who underwent G-CSF mobilization for autologous HSC transplantation. All G-CSF samples were de-identified and no further identifying information was associated with the cells used for these studies. The cells were added drop wise to 10 ml of FCB media. The cells were washed twice in FCB media and treated with 5 µg/ml recombinant TAT-Myc and 10 µg/ml recombinant TAT-Bcl-2 in a 10 ml volume. Cells (5×10⁶) were seeded in the G-Rex 100 cell expansion device (Wilson Wolf Manufacturing) according to the manufacturer's recommendation.

Figure 21A:
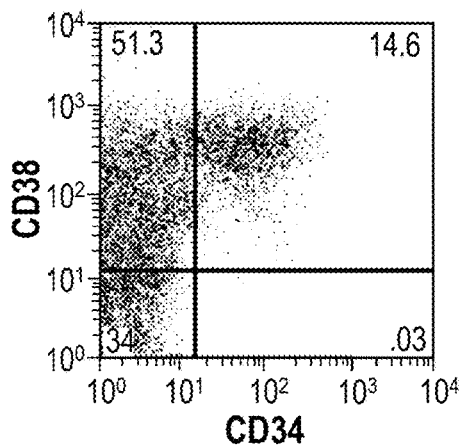
FIGS. 21A-21G depict a graphical representation of the expansion of adult human G-CSF mobilized HSCs in vitro with Tat-Myc and Tat-Bcl-2.
Figure 21B:
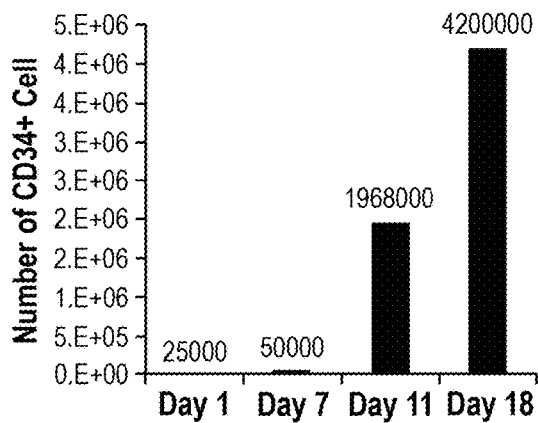

The cells were expanded in media supplemented with cytokines plus TAT-Myc and TAT-Bcl2 14 days. The FACS profile of the expanded HSCs shows a distinct population of hCD45+, CD34+, CD38hi, CD133+ cells (FIG. 21A). The kinetics of cell expansion are illustrated in FIG. 21B.

Figure 21C:
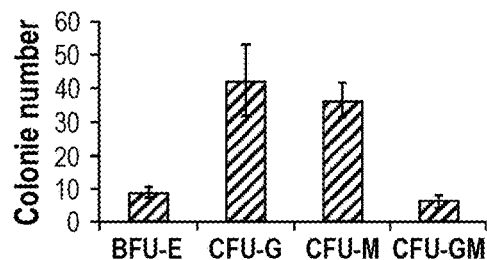

The expanded adult GCS-F mobilized HSCs were then plated on MethoCult Optimum in order to characterize their differentiation potential in vitro. The four colony types normally observed in the media that supports myeloerythroid differentiation were obtained (FIG. 21C), and some of these colony types were also observed upon serial replating.

Figure 21D:
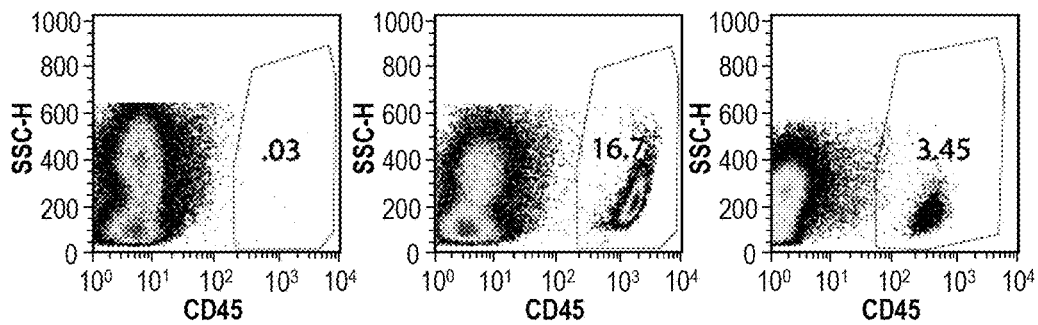

The expanded adult HSCs were able to reconstitute sublethally irradiated NSG mice. FIG. 21D shows a FACS analysis of the CD45+ staining of bone marrow from NSG mice transplanted 12 weeks earlier with either 10⁶ expanded G-CSF and TAT-Myc/TAT-Bcl-2 mobilized HSCs (first panel) or 5×10⁶ fresh un-manipulated cord blood cells (second panel).

Figure 21E:
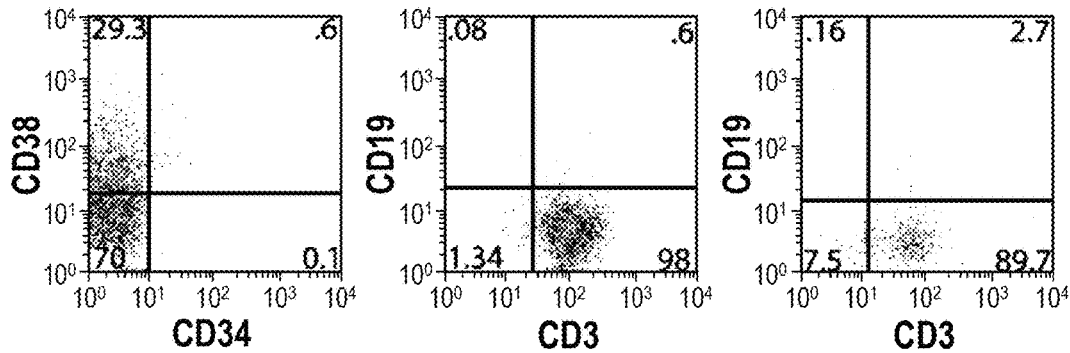

The NSG xenochimeric mice generated with G-CSF mobilized cells cultured with TAT-Myc and TAT-Bcl-2 were euthanized, and bone marrow, spleen and thymus were collected for further analysis. The analysis of lymphoid organs from xenochimeric NSG mice reconstituted with expanded adult HSCs showed that there were human CD45+, CD34+CD3810 cells in the bone marrow (FIG. 21E; first panel), human CD45+, CD3+ lymphoid cells in the spleen (FIG. 21E; second panel) and thymus (FIG. 21E; third panel) of those mice. Together, these data demonstrate that one can successfully expand the HSC population obtained from human G-CSF mobilized adult blood.

Figure 21F:
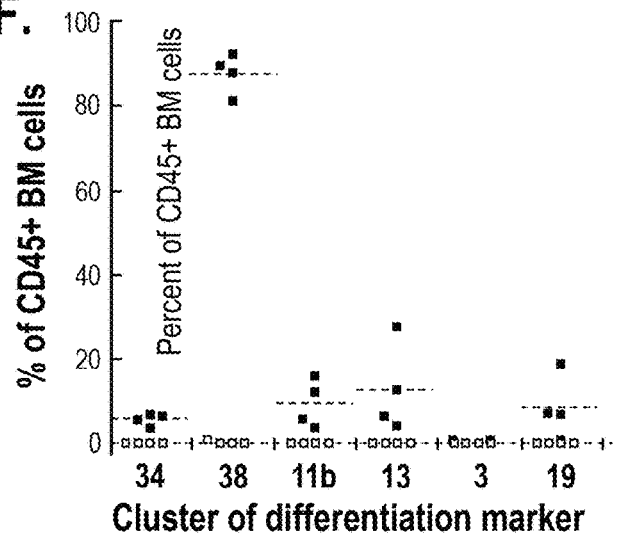
Figure 21G:
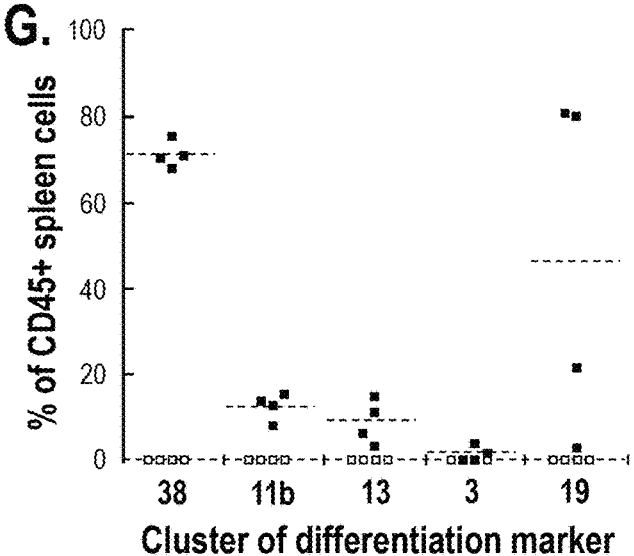

A cohort of xenochimeric mice engrafted with 10⁶ expanded G-CSF mobilized cells expanded in vitro in a cocktail of cytokines supplemented with TAT-Myc and TAT-Bcl-2 (black squares) were assessed for myeloid and lymphoid cell differentiation. The CD45 positive population of bone marrow cells (FIG. 21F) and spleen cells (FIG. 21G) were analyzed for CD11b, CD33, CD3, and CD19 expression. Both myeloid and lymphoid cell differentiation was observed in the bone marrow and spleen of these xenochimeric mice.

This method is able to generate a sufficient number of HSCs needed for transplantation of an average size adult according to current approaches (Sideri, A., et al. (2011). *Hematologica* 96, 1213-20.).

Example 23: Generation of Biologically Active Myc Fusion Proteins

Figures 22A, 22B:
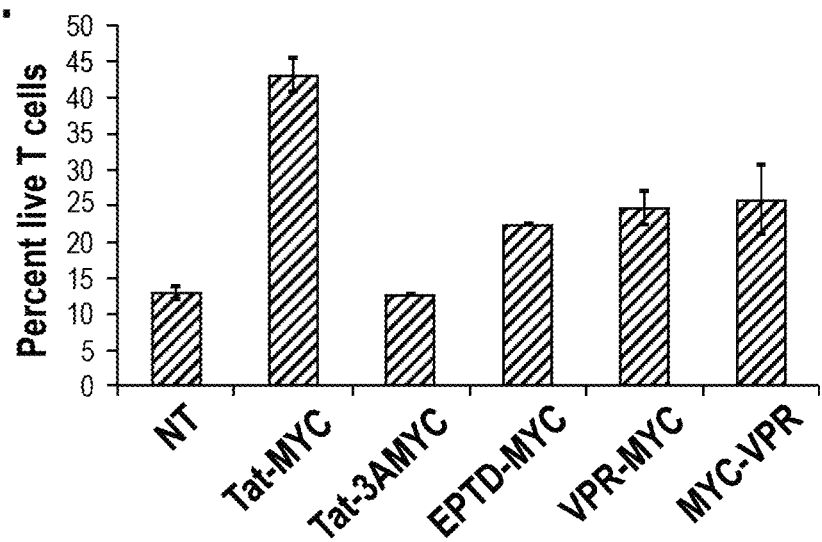
FIGS. 22A and 22B depict the activity of various Myc fusion protein constructs in an activated T cell viability assay.
Figure 23A:
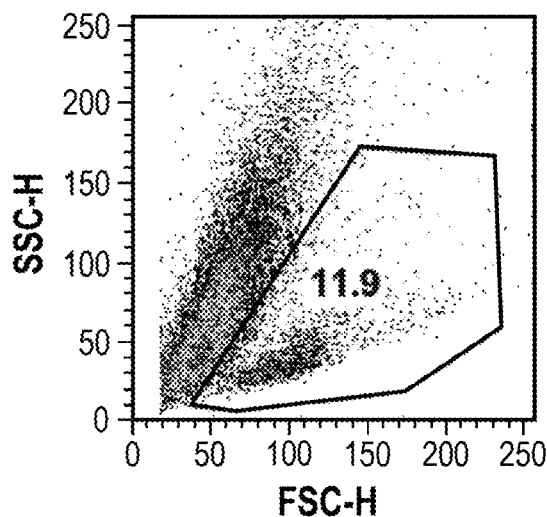
FIGS. 23A-23D depict the activity of various Tat-fusion proteins (each at 50 ug/ml) in an activated T cell viability assay.
Figure 23B:
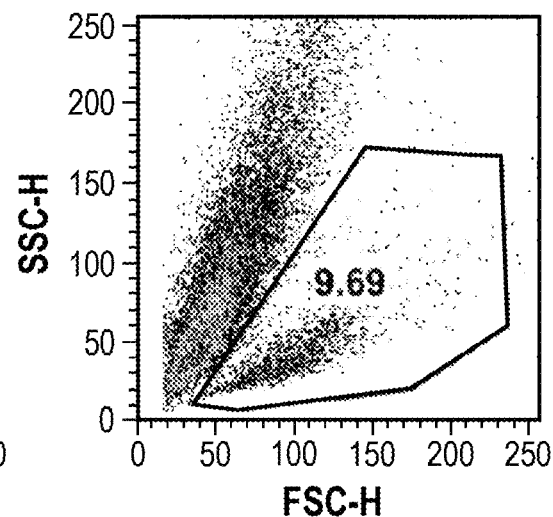
Figure 23C:
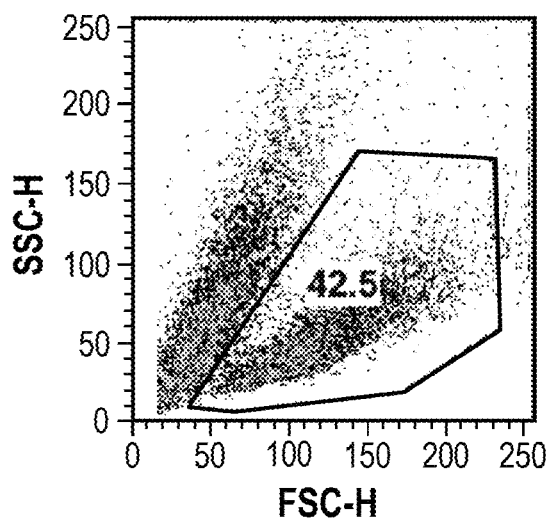
Figure 23D:
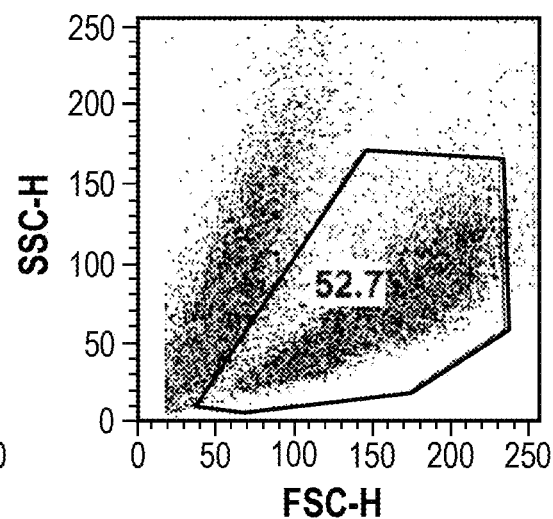

Five Myc fusion proteins in addition to the TAT-Myc fusion protein described in Example 18 were generated and purified using the same approach described there. The plasmids were made by PCR amplification of the coding region using a forward primer that contains an in frame N-terminal PTD-amino-acid sequence and a reverse primer that removed the stop codon. The PCR product was then cloned into pET101/D-Topo (Invitrogen) vector, which includes a C-terminal V5 epitope and 6x-histidine purification tag. FIG. 22A shows a diagrammatic representation of the Myc fusion proteins as compared with TAT-Myc from Example 18. In each, a protein transduction (PTD) is fused in frame before or after the Myc polypeptide.

Protein transduction domains included TAT, EPTD, and VPR. EPTD is an optimized protein transduction domain (YARAAARQARA) taken from Ho, A. et al. (Synthetic protein transduction domains: enhanced transduction potential in vitro and in vivo. *Cancer Res.* (2001) 61:474-477). VPR transduction domain was as identified by Taguchi, T. et al. (Nuclear trafficking of macromolecules by an oligopeptide derived from VPR of human immunodeficiency virus type-1. *Biochem. Biophys. Res. Commun.* (2004) 320(1):18-26).

Myc was either the ORF of the polypeptide as described in Example 1, or of the 3AMyc sequence previously described by Huang, Z. et al. (Negative control of the Myc protein by the stress-responsive kinase Pak-2. Mol Cell Biol (2004) 24(4):1582-94). The recombinant proteins also encoded a V5 peptide tag and a 6– His tag, to facilitate detection and purification. (FIG. 22A).

Example 24: Activated T Cell Survival Assays

The Myc fusion proteins described in Example 23 (TAT-Myc, TAT-3AMyc, EPTD-Myc, VPR-Myc, and Myc-VPR) were tested for Myc biological activity in an activated T cell viability assay (FIG. 22B). A spleen was harvested from a C57BL.6j (Jackson) mouse, and mechanically dissociated through wire mess. The red blood cells were removed, and the T cells were activated with 1 µg/ml anti-CD3 (2c11). The cells were plated into a 24 well cluster dish at 3×10^6 cells per well in 1 ml of media. 48 hrs later, the live cells were captured on a Ficol cushion, washed, and plated in a 24 well cluster dishes at 1-1.5×1^6 cells per well. The PTD-Myc proteins were titrated onto the T cells at 0.5, 1, 5, 10, 25, or 50 ug/ml. 48 hrs after the PTD-Myc protein treatment, the cells were assessed for viability by flow cytometry (forward x side-scatter). In FIG. 22B, the data presented are for the 25 ug/ml protein treatment.

As shown in FIG. 22B, all the constructs tested, except TAT-3AMyc, resulted in greater T cell viability after 48 hours than the untreated control. However, no construct resulted in greater T cell viability than TAT-Myc described in Example 1.

In a similar experiment, the activity of TAT-Myc and TAT-Bcl-2 at various concentrations is shown in Table 5, below. T cells from spleens of C57BL.6j (Jackson) mice are activated with 1 μg/ml anti-CD3 (2c11). Following activation (48 hours later), the cells were washed, were plated at about 1-1.5×10⁶ cells/well, and fusion proteins (TAT-Myc or TAT-Bcl-2) at various concentrations (0.5, 1, 5, 10, 25, or 50 ug/ml) were added. After 48 hours, the percent of live cells was determined by flow cytometry (forward x side scatter) as shown in Table 5, below.

TABLE 5

| Concentration [ug/ml] | TAT-Bcl2 (% viable) | TAT-Myc (% viable) |
| --- | --- | --- |
| 0 | 8.5 | 3.1 |
| 0.5 | 9.5 | 5 |
| 1 | 11.4 | 7.68 |
| 5 | 21.1 | 14.3 |
| 10 | 22.4 | 24.4 |
| 25 | 31.9 | 25 |
| 50 | 32.8 | 19.8 |

For both TAT-Myc and TAT-Bcl-2, and at all concentrations tested, cell viability and/or proliferation is increased as compared with cells incubated in the absence of either fusion protein.

In a separate experiment using the same methods, FIG. 23 provides the FACS data for the live gate for activated T cells treated with 50 ug/ml of fusion proteins; TAT-Bcl-2 and TAT-Myc are compared with control (TAT-Cre or no treatment). As shown, both TAT-Myc and TAT-Bcl-2 treatments result in significantly improved T cell survival and/or proliferation.

Example 25: Evaluation of Bcl-2

3T3 cells were transduced with TAT-Bcl2 for 1 hour followed by 3 PBS washes. Two hours post-transduction, the cells were Trypsanized, counted, and 5×10⁶ were harvested. The nuclear and cytoplasmic fractions were isolated. 5×10⁶ cells were harvested every 24 hours for the next 5 days. Nuclear and cytoplasmic proteins were prepared by lysing cells in 10 mMHEPES (pH 7.6), 10 mM NaCl$_2$, 3 mM CaCl$_2$, and 0.5% NP40. Nuclei were pelleted, and the cytoplasmic-containing supernatant fraction was precipitated with trichloroacetic acid (TCA). Western blots were probed with anti-VS antibody (Invitrogen), and goat anti-mouse IgG-HRP (Santa Cruz Biotechnology).

TAT-Bcl2 was observed in the cytoplasmic fraction at 24 and 48 hours. The signal began to diminish by 72 hrs post transduction and was no longer observed at the 96 hour time point.

Plasmids expressing TAT-Bcl2, TAT-Bcl2Δ, EPTD-Bcl2, VPR-Bcl2, VPR-Bcl2Δ, and VPR-BclXL were created. pPTD-Bcl2-V5-6× His(Amp$^R$): plasmids were generated by PCR amplification of a cDNA encoding human Bcl2 using a forward primer encoding an in frame PTD (TAT, EPTD or VPR) protein transduction domain. The PCR products were cloned into pET101/D-Topo (Invitrogen) vector. To generate the Bcl2Δ the unstructured loop (A.A. #27-80) was removed from the BCL-2 coding sequence using a Quick Change site directed mutagenesis kit (Stratagene #200521-5). VPR-BclXL was made in a similar fashion as the PTD-Bcl 2 described above, but using the cDNA of human BclXL rather than Bcl2.

The amino acid sequence and nucleic acid sequence of TAT-Bcl-2Δ are shown in FIG. 25.

Example 26: Generation of Mature RBCs from HSCs

CD34+ cell were purified from mobilized peripheral blood using Dynal CD34 positive selection beads according to the manufacturer's protocol. The CD34+ cells were treated for 1 hour at 37° C. with 5 ug/ml TAT-MYC and 5 ug/ml TAT-Bcl2 in iscoves media supplemented with 15% human plamsa, and 100 units/ml penn strep. Following the treatment with TAT-MYC and TAT-Bcl2, the cells are spun down at 1200 rpm for 5 minutes and the media is removed from the cell pellet. The treated primary CD34+ cells are seeded in erythroid differentiation media (Iscoves media supplemented with 15% human plasma, 100 units/ml penn strep, 100 units/ml EPO, and 3.2 ng/ml IL3) shifting their cellular programming away from being HSCs and towards erythroid cells because of the presence of the IL3 and EPO cytokines in the RBC media.

Treating the purified CD34+ cells with this single bolus TAT-MYC and TAT-Bcl2 improves these differentiation cultures in 2 ways. First, primary CD34+ cell treated with TAT-fusion proteins show improved viability during their differentiation resulting in the production of a greater number of mature red blood cells. Second, primary CD34+ cell treated with TAT-MYC and TAT-Bcl2 and seeded in RBC differentiation media show a better commitment to differentiating down the erythroid lineage rather then differentiating into other myeloid cells.

Figure 26A:
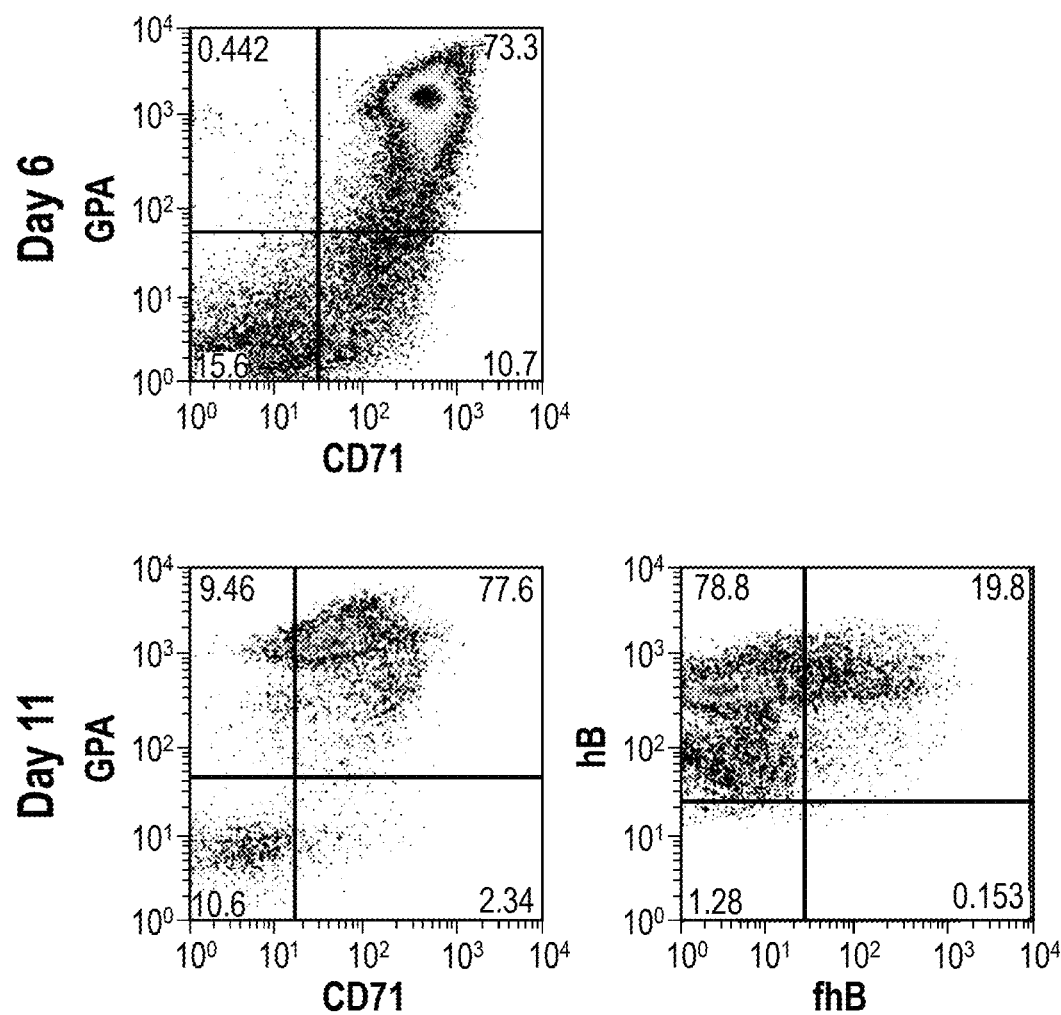
FIGS. 26A and 26B depict primary HSCs also differentiate into mature red blood cells using differentiation media including Tat-Myc.

After the TAT-MYC and TAT-Bcl2 treatment, the CD34+ cells were seeded in wells of a 24 well cluster dish at 5×10^4 cells per well in RBC differentiation media described above. The cells were allowed to differentiate for 11 days. On day 6 and 11, cells were assessed for GPAxCD71 erythroid surface markers (FIG. 26A). The TAT-Myc and TAT-Bcl2 treated cells differentiate into erythroid cells as indicated by the 74% and 87.6% GPAxCD71 double positive cells (FIG. 26.A; day 6 and 11 respectively). Additionally, these erythroid cells continue to express adult hemoglobin over fetal hemoglobin indicated by the 78.8% of the cells that uniquely express adult hemoglobin compared to the 19.8% of the cells that express fetal hemoglobin (FIG. 26A; day 11 hB×fhB panel).

Figure 26B:
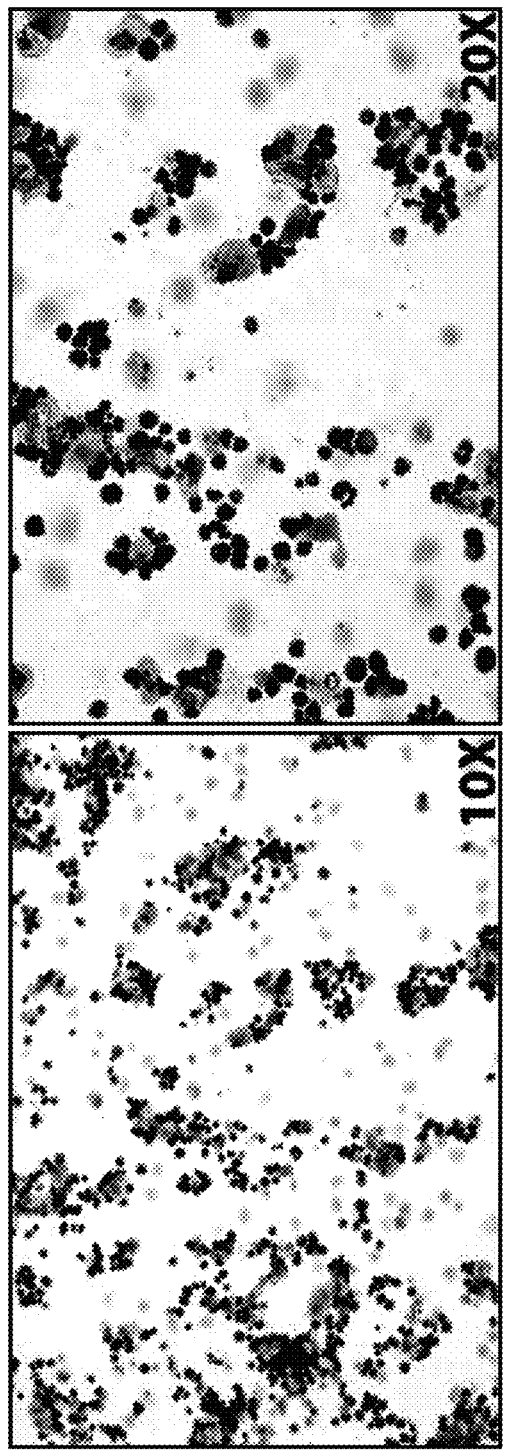

On day 10, a sample from the differentiation culture was cytospun on to a coverslip for H&E staining. Images are 10× and 20× magnification (FIG. 26B). Hemoglobin expressing cells that have become anucleated were observed, as indicated by the red staining cells that lack a dark staining nucleus in the center of the (FIG. 26B).

What is claimed is:

1. A method for increasing the viability of a population of primary mature red blood cells in vitro comprising:
   treating the population of primary mature red blood cells in a culture media comprising a TAT-Bcl-2 fusion protein, wherein said treating results in increased viability in the population of primary mature red blood cells when compared to an untreated control.

2. The method of claim 1, wherein the population of primary mature red blood cells is produced by in vitro differentiation of hematopoietic stem cells.

3. The method of claim 1, wherein the population of primary mature red blood cells is obtained from peripheral blood of a subject.

4. The method of claim 1, wherein the population of primary mature red blood cells is an RBC concentrate.

5. The method of claim 1, wherein the population of primary mature red blood cells is a clinical RBC product.

6. The method of claim 1, wherein the culture media is a red blood cell storage media.

7. The method of claim 1, wherein the TAT-Bcl-2 fusion protein is provided in the culture media as a single bolus or provided in the culture media at intervals.

8. The method of claim 1, wherein the TAT-Bcl-2 fusion protein is provided in the culture media every 24 hours, every 48 hours, every 72 hours, or every 96 hours.

9. The method of claim 1, wherein the TAT-Bcl-2 fusion protein is provided in the culture media at a concentration of 0.5 µg/ml to 100 µg/ml.

10. The method of claim 1, wherein the TAT-Bcl-2 fusion protein is provided in the culture media at a concentration of 1 µg/ml, 5 µg/ml, 10 µg/ml, 25 µg/ml, or 50 µg/ml.

* * * * *